US012778126B2

(12) United States Patent
Kuzmina et al.

(10) Patent No.: US 12,778,126 B2
(45) Date of Patent: Nov. 3, 2026

(54) MESOIONIC IMIDAZOLIUM COMPOUNDS AND DERIVATIVES FOR COMBATING ANIMAL PESTS

(71) Applicant: BASF SE, Ludwigshafen (DE)

(72) Inventors: Olesya Kuzmina, Ludwigshafen (DE); Ashokkumar Adisechan, Navi Mumbai (IN); Joachim Dickhaut, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 1070 days.

(21) Appl. No.: 17/607,072

(22) PCT Filed: May 19, 2020

(86) PCT No.: PCT/EP2020/063883

§ 371 (c)(1),
(2) Date: Oct. 28, 2021

(87) PCT Pub. No.: WO2020/239517

PCT Pub. Date: Dec. 3, 2020

(65) Prior Publication Data

US 2022/0202017 A1 Jun. 30, 2022

(30) Foreign Application Priority Data

May 29, 2019 (IN) ............................ 2019 21021350
Jul. 22, 2019 (EP) .................................... 19187583

(51) Int. Cl.

| | |
|---|---|
| ***C07D 487/04*** | (2006.01) |
| ***A01N 43/50*** | (2006.01) |
| ***A01N 43/90*** | (2006.01) |
| ***A01P 7/04*** | (2006.01) |
| ***C07D 513/04*** | (2006.01) |

(52) U.S. Cl.

CPC ................ *A01N 43/90* (2013.01); *A01P 7/04* (2021.08); *C07D 487/04* (2013.01); *C07D 513/04* (2013.01)

(58) Field of Classification Search

CPC ...... C07D 487/04; A01N 43/90; A01N 43/50; A01P 7/04

See application file for complete search history.

(56) References Cited

FOREIGN PATENT DOCUMENTS

| | | | |
|---|---|---|---|
| WO | WO-2014/167084 | A1 | 10/2014 |
| WO | WO-2017/093214 | A1 | 6/2017 |
| WO | WO-2018/108730 | A1 | 6/2018 |
| WO | WO-2018/189077 | A1 | 10/2018 |
| WO | WO-2018/192872 | A1 | 10/2018 |
| WO | WO-2018/208595 | A1 | 11/2018 |
| WO | WO-2018/229202 | A1 | 12/2018 |
| WO | WO-2019/086474 | A1 | 5/2019 |

OTHER PUBLICATIONS

Ichinari et al., Formation and Reaction of Mesoionic Imidazolo[2,3-b][1,3]thiazines and [1,2,4,6]Thiatriazino[3,2-b][1,3]thiazin-4-one 2,2-Diosides from 2-Arylimino-1,3-thiazines, Heterocycles, 27(1):227-35 (1988).

International Application No. PCT/EP2020/063883, International Search Report and Written Opinion, mailed Jul. 30, 2020.

European Search Report for EP Patent Application No. 19187583.0, Issued on Dec. 13, 2019, 3 pages.

*Primary Examiner* — Brenda L Coleman

(57) ABSTRACT

Mesoionic imidazolium compounds of formula (I) and their uses for combating animal pests. The present invention relates to compounds of formula (I), wherein A, W, Y, T and $R^1$ are defined as in the description, and to the stereoisomers, salts, tautomers and N-oxides thereof and to compositions comprising such compounds. The invention also relates to methods and uses of these compounds and of compositions thereof, for combating and controlling animal pests. Furthermore the invention relates also to pesticidal methods of applying such substituted pyrimidinium compounds.

(I)

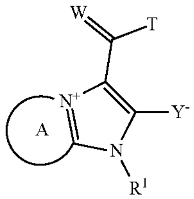

15 Claims, No Drawings

MESOIONIC IMIDAZOLIUM COMPOUNDS AND DERIVATIVES FOR COMBATING ANIMAL PESTS

CROSS-REFERENCE TO RELATED APPLICATIONS

This is the U.S. national phase of International Application No. PCT/EP2020/063883, filed May 19, 2020, which claims the benefit of Indian Patent Application number 201921021350, filed May 29, 2019, and European Patent Application No. 19187583.0, filed on Jul. 22, 2019.

The present invention relates to insecticidal substituted imidazolium compounds and/or to the compositions comprising such compounds for combating invertebrate pests. The invention also relates to pesticidal methods, to uses and to applications of substituted imidazolium compounds as described in the present invention and the stereoisomers, salts, tautomers and N-oxides thereof as well as compositions comprising them.

Invertebrate pests and in particular insects, arthropods and nematodes destroy growing and harvested crops and attack wooden dwelling and commercial structures, thereby causing large economic loss to the food supply and to property. While a large number of pesticidal agents are known, due to the ability of target pests to develop resistance to said agents, there is an ongoing need for new agents for combating invertebrate pests such as insects, arachnids and nematodes. It is therefore an object of the present invention to provide compounds having a good pesticidal activity and showing a broad activity spectrum against a large number of different invertebrate pests, especially against difficult to control insects, arachnids and nematodes.

It has been found that these objectives can be achieved by compounds of the general formula (I), as defined below, including their stereoisomers, their salts, in particular their agriculturally or veterinary acceptable salts, their tautomers and their N-oxides.

Therefore, in a first aspect the present invention provides compounds of formula (I)

I

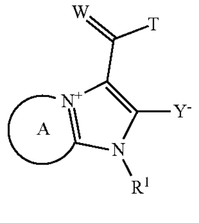

Y is O or S

W is O, S, $NOR^{15}$

T is $R^5$, $OR^6$, $—N(R^7)(R^8)$ or $—N(R^{7a})—N(R^7)(R^8)$, $C(=Z)R^{12}$, $C(=Z)OR^{13}$, or $C(=O)NR^{14a}R^{14b}$;

Z is O, S, or $N—OR^{15}$, $R^1$ is $NO_2$, CN $C_1$-$C_8$-alkyl, $C_2$-$C_8$-alkenyl, $C_2$-$C_8$-alkynyl, $C_3$-$C_{10}$-cycloalkyl, $C_4$-$C_{10}$-cycloalkenyl, $C_5$-$C_{14}$-cycloalkylcycloalkyl or $R^1$ may form a three- to eleven-membered saturated, or partially unsaturated or aromatic carbo- or heterocyclic ring or ring system, which may contain 1 to 4 heteroatoms selected from $N(R^c)_p$, O, and S, wherein S may be oxidized, and wherein the aforementioned groups and the carbo- or heterocyclic rings system may be unsubstituted, partially or fully substituted with $R^a$;

or $R^1$ is $C(=O)R^b$, $C(=O)OR^e$, $NR^bR^c$, $C(=O)NR^bR^c$, $C(=S)NR^bR^c$, $SO_2NR^bR^c$, $OC(=O)R^c$, $OC(=O)OR^e$, $OC(=O)NR^bR^e$, $N(R^c)C(=O)R^c$, $N(R^c)C(=O)OR^e$, $N(R^c)C(=O)NR^bR^c$, $NR^cSO_2R^b$, $NR^cSO_2NR^bR^c$, $Si(R^d)_3$, $C(=NR^c)R^c$, $C(=NOR^c)R^c$, $C(=NNR^bR^c)R^c$, $C(=NN(C(=O)R^b)R^c)R^c$, $C(=NN(C=O)OR^c)(R^c)_2$, $S(=O)_o(=NR^b)_qR^c$ or $N=CR^bR^c$;

A is a four- to seven-membered saturated or partially unsaturated ring, taken together with the carbon and nitrogen of the imidazole ring in formula (I), wherein each remaining ring member is selected from carbon atoms and up to 3 heteroatoms independently selected from up to 2 O, up to 2 S, and up to 3 N, wherein up to 2 carbon atom ring members are independently selected from C(=O) and C(=S), and the sulfur atom ring members are independently selected from $S(=O)_m$, wherein each ring member may be substituted with $R^a$ and/or $R^c$;

wherein the ring A is substituted with one $R^4$;

$R^4$ is Het or $R^{4a}$;

Het is a three- to ten-membered heterocyclic ring or a seven- to eleven-membered heterocyclic ring system, each ring or ring system member selected from carbon atoms and up to 4 heteroatoms independently selected from up to 2 O, up to 2 S, and up to 4 $N(R^c)_p$, wherein up to 3 carbon atom ring members are independently selected from C(=O) and C(=S) and the sulfur atom ring members are independently selected from $S(=O)_o(=NR^b)_q$, each ring or ring system optionally substituted with up to 5 $R^a$;

o, q are each independently 0, 1 or 2, provided that the sum (o+q) is 0, 1 or 2 for each ring;

$R^{4a}$ is $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_7$-cycloalkyl, $C_3$-$C_7$-halocycloalkyl, $C_4$-$C_8$-alkylcycloalkyl, $C_4$-$C_8$-haloalkylcycloalkyl, $C_4$-$C_8$-cycloalkylalkyl, $C_4$-$C_8$-halocycloalkylalkyl, $C_1$-$C_6$-alkoxy, $C_1$-$C_6$-haloalkoxy, $C_2$-$C_6$-alkylcarbonyl, $C_2$-$C_6$-haloalkylcarbonyl, CN;

each optionally substituted with one or more substituents selected from CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_cR^c$, $SO_2NR^b(=O)NR^bR^c$, $P(=W)R^bR^c$, $OP(=W)(O_pR^c)R^b$, $OP(=W)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^{b}$-$NR^bC(=W)NR^bR^c$, $NR^bNR^bSO_2NR^bR^c$, or $N=S(=O)_pR^cR^c$, or two geminally bound groups $R^{4a}$ together may form a group selected from =O, =S, $=CR^bR^c$, $=NR^c$, $=NOR^c$, and $=NNR^cR^c$;

or $R^{4a}$ is phenyl optionally substituted with one or more substituents selected from halogen, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, C(=N $(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=W)R^bR^c$, $OP(=W)(O_pR^c)R^b$, $OP(=W)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=W)NR^bR^c$, $NR^bNR^bSO_2NR^bR^c$, or $N=S(=O)_pR^cR^c$, or $R^{4a}$ is phenyl optionally substituted with one or more substituents selected from $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_7$-cycloalkyl, $C_3$-$C_7$-halocycloalkyl, $C_4$-$C_8$-alkylcycloalkyl, $C_4$-$C_8$-haloalkylcycloalkyl, $C_4$-$C_8$-cycloalkylalkyl, $C_4$-$C_8$-halocycloalkylalkyl, $C_1$-$C_6$-alkoxy, $C_1$-$C_6$-haloalkoxy, $C_2$-$C_6$-alkylcarbonyl, $C_2$-$C_6$-haloalkylcarbonyl, which groups may optionally be substituted with halogen, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=W)R^bR^c$, $OP(=W)(O_pR^c)R^b$, $OP(=W)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=W)NR^bR^c$, $NR^bNR^bSO_2NR^bR^c$, or $N=S(=O)_pR^cR^c$;

$R^a$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $N=S(=O)_pR^cR^c$, $S(=O)_o(=NR^b)_qR^c$, $SF_5$, OCN, SCN, $Si(R^d)_3$ or a three- to six-membered saturated, or partially unsaturated or aromatic carbo- or heterocyclic ring, which may contain 1 to 3 heteroatoms selected from $N-(R^c)_p$, O, and S which may be oxidized, and wherein the aforementioned groups and the carbo- or heterocyclic ring may be partially or fully substituted with $R^{aa}$, or two geminally bound groups $R^a$ together may form a group selected from $=O$, $=S$, $=CR^bR^c$, $=NR^c$, $=NOR^c$, and $=NNR^cR^c$;

$R^{aa}$ is each independently halogen, $C_1$-$C_6$-alkyl, $C_1$-$C_6$-haloalkyl, $C_1$-$C_6$-alkoxy or $C_1$-$C_6$-haloalkoxy;

$R^b$ is each independently hydrogen, $C_1$-$C_6$-alkyl, $C_1$-$C_6$-haloalkyl, $C_1$-$C_6$-alkoxy, $C_1$-$C_6$-haloalkoxy or a three- to six-membered saturated, or partially unsaturated or aromatic carbo- or heterocyclic ring, which may contain 1 to 3 heteroatoms selected from $N(R^c)_p$, O, and S, wherein S may be oxidized and which carbo- or heterocyclic ring may be partially or fully substituted with $R^{aa}$;

$R^c$ is each independently hydrogen, $C_1$-$C_4$-alkyl, $C_1$-$C_4$-haloalkyl, $C_1$-$C_4$-alkylcarbonyl, $C_1$-$C_6$ cycloalkyl, or a three- to six-membered saturated, partially unsaturated or aromatic carbo- or heterocyclic ring, which may contain 1 to 3 heteroatoms selected from $N(R^{aa})_p$, O and S, wherein S may be oxidized and wherein the carbo- or heterocyclic ring may be partially or fully substituted with $R^{aa}$;

wherein two geminally bound groups $R^bR^b$, $R^cR^b$ or $R^cR^c$ together with the atom to which they are bound, may form a 3-, 4-, 5-, 6- or 7-membered saturated, partially unsaturated or aromatic carbo- or heterocyclic ring, which may contain 1 to 2 heteroatoms or heteroatoms groups selected from N, O, S, NO, SO and $SO_2$ and wherein the carbo- or heterocyclic ring may be partially or fully substituted with $R^a$;

$R^d$ is each independently hydrogen, phenyl, $C_1$-$C_6$-alkyl, $C_2$-$C_6$-alkenyl, $C_2$-$C_6$-alkynyl, $C_3$-$C_8$-cycloalkyl, or $C_1$-$C_6$-alkoxyalkyl, wherein the above mentioned groups may be substituted with one or more halogen;

$R^e$ is each independently $C_1$-$C_4$-alkyl, $C_1$-$C_4$-haloalkyl, $C_1$-$C_4$-alkylcarbonyl, $C_1$-$C_6$ cycloalkyl, or a three- to six-membered saturated, partially unsaturated or aromatic carbo- or heterocyclic ring, which may contain 1 to 3 heteroatoms selected from $N(R^{aa})_p$, O and S, wherein S may be oxidized and wherein the carbo- or heterocyclic ring may be partially or fully substituted with $R^{aa}$;

m is 0, 1, or 2;

n is 0, 1 or 2;

p is 0 or 1;

$R^5$ is hydrogen, $C_1$-$C_8$-alkyl, $C_2$-$C_8$-alkenyl, $C_2$-$C_8$-alkynyl, which groups may be independently from each other substituted with one to five substituents selected from halogen, $NO_2$, CN, OH, $C_1$-$C_6$-alkyl, $C_3$-$C_6$-cycloalkyl, $C_1$-$C_6$-alkoxy-$C_1$-$C_6$-alkyl, $C_1$-$C_6$-haloalkyl, $C_3$-$C_6$-halocycloalkyl, $C_3$-$C_6$-cycloalkyl-$C_1$-$C_6$-alkyl, $C_3$-$C_6$-halocycloalkyl-$C_1$-$C_6$-alkyl, cyano-$C_1$-$C_6$-alkyl, cyano-$C_1$-$C_6$-haloalkyl, $O-R^{51}$, $-S(O)_q-R^{52}$, $-N(R^{53})(R^{54})$, $-C(=O)N(R^{53})(R^{54})$, $-O-C(=O)-R^{55}$, $-C(=O)-OR^{55}$, $-C(=O)-R^{55}$, $O-SO_2-R^{56}$, aryl, hetaryl, heterocyclyl and oxoheterocyclyl, wherein aryl, hetaryl, heterocyclyl or oxoheterocyclyl may in turn be substituted with 1 to 3 substituents selected from halogen, $NO_2$, CN, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, $C_1$-$C_6$-alkylcarbonylamino, aryl, and hetaryl;

wherein aryl and hetaryl may be substituted with one or more, identical or different, halogen, CN, $NO_2$, hydroxy, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, or $C_1$-$C_6$-alkylthio;

or $R^5$ is $C_3$-$C_6$-cycloalkyl, $C_3$-$C_6$-heterocyclyl, $C_3$-$C_8$-oxo-heterocyclyl or $C_3$-$C_8$-dioxo-heterocyclyl, which groups may be independently from each other substituted with substituents selected from halogen, CN, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, $C_1$-$C_6$-alkylthio, $C_1$-$C_6$-alkylsulfinyl, $C_1$-$C_6$-alkylsulfonyl, aryl, hetaryl, aryl-$C_1$-$C_6$-alkyl and hetaryl-$C_1$-$C_6$-alkyl, wherein aryl, hetaryl, aryl-$C_1$-$C_6$-alkyl and hetaryl-$C_1$-$C_6$-alkyl may be substituted with one to three halogen, CN, $NO_2$, $C_1$-$C_4$-alkyl, $C_1$-$C_4$-haloalkyl, $C_1$-$C_4$-alkoxy, $C_1$-$C_4$-haloalkoxy;

or $R^5$ is aryl, $C_1$-$C_6$-alkylenedioxyaryl, or hetaryl, which groups may be independently from each other substituted with one to three substituents independently selected from halogen, $NO_2$, amino, CN, $SF_5$, SCN, OH, COOH, $CONH_2$, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_3$-$C_6$-cycloalkyl-$C_1$-$C_6$-alkyl, $C_3$-$C_6$-halocycloalkyl-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkoxy, $C_1$-$C_6$-alkoxy-$C_1$-$C_6$-alkyloxy, cyano-$C_1$-$C_6$-alkyl, cyano-$C_1$-$C_6$-haloalkyl, $C_3$-$C_6$-cycloalkyl-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, SH, $C_1$-$C_6$-alkylthio, $C_1$-$C_6$-alkylsulfonyl, $C_1$-$C_6$-alkylsulfinyl, $C_1$-$C_6$-haloalkylthio, $C_1$-$C_6$-haloalkylsulfonyl, $C_1$-$C_6$-haloalkylsulfinyl, $C_1$-$C_6$-alkylcarbonyl, $C_3$-$C_6$-cycloalkylcarbonyl, $C_3$-$C_6$-halocycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-haloalkoxycarbonyl, $C_1$-$C_6$-alkylamino, di-($C_1$-$C_6$)-alkylamino, $C_3$-$C_6$-cycloalkylamino, di-($C_3$-$C_6$)-cycloalkylamino, $C_1$-$C_6$-alkylcarbonylamino, $C_1$-$C_6$-haloalkylcarbonylamino, $C_3$-$C_6$-cycloalkylcarbonylamino, $C_3$-$C_6$-halocycloalkylcarbonylamino, $C_1$-$C_6$-alkylaminocarbonyl, $C_1$-$C_6$-haloalkylaminocarbonyl, $C_3$-$C_6$-cycloalkylaminocarbonyl, $C_3$-$C_6$-halocycloalkylaminocarbonyl, di-($C_1$-$C_6$)-alkylaminocarbonyl, or tri-($C_1$-$C_6$-alkyl)-silyl, aryl, hetaryl, heterocyclyl, aryl-$C_1$-$C_6$-alkyl and hetaryl-$C_1$-$C_6$-alkyl, wherein aryl, hetaryl, aryl-$C_1$-$C_6$-alkyl and hetaryl-$C_1$-$C_6$-alkyl may each in turn optionally be substituted with 1 to 3 substituents selected independently of one another from halogen, CN, $NO_2$, $C_1$-$C_4$-haloalkyl, $C_1$-$C_4$-alkoxy, and $C_1$-$C_4$-haloalkoxy;

q is 0, 1 or 2;

$R^{51}$ is hydrogen, $C_1$-$C_6$-alkyl, $C_2$-$C_6$-alkenyl, $C_2$-$C_6$-alkynyl, $C_3$-$C_6$-cycloalkyl or $C_3$-$C_6$-heterocyclyl, which groups may be independently from each other substituted with one to three halogen or one $NO_2$, CN, $C_3$-$C_6$-cycloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-alkylcarbonyl, $C_1$-$C_6$-alkoxyimino-$C_1$-$C_6$-alkyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, aryl or hetaryl, wherein aryl and hetaryl may be substituted with one to three halogen, CN, $NO_2$, $C_1$-$C_4$-alkyl, $C_1$-$C_4$-haloalkyl, $C_1$-$C_4$-alkoxy or $C_1$-$C_4$-haloalkoxy;

or $R^{51}$ is aryl or hetaryl, which groups may be independently from each other substituted with one to three halogen, $NO_2$, amino, CN, $SF_5$, SCN, $C_1$-$C_6$-alkylamino, di-($C_1$-$C_6$)-alkylamino, hydroxy, COOH, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_3$-$C_6$-halocycloalkyl-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, SH, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, or tri-($C_1$-$C_6$-alkyl)-silyl;

$R^{52}$ is $C_1$-$C_6$-alkyl, $C_2$-$C_6$-alkenyl, $C_2$-$C_6$-alkynyl, $C_3$-$C_6$-cycloalkyl or $C_3$-$C_6$-heterocyclyl, which groups may be independently from each other substituted with one to three halogen, $NO_2$, CN, $C_3$-$C_6$-cycloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-alkylcarbonyl, $C_1$-$C_6$-alkoxyimino-$C_1$-$C_6$-alkyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, aryl or hetaryl, wherein aryl and hetaryl may be substituted with one to three halogen, CN, $NO_2$, $C_1$-$C_4$-alkyl, $C_1$-$C_4$-haloalkyl, $C_1$-$C_4$-alkoxy or $C_1$-$C_4$-haloalkoxy;

or $R^{52}$ is aryl or hetaryl, which groups may be independently from each other substituted with one to three halogen, $NO_2$, amino, CN, $SF_5$, SCN, $C_1$-$C_6$-alkylamino, di-($C_1$-$C_6$)-alkylamino, hydroxy, COOH, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_3$-$C_6$-halocycloalkyl-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, or tri-($C_1$-$C_6$-alkyl)-silyl;

$R^{53}$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-alkoxy-$C_1$-$C_6$-alkyl, $C_1$-$C_6$-alkoxycarbonyl, $C_1$-$C_6$-alkylcarbonyl, aryl, hetaryl, arylcarbonyl or hetarylcarbonyl, wherein aryl and hetaryl may be substituted with one to three halogen, CN, $NO_2$, $C_1$-$C_4$-alkyl, $C_1$-$C_4$-haloalkyl, $C_1$-$C_4$-alkoxy or $C_1$-$C_4$-haloalkoxy;

$R^{54}$ is hydrogen, $C_1$-$C_6$-alkyl, $C_2$-$C_6$-alkenyl, $C_2$-$C_6$-alkynyl, $C_3$-$C_6$-cycloalkyl or $C_3$-$C_6$-cycloalkyl-$C_1$-$C_6$-alkyl, which groups may be independently from each other substituted with one to five halogen or one CN, $NO_2$, hydroxy, $C_1$-$C_6$-alkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-alkoxycarbonyl, $C_1$-$C_6$-alkylcarbonyl or tri-($C_1$-$C_6$-alkyl)-silyl;

or $R^{54}$ is aryl, hetaryl, aryl-$C_1$-$C_6$-alkyl or hetaryl-$C_1$-$C_6$-alkyl, which groups may be independently from each other substituted with halogen, CN, $NO_2$, hydroxy, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl or $C_2$-$C_6$-alkylcarbonyl, or $R^{53}$ and $R^{54}$ are connected through two to six carbon atoms and form a ring, which may comprise an additional atom selected from O, S or N, and which may be substituted with one to four $C_1$-$C_2$-alkyl, halogen, CN, amino or $C_1$-$C_2$-alkoxy;

$R^{55}$ is $C_1$-$C_6$-alkyl, $C_3$-$C_6$-cycloalkyl, $C_1$-$C_6$-haloalkyl, $C_3$-$C_6$-halocycloalkyl, $C_3$-$C_6$-cycloalkyl-$C_1$-$C_6$-alkyl, $C_3$-$C_6$-halocycloalkyl-$C_1$-$C_6$-alkyl, cyano-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, aryl, hetaryl, aryl-$C_1$-$C_6$-alkyl or hetaryl-$C_1$-$C_6$-alkyl, wherein aryl, hetaryl, aryl-$C_1$-$C_6$-alkyl and hetaryl-$C_1$-$C_6$-alkyl, may be substituted with one or more, identical or different, halogen, CN, $NO_2$, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl or $C_1$-$C_6$-alkoxy-$C_1$-$C_6$-alkyl;

$R^{56}$ is $C_1$-$C_6$-alkyl, $C_3$-$C_6$-cycloalkyl, $C_3$-$C_6$-halocycloalkyl, $C_3$-$C_6$-cycloalkyl-$C_1$-$C_6$-alkyl, $C_3$-$C_6$-halocycloalkyl-$C_1$-$C_6$-alkyl, cyano-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, aryl, hetaryl or aryl-$C_1$-$C_6$-alkyl, wherein aryl, hetaryl and aryl-$C_1$-$C_6$-alkyl may be substituted with one or more, identical or different, halogen, CN, $NO_2$, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl or $C_1$-$C_6$-alkoxy-$C_1$-$C_6$-alkyl;

$R^6$ is $C_1$-$C_6$-alkyl, $C_3$-$C_6$-cycloalkyl, $C_1$-$C_6$-haloalkyl, $C_3$-$C_6$-halocycloalkyl, $C_3$-$C_6$-cycloalkyl-$C_1$-$C_6$-alkyl, $C_3$-$C_6$-halocycloalkyl-$C_1$-$C_6$-alkyl, cyano-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, aryl, hetaryl, aryl-$C_1$-$C_6$-alkyl or hetaryl-$C_1$-$C_6$-alkyl, wherein aryl, hetaryl, aryl-$C_1$-$C_6$-alkyl and hetaryl-$C_1$-$C_6$-alkyl, may be substituted with one or more, identical or different, halogen, CN, $NO_2$, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl or $C_1$-$C_6$-alkoxy-$C_1$-$C_6$-alkyl;

$R^7$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkoxy-$C_1$-$C_6$-alkyl, $C_1$-$C_6$-alkoxycarbonyl, $C_1$-$C_6$-alkylcarbonyl;

$R^{7a}$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy-$C_1$-$C_6$-alkyl, $C_1$-$C_6$-alkoxycarbonyl, $C_1$-$C_6$-alkylcarbonyl;

$R^8$ is hydrogen, $C_1$-$C_6$-alkyl, $C_2$-$C_6$-alkenyl, $C_2$-$C_6$-alkynyl, which groups may be independently from each other substituted with one to five halogen or one CN, $NO_2$, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_1$-$C_4$-alkylsulfimino-$C_1$-$C_4$-alkyl, $C_1$-$C_4$-alkylsulfimino-$C_2$-$C_6$-alkylcarbonyl, $C_1$-$C_4$-alkylsulfoximino, $C_1$-$C_4$-alkylsulfoximino-$C_1$-$C_4$-alkyl, $C_1$-$C_4$-alkylsulfoximino-$C_2$-$C_5$-alkylcarbonyl, $C_1$-$C_6$-alkoxycarbonyl, $C_1$-$C_6$-alkylcarbonyl or $C_3$-$C_6$-trialkylsilyl;

or $R^8$ is aryl-$C_1$-$C_6$-alkyl or hetaryl-$C_1$-$C_6$-alkyl, $C_3$-$C_{12}$-cycloalkyl, $C_3$-$C_{12}$-cycloalkyl-$C_1$-$C_6$-alkyl or $C_4$-$C_{12}$-bicycloalkyl, which groups may be substituted with halogen, CN, $NO_2$, hydroxy, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl or $C_2$-$C_6$-alkylcarbonyl, or $R^8$ is a five- to ten-membered aromatic or heteroaromatic ring which may be substituted with one or more identical or different substituents, a four- to six-membered partially saturated ring, a saturated heterocyclic ring, or a saturated or aromatic heterobicyclic ring which may comprise one to three heteroatoms from O, S or N and which may be substituted with one or more substituents, wherein the substituents are independently from each other halogen, CN, $NO_2$, hydroxy, amino, $C_1$-$C_6$-alkyl, $C_2$-$C_6$-alkynyl, $C_1$-$C_6$-haloalkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl or $C_2$-$C_6$-alkylcarbonyl, or $R^7$ and $R^8$ are connected through two to six carbon atoms and form a ring, which may comprise an additional atom selected from O, S or N, and which may be substituted with one to four $C_1$-$C_2$-alkyl, halogen, CN, amino or $C_1$-$C_2$-alkoxy;

$R^{12}$ is H, $C_1$-$C_6$-alkyl, $C_2$-$C_6$-alkenyl, $C_2$-$C_6$-alkynyl, $C_3$-$C_6$-cycloalkyl, $C_3$-$C_6$-heterocyclyl, wherein $C_1$-$C_6$-alkyl, $C_2$-$C_6$-alkenyl, $C_2$-$C_6$-alkynyl, $C_3$-$C_6$-cycloalkyl, $C_3$-$C_6$-heterocyclyl groups may each optionally be substituted with 1 to 3 substituents independently selected from halogen, $NO_2$, CN, $C_3$-$C_6$-cycloalkyl, $C_1$-$C_6$-alkoxy, $C_1$-$C_6$-haloalkoxy, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, $C_1$-$C_6$-alkylthio, $C_1$-$C_6$-haloalkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, $C_1$-$C_6$-alkylcarbonylamino, aryl or hetaryl, $C_3$-$C_6$-heterocyclyl, or $C_3$-$C_6$-oxoheterocyclyl;

wherein aryl, hetaryl, $C_3$-$C_6$-heterocyclyl, and $C_3$-$C_6$-oxoheterocyclyl may be substituted with one or more, identical or different, halogen, CN, $NO_2$, hydroxy, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_3$-$C_6$-cycloalkyl-$C_1$-$C_6$-alkyl, cyano-$C_1$-$C_6$-alkyl, or $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylthio, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, $C_1$-$C_6$-alkylcarbonylamino, aryl, or hetaryl;

or $R^{12}$ is aryl or heteroaryl, which is optionally substituted with 1 to 3 substituents independently selected from halogen, $NO_2$, CN, amino, $SF_5$, SCN, $C_1$-$C_6$-alkylamino, di-($C_1$-$C_6$)-alkylamino, OH, COOH, $C_1$-$C_6$-alkyl, $C_3$-$C_6$-cycloalkyl, $C_1$-$C_6$-alkoxy, $C_1$-$C_6$-haloalkyl, $C_1$-$C_6$-haloalkoxy, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_3$-$C_6$-halocycloalkyl-$C_1$-$C_6$-alkyl, $C_1$-$C_6$-alkoxy-$C_1$-$C_6$-alkyloxy, $C_1$-$C_6$-haloalkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, $C_1$-$C_6$- alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, and tri-($C_1$-$C_6$-alkyl)silyl;

$R^{13}$ is H, $C_1$-$C_6$-alkyl, $C_2$-$C_6$-alkenyl, $C_2$-$C_6$-alkynyl, $C_3$-$C_6$-cycloalkyl, $C_3$-$C_6$-heterocyclyl, aryl, heteroaryl, aryl-$C_1$-$C_6$-alkyl, heteroaryl-$C_1$-$C_6$-alkyl, $C_3$-$C_6$-oxo-heterocyclyl or $C_3$-$C_6$-dioxo-heterocyclyl, wherein each group may optionally be substituted with 1 to 3 substituents independently selected from halogen, $NO_2$, CN, $C_3$-$C_6$-cycloalkyl, $C_1$-$C_6$-alkoxy, $C_1$-$C_6$-haloalkoxy, $C_1$-$C_6$-alkoxyamino-$C_1$-$C_6$-alkyl, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfinyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, aryl, and heteroaryl, wherein aryl, heteroaryl, may be substituted with one or more, identical or different, halogen, CN, $NO_2$, OH, $C_1$-$C_6$-alkyl, $C_1$-$C_6$-haloalkyl, $C_1$-$C_6$-alkoxy, and $C_1$-$C_6$-haloalkoxy;

$R^{14a}$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkoxy-$C_1$-$C_6$-alkyl, $C_1$-$C_6$-alkoxycarbonyl, $C_1$-$C_6$-alkylcarbonyl;

$R^{14b}$ is hydrogen, $C_1$-$C_6$-alkyl, $C_2$-$C_6$-alkenyl, $C_2$-$C_6$-alkynyl, C(=O)N($R^7$)($R^8$), wherein $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkoxy-$C_1$-$C_6$-alkyl, $C_1$-$C_6$-alkoxycarbonyl groups may be independently from each other substituted with one to five halogen or one CN, $NO_2$, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_1$-$C_4$-alkylsulfimino-$C_1$-$C_4$-alkyl, $C_1$-$C_4$-alkylsulfimino-$C_2$-$C_5$-alkylcarbonyl, $C_1$-$C_4$-alkylsulfoximino, $C_1$-$C_4$-alkylsulfoximino-$C_1$-$C_4$-alkyl, $C_1$-$C_4$-alkylsulfoximino-$C_2$-$C_5$-alkylcarbonyl, $C_1$-$C_6$-alkoxycarbonyl, $C_1$-$C_6$-alkylcarbonyl or $C_3$-$C_6$-trialkylsilyl;

or $R^{14b}$ is aryl-$C_1$-$C_6$-alkyl or hetaryl-$C_1$-$C_6$-alkyl, $C_3$-$C_{12}$-cycloalkyl, $C_3$-$C_{12}$-cycloalkyl-$C_1$-$C_6$-alkyl or $C_4$-$C_{12}$-bicycloalkyl, which groups may be substituted with halogen, CN, $NO_2$, hydroxy, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl or $C_2$-$C_6$-alkylcarbonyl, or $R^{14b}$ is a five- to six-membered aromatic or heteroaromatic ring which may be substituted with one or more identical or different substituents, a four- to six-membered partially saturated ring, a saturated heterocyclic ring, or a saturated or aromatic heterobicyclic ring which may comprise one to three heteroatoms from O, S or N and which may be substituted with one or more substituents, wherein the substituents are independently from each other halogen, CN, $NO_2$, hydroxy, amino, $C_1$-$C_6$-alkyl, $C_2$-$C_6$-alkynyl, $C_1$-$C_6$-haloalkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl or $C_2$-$C_6$-alkylcarbonyl, or $R^{14a}$ and $R^{14b}$ are connected through two to six carbon atoms and form a ring, which may comprise an additional atom selected from O, S or N, and which may be substituted with one to four $C_1$-$C_2$-alkyl, halogen, CN, amino or $C_1$-$C_2$-alkoxy;

$R^{15}$ is H or $C_1$-$C_6$-alkyl, wherein alkyl group is optionally substituted with one or more substituents independently selected from halogen, $NO_2$, CN, $C_3$-$C_6$-cycloalkyl, $C_1$-$C_6$-alkoxy, $C_1$-$C_6$-haloalkoxy, aryl, and heteroaryl, wherein aryl, heteroaryl, may optionally be substituted with one or more, identical or different, halogen, CN, $NO_2$, OH, $C_1$-$C_6$-alkyl, $C_1$-$C_6$-haloalkyl, $C_1$-$C_6$-alkoxy, and $C_1$-$C_6$-haloalkoxy, $C_1$-$C_6$-alkylthio, $C_1$-$C_6$-alkylcarbonyl, $C_1$-$C_6$-haloalkylcarbonyl, $C_1$-$C_6$-alkoxycarbonyl, $C_1$-$C_6$-alkylsulfinyl, $C_1$-$C_6$-alkylsulfonyl, $C_1$-$C_6$-haloalkylsulfonyl, and $C_1$-$C_6$-alkylcarbonylamino;

or a stereoisomer, tautomer, salt, or N-oxide thereof.

WO2017/093214, WO2018/189077, WO 2018/108730, WO2018/192872, WO2018/208595, WO2019/086474 describes certain mesoionic imidazolium compounds.

WO2014/167084 describes certain substituted pyrimidinium compounds with heterocyclic substituents for combating invertebrate pests.

The substituted imidazolium compounds of formula (I) according to the present invention, with their characteristic core and substitution pattern, have not yet been described for pesticidal uses or pesticidal applications in agricultural industry or veterinary practice.

The substituted compounds of the formula (I), and their agriculturally acceptable salts are highly active against animal pest, i.e. harmful arthropods and nematodes, especially against insects and acaridae which are difficult to control by other means.

Moreover, the present invention relates to and includes the following embodiments:

compositions comprising at least one compound of formula (I) as defined above;

agricultural and veterinary compositions comprising an amount of at least one compound of formula (I) or an enantiomer, diastereomer or salt thereof as defined above;

a method for combating invertebrate pests, infestation, or infection by invertebrate pests, which method comprises contacting said pest or its food supply, habitat or breeding grounds with a pesticidally effective amount of at least one compound of formula (I) as defined above or a composition thereof;

a method for controlling invertebrate pests, infestation, or infection by invertebrate pests, which method comprises contacting said pest or its food supply, habitat or breeding grounds with a pesticidally effective amount of at least one compound of formula (I) as defined above or a composition comprising at least one compound of formula (I);

a method for preventing or protecting against invertebrate pests comprising contacting the invertebrate pests, or their food supply, habitat or breeding grounds with substituted imidazolium compounds of the general formula (I) as defined above or a composition comprising at least one compound of formula (I) as defined above or a composition comprising at least one compound of formula (I);

a method for protecting crops, plants, plant propagation material and/or growing plants from attack or infestation by invertebrate pests comprising contacting or treating the crops, plants, plant propagation material and growing plants, or soil, material, surface, space, area or water in which the crops, plants, plant propagation material is stored or the plant is growing, with a pesticidally effective amount of at least one compound of formula (I) as defined above or a composition comprising at least one compound of formula (I);

a non-therapeutic method for treating animals infested or infected by parasites or preventing animals of getting infected or infested by parasites or protecting animals against infestation or infection by parasites which comprises orally, topically or parenterally administering or applying to the animals a parasiticidally effective amount of a compound of formula (I) as defined above or a composition comprising at least one compound of formula (I);

a method for treating, controlling, preventing or protecting animals against infestation or infection by parasites by administering or applying orally, topically or parenterally to the animals a substituted imidazolium compound of the general formula (I) as defined above or a composition comprising at least one compound of formula (I);

seed comprising a compound of formula (I) as defined above, in an amount of from 0.1 g to 10 kg per 100 kg of seed;

the use of the compounds of formula (I) as defined above for protecting growing plants or plant propagation material from attack or infestation by invertebrate pests;

the use of compounds of formula (I) or the enantiomers, diastereomers or veterinary acceptable salts thereof for combating parasites in and on animals;

a process for the preparation of a veterinary composition for treating, controlling, preventing or protecting animals against infestation or infection by parasites which comprises adding a parasiticidally effective amount of an compound of formula (I) or the enantiomers, diastereomers and/or veterinary acceptable salt thereof to a carrier composition suitable for veterinary use;

the use of a compound of formula (I) or the enantiomers, diastereomers and/or veterinary acceptable salt thereof for the preparation of a medicament for treating, controlling, preventing or protecting animals against infestation or infection by parasites.

All the compounds of the present invention including if applicable their stereoisomers, their tautomers, their salts or their N-oxides as well as compositions thereof are particularly useful for controlling invertebrate pests, in particular for controlling arthropods and nematodes and especially insects. Therefore, the invention relates to the use of a compound as disclosed in the present invention, for combating or controlling invertebrate pests, in particular invertebrate pests of the group of insects, arachnids or nematodes.

The term "compound(s) according to the invention" or "compound(s) of formula (I)" as used in the present invention refers to and comprises the compound(s) as defined herein and/or stereoisomer(s), salt(s), tautomer(s) or N-oxide(s) thereof. The term "compound(s) of the present invention" is to be understood as equivalent to the term "compound(s) according to the invention", therefore also comprising stereoisomer(s), salt(s), tautomer(s) or N-oxide(s) of compounds of formula (I).

The term "composition(s) according to the invention" or "composition(s) of the present invention" encompasses composition(s) comprising at least one compound of formula (I) according to the invention as defined above, therefore also including a stereoisomer, an agriculturally or veterinary acceptable salt, tautomer or an N-oxide of the compounds of formula (I).

The compounds of the formula (I) are present in mesomeric forms.

These forms may be expressed in different isoelectronic formulae, each having the formal positive and negative charges on different atoms (as shown below). The present invention extends to all representative isoelectronic structures of compounds of formula I.

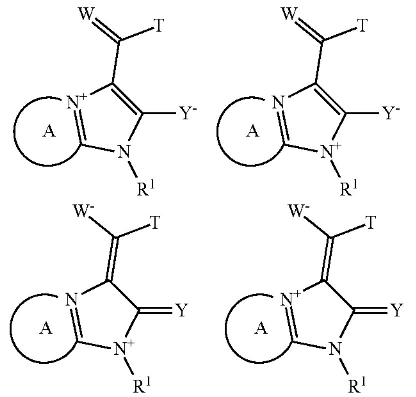

The compounds of the formula (I) may have one or more centers of chirality, i.e. they are present as mixtures of enantiomers or diastereomers. The invention provides both the single pure enantiomers or pure diastereomers of the compounds of formula (I), and their mixtures and the use according to the invention of the pure enantiomers or pure diastereomers of the compound of formula (I) or its mixtures. Suitable compounds of the formula (I) also include all possible geometrical stereoisomers (cis/trans isomers) and mixtures thereof. Cis/trans isomers may be present with respect to an alkene, carbon-nitrogen double-bond or amide group. The term "stereoisomer(s)" encompasses both optical isomers, such as enantiomers or diastereomers, the latter existing due to more than one center of chirality in the molecule, as well as geometrical isomers (cis/trans isomers). The present invention relates to every possible stereoisomer of the compounds of formula (I), i.e. to single enantiomers or diastereomers, as well as to mixtures thereof.

The compounds of the present invention may be amorphous or may exist in one or more different crystalline states (polymorphs) or modifications which may have a different macroscopic properties such as stability or show different biological properties such as activities. The present invention includes both amorphous and crystalline compounds of the formula (I), mixtures of different crystalline states or modifications of the respective compound I, as well as amorphous or crystalline salts thereof.

Salts of the compounds of the formula (I) are preferably agriculturally and/or veterinary acceptable salts. They can be formed in a customary method, e.g. by reacting the compound with an acid of the anion in question if the compound of formula (I) has a basic functionality or by reacting an acidic compound of formula (I) with a suitable base.

Suitable agriculturally or veterinary useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy) ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae I with an acid of the corresponding anion, preferably of hydrochloric acid, hydrobromic acid, sulfuric acid, phosphoric acid or nitric acid.

The term "N-oxide" includes any compound of the present invention which has at least one tertiary nitrogen atom that is oxidized to an N-oxide moiety.

The organic moieties groups mentioned in the above definitions of the variables are—like the term halogen—collective terms for individual listings of the individual group members. The prefix $C_n$-$C_m$ indicates in each case the possible number of carbon atoms in the group.

"Halogen" will be taken to mean fluoro, chloro, bromo and iodo.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl. Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen (or sulfur linkages, respectively) at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or $C_n$-$C_m$-haloalkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl. The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term "$C_n$-$C_m$-alkoxy-$C_n$-$C_m$-alkyl" as used herein refers to alkyl having n to m carbon atoms, e.g. like specific examples mentioned above, wherein one hydrogen atom of the alkyl radical is replaced by an $C_n$-$C_m$-alkoxy group; wherein the value of n and m of the alkoxy group are independently chosen from that of the alkyl group.

The suffix "-carbonyl" in a group or "C(═O)" denotes in each case that the group is bound to the remainder of the molecule via a carbonyl C═O group. This is the case e.g. in alkylcarbonyl, haloalkylcarbonyl, aminocarbonyl, alkylaminocarbonyl, dialkylaminocarbonyl, alkoxycarbonyl, haloalkoxycarbonyl.

The term "aryl" as used herein refers to a mono-, bi- or tricyclic aromatic hydrocarbon radical such as phenyl or naphthyl, in particular phenyl (also referred as to $C_6H_5$ as substituent).

The term "ring system" denotes two or more directly connected rings.

The term "$C_3$-$C_m$-cycloalkyl" as used herein refers to a monocyclic ring of 3- to m-membered saturated cycloaliphatic radicals, e.g. cyclopropyl, cyclobutyl, cyclopentyl, cyclohexyl, cycloheptyl, cyclooctyl and cyclodecyl.

The term "alkylcycloalkyl" denotes as well as the term "alkyl which may be substituted with cycloalkyl" an alkyl group which is substituted with a cycloalkyl ring, wherein alkyl and cycloalkyl are as herein defined.

The term "cycloalkylalkyl" denotes as well as the term "cycloalkyl which may be substituted with alkyl" a cycloalkyl ring which is substituted with an alkyl group, wherein alkyl and cycloalkyl are as herein defined.

The term "alkylcycloalkylalkyl" denotes as well as the term "alkylcycloalkyl which may be substituted with alkyl" an alkylcycloalkyl group which is substituted with an alkyl, wherein alkyl and alkylcycloalkyl are as herein defined.

The term "$C_3$-$C_m$-cycloalkenyl" as used herein refers to a monocyclic ring of 3- to m-membered partially unsaturated cycloaliphatic radicals.

The term "cycloalkylcycloalkyl" denotes as well as the term "cycloalkyl which may be substituted with cycloalkyl" a cycloalkyl substitution on another cycloalkyl ring, wherein each cycloalkyl ring independently has from 3 to 7 carbon atom ring members and the cycloalkyls are linked through one single bond or have one common carbon atom. Examples of cycloalkylcycloalkyl include cyclopropylcyclopropyl (e.g. 1,1'-bicyclopropyl-2-yl), cyclohexylcyclohexyl wherein the two rings are linked through one single common carbon atom (e.g. 1,1'-bicyclohexyl-2-yl), cyclohexylcyclopentyl wherein the two rings are linked through one single bond (e.g. 4-cyclopentylcyclohexyl) and their different stereoisomers such as (1R,2S)-1,1'-bicyclopropyl-2-yl and (1R,2R)-1,1'-bicyclopropyl-2-yl.

The term "3- to 6-membered carbocyclic ring" as used herein refers to cyclopropane, cyclobutane, cyclopentane and cyclohexane rings.

The term "3-, 4-, 5-, 6- or 7-membered saturated, partially unsaturated or aromatic heterocyclic ring which may contain 1, 2, 3 or 4 heteroatoms" or "containing heteroatom groups", wherein those heteroatom(s) (group(s)) are selected from N (N-substituted groups), O and S (S-substituted groups) as used herein refers to monocyclic radicals, the monocyclic radicals being saturated, partially unsaturated or aromatic (completely unsaturated). The heterocyclic radical may be attached to the remainder of the molecule via a carbon ring member or via a nitrogen ring member.

Examples of 3-, 4-, 5-, 6- or 7-membered saturated heterocyclyl or heterocyclic rings include: oxiranyl, aziridinyl, azetidinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin 5 yl, 1,2,4-thiadiazolidin-3-yl, 1,2,4-thiadiazolidin-5-yl, 1,2,4-triazolidin-3-yl,-1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl or heterocyclic rings include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin 3 yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7 tetrahydro[1H]azepin-1-, -2-, -3-, -4-, -5-, -6- or -7-yl, 2,3,6,7 tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7 tetrahydro[1H]oxepin-2-, -3-, -4-, -5-, -6- or -7-yl, 2,3,6,7 tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples of 5- or 6-membered aromatic heterocyclic (hetaryl) or heteroaromatic rings are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

A "$C_2$-$C_m$-alkylene" is divalent branched or preferably unbranched saturated aliphatic chain having 2 to m, e.g. 2 to 7 carbon atoms, for example $CH_2CH_2$, —$CH(CH_3)$—, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$.

Embodiments and preferred compounds of the present invention for use in pesticidal methods and for insecticidal application purposes are outlined in the following paragraphs.

The remarks made below concerning preferred embodiments of the variables (substituents) of the compounds according to the invention, especially with respect to their substituents W, Y, T, A, $R^1$, $R^4$, Het, $R^{4a}$, $R^a$, $R^{aa}$, $R^b$, $R^c$, $R^d$, $R^e$, m, n, p, $R^5$, $R^{51}$, $R^{52}$, $R^{53}$, $R^{54}$, $R^{55}$, $R^6$, $R^7$, $R^{7a}$ and $R^8$, $R^{13}$, $R^{14a}$, $R^{14b}$, $R^{15}$ are valid both on their own and, in particular, in every possible combination with each other and where applicable, the uses, the methods and the compositions according to the invention.

In a particular embodiment, the variables of the compounds of formula (I) have the following meanings, these meanings, both on their own and in combination with one another, being particular embodiments of the compounds of the formula (I):

In one embodiment of the invention, Y is O;

In further embodiment of the invention, Y is S;

In one embodiment of the invention, W is O;

In further embodiment of the invention, W is S;

In further embodiment of the invention, W is $NOR^{15}$;

In further embodiment of the invention, W is O or $NOR^{15}$;

In further embodiment of the invention, W is S or $NOR^{15}$;

In further embodiment of the invention, W is O or S;

In one embodiment of the invention, T is $R^5$;

In further embodiment of the invention, T is $OR^6$;

In further embodiment of the invention, T is —$N(R^7)(R^8)$;

In further embodiment of the invention, T is —$N(R^{7a})$—$N(R^7)(R^8)$;

In further embodiment of the invention, T is $C(=Z)R^{12}$;

In further embodiment of the invention, T is $C(=Z)OR^{13}$;

In further embodiment of the invention, T is $C(=O)NR^{14a}R^{14b}$;

In one embodiment of the invention, Z is O;

In further embodiment of the invention, Z is S;

In further embodiment of the invention, Z is $NOR^{15}$;

In further embodiment of the invention, T is $R^5$, $OR^6$, —$N(R^7)(R^8)$ or —$N(R^{7a})$—$N(R^7)(R^8)$, $C(=Z)R^{12}$, or $C(=Z)OR^{13}$, wherein Z is O, S, or N—$OR^{15}$, $R^5$ is $C_1$-$C_8$-alkyl, which may be independently from each other substituted with one to five substituents selected from halogen, aryl, hetaryl, wherein aryl, hetaryl, may in turn be substituted with 1 to 3 halogen, or $R^5$ is aryl, or hetaryl, which groups may be independently from each other substituted with one to three substituents independently selected from halogen, CN, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_1$-$C_6$-alkylthio;

$R^7$ is hydrogen;

$R^{7a}$ is hydrogen;

$R^8$ is $C_1$-$C_6$-alkyl;

or $R^8$ is aryl-$C_1$-$C_6$-alkyl, or $R^8$ is a five- to ten-membered aromatic ring which may be substituted with one or more halogen;

$R^{12}$ is $C_1$-$C_6$-alkyl, may each optionally be substituted with 1 to 3 substituents independently selected from halogen, and $C_1$-$C_6$-haloalkylthio;

$R^{13}$ is $C_1$-$C_6$-alkyl, may optionally be substituted with 1 to 3 halogens;

$R^{14a}$ is hydrogen;

$R^{14b}$ is $C(=O)N(R^7)(R^8)$;

$R^{15}$ is $C_1$-$C_6$-alkyl, optionally substituted with one or more halogen;

Preferred T groups are T-1 to T-64 as listed in Table T,

TABLE T

| No. | T |
|---|---|
| T-1 | $CH_3$ |
| T-2 | $CH_2$—Cl |
| T-3 | $CH_2$—$OCH_3$ |
| T-4 | $CH_2$—$OCH(CH_3)_2$ |
| T-5 | $OCH_3$ |
| T-6 | $CH_2$—$SCH_3$ |
| T-7 | $CH_2$—$SCH_2CH_3$ |
| T-8 | $CH_2$—$S(O)CH_2CH_3$ |
| T-9 | $CH_2$—$NHCH_3$ |
| T-10 | $CH_2$—$NHCH_2CH_3$ |
| T-11 | 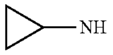 |
| T-12 | $CHF_2$ |
| T-13 | $C_2F_5$ |
| T-14 | $CClF_2$ |
| T-15 | $C_4F_9$ |
| T-16 | $OC_2H_5$ |

TABLE T-continued
| No. | T |
|---|---|
| T-17 | 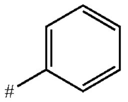 |
| T-18 | 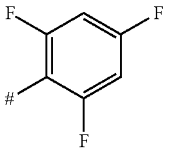 |
| T-19 | 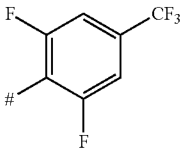 |
| T-20 | 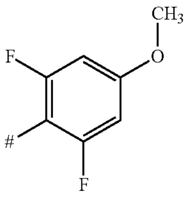 |
| T-21 | 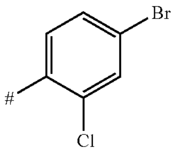 |
| T-22 | 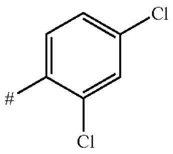 |
| T-23 | 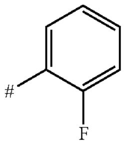 |
| T-24 | 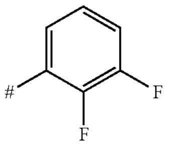 |
| T-25 | 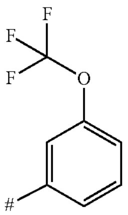 |
TABLE T-continued
| No. | T |
|---|---|
| T-26 | 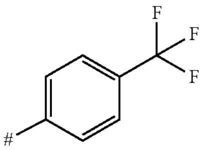 |
| T-27 | 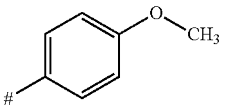 |
| T-28 | 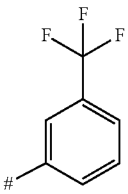 |
| T-29 | 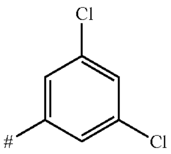 |
| T-30 | 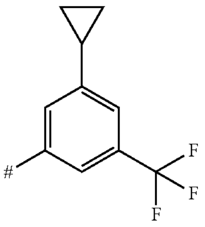 |
| T-31 | 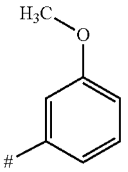 |
| T-32 | 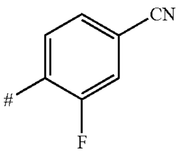 |
| T-33 | 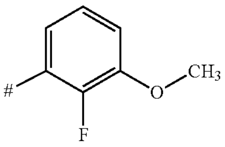 |

TABLE T-continued
| No. | T |
|---|---|
| T-34 | 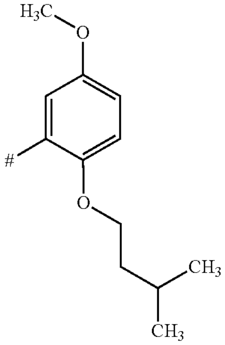 |
| T-35 | 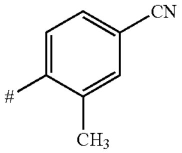 |
| T-36 | 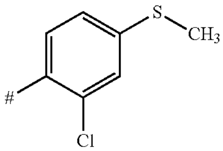 |
| T-37 | 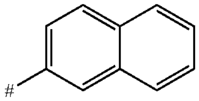 |
| T-38 | 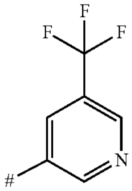 |
| T-39 | 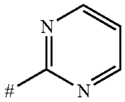 |
| T-40 | 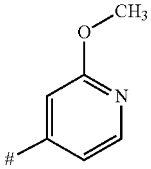 |
| T-41 | 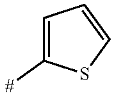 |
| T-42 | 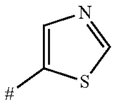 |
TABLE T-continued
| No. | T |
|---|---|
| T-43 | 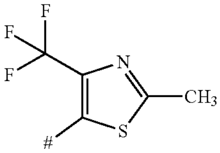 |
| T-44 | 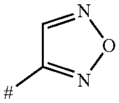 |
| T-45 | 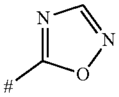 |
| T-46 | 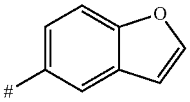 |
| T-47 | 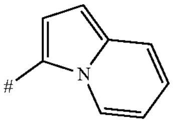 |
| T-48 | 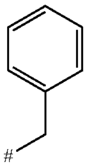 |
| T-49 | 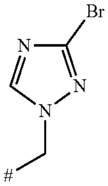 |
| T-50 | 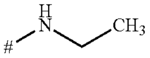 |
| T-51 | 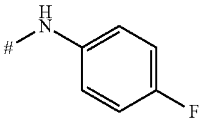 |
| T-52 | 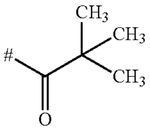 |
| T-53 | 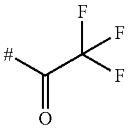 |

TABLE T-continued

| No. | T |
| --- | --- |
| T-54 | 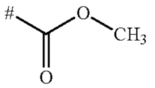 |
| T-55 | 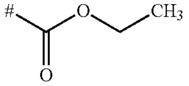 |
| T-56 | 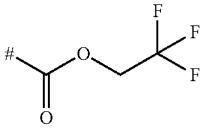 |
| T-57 | 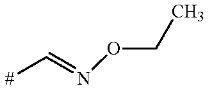 |
| T-58 | 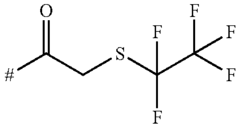 |
| T-59 | 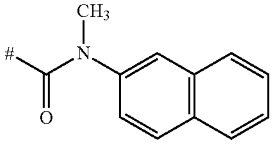 |
| T-60 | 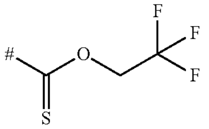 |
| T-61 | 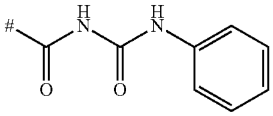 |
| T-62 | 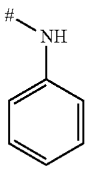 |
| T-63 | 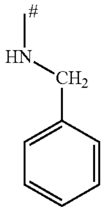 |

TABLE T-continued

| No. | T |
| --- | --- |
| T-64 | 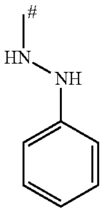 |

In one embodiment of the invention, the ring A is a five- or six-membered ring, taken together with the carbon and nitrogen of the imidazole ring in formula (I), wherein each remaining ring member is selected from carbon atoms and up to 3 heteroatoms independently selected from up to 2 O, up to 2 S, and up to 3 N, wherein up to 2 carbon atom ring members are independently selected from C(═O) and C(═S), and the sulfur atom ring members are independently selected from $S(═O)_m$, wherein each ring member may be substituted with $R^a$ and/or $R^c$; and wherein the ring is substituted with one $R^4$.

In one embodiment of the invention, the ring A is a five-membered ring, taken together with the carbon and nitrogen of the imidazole ring in formula (I), wherein each remaining ring member is selected from carbon atoms and up to 3 heteroatoms independently selected from up to 2 O, up to 2 S, and up to 3 N, wherein up to 2 carbon atom ring members are independently selected from C(═O) and C(═S), and the sulfur atom ring members are independently selected from $S(═O)_m$, wherein each ring member may be substituted with $R^a$ and/or $R^c$; and wherein the ring is substituted with one $R^4$.

In one embodiment of the invention, the ring A is a six-membered ring, taken together with the carbon and nitrogen of the imidazole ring in formula (I), wherein each remaining ring member is selected from carbon atoms and up to 3 heteroatoms independently selected from up to 2 O, up to 2 S, and up to 3 N, wherein up to 2 carbon atom ring members are independently selected from C(═O) and C(═S), and the sulfur atom ring members are independently selected from $S(═O)_m$, wherein each ring member may be substituted with $R^a$ and/or $R^c$; and wherein the ring is substituted with one $R^4$.

In one embodiment of the invention, the ring A is a five- or six-membered ring, taken together with the carbon and nitrogen of the imidazole ring in formula (I), wherein each remaining ring member is selected from carbon atoms and up to 2 heteroatoms independently selected from up to 2 O, up to 1 S, and up to 2 N, wherein up to 2 carbon atom ring members are independently selected from C(═O) and C(═S), and the sulfur atom ring members are independently selected from $S(═O)_m$, wherein each ring member may be substituted with $R^a$ and/or $R^c$; and wherein the ring is substituted with one $R^4$.

In one embodiment <W-1> of the invention, in the compounds of formula (I), W is O, and T is $R^5$.

In a further embodiment <W-2> of the invention, W is O, and T is $C_1$-$C_6$-alkyl, $C_1$-$C_6$-alkoxy, $C_2$-$C_6$-alkenyl, $C_2$-$C_6$-alkynyl, each optionally substituted with one or up to five halogen or with one $NO_2$, CN, $C_3$-$C_6$-cycloalkyl, O—$R^{51}$, —$S(O)_q$—$R^{52}$, —$N(R^{53})(R^{54})$.

In a further embodiment <W-3>, W is O and T is methyl, optionally substituted with halogen, cyano, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_6$-cycloalkyl.

In a further embodiment <W-4>, W is O and T is $OR^6$, wherein $R^6$ is $C_1$-$C_6$-alkyl, $C_3$-$C_6$-cycloalkyl, $C_1$-$C_6$-haloalkyl, optionally substituted with halogen, cyano, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_6$-cycloalkyl.

In a further embodiment <W-5>, W is O and T is $N(R^7)(R^8)$, wherein $R^7$ and $R^8$ independently are selected from H, $C_1$-$C_6$-alkyl, $C_3$-$C_6$-cycloalkyl, $C_6H_5$, $CH_2C_6H_5$, which are optionally substituted with halogen, cyano, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_6$-cycloalkyl.

In a further embodiment <W-6>, W is O and T is $—N(R^{7a})—N(R^7)(R^8)$, wherein $R^7$, $R^{7a}$ and $R^8$ independently are selected from H, $C_1$-$C_6$-alkyl, $C_3$-$C_6$-cycloalkyl, $C_6H_5$, $CH_2C_6H_5$, which are optionally substituted with halogen, cyano, $C_1$-$C_6$-alkoxy, $C_1$-$C_6$-alkylthio, $C_1$-$C_6$-alkylsulfinyl, $C_1$-$C_6$-alkylsulfonyl, $C_3$-$C_6$-cycloalkyl.

In an embodiment <1-1>, $R^1$ is $NO_2$, CN, $C_2$-$C_8$-alkenyl, $C_2$-$C_8$-alkynyl, $C_1$-$C_6$-alkoxy, $C_3$-$C_6$-cycloalkyl, $C_4$-$C_{10}$-cycloalkenyl or $C_5$-$C_{11}$-cycloalkylcycloalkyl, wherein the C-atoms of the aforementioned groups may be unsubstituted, or partially or fully substituted with $R^a$, wherein $R^a$ has the meaning as hereunder described.

In another embodiment <1-2>, $R^1$ is a three- to ten-membered saturated, or partially saturated or heterocyclic ring system, which may contain 1 to 3 heteroatoms selected from $N(R^c)_p$, O, and S, wherein S may be oxidized and which heterocyclic ring may be unsubstituted or substituted with $R^a$.

In a further embodiment <1-3>, $R^1$ is $C_1$-$C_4$-alkyl, $C_2$-$C_8$-alkenyl, $C_1$-$C_6$-alkoxy, $C_3$-$C_6$-cycloalkyl or $C_5$-$C_{11}$-cycloalkylcycloalkyl, wherein the C-atoms of the aforementioned groups may be unsubstituted, or partially or fully substituted with halogen.

In a further embodiment <1-4>, $R^1$ is $C_1$-$C_4$-alkyl, $C_2$-$C_8$-alkenyl, $C_3$-$C_6$-cycloalkyl, phenyl or benzyl, wherein the C-atoms of the aforementioned groups may be unsubstituted, or partially or fully substituted with $R^a$, wherein $R^a$ has the meaning as hereunder described.

In a further embodiment <1-5>, $R^1$ is $C_1$-$C_4$-alkyl, $C_3$-$C_6$-cycloalkyl or phenyl, wherein the C-atoms of the aforementioned groups may be unsubstituted, or partially or fully substituted with halogen or $C_1$-$C_4$-alkyl.

In a further embodiment <1-6>, $R^1$ is $C_1$-$C_4$-alkyl, $C_2$-$C_4$-alkenyl, phenyl or benzyl, wherein the c-atoms of the aforementioned groups may be partially or fully substituted with halogen, preferably Cl or F.

In a further embodiment <1-7>, $R^1$ is $C_1$-$C_4$-alkyl, $C_3$-$C_6$-cycloalkyl or phenyl, preferably $CH_3$, $CH_2CH_3$, $CH(CH_3)_2$, cyclopropyl or phenyl.

In a further embodiment <1-8>, $R^1$ is $C_1$-$C_3$-alkyl, preferably $CH_3$, $CH_2CH_3$ or $CH(CH_3)_2$, particularly $R^1$ is $CH_3$, particularly $R^1$ is $CH_2CH_3$.

In a further embodiment <1-9>, $R^1$ is $C_1$-$C_4$-alkyl, $C_3$-$C_6$-cycloalkyl, $C_2$-$C_4$-alkenyl, benzyl or phenyl, which groups may be partially or fully substituted with halogen or $C_1$-$C_4$-alkyl.

In a further embodiment <2-1>, A together with the nitrogen and the carbon atom of the imidazolium ring, form a five or six membered saturated or partially unsaturated ring, wherein each remaining ring member is selected from carbon atoms and up to one heteroatoms independently selected from O, S, and $N(R^c)_p$, wherein each ring may be substituted with up to one $R^a$, wherein $R^a$ has the meaning as hereunder described.

In a further embodiment <2-2>, A together with the nitrogen and the carbon atom of the imidazolium ring, form a five membered saturated or partially unsaturated ring, wherein each remaining ring member is selected from carbon atoms and up to one heteroatoms independently selected from O, S, and $N(R^c)_p$.

In a further embodiment <2-3>, A together with the nitrogen and the carbon atom of the imidazolium ring, form a six membered saturated or partially unsaturated ring, wherein each remaining ring member is selected from carbon atoms and up to one heteroatoms independently selected from O, S, and $N(R^c)_p$.

In a further embodiment <2-4>, A together with the nitrogen and the carbon atom of the imidazolium ring, form a five or six membered saturated or partially unsaturated ring resulting in the compounds of formula (II) selected from the group of compounds of formulae II-1 to II-16:

(II-1)

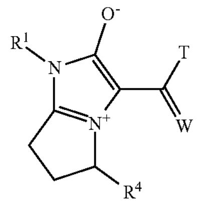

(II-2)

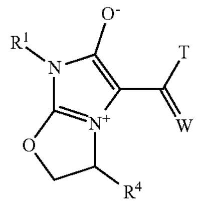

(II-3)

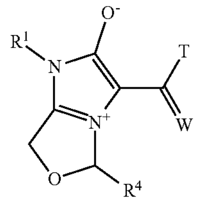

(II-4)

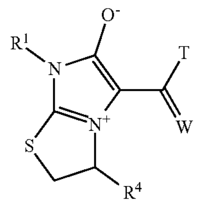

(II-5)

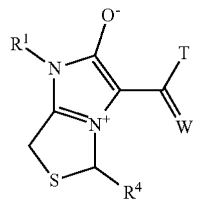

-continued (II-6)

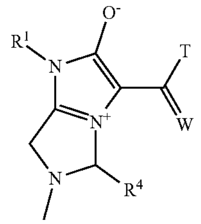

(II-7)

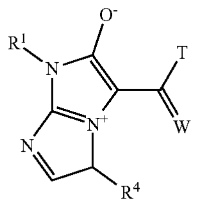

(II-8)

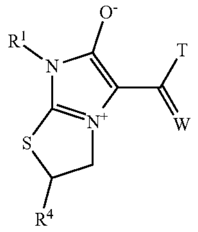

(II-9)

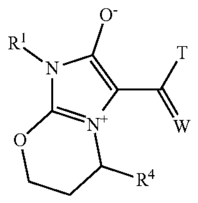

(II-10)

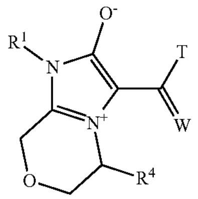

(II-11)

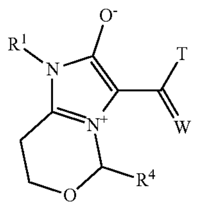

(II-12)

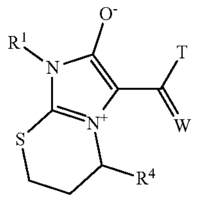

-continued (II-13)

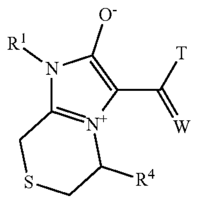

(II-14)

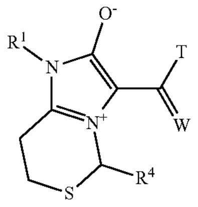

(II-15)

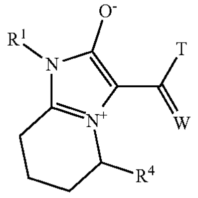

(II-16)

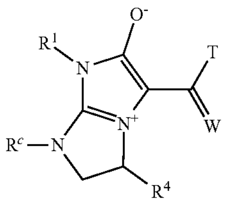

In a further embodiment, compounds of formula (I) are selected from the group of compounds of formulae II-2, II-4, II-9, II-12.

In a further embodiment, compounds of formula (I) are selected from the group of compounds of formulae II-2, II-4, II-16.

In a further embodiment, compounds of formula (I) are selected from the group of compounds of formulae II-4, II-16.

In a further embodiment, compounds of formula (I) are selected from the compounds of formula II-4.

In an embodiment <4-1>, $R^4$ is Het, and Het is selected from any one of the following ring systems D-1 to D-56:

D-1

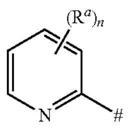

D-2

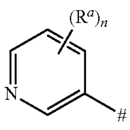

D-3

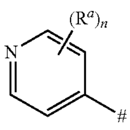

-continued
D-4
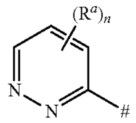
D-5
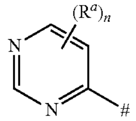
D-6
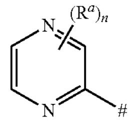
D-7
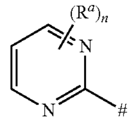
D-8
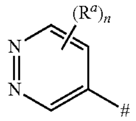
D-9
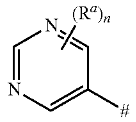
D-10
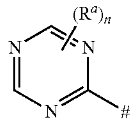
D-11
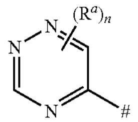
D-12
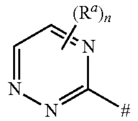
D-13
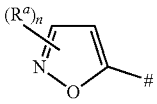
D-14
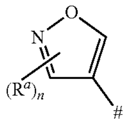
D-15
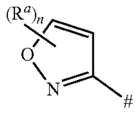
-continued
D-16
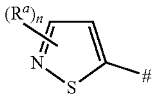
D-17
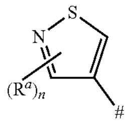
D-18
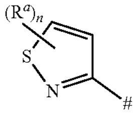
D-19
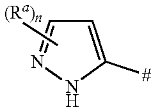
D-20
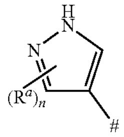
D-21
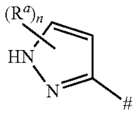
D-22
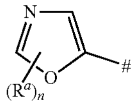
D-23
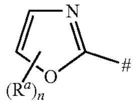
D-24
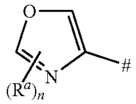
D-25
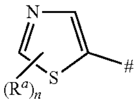
D-26
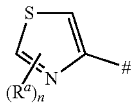
D-27
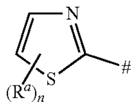
D-28
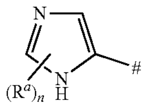

-continued
D-29
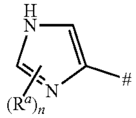
D-30
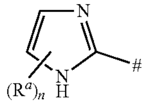
D-31
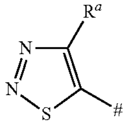
D-32
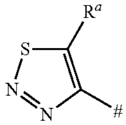
D-33
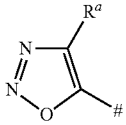
D-34
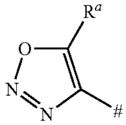
D-35
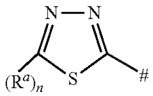
D-36
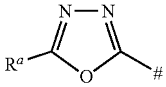
D-37
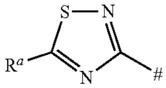
D-38
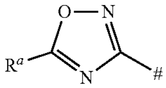
D-39
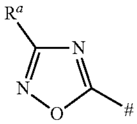
D-40
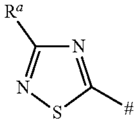
D-41
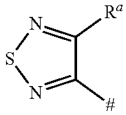
-continued
D-42
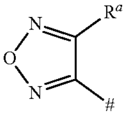
D-43
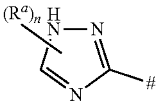
D-44
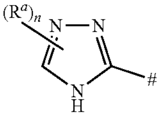
D-45
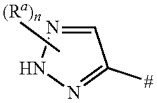
D-46
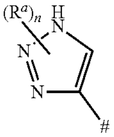
D-47
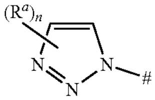
D-48
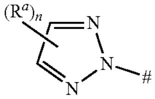
D-49
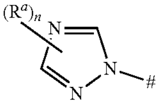
D-50
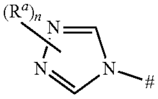
D-51
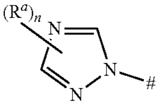
D-52
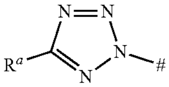
D-53
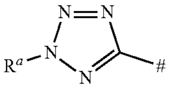
D-54
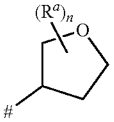

-continued
D-55
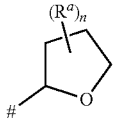
D-56
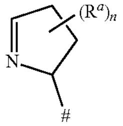
Wherever used in a structure, the following: #denotes the bond to A in formula (I)
In a further embodiment Het is selected from any one of the following ring systems:
D-1
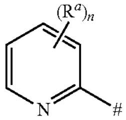
D-2
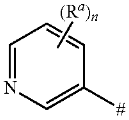
D-3
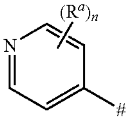
D-5
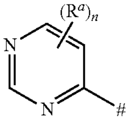
D-6
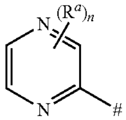
D-7
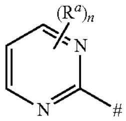
D-16
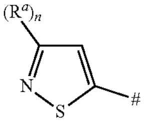
D-17
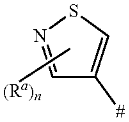
-continued
D-20
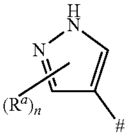
D-22
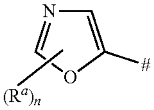
D-23
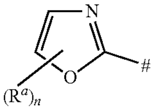
D-24
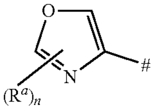
D-25
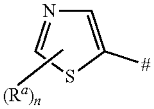
D-26
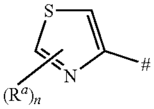
D-27
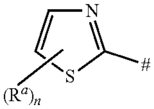
D-28
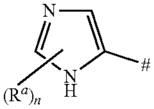
D-29
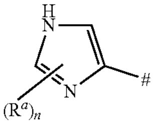
D-30
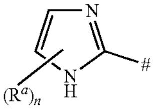
D-35
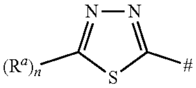
D-36
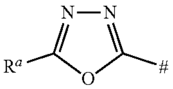

-continued

D-54

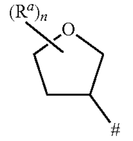

D-55

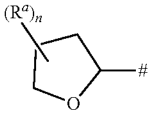

D-56

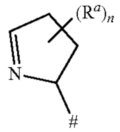

In a further embodiment <4-2>, Het is selected from the following rings systems D-2, D-9, D-22, D-25, D-28, D-29 and D-54:

D-2

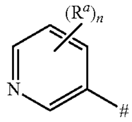

D-9

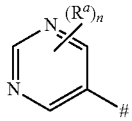

D-22

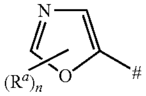

D-25

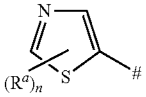

D-28

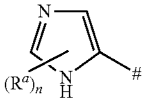

D-29

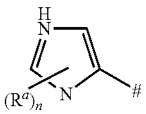

D-54

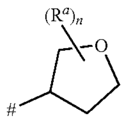

D-56

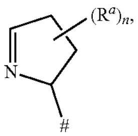

wherein $R^a$ is halogen, $C_1$-$C_4$-haloalkyl, $C_1$-$C_4$-alkoxy or $C_1$-$C_4$-alkylthio or phenyl; preferably $R^a$ is halogen or halomethyl.

In a further embodiment <4-3>, Het is selected from the following rings systems D-2, D-9, D-25 and D-56:

D-2

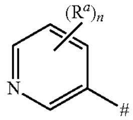

D-9

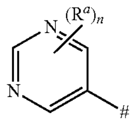

D-25

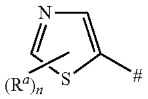

D-56

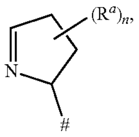

wherein $R^a$ is halogen, $C_1$-$C_4$-haloalkyl, $C_1C_4$-alkoxy or $C_1$-$C_4$-alkylthio or phenyl, preferably halogen or $C_1$-$C_4$-haloalkyl; more preferably $R^a$ is Cl, Br, F or $CF_3$, most preferably $R^a$ is Cl or $CF_3$.

In a further embodiment <4-4>, Het is selected from the following rings systems D-2, D-25 or D-54:

D-2

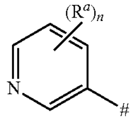

D-25

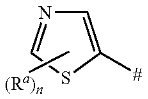

D-54

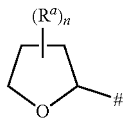

wherein $R^a$ is halogen or $C_1$-$C_4$-haloalkyl; preferably $R^a$ is Cl, Br, F or $CF_3$, most preferably $R^a$ is Cl or $CF_3$.

In another embodiment <4-5>, Het is selected from the following rings systems D-2a, D-2b, D-2c, D-25, D-25a, preferably D-25a substituted with Cl, and D-56a:

D-2a

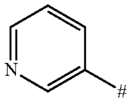

-continued

D-9a

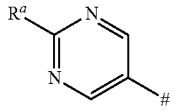

D-9b

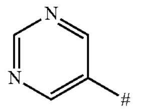

D-2b

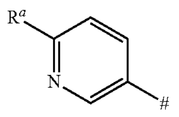

D-2c

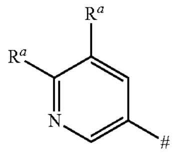

D-25

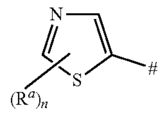

D-25a

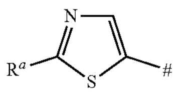

D-54a

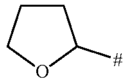

D-56

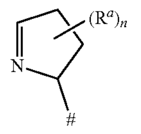

D-56a

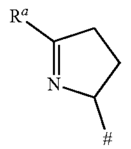

wherein $R^a$ are independently from each other selected from Cl, Br, F and $CF_3$.

In another embodiment <4-6>, Het is D-2, preferably D-2b or D-2c, particularly D-2b, wherein $R^a$ is Cl or $CF_3$.

In another embodiment <4-7>, Het is selected from D-2a, D-25, preferably D-25a substituted with Cl, D-9, preferably D-9a or D9b, D-56, preferably D-56a.

In another embodiment, Het is D-2a.

In another embodiment, Het is D-25, preferably D-25a substituted with Cl.

In another embodiment, Het is D-9, preferably D-9a or D9b.

In another embodiment, Het is D-56, preferably D-56a.

In a further embodiment <4-8>, $R^4$ is $R^{4a}$, which is $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_7$-cycloalkyl, $C_3$-$C_7$-halocycloalkyl, $C_4$-$C_8$-alkylcycloalkyl, $C_4$-$C_8$-haloalkylcycloalkyl, $C_4$-$C_8$-cycloalkylalkyl, $C_4$-$C_8$-halocycloalkylalkyl, $C_1$-$C_6$-alkoxy, $C_1$-$C_6$-haloalkoxy, $C_2$-$C_6$-alkylcarbonyl, $C_2$-$C_6$-haloalkylcarbonyl, CN; each optionally substituted with one or more substituents selected from $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, In a further embodiment <4-9>, $R^4$ is $C_1$-$C_4$-alkyl, $C_1$-$C_4$-haloalkyl, each optionally substituted with one or more substituents selected from CN, $NO_2$.

In a further embodiment <4-10>, $R^4$ is $CH_2CH_2CN$ or $CH_2CN$, preferably $CH_2CN$.

In an embodiment, $R^a$ is halogen, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, CN, $OR^c$, $NR^bR^c$, $NO_2$, phenyl, pyridyl, thiazyl, furanyl, pyrimidinyl or thienyl, wherein the C-atoms aforementioned which groups may be unsubstituted or substituted with one or more $R^{aa}$, wherein $R^{aa}$ is as hereunder defined.

In a further embodiment, $R^a$ is halogen, $C_1$-$C_4$-alkyl, $C_1$-$C_4$-haloalkyl or $C_3$-$C_6$-cycloalkyl.

In a further embodiment, $R^a$ is halogen, $C_1$-$C_4$-alkyl, $C_1$-$C_4$-haloalkyl or $C_3$-$C_6$-cycloalkyl.

In a further embodiment, $R^a$ is halogen.

In an embodiment, $R^a$ is halogen, CN, $NO_2$, $S(O)_mR^b$, $C(O)R^c$, $C(O)OR^c$, $C(O)NR^bR^c$, $C(=S)NR^bR^c$, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, wherein the C-atoms of the aforementioned groups may be unsubstituted, partially or fully substituted with $R^{aa}$, wherein is as hereunder defined.

In a further embodiment, $R^a$ is halogen, CN, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, which C-atoms of the aforementioned groups may be unsubstituted, partially or fully substituted with $R^{aa}$, wherein $R^{aa}$ is as hereunder defined.

In a further embodiment, $R^a$ is halogen, CN, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, wherein the C-atoms of the aforementioned groups may be unsubstituted, partially or fully substituted with halogen.

In a further embodiment, $R^a$ is halogen, $C_1$-$C_6$-haloalkyl or $C_1$-$C_6$-alkoxy.

In a further embodiment, $R^a$ is halogen, CN or $C_1$-$C_2$-haloalkyl.

In a further embodiment, $R^a$ is halogen or $C_1$-$C_2$-haloalkyl.

In an embodiment, $R^a$ is halogen, preferably Br, Cl or F, particularly Cl.

In another embodiment, $R^a$ is $C_1$-$C_2$-haloalkyl, preferably halomethyl such as $CHF_2$ or $CF_3$, particularly $CF_3$.

In an embodiment, two geminally bound groups $R^a$ together may form a group selected from =O, =S, $=CR^bR^c$, $=NR^c$, $=NOR^c$, and $=NNR^cR^c$;

In another embodiment, two geminally bound groups $R^a$ together may form a group selected from $=CR^bR^c$, $=NR^c$, $=NOR^c$, and $=NNR^cR^c$;

In another embodiment, two geminally bound groups $R^a$ together may form a group selected from =O, =S and $=N(C_1$-$C_6$-alkyl).

In another embodiment, two geminally bound groups $R^a$ together may form a $=N(C_1$-$C_6$-alkyl) group.

In an embodiment, $R^b$ is hydrogen, $C_1$-$C_6$-alkyl, $C_1$-$C_6$-haloalkyl, $C_1$-$C_6$-alkoxy, $C_1$-$C_6$-haloalkoxy, phenyl, pyridyl, thiazyl or thienyl, wherein the C-atoms of the aforementioned groups may be substituted with $R^{aa}$, wherein $R^{aa}$ is as hereunder defined. In a further embodiment, $R^b$ is hydrogen, $C_1$-$C_6$-alkyl, $C_1$-$C_6$-haloalkyl, $C_1$-$C_6$-alkoxy or $C_1$-$C_6$-haloalkoxy. In a further embodiment, $R^b$ is hydrogen, $C_1$-$C_6$-alkyl or $C_1$-$C_6$-haloalkyl. In an embodiment, $R^b$ is $C_1$-$C_6$-alkyl or $C_1$-$C_6$-haloalkyl. In an embodiment, $R^b$ is H.

In an embodiment, $R^c$ is hydrogen, $C_1$-$C_4$-alkyl, $C_1$-$C_4$-haloalkyl, $C_1$-$C_4$-alkylcarbonyl, $C_1$-$C_6$ cycloalkyl, phenyl, pyridyl, thiazyl or thienyl wherein the C-atoms of the aforementioned groups may be substituted with $R^{aa}$, wherein $R^{aa}$ is as hereunder defined. In a further embodiment, $R^c$ is hydrogen, $C_1$-$C_4$-alkyl, $C_1$-$C_4$-haloalkyl, $C_1$-$C_4$-alkylcarbonyl, or $C_1$-$C_6$-cycloalkyl. In an embodiment, $R^c$ is hydrogen, $C_1$-$C_6$-alkyl or $C_1$-$C_6$-haloalkyl. In an embodiment, $R^c$ is $C_1$-$C_6$-alkyl or $C_1$-$C_6$-haloalkyl. In an embodiment, $R^c$ is H.

In an embodiment, two geminally bound groups $R^bR^b$, $R^cR^b$ or $R^cR^c$ together with the atom to which they are bound, may form a 3-, 4-, 5-, 6- or 7-membered saturated, partially unsaturated or aromatic carbo- or heterocyclic ring, which may contain 1 to 2 heteroatoms or heteroatoms groups selected from N, O, S, NO, SO and $SO_2$ and wherein the carbo- or heterocyclic ring may be partially or fully substituted with $R^a$.

In another embodiment, two geminally bound groups $R^bR^b$, $R^cR^b$ or $R^cR^c$ together with the atom to which they are bound, may form a 5- or 6-membered saturated, partially unsaturated or aromatic carbocyclic ring, which ring may be partially or fully substituted with $R^a$, and wherein $R^a$ is as hereunder defined.

In another embodiment, two geminally bound groups $R^bR^b$, $R^cR^b$ or $R^cR^c$ together with the atom to which they are bound, may form a 5- or 6-membered saturated, partially unsaturated or aromatic heterocyclic ring, which may contain 1 to 2 heteroatoms or heteroatoms groups selected from N, O, S, NO, SO and $SO_2$, wherein the heterocyclic ring may be partially or fully substituted with $R^a$, and wherein $R^a$ is as hereunder defined.

In an embodiment, $R^d$ is hydrogen, phenyl, $C_1$-$C_4$-alkyl or $C_2$-$C_6$-alkenyl, wherein the aforementioned groups may be substituted with one or more halogen. In a further embodiment, $R^d$ is $C_1$-$C_4$-alkyl or phenyl, which may be substituted with halogen. In another embodiment, $R^c$ $C_1$-$C_4$-alkyl, preferably $CH_3$.

In an embodiment, $R^e$ is $C_1$-$C_4$-alkyl, $C_1$-$C_4$-haloalkyl, $C_1$-$C_4$-alkylcarbonyl, $C_1$-$C_6$ cycloalkyl, phenyl, pyridyl, thiazyl or thienyl wherein the aforementioned groups may be substituted with $R^{aa}$, wherein $R^{aa}$ is as hereunder defined. In a further embodiment, $R^e$ is $C_1$-$C_4$-alkyl, $C_1$-$C_4$-haloalkyl, $C_1$-$C_4$-alkylcarbonyl, or $C_1$-$C_6$-cycloalkyl. In a further embodiment, $R^e$ is $C_1$-$C_4$-alkyl or $C_1$-$C_4$-haloalkyl.

In an embodiment, $R^{aa}$ is halogen, $C_1$-$C_6$-alkyl or $C_1$-$C_6$-haloalkyl. In another embodiment, $R^{aa}$ is $C_1$-$C_6$-alkoxy or $C_1$-$C_6$-haloalkoxy. In an embodiment, $R^{aa}$ is halogen.

In an embodiment, $R^{2a}$ is halogen, $C_1$-$C_6$-haloalkyl, $C_1$-$C_6$-alkoxy, $C_1$-$C_6$-haloalkoxy, $OR^c$, $C(=O)OR^c$, $C(=O)NR^bR^c$, or phenyl, wherein the C-atoms of the aforementioned groups may be unsubstituted or substituted with one or more $R^{2aa}$, wherein $R^{2aa}$ is as hereunder defined, particularly $R^{2a}$ is halogen, $C_1$-$C_6$-alkoxy, or $C_1$-$C_6$-haloalkoxy.

In an embodiment, two geminally bound groups $R^{2a}$ together may form a group selected from =O, =S and =N($C_1$-$C_6$-alkyl).

In an embodiment, $R^{2a}$ is halogen, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, CN, $OR^c$, $NR^bR^c$, $NO_2$, phenyl, pyridyl, thiazyl, furanyl, pyrimidinyl or thienyl, wherein the C-atoms of the aforementioned groups may be unsubstituted or substituted with one or more $R^{2aa}$, wherein $R^{2aa}$ is as hereunder defined.

In a further embodiment, $R^{2a}$ is halogen, $C_1$-$C_4$-haloalkyl or $C_3$-$C_6$-haloalkoxy.

In another embodiment, $R^{2a}$ is phenyl which may be substituted with one or more $R^{2aa}$.

In another embodiment, $R^{2a}$ is halogen. In another embodiment, $R^{2a}$ is $C_1$-$C_6$-haloalkyl. In another embodiment, $R^{2a}$ is $C_1$-$C_6$-haloalkoxy.

In another embodiment, $R^{2a}$ is halogen, CN, $NO_2$, $S(O)_mR^b$, $C(=O)R^c$, $C(=O)OR^c$, $C(O)NR^bR^c$, $C(=S)NR^bR^c$, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, which C-atoms of the aforementioned groups may be unsubstituted, partially or fully substituted with $R^{aa}$, wherein is as hereunder defined.

In a further embodiment, $R^{2a}$ is, $C(=O)OR^c$ or $C(=O)NR^bR^c$.

In another embodiment, $R^{2a}$ is halogen, CN, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_2$-$C_6$-alkenyloxy or $C_2$-$C_6$-alkynyloxy, which C-atoms of the aforementioned groups may be unsubstituted, partially or fully substituted with $R^{2aa}$, wherein $R^{2aa}$ is as hereunder defined.

In an embodiment, $R^{2a}$ is Br, Cl or F, particularly Cl.

In another embodiment, $R^{2a}$ is $C_1$-$C_2$-haloalkyl, preferably halomethyl such as $CHF_2$ or $CF_3$, particularly $CF_3$.

In an embodiment, $R^{2aa}$ is halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, N($C_1$-$C_6$-alkyl)($C_1$-$C_6$-alkyl), $C(=O)(O)_p$($C_1$-$C_6$-alkyl), C(=O)N($C_1$-$C_6$-alkyl)($C_1$-$C_6$-alkyl), $(S(O)_m$($C_1$-$C_6$-alkyl), $SO_2$N($C_1$-$C_6$-alkyl)($C_1$-$C_6$-alkyl), $OSO_2$($C_1$-$C_6$-alkyl), N($C_1$-$C_6$-alkyl)$SO_2$($C_1$-$C_6$-alkyl), or $S(=O)_p$(=N($C_1$-$C_6$-alkyl))($C_1$-$C_6$-alkyl) or two geminally bound groups $R^{2aa}$ together may form a group selected from =O, =S and =N($C_1$-$C_6$-alkyl).

In an embodiment, $R^{2aa}$ is halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, N($C_1$-$C_6$-alkyl)($C_1$-$C_6$-alkyl), $C(=O)(O)_p$($C_1$-$C_6$-alkyl), C(=O)N($C_1$-$C_6$-alkyl)($C_1$-$C_6$-alkyl), $(S(O)_m$($C_1$-$C_6$-alkyl), $SO_2$N($C_1$-$C_6$-alkyl)($C_1$-$C_6$-alkyl), $OSO_2$($C_1$-$C_6$-alkyl), N($C_1$-$C_6$-alkyl)$SO_2$($C_1$-$C_6$-alkyl), or $S(=O)_p$(=N($C_1$-$C_6$-alkyl))($C_1$-$C_6$-alkyl). In another embodiment, two geminally bound groups $R^{2aa}$ together may form a group selected from =O, =S and =N($C_1$-$C_6$-alkyl).

In an embodiment, compound of formula I is formula II-4 or II-16, wherein $R^1$ is alkyl, preferably $CH_3$;

W is O;

T is haloalkyl, preferably $-CH_2-Cl$;

$R^c$ is H or $C_1$-$C_6$-alkyl;

$R^4$ is D-25, preferably D-25a substituted with Cl;

or $R^4$ is $CH_2CN$;

In an embodiment, compound of formula I is formula II-4 or II-16, wherein $R^1$ is alkyl, preferably $CH_3$ or $C_2H_5$;

W is O;

T is selected from T-1 to T-64, preferably from T-1, T-12, T-13, T-17, T-41, T-55, and T-56;

$R^c$ is H or $C_1$-$C_6$-alkyl;

$R^4$ is D-1 or D-25;

n is 1;

$R^a$ is halogen;

or $R^4$ is $CH_2CN$.

In an embodiment, m is 0. In another embodiment, m is 1. In another embodiment, m is 2.

In an embodiment, n is 0. In another embodiment, n is 1. In another embodiment, n is 2.

In an embodiment, p is 0. In another embodiment, p is 1.

Preferred embodiment combinations are as shown in the following table:

Table of embodiment combinations

| No | W/T | $R^1$ | A | $R^4$ |
|---|---|---|---|---|
| A-1 | <W-1> | <1-1> | <2-1> | <4-1> |
| A-2 | <W-1> | <1-1> | <2-1> | <4-2> |
| A-3 | <W-1> | <1-1> | <2-1> | <4-3> |
| A-4 | <W-1> | <1-1> | <2-1> | <4-4> |
| A-5 | <W-1> | <1-1> | <2-1> | <4-5> |
| A-6 | <W-1> | <1-1> | <2-1> | <4-6> |
| A-7 | <W-1> | <1-1> | <2-1> | <4-7> |
| A-8 | <W-1> | <1-1> | <2-1> | <4-8> |
| A-9 | <W-1> | <1-1> | <2-1> | <4-9 |
| A-10 | <W-1> | <1-1> | <2-1> | <4-10> |
| A-11 | <W-1> | <1-1> | <2-2> | <4-1> |
| A-12 | <W-1> | <1-1> | <2-2> | <4-2> |
| A-13 | <W-1> | <1-1> | <2-2> | <4-3> |
| A-14 | <W-1> | <1-1> | <2-2> | <4-4> |
| A-15 | <W-1> | <1-1> | <2-2> | <4-5> |
| A-16 | <W-1> | <1-1> | <2-2> | <4-6> |
| A-17 | <W-1> | <1-1> | <2-2> | <4-7> |
| A-18 | <W-1> | <1-1> | <2-2> | <4-8> |
| A-19 | <W-1> | <1-1> | <2-2> | <4-9 |
| A-20 | <W-1> | <1-1> | <2-2> | <4-10> |
| A-21 | <W-1> | <1-1> | <2-3> | <4-1> |
| A-22 | <W-1> | <1-1> | <2-3> | <4-2> |
| A-23 | <W-1> | <1-1> | <2-3> | <4-3> |
| A-24 | <W-1> | <1-1> | <2-3> | <4-4> |
| A-25 | <W-1> | <1-1> | <2-3> | <4-5> |
| A-26 | <W-1> | <1-1> | <2-3> | <4-6> |
| A-27 | <W-1> | <1-1> | <2-3> | <4-7> |
| A-28 | <W-1> | <1-1> | <2-3> | <4-8> |
| A-29 | <W-1> | <1-1> | <2-3> | <4-9 |
| A-30 | <W-1> | <1-1> | <2-3> | <4-10> |
| A-31 | <W-1> | <1-1> | <2-4> | <4-1> |
| A-32 | <W-1> | <1-1> | <2-4> | <4-2> |
| A-33 | <W-1> | <1-1> | <2-4> | <4-3> |
| A-34 | <W-1> | <1-1> | <2-4> | <4-4> |
| A-35 | <W-1> | <1-1> | <2-4> | <4-5> |
| A-36 | <W-1> | <1-1> | <2-4> | <4-6> |
| A-37 | <W-1> | <1-1> | <2-4> | <4-7> |
| A-38 | <W-1> | <1-1> | <2-4> | <4-8> |
| A-39 | <W-1> | <1-1> | <2-4> | <4-9 |
| A-40 | <W-1> | <1-1> | <2-4> | <4-10> |
| A-41 | <W-1> | <1-2> | <2-1> | <4-1> |
| A-42 | <W-1> | <1-2> | <2-1> | <4-2> |
| A-43 | <W-1> | <1-2> | <2-1> | <4-3> |
| A-44 | <W-1> | <1-2> | <2-1> | <4-4> |
| A-45 | <W-1> | <1-2> | <2-1> | <4-5> |
| A-46 | <W-1> | <1-2> | <2-1> | <4-6> |
| A-47 | <W-1> | <1-2> | <2-1> | <4-7> |
| A-48 | <W-1> | <1-2> | <2-1> | <4-8> |
| A-49 | <W-1> | <1-2> | <2-1> | <4-9 |
| A-50 | <W-1> | <1-2> | <2-1> | <4-10> |
| A-51 | <W-1> | <1-2> | <2-2> | <4-1> |
| A-52 | <W-1> | <1-2> | <2-2> | <4-2> |
| A-53 | <W-1> | <1-2> | <2-2> | <4-3> |
| A-54 | <W-1> | <1-2> | <2-2> | <4-4> |
| A-55 | <W-1> | <1-2> | <2-2> | <4-5> |
| A-56 | <W-1> | <1-2> | <2-2> | <4-6> |
| A-57 | <W-1> | <1-2> | <2-2> | <4-7> |
| A-58 | <W-1> | <1-2> | <2-2> | <4-8> |
| A-59 | <W-1> | <1-2> | <2-2> | <4-9 |
| A-60 | <W-1> | <1-2> | <2-2> | <4-10> |
| A-61 | <W-1> | <1-2> | <2-3> | <4-1> |
| A-62 | <W-1> | <1-2> | <2-3> | <4-2> |
| A-63 | <W-1> | <1-2> | <2-3> | <4-3> |
| A-64 | <W-1> | <1-2> | <2-3> | <4-4> |
| A-65 | <W-1> | <1-2> | <2-3> | <4-5> |
| A-66 | <W-1> | <1-2> | <2-3> | <4-6> |
| A-67 | <W-1> | <1-2> | <2-3> | <4-7> |
| A-68 | <W-1> | <1-2> | <2-3> | <4-8> |
| A-69 | <W-1> | <1-2> | <2-3> | <4-9 |
| A-70 | <W-1> | <1-2> | <2-3> | <4-10> |

-continued

Table of embodiment combinations

| No | W/T | $R^1$ | A | $R^4$ |
|---|---|---|---|---|
| A-71 | <W-1> | <1-2> | <2-4> | <4-1> |
| A-72 | <W-1> | <1-2> | <2-4> | <4-2> |
| A-73 | <W-1> | <1-2> | <2-4> | <4-3> |
| A-74 | <W-1> | <1-2> | <2-4> | <4-4> |
| A-75 | <W-1> | <1-2> | <2-4> | <4-5> |
| A-76 | <W-1> | <1-2> | <2-4> | <4-6> |
| A-77 | <W-1> | <1-2> | <2-4> | <4-7> |
| A-78 | <W-1> | <1-2> | <2-4> | <4-8> |
| A-79 | <W-1> | <1-2> | <2-4> | <4-9 |
| A-80 | <W-1> | <1-2> | <2-4> | <4-10> |
| A-81 | <W-1> | <1-3> | <2-1> | <4-1> |
| A-82 | <W-1> | <1-3> | <2-1> | <4-2> |
| A-83 | <W-1> | <1-3> | <2-1> | <4-3> |
| A-84 | <W-1> | <1-3> | <2-1> | <4-4> |
| A-85 | <W-1> | <1-3> | <2-1> | <4-5> |
| A-86 | <W-1> | <1-3> | <2-1> | <4-6> |
| A-87 | <W-1> | <1-3> | <2-1> | <4-7> |
| A-88 | <W-1> | <1-3> | <2-1> | <4-8> |
| A-89 | <W-1> | <1-3> | <2-1> | <4-9 |
| A-90 | <W-1> | <1-3> | <2-1> | <4-10> |
| A-91 | <W-1> | <1-3> | <2-2> | <4-1> |
| A-92 | <W-1> | <1-3> | <2-2> | <4-2> |
| A-93 | <W-1> | <1-3> | <2-2> | <4-3> |
| A-94 | <W-1> | <1-3> | <2-2> | <4-4> |
| A-95 | <W-1> | <1-3> | <2-2> | <4-5> |
| A-96 | <W-1> | <1-3> | <2-2> | <4-6> |
| A-97 | <W-1> | <1-3> | <2-2> | <4-7> |
| A-98 | <W-1> | <1-3> | <2-2> | <4-8> |
| A-99 | <W-1> | <1-3> | <2-2> | <4-9 |
| A-100 | <W-1> | <1-3> | <2-2> | <4-10> |
| A-101 | <W-1> | <1-3> | <2-3> | <4-1> |
| A-102 | <W-1> | <1-3> | <2-3> | <4-2> |
| A-103 | <W-1> | <1-3> | <2-3> | <4-3> |
| A-104 | <W-1> | <1-3> | <2-3> | <4-4> |
| A-105 | <W-1> | <1-3> | <2-3> | <4-5> |
| A-106 | <W-1> | <1-3> | <2-3> | <4-6> |
| A-107 | <W-1> | <1-3> | <2-3> | <4-7> |
| A-108 | <W-1> | <1-3> | <2-3> | <4-8> |
| A-109 | <W-1> | <1-3> | <2-3> | <4-9 |
| A-110 | <W-1> | <1-3> | <2-3> | <4-10> |
| A-111 | <W-1> | <1-3> | <2-4> | <4-1> |
| A-112 | <W-1> | <1-3> | <2-4> | <4-2> |
| A-113 | <W-1> | <1-3> | <2-4> | <4-3> |
| A-114 | <W-1> | <1-3> | <2-4> | <4-4> |
| A-115 | <W-1> | <1-3> | <2-4> | <4-5> |
| A-116 | <W-1> | <1-3> | <2-4> | <4-6> |
| A-117 | <W-1> | <1-3> | <2-4> | <4-7> |
| A-118 | <W-1> | <1-3> | <2-4> | <4-8> |
| A-119 | <W-1> | <1-3> | <2-4> | <4-9 |
| A-120 | <W-1> | <1-3> | <2-4> | <4-10> |
| A-121 | <W-1> | <1-4> | <2-1> | <4-1> |
| A-122 | <W-1> | <1-4> | <2-1> | <4-2> |
| A-123 | <W-1> | <1-4> | <2-1> | <4-3> |
| A-124 | <W-1> | <1-4> | <2-1> | <4-4> |
| A-125 | <W-1> | <1-4> | <2-1> | <4-5> |
| A-126 | <W-1> | <1-4> | <2-1> | <4-6> |
| A-127 | <W-1> | <1-4> | <2-1> | <4-7> |
| A-128 | <W-1> | <1-4> | <2-1> | <4-8> |
| A-129 | <W-1> | <1-4> | <2-1> | <4-9 |
| A-130 | <W-1> | <1-4> | <2-1> | <4-10> |
| A-131 | <W-1> | <1-4> | <2-2> | <4-1> |
| A-132 | <W-1> | <1-4> | <2-2> | <4-2> |
| A-133 | <W-1> | <1-4> | <2-2> | <4-3> |
| A-134 | <W-1> | <1-4> | <2-2> | <4-4> |
| A-135 | <W-1> | <1-4> | <2-2> | <4-5> |
| A-136 | <W-1> | <1-4> | <2-2> | <4-6> |
| A-137 | <W-1> | <1-4> | <2-2> | <4-7> |
| A-138 | <W-1> | <1-4> | <2-2> | <4-8> |
| A-139 | <W-1> | <1-4> | <2-2> | <4-9 |
| A-140 | <W-1> | <1-4> | <2-2> | <4-10> |
| A-141 | <W-1> | <1-4> | <2-3> | <4-1> |
| A-142 | <W-1> | <1-4> | <2-3> | <4-2> |
| A-143 | <W-1> | <1-4> | <2-3> | <4-3> |
| A-144 | <W-1> | <1-4> | <2-3> | <4-4> |
| A-145 | <W-1> | <1-4> | <2-3> | <4-5> |

-continued

Table of embodiment combinations

| No | W/T | $R^1$ | A | $R^4$ |
|---|---|---|---|---|
| A-146 | <W-1> | <1-4> | <2-3> | <4-6> |
| A-147 | <W-1> | <1-4> | <2-3> | <4-7> |
| A-148 | <W-1> | <1-4> | <2-3> | <4-8> |
| A-149 | <W-1> | <1-4> | <2-3> | <4-9 |
| A-150 | <W-1> | <1-4> | <2-3> | <4-10> |
| A-151 | <W-1> | <1-4> | <2-4> | <4-1> |
| A-152 | <W-1> | <1-4> | <2-4> | <4-2> |
| A-153 | <W-1> | <1-4> | <2-4> | <4-3> |
| A-154 | <W-1> | <1-4> | <2-4> | <4-4> |
| A-155 | <W-1> | <1-4> | <2-4> | <4-5> |
| A-156 | <W-1> | <1-4> | <2-4> | <4-6> |
| A-157 | <W-1> | <1-4> | <2-4> | <4-7> |
| A-158 | <W-1> | <1-4> | <2-4> | <4-8> |
| A-159 | <W-1> | <1-4> | <2-4> | <4-9 |
| A-160 | <W-1> | <1-4> | <2-4> | <4-10> |
| A-161 | <W-1> | <1-5> | <2-1> | <4-1> |
| A-162 | <W-1> | <1-5> | <2-1> | <4-2> |
| A-163 | <W-1> | <1-5> | <2-1> | <4-3> |
| A-164 | <W-1> | <1-5> | <2-1> | <4-4> |
| A-165 | <W-1> | <1-5> | <2-1> | <4-5> |
| A-166 | <W-1> | <1-5> | <2-1> | <4-6> |
| A-167 | <W-1> | <1-5> | <2-1> | <4-7> |
| A-168 | <W-1> | <1-5> | <2-1> | <4-8> |
| A-169 | <W-1> | <1-5> | <2-1> | <4-9 |
| A-170 | <W-1> | <1-5> | <2-1> | <4-10> |
| A-171 | <W-1> | <1-5> | <2-2> | <4-1> |
| A-172 | <W-1> | <1-5> | <2-2> | <4-2> |
| A-173 | <W-1> | <1-5> | <2-2> | <4-3> |
| A-174 | <W-1> | <1-5> | <2-2> | <4-4> |
| A-175 | <W-1> | <1-5> | <2-2> | <4-5> |
| A-176 | <W-1> | <1-5> | <2-2> | <4-6> |
| A-177 | <W-1> | <1-5> | <2-2> | <4-7> |
| A-178 | <W-1> | <1-5> | <2-2> | <4-8> |
| A-179 | <W-1> | <1-5> | <2-2> | <4-9 |
| A-180 | <W-1> | <1-5> | <2-2> | <4-10> |
| A-181 | <W-1> | <1-5> | <2-3> | <4-1> |
| A-182 | <W-1> | <1-5> | <2-3> | <4-2> |
| A-183 | <W-1> | <1-5> | <2-3> | <4-3> |
| A-184 | <W-1> | <1-5> | <2-3> | <4-4> |
| A-185 | <W-1> | <1-5> | <2-3> | <4-5> |
| A-186 | <W-1> | <1-5> | <2-3> | <4-6> |
| A-187 | <W-1> | <1-5> | <2-3> | <4-7> |
| A-188 | <W-1> | <1-5> | <2-3> | <4-8> |
| A-189 | <W-1> | <1-5> | <2-3> | <4-9 |
| A-190 | <W-1> | <1-5> | <2-3> | <4-10> |
| A-191 | <W-1> | <1-5> | <2-4> | <4-1> |
| A-192 | <W-1> | <1-5> | <2-4> | <4-2> |
| A-193 | <W-1> | <1-5> | <2-4> | <4-3> |
| A-194 | <W-1> | <1-5> | <2-4> | <4-4> |
| A-195 | <W-1> | <1-5> | <2-4> | <4-5> |
| A-196 | <W-1> | <1-5> | <2-4> | <4-6> |
| A-197 | <W-1> | <1-5> | <2-4> | <4-7> |
| A-198 | <W-1> | <1-5> | <2-4> | <4-8> |
| A-199 | <W-1> | <1-5> | <2-4> | <4-9 |
| A-200 | <W-1> | <1-5> | <2-4> | <4-10> |
| A-201 | <W-1> | <1-6> | <2-1> | <4-1> |
| A-202 | <W-1> | <1-6> | <2-1> | <4-2> |
| A-203 | <W-1> | <1-6> | <2-1> | <4-3> |
| A-204 | <W-1> | <1-6> | <2-1> | <4-4> |
| A-205 | <W-1> | <1-6> | <2-1> | <4-5> |
| A-206 | <W-1> | <1-6> | <2-1> | <4-6> |
| A-207 | <W-1> | <1-6> | <2-1> | <4-7> |
| A-208 | <W-1> | <1-6> | <2-1> | <4-8> |
| A-209 | <W-1> | <1-6> | <2-1> | <4-9 |
| A-210 | <W-1> | <1-6> | <2-1> | <4-10> |
| A-211 | <W-1> | <1-6> | <2-2> | <4-1> |
| A-212 | <W-1> | <1-6> | <2-2> | <4-2> |
| A-213 | <W-1> | <1-6> | <2-2> | <4-3> |
| A-214 | <W-1> | <1-6> | <2-2> | <4-4> |
| A-215 | <W-1> | <1-6> | <2-2> | <4-5> |
| A-216 | <W-1> | <1-6> | <2-2> | <4-6> |
| A-217 | <W-1> | <1-6> | <2-2> | <4-7> |
| A-218 | <W-1> | <1-6> | <2-2> | <4-8> |
| A-219 | <W-1> | <1-6> | <2-2> | <4-9 |
| A-220 | <W-1> | <1-6> | <2-2> | <4-10> |

-continued

Table of embodiment combinations

| No | W/T | $R^1$ | A | $R^4$ |
|---|---|---|---|---|
| A-221 | <W-1> | <1-6> | <2-3> | <4-1> |
| A-222 | <W-1> | <1-6> | <2-3> | <4-2> |
| A-223 | <W-1> | <1-6> | <2-3> | <4-3> |
| A-224 | <W-1> | <1-6> | <2-3> | <4-4> |
| A-225 | <W-1> | <1-6> | <2-3> | <4-5> |
| A-226 | <W-1> | <1-6> | <2-3> | <4-6> |
| A-227 | <W-1> | <1-6> | <2-3> | <4-7> |
| A-228 | <W-1> | <1-6> | <2-3> | <4-8> |
| A-229 | <W-1> | <1-6> | <2-3> | <4-9 |
| A-230 | <W-1> | <1-6> | <2-3> | <4-10> |
| A-231 | <W-1> | <1-6> | <2-4> | <4-1> |
| A-232 | <W-1> | <1-6> | <2-4> | <4-2> |
| A-233 | <W-1> | <1-6> | <2-4> | <4-3> |
| A-234 | <W-1> | <1-6> | <2-4> | <4-4> |
| A-235 | <W-1> | <1-6> | <2-4> | <4-5> |
| A-236 | <W-1> | <1-6> | <2-4> | <4-6> |
| A-237 | <W-1> | <1-6> | <2-4> | <4-7> |
| A-238 | <W-1> | <1-6> | <2-4> | <4-8> |
| A-239 | <W-1> | <1-6> | <2-4> | <4-9 |
| A-240 | <W-1> | <1-6> | <2-4> | <4-10> |
| A-241 | <W-1> | <1-7> | <2-1> | <4-1> |
| A-242 | <W-1> | <1-7> | <2-1> | <4-2> |
| A-243 | <W-1> | <1-7> | <2-1> | <4-3> |
| A-244 | <W-1> | <1-7> | <2-1> | <4-4> |
| A-245 | <W-1> | <1-7> | <2-1> | <4-5> |
| A-246 | <W-1> | <1-7> | <2-1> | <4-6> |
| A-247 | <W-1> | <1-7> | <2-1> | <4-7> |
| A-248 | <W-1> | <1-7> | <2-1> | <4-8> |
| A-249 | <W-1> | <1-7> | <2-1> | <4-9 |
| A-250 | <W-1> | <1-7> | <2-1> | <4-10> |
| A-251 | <W-1> | <1-7> | <2-2> | <4-1> |
| A-252 | <W-1> | <1-7> | <2-2> | <4-2> |
| A-253 | <W-1> | <1-7> | <2-2> | <4-3> |
| A-254 | <W-1> | <1-7> | <2-2> | <4-4> |
| A-255 | <W-1> | <1-7> | <2-2> | <4-5> |
| A-256 | <W-1> | <1-7> | <2-2> | <4-6> |
| A-257 | <W-1> | <1-7> | <2-2> | <4-7> |
| A-258 | <W-1> | <1-7> | <2-2> | <4-8> |
| A-259 | <W-1> | <1-7> | <2-2> | <4-9 |
| A-260 | <W-1> | <1-7> | <2-2> | <4-10> |
| A-261 | <W-1> | <1-7> | <2-3> | <4-1> |
| A-262 | <W-1> | <1-7> | <2-3> | <4-2> |
| A-263 | <W-1> | <1-7> | <2-3> | <4-3> |
| A-264 | <W-1> | <1-7> | <2-3> | <4-4> |
| A-265 | <W-1> | <1-7> | <2-3> | <4-5> |
| A-266 | <W-1> | <1-7> | <2-3> | <4-6> |
| A-267 | <W-1> | <1-7> | <2-3> | <4-7> |
| A-268 | <W-1> | <1-7> | <2-3> | <4-8> |
| A-269 | <W-1> | <1-7> | <2-3> | <4-9 |
| A-270 | <W-1> | <1-7> | <2-3> | <4-10> |
| A-271 | <W-1> | <1-7> | <2-4> | <4-1> |
| A-272 | <W-1> | <1-7> | <2-4> | <4-2> |
| A-273 | <W-1> | <1-7> | <2-4> | <4-3> |
| A-274 | <W-1> | <1-7> | <2-4> | <4-4> |
| A-275 | <W-1> | <1-7> | <2-4> | <4-5> |
| A-276 | <W-1> | <1-7> | <2-4> | <4-6> |
| A-277 | <W-1> | <1-7> | <2-4> | <4-7> |
| A-278 | <W-1> | <1-7> | <2-4> | <4-8> |
| A-279 | <W-1> | <1-7> | <2-4> | <4-9 |
| A-280 | <W-1> | <1-7> | <2-4> | <4-10> |
| A-281 | <W-1> | <1-8> | <2-1> | <4-1> |
| A-282 | <W-1> | <1-8> | <2-1> | <4-2> |
| A-283 | <W-1> | <1-8> | <2-1> | <4-3> |
| A-284 | <W-1> | <1-8> | <2-1> | <4-4> |
| A-285 | <W-1> | <1-8> | <2-1> | <4-5> |
| A-286 | <W-1> | <1-8> | <2-1> | <4-6> |
| A-287 | <W-1> | <1-8> | <2-1> | <4-7> |
| A-288 | <W-1> | <1-8> | <2-1> | <4-8> |
| A-289 | <W-1> | <1-8> | <2-1> | <4-9 |
| A-290 | <W-1> | <1-8> | <2-1> | <4-10> |
| A-291 | <W-1> | <1-8> | <2-2> | <4-1> |
| A-292 | <W-1> | <1-8> | <2-2> | <4-2> |
| A-293 | <W-1> | <1-8> | <2-2> | <4-3> |
| A-294 | <W-1> | <1-8> | <2-2> | <4-4> |
| A-295 | <W-1> | <1-8> | <2-2> | <4-5> |

-continued

Table of embodiment combinations

| No | W/T | $R^1$ | A | $R^4$ |
|---|---|---|---|---|
| A-296 | <W-1> | <1-8> | <2-2> | <4-6> |
| A-297 | <W-1> | <1-8> | <2-2> | <4-7> |
| A-298 | <W-1> | <1-8> | <2-2> | <4-8> |
| A-299 | <W-1> | <1-8> | <2-2> | <4-9 |
| A-300 | <W-1> | <1-8> | <2-2> | <4-10> |
| A-301 | <W-1> | <1-8> | <2-3> | <4-1> |
| A-302 | <W-1> | <1-8> | <2-3> | <4-2> |
| A-303 | <W-1> | <1-8> | <2-3> | <4-3> |
| A-304 | <W-1> | <1-8> | <2-3> | <4-4> |
| A-305 | <W-1> | <1-8> | <2-3> | <4-5> |
| A-306 | <W-1> | <1-8> | <2-3> | <4-6> |
| A-307 | <W-1> | <1-8> | <2-3> | <4-7> |
| A-308 | <W-1> | <1-8> | <2-3> | <4-8> |
| A-309 | <W-1> | <1-8> | <2-3> | <4-9 |
| A-310 | <W-1> | <1-8> | <2-3> | <4-10> |
| A-311 | <W-1> | <1-8> | <2-4> | <4-1> |
| A-312 | <W-1> | <1-8> | <2-4> | <4-2> |
| A-313 | <W-1> | <1-8> | <2-4> | <4-3> |
| A-314 | <W-1> | <1-8> | <2-4> | <4-4> |
| A-315 | <W-1> | <1-8> | <2-4> | <4-5> |
| A-316 | <W-1> | <1-8> | <2-4> | <4-6> |
| A-317 | <W-1> | <1-8> | <2-4> | <4-7> |
| A-318 | <W-1> | <1-8> | <2-4> | <4-8> |
| A-319 | <W-1> | <1-8> | <2-4> | <4-9 |
| A-320 | <W-1> | <1-8> | <2-4> | <4-10> |
| A-321 | <W-1> | <1-9> | <2-1> | <4-1> |
| A-322 | <W-1> | <1-9> | <2-1> | <4-2> |
| A-323 | <W-1> | <1-9> | <2-1> | <4-3> |
| A-324 | <W-1> | <1-9> | <2-1> | <4-4> |
| A-325 | <W-1> | <1-9> | <2-1> | <4-5> |
| A-326 | <W-1> | <1-9> | <2-1> | <4-6> |
| A-327 | <W-1> | <1-9> | <2-1> | <4-7> |
| A-328 | <W-1> | <1-9> | <2-1> | <4-8> |
| A-329 | <W-1> | <1-9> | <2-1> | <4-9 |
| A-330 | <W-1> | <1-9> | <2-1> | <4-10> |
| A-331 | <W-1> | <1-9> | <2-2> | <4-1> |
| A-332 | <W-1> | <1-9> | <2-2> | <4-2> |
| A-333 | <W-1> | <1-9> | <2-2> | <4-3> |
| A-334 | <W-1> | <1-9> | <2-2> | <4-4> |
| A-335 | <W-1> | <1-9> | <2-2> | <4-5> |
| A-336 | <W-1> | <1-9> | <2-2> | <4-6> |
| A-337 | <W-1> | <1-9> | <2-2> | <4-7> |
| A-338 | <W-1> | <1-9> | <2-2> | <4-8> |
| A-339 | <W-1> | <1-9> | <2-2> | <4-9 |
| A-340 | <W-1> | <1-9> | <2-2> | <4-10> |
| A-341 | <W-1> | <1-9> | <2-3> | <4-1> |
| A-342 | <W-1> | <1-9> | <2-3> | <4-2> |
| A-343 | <W-1> | <1-9> | <2-3> | <4-3> |
| A-344 | <W-1> | <1-9> | <2-3> | <4-4> |
| A-345 | <W-1> | <1-9> | <2-3> | <4-5> |
| A-346 | <W-1> | <1-9> | <2-3> | <4-6> |
| A-347 | <W-1> | <1-9> | <2-3> | <4-7> |
| A-348 | <W-1> | <1-9> | <2-3> | <4-8> |
| A-349 | <W-1> | <1-9> | <2-3> | <4-9 |
| A-350 | <W-1> | <1-9> | <2-3> | <4-10> |
| A-351 | <W-1> | <1-9> | <2-4> | <4-1> |
| A-352 | <W-1> | <1-9> | <2-4> | <4-2> |
| A-353 | <W-1> | <1-9> | <2-4> | <4-3> |
| A-354 | <W-1> | <1-9> | <2-4> | <4-4> |
| A-355 | <W-1> | <1-9> | <2-4> | <4-5> |
| A-356 | <W-1> | <1-9> | <2-4> | <4-6> |
| A-357 | <W-1> | <1-9> | <2-4> | <4-7> |
| A-358 | <W-1> | <1-9> | <2-4> | <4-8> |
| A-359 | <W-1> | <1-9> | <2-4> | <4-9 |
| A-360 | <W-1> | <1-9> | <2-4> | <4-10> |

In the same way, the combinations A-361 to A-720 are part of the invention, wherein <W-2> is used instead of <W-1>.

In the same way, the combinations A-721 to A-1080 are part of the invention, wherein <W-3> is used instead of <W-1>.

In the same way, the combinations A-1081 to A-1440 are part of the invention, wherein <W-4> is used instead of <W-1>.

In particular, with a view to their use, preference is given to the compounds of the formula (I) compiled in the tables below, and to the preferred compounds of formula II-1, II-2, II-3, II-4, II-5, II-6, II-7, and II-16. Each of the groups mentioned for the substituents in the tables are furthermore per se, independently of the combination in which they are mentioned, a particularly preferred aspect of the substituent in question. Further, each individual meaning of a substituent in the tables constitutes a particularly preferred embodiment of the substituents in question.

TABLE 1

Compounds of the formula (III-1) corresponding to the compounds of the formula II-1, in which the combination of $R^1$, $R^4$ and T for a compound corresponds in each case to one line of Table A:

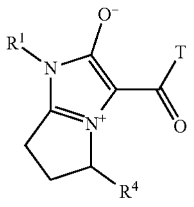

(III-1)

TABLE 2

Compounds of the formula (III-2) corresponding to the compounds of the formula II-2, in which the combination of $R^1$, $R^4$ and T for a compound corresponds in each case to one line of Table A:

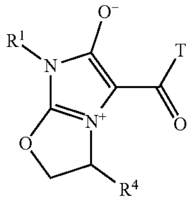

(III-2)

TABLE 3

Compounds of the formula (III-3) corresponding to the compounds of the formula II-3, in which the combination of $R^1$, $R^4$ and T for a compound corresponds in each case to one line of Table A:

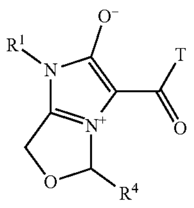

(III-3)

TABLE 4

| |
|---|
| Compounds of the formula (III-4) corresponding to the compounds of the formula II-4, in which the combination of $R^1$, $R^4$ and T for a compound corresponds in each case to one line of Table A: |
| 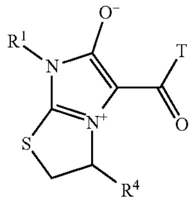 (III-4) |

TABLE 5

| |
|---|
| Compounds of the formula (II-5) corresponding to the compounds of the formula II-5, in which the combination of $R^1$, $R^4$ and T for a compound corresponds in each case to one line of Table A: |
| 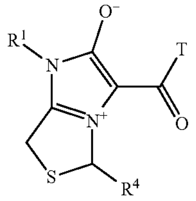 (III-5) |

TABLE 6

| |
|---|
| Compounds of the formula (III-6) corresponding to the compounds of the formula II-6, in which the combination of $R^1$, $R^4$ and T for a compound corresponds in each case to one line of Table A: |
| 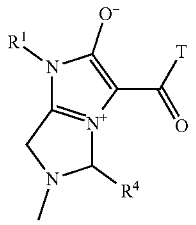 (III-6) |

TABLE 7

| |
|---|
| Compounds of the formula (III-7) corresponding to the compounds of the formula II-7, in which the combination of $R^1$, $R^4$ and T for a compound corresponds in each case to one line of Table A: |
| 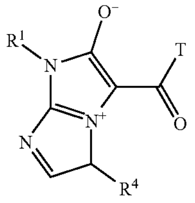 (III-7) |

TABLE 8

| |
|---|
| Compounds of the formula (III-8) corresponding to the compounds of the formula II-8, in which the combination of $R^1$, $R^4$ and T for a compound corresponds in each case to one line of Table A: |
| 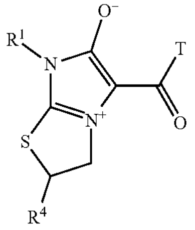 (III-8) |

TABLE 9

| |
|---|
| Compounds of the formula (III-9) corresponding to the compounds of the formula II-9, in which the combination of $R^1$, $R^4$ and T for a compound corresponds in each case to one line of Table A: |
| 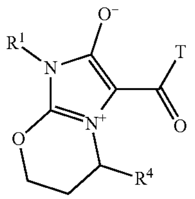 (III-9) |

TABLE 10

Compounds of the formula (III-10) corresponding to the compounds of the formula II-10, in which the combination of $R^1$, $R^4$ and T for a compound corresponds in each case to one line of Table A:

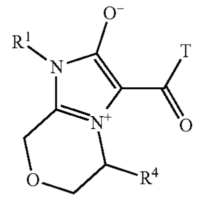

(III-10)

TABLE 11

Compounds of the formula (III-11) corresponding to the compounds of the formula II-15, in which the combination of $R^1$, $R^4$ and T for a compound corresponds in each case to one line of Table A:

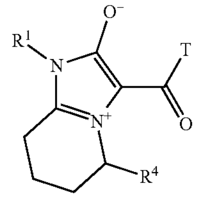

(III-11)

TABLE 12

Compounds of the formula (III-12) corresponding to the compounds of the formula II-16, in which the combination of $R^1$, $R^4$ and T for a compound corresponds in each case to oneline of Table A:

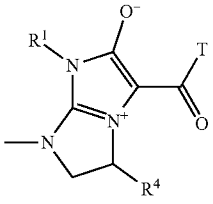

(III-12)

TABLE 13

Compounds of the formula (IIIA-1) corresponding to the compounds of the formula II-1, in which the combination of $R^1$, $R^4$ and T for a compound corresponds in each case to one line of Table A:

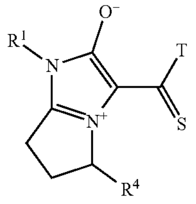

(IIIA-1)

TABLE 14

Compounds of the formula (IIIA-2) corresponding to the compounds of the formula II-2, in which the combination of $R^1$, $R^4$ and T for a compound corresponds in each case to one line of Table A:

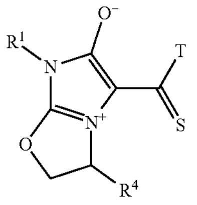

(IIIA-2)

TABLE 15

Compounds of the formula (IIIA-3) corresponding to the compounds of the formula II-3, in which the combination of $R^1$, $R^4$ and T for a compound corresponds in each case to one line of Table A:

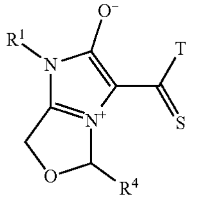

(IIIA-3)

TABLE 16

Compounds of the formula (IIIA-4) corresponding to the compounds of the formula II-4, in which the combination of $R^1$, $R^4$ and T for a compound corresponds in each case to one line of Table A:

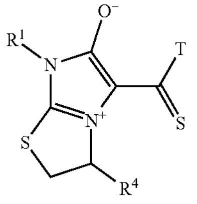

(IIIA-4)

TABLE 17

| Compounds of the formula (IIIA-5) corresponding to the compounds of the formula II-5, in which the combination of $R^1$, $R^4$ and T for a compound corresponds in each case to one line of Table A: |
|---|
| 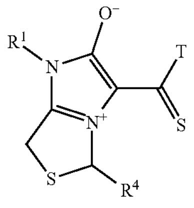 (IIIA-5) |

TABLE 18

| Compounds of the formula (IIIA-6) corresponding to the compounds of the formula II-6, in which the combination of $R^1$, $R^4$ and T for a compound corresponds in each case to one line of Table A: |
|---|
| 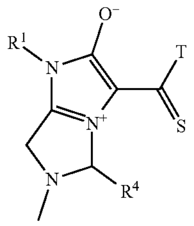 (IIIA-6) |

TABLE 19

| Compounds of the formula (IIIA-7) corresponding to the compounds of the formula II-7, in which the combination of $R^1$, $R^4$ and T for a compound corresponds in each case to one line of Table A: |
|---|
| 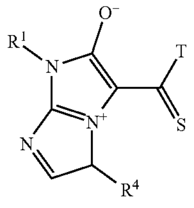 (IIIA-7) |

TABLE 20

| Compounds of the formula (IIIA-8) corresponding to the compounds of the formula II-8, in which the combination of $R^1$, $R^4$ and T for a compound corresponds in each case to one line of Table A: |
|---|
| 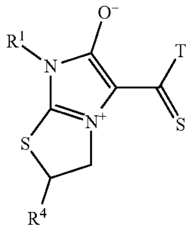 (IIIA-8) |

TABLE 21

| Compounds of the formula (IIIA-9) corresponding to the compounds of the formula II-9, in which the combination of $R^1$, $R^4$ and T for a compound corresponds in each case to one line of Table A: |
|---|
| 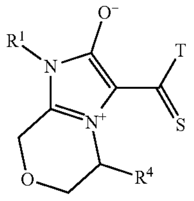 (IIIA-9) |

TABLE 22

| Compounds of the formula (IIIA-10) corresponding to the compounds of the formula II-10, in which the combination of $R^1$, $R^4$ and T for a compound corresponds in each case to one line of Table A: |
|---|
| 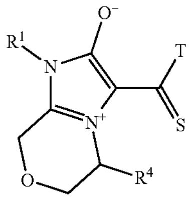 (IIIA-10) |

TABLE 23

| Compounds of the formula (IIIA-11) corresponding to the compounds of the formula II-15, in which the combination of $R^1$, $R^4$ and T for a compound corresponds in each case to one line of Table A: |
|---|
| 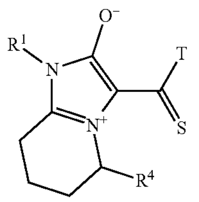 (IIIA-11) |

TABLE 24

| Compounds of the formula (IIIA-12) corresponding to the compounds of the formula II-16, in which the combination of $R^1$, $R^4$ and T for a compound corresponds in each case to one line of Table A: |
|---|
| 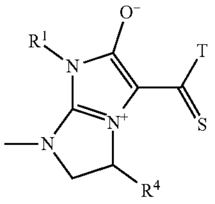 (IIIA-12) |

TABLE A

| No. | T | $R^4$ | $R^1$ |
|---|---|---|---|
| C-1 | T-1 | 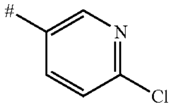 = D2b.1 | $CH_3$ |
| C-2 | T-2 | D2b.1 | $CH_3$ |
| C-3 | T-3 | D2b.1 | $CH_3$ |
| C-4 | T-4 | D2b.1 | $CH_3$ |
| C-5 | T-5 | D2b.1 | $CH_3$ |
| C-6 | T-6 | D2b.1 | $CH_3$ |
| C-7 | T-7 | D2b.1 | $CH_3$ |
| C-8 | T-8 | D2b.1 | $CH_3$ |
| C-9 | T-9 | D2b.1 | $CH_3$ |
| C-10 | T-10 | D2b.1 | $CH_3$ |
| C-11 | T-11 | D2b.1 | $CH_3$ |
| C-12 | T-12 | D2b.1 | $CH_3$ |
| C-13 | T-13 | D2b.1 | $CH_3$ |
| C-14 | T-14 | D2b.1 | $CH_3$ |
| C-15 | T-15 | D2b.1 | $CH_3$ |
| C-16 | T-16 | D2b.1 | $CH_3$ |
| C-17 | T-17 | D2b.1 | $CH_3$ |
| C-18 | T-18 | D2b.1 | $CH_3$ |
| C-19 | T-19 | D2b.1 | $CH_3$ |
| C-20 | T-20 | D2b.1 | $CH_3$ |
| C-21 | T-21 | D2b.1 | $CH_3$ |
| C-22 | T-22 | D2b.1 | $CH_3$ |
| C-23 | T-23 | D2b.1 | $CH_3$ |
| C-24 | T-24 | D2b.1 | $CH_3$ |
| C-25 | T-25 | D2b.1 | $CH_3$ |
| C-26 | T-26 | D2b.1 | $CH_3$ |
| C-27 | T-27 | D2b.1 | $CH_3$ |
| C-28 | T-28 | D2b.1 | $CH_3$ |

TABLE A-continued

| No. | T | $R^4$ | $R^1$ |
|---|---|---|---|
| C-29 | T-29 | D2b.1 | $CH_3$ |
| C-30 | T-30 | D2b.1 | $CH_3$ |
| C-31 | T-31 | D2b.1 | $CH_3$ |
| C-32 | T-32 | D2b.1 | $CH_3$ |
| C-33 | T-33 | D2b.1 | $CH_3$ |
| C-34 | T-34 | D2b.1 | $CH_3$ |
| C-35 | T-35 | D2b.1 | $CH_3$ |
| C-36 | T-36 | D2b.1 | $CH_3$ |
| C-37 | T-37 | D2b.1 | $CH_3$ |
| C-38 | T-38 | D2b.1 | $CH_3$ |
| C-39 | T-39 | D2b.1 | $CH_3$ |
| C-40 | T-40 | D2b.1 | $CH_3$ |
| C-41 | T-41 | D2b.1 | $CH_3$ |
| C-42 | T-42 | D2b.1 | $CH_3$ |
| C-43 | T-43 | D2b.1 | $CH_3$ |
| C-44 | T-44 | D2b.1 | $CH_3$ |
| C-45 | T-45 | D2b.1 | $CH_3$ |
| C-46 | T-46 | D2b.1 | $CH_3$ |
| C-47 | T-47 | D2b.1 | $CH_3$ |
| C-48 | T-48 | D2b.1 | $CH_3$ |
| C-49 | T-49 | D2b.1 | $CH_3$ |
| C-50 | T-50 | D2b.1 | $CH_3$ |
| C-51 | T-51 | D2b.1 | $CH_3$ |
| C-52 | T-52 | D2b.1 | $CH_3$ |
| C-53 | T-53 | D2b.1 | $CH_3$ |
| C-54 | T-54 | D2b.1 | $CH_3$ |
| C-55 | T-55 | D2b.1 | $CH_3$ |
| C-56 | T-56 | D2b.1 | $CH_3$ |
| C-57 | T-57 | D2b.1 | $CH_3$ |
| C-58 | T-58 | D2b.1 | $CH_3$ |
| C-59 | T-59 | D2b.1 | $CH_3$ |
| C-60 | T-60 | D2b.1 | $CH_3$ |
| C-61 | T-61 | D2b.1 | $CH_3$ |
| C-62 | T-62 | D2b.1 | $CH_3$ |
| C-63 | T-63 | D2b.1 | $CH_3$ |
| C-64 | T-64 | D2b.1 | $CH_3$ |
| C-65 | T-1 | 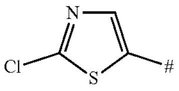 = D25a.1 | $CH_3$ |
| C-66 | T-2 | D25a.1 | $CH_3$ |
| C-67 | T-3 | D25a.1 | $CH_3$ |
| C-68 | T-4 | D25a.1 | $CH_3$ |
| C-69 | T-5 | D25a.1 | $CH_3$ |
| C-70 | T-6 | D25a.1 | $CH_3$ |
| C-71 | T-7 | D25a.1 | $CH_3$ |
| C-72 | T-8 | D25a.1 | $CH_3$ |
| C-73 | T-9 | D25a.1 | $CH_3$ |
| C-74 | T-10 | D25a.1 | $CH_3$ |
| C-75 | T-11 | D25a.1 | $CH_3$ |
| C-76 | T-12 | D25a.1 | $CH_3$ |
| C-77 | T-13 | D25a.1 | $CH_3$ |
| C-78 | T-14 | D25a.1 | $CH_3$ |
| C-79 | T-15 | D25a.1 | $CH_3$ |
| C-80 | T-16 | D25a.1 | $CH_3$ |
| C-81 | T-17 | D25a.1 | $CH_3$ |
| C-82 | T-18 | D25a.1 | $CH_3$ |
| C-83 | T-19 | D25a.1 | $CH_3$ |
| C-84 | T-20 | D25a.1 | $CH_3$ |
| C-85 | T-21 | D25a.1 | $CH_3$ |
| C-86 | T-22 | D25a.1 | $CH_3$ |
| C-87 | T-23 | D25a.1 | $CH_3$ |
| C-88 | T-24 | D25a.1 | $CH_3$ |
| C-89 | T-25 | D25a.1 | $CH_3$ |
| C-90 | T-26 | D25a.1 | $CH_3$ |
| C-91 | T-27 | D25a.1 | $CH_3$ |
| C-92 | T-28 | D25a.1 | $CH_3$ |
| C-93 | T-29 | D25a.1 | $CH_3$ |
| C-94 | T-30 | D25a.1 | $CH_3$ |
| C-95 | T-31 | D25a.1 | $CH_3$ |
| C-96 | T-32 | D25a.1 | $CH_3$ |
| C-97 | T-33 | D25a.1 | $CH_3$ |
| C-98 | T-34 | D25a.1 | $CH_3$ |
| C-99 | T-35 | D25a.1 | $CH_3$ |

TABLE A-continued

| No. | T | $R^4$ | $R^1$ |
|---|---|---|---|
| C-100 | T-36 | D25a.1 | $CH_3$ |
| C-101 | T-37 | D25a.1 | $CH_3$ |
| C-102 | T-38 | D25a.1 | $CH_3$ |
| C-103 | T-39 | D25a.1 | $CH_3$ |
| C-104 | T-40 | D25a.1 | $CH_3$ |
| C-105 | T-41 | D25a.1 | $CH_3$ |
| C-106 | T-42 | D25a.1 | $CH_3$ |
| C-107 | T-43 | D25a.1 | $CH_3$ |
| C-108 | T-44 | D25a.1 | $CH_3$ |
| C-109 | T-45 | D25a.1 | $CH_3$ |
| C-110 | T-46 | D25a.1 | $CH_3$ |
| C-111 | T-47 | D25a.1 | $CH_3$ |
| C-112 | T-48 | D25a.1 | $CH_3$ |
| C-113 | T-49 | D25a.1 | $CH_3$ |
| C-114 | T-50 | D25a.1 | $CH_3$ |
| C-115 | T-51 | D25a.1 | $CH_3$ |
| C-116 | T-52 | D25a.1 | $CH_3$ |
| C-117 | T-53 | D25a.1 | $CH_3$ |
| C-118 | T-54 | D25a.1 | $CH_3$ |
| C-119 | T-55 | D25a.1 | $CH_3$ |
| C-120 | T-56 | D25a.1 | $CH_3$ |
| C-121 | T-57 | D25a.1 | $CH_3$ |
| C-122 | T-58 | D25a.1 | $CH_3$ |
| C-123 | T-59 | D25a.1 | $CH_3$ |
| C-124 | T-60 | D25a.1 | $CH_3$ |
| C-125 | T-61 | D25a.1 | $CH_3$ |
| C-126 | T-62 | D25a.1 | $CH_3$ |
| C-127 | T-63 | D25a.1 | $CH_3$ |
| C-128 | T-64 | D25a.1 | $CH_3$ |
| C-129 | T-1 | 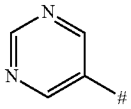 = D9b | $CH_3$ |
| C-130 | T-2 | D9b | $CH_3$ |
| C-131 | T-3 | D9b | $CH_3$ |
| C-132 | T-4 | D9b | $CH_3$ |
| C-133 | T-5 | D9b | $CH_3$ |
| C-134 | T-6 | D9b | $CH_3$ |
| C-135 | T-7 | D9b | $CH_3$ |
| C-136 | T-8 | D9b | $CH_3$ |
| C-137 | T-9 | D9b | $CH_3$ |
| C-138 | T-10 | D9b | $CH_3$ |
| C-139 | T-11 | D9b | $CH_3$ |
| C-140 | T-12 | D9b | $CH_3$ |
| C-141 | T-13 | D9b | $CH_3$ |
| C-142 | T-14 | D9b | $CH_3$ |
| C-143 | T-15 | D9b | $CH_3$ |
| C-144 | T-16 | D9b | $CH_3$ |
| C-145 | T-17 | D9b | $CH_3$ |
| C-146 | T-18 | D9b | $CH_3$ |
| C-147 | T-19 | D9b | $CH_3$ |
| C-148 | T-20 | D9b | $CH_3$ |
| C-149 | T-21 | D9b | $CH_3$ |
| C-150 | T-22 | D9b | $CH_3$ |
| C-151 | T-23 | D9b | $CH_3$ |
| C-152 | T-24 | D9b | $CH_3$ |
| C-153 | T-25 | D9b | $CH_3$ |
| C-154 | T-26 | D9b | $CH_3$ |
| C-155 | T-27 | D9b | $CH_3$ |
| C-156 | T-28 | D9b | $CH_3$ |
| C-157 | T-29 | D9b | $CH_3$ |
| C-158 | T-30 | D9b | $CH_3$ |
| C-159 | T-31 | D9b | $CH_3$ |
| C-160 | T-32 | D9b | $CH_3$ |
| C-161 | T-33 | D9b | $CH_3$ |
| C-162 | T-34 | D9b | $CH_3$ |
| C-163 | T-35 | D9b | $CH_3$ |
| C-164 | T-36 | D9b | $CH_3$ |
| C-165 | T-37 | D9b | $CH_3$ |
| C-166 | T-38 | D9b | $CH_3$ |
| C-167 | T-39 | D9b | $CH_3$ |
| C-168 | T-40 | D9b | $CH_3$ |
| C-169 | T-41 | D9b | $CH_3$ |

TABLE A-continued

| No. | T | $R^4$ | $R^1$ |
|---|---|---|---|
| C-170 | T-42 | D9b | $CH_3$ |
| C-171 | T-43 | D9b | $CH_3$ |
| C-172 | T-44 | D9b | $CH_3$ |
| C-173 | T-45 | D9b | $CH_3$ |
| C-174 | T-46 | D9b | $CH_3$ |
| C-175 | T-47 | D9b | $CH_3$ |
| C-176 | T-48 | D9b | $CH_3$ |
| C-177 | T-49 | D9b | $CH_3$ |
| C-178 | T-50 | D9b | $CH_3$ |
| C-179 | T-51 | D9b | $CH_3$ |
| C-180 | T-52 | D9b | $CH_3$ |
| C-181 | T-53 | D9b | $CH_3$ |
| C-182 | T-54 | D9b | $CH_3$ |
| C-183 | T-55 | D9b | $CH_3$ |
| C-184 | T-56 | D9b | $CH_3$ |
| C-185 | T-57 | D9b | $CH_3$ |
| C-186 | T-58 | D9b | $CH_3$ |
| C-187 | T-59 | D9b | $CH_3$ |
| C-188 | T-60 | D9b | $CH_3$ |
| C-189 | T-61 | D9b | $CH_3$ |
| C-190 | T-62 | D9b | $CH_3$ |
| C-191 | T-63 | D9b | $CH_3$ |
| C-192 | T-64 | D9b | $CH_3$ |
| C-193 | T-1 | $CH_2$—CN | $CH_3$ |
| C-194 | T-2 | $CH_2$—CN | $CH_3$ |
| C-195 | T-3 | $CH_2$—CN | $CH_3$ |
| C-196 | T-4 | $CH_2$—CN | $CH_3$ |
| C-197 | T-5 | $CH_2$—CN | $CH_3$ |
| C-198 | T-6 | $CH_2$—CN | $CH_3$ |
| C-199 | T-7 | $CH_2$—CN | $CH_3$ |
| C-200 | T-8 | $CH_2$—CN | $CH_3$ |
| C-201 | T-9 | $CH_2$—CN | $CH_3$ |
| C-202 | T-10 | $CH_2$—CN | $CH_3$ |
| C-203 | T-11 | $CH_2$—CN | $CH_3$ |
| C-204 | T-12 | $CH_2$—CN | $CH_3$ |
| C-205 | T-13 | $CH_2$—CN | $CH_3$ |
| C-206 | T-14 | $CH_2$—CN | $CH_3$ |
| C-207 | T-15 | $CH_2$—CN | $CH_3$ |
| C-208 | T-16 | $CH_2$—CN | $CH_3$ |
| C-209 | T-17 | $CH_2$—CN | $CH_3$ |
| C-210 | T-18 | $CH_2$—CN | $CH_3$ |
| C-211 | T-19 | $CH_2$—CN | $CH_3$ |
| C-212 | T-20 | $CH_2$—CN | $CH_3$ |
| C-213 | T-21 | $CH_2$—CN | $CH_3$ |
| C-214 | T-22 | $CH_2$—CN | $CH_3$ |
| C-215 | T-23 | $CH_2$—CN | $CH_3$ |
| C-216 | T-24 | $CH_2$—CN | $CH_3$ |
| C-217 | T-25 | $CH_2$—CN | $CH_3$ |
| C-218 | T-26 | $CH_2$—CN | $CH_3$ |
| C-219 | T-27 | $CH_2$—CN | $CH_3$ |
| C-220 | T-28 | $CH_2$—CN | $CH_3$ |
| C-221 | T-29 | $CH_2$—CN | $CH_3$ |
| C-222 | T-30 | $CH_2$—CN | $CH_3$ |
| C-223 | T-31 | $CH_2$—CN | $CH_3$ |
| C-224 | T-32 | $CH_2$—CN | $CH_3$ |
| C-225 | T-33 | $CH_2$—CN | $CH_3$ |
| C-226 | T-34 | $CH_2$—CN | $CH_3$ |
| C-227 | T-35 | $CH_2$—CN | $CH_3$ |
| C-228 | T-36 | $CH_2$—CN | $CH_3$ |
| C-229 | T-37 | $CH_2$—CN | $CH_3$ |
| C-230 | T-38 | $CH_2$—CN | $CH_3$ |
| C-231 | T-39 | $CH_2$—CN | $CH_3$ |
| C-232 | T-40 | $CH_2$—CN | $CH_3$ |
| C-233 | T-41 | $CH_2$—CN | $CH_3$ |
| C-234 | T-42 | $CH_2$—CN | $CH_3$ |
| C-235 | T-43 | $CH_2$—CN | $CH_3$ |
| C-236 | T-44 | $CH_2$—CN | $CH_3$ |
| C-237 | T-45 | $CH_2$—CN | $CH_3$ |
| C-238 | T-46 | $CH_2$—CN | $CH_3$ |
| C-239 | T-47 | $CH_2$—CN | $CH_3$ |
| C-240 | T-48 | $CH_2$—CN | $CH_3$ |
| C-241 | T-49 | $CH_2$—CN | $CH_3$ |
| C-242 | T-50 | $CH_2$—CN | $CH_3$ |
| C-243 | T-51 | $CH_2$—CN | $CH_3$ |
| C-244 | T-52 | $CH_2$—CN | $CH_3$ |
| C-245 | T-53 | $CH_2$—CN | $CH_3$ |
| C-246 | T-54 | $CH_2$—CN | $CH_3$ |
| C-247 | T-55 | $CH_2$—CN | $CH_3$ |

TABLE A-continued

| No. | T | $R^4$ | $R^1$ |
|---|---|---|---|
| C-248 | T-56 | $CH_2$—CN | $CH_3$ |
| C-249 | T-57 | $CH_2$—CN | $CH_3$ |
| C-250 | T-58 | $CH_2$—CN | $CH_3$ |
| C-251 | T-59 | $CH_2$—CN | $CH_3$ |
| C-252 | T-60 | $CH_2$—CN | $CH_3$ |
| C-253 | T-61 | $CH_2$—CN | $CH_3$ |
| C-254 | T-62 | $CH_2$—CN | $CH_3$ |
| C-255 | T-63 | $CH_2$—CN | $CH_3$ |
| C-256 | T-64 | $CH_2$—CN | $CH_3$ |
| C-257 | T-1 | D2b.1 | $CH_2CH_3$ |
| C-258 | T-2 | D2b.1 | $CH_2CH_3$ |
| C-259 | T-3 | D2b.1 | $CH_2CH_3$ |
| C-260 | T-4 | D2b.1 | $CH_2CH_3$ |
| C-261 | T-5 | D2b.1 | $CH_2CH_3$ |
| C-262 | T-6 | D2b.1 | $CH_2CH_3$ |
| C-263 | T-7 | D2b.1 | $CH_2CH_3$ |
| C-264 | T-8 | D2b.1 | $CH_2CH_3$ |
| C-265 | T-9 | D2b.1 | $CH_2CH_3$ |
| C-266 | T-10 | D2b.1 | $CH_2CH_3$ |
| C-267 | T-11 | D2b.1 | $CH_2CH_3$ |
| C-268 | T-12 | D2b.1 | $CH_2CH_3$ |
| C-269 | T-13 | D2b.1 | $CH_2CH_3$ |
| C-270 | T-14 | D2b.1 | $CH_2CH_3$ |
| C-271 | T-15 | D2b.1 | $CH_2CH_3$ |
| C-272 | T-16 | D2b.1 | $CH_2CH_3$ |
| C-273 | T-17 | D2b.1 | $CH_2CH_3$ |
| C-274 | T-18 | D2b.1 | $CH_2CH_3$ |
| C-275 | T-19 | D2b.1 | $CH_2CH_3$ |
| C-276 | T-20 | D2b.1 | $CH_2CH_3$ |
| C-277 | T-21 | D2b.1 | $CH_2CH_3$ |
| C-278 | T-22 | D2b.1 | $CH_2CH_3$ |
| C-279 | T-23 | D2b.1 | $CH_2CH_3$ |
| C-280 | T-24 | D2b.1 | $CH_2CH_3$ |
| C-281 | T-25 | D2b.1 | $CH_2CH_3$ |
| C-282 | T-26 | D2b.1 | $CH_2CH_3$ |
| C-283 | T-27 | D2b.1 | $CH_2CH_3$ |
| C-284 | T-28 | D2b.1 | $CH_2CH_3$ |
| C-285 | T-29 | D2b.1 | $CH_2CH_3$ |
| C-286 | T-30 | D2b.1 | $CH_2CH_3$ |
| C-287 | T-31 | D2b.1 | $CH_2CH_3$ |
| C-288 | T-32 | D2b.1 | $CH_2CH_3$ |
| C-289 | T-33 | D2b.1 | $CH_2CH_3$ |
| C-290 | T-34 | D2b.1 | $CH_2CH_3$ |
| C-291 | T-35 | D2b.1 | $CH_2CH_3$ |
| C-292 | T-36 | D2b.1 | $CH_2CH_3$ |
| C-293 | T-37 | D2b.1 | $CH_2CH_3$ |
| C-294 | T-38 | D2b.1 | $CH_2CH_3$ |
| C-295 | T-39 | D2b.1 | $CH_2CH_3$ |
| C-296 | T-40 | D2b.1 | $CH_2CH_3$ |
| C-297 | T-41 | D2b.1 | $CH_2CH_3$ |
| C-298 | T-42 | D2b.1 | $CH_2CH_3$ |
| C-299 | T-43 | D2b.1 | $CH_2CH_3$ |
| C-300 | T-44 | D2b.1 | $CH_2CH_3$ |
| C-301 | T-45 | D2b.1 | $CH_2CH_3$ |
| C-302 | T-46 | D2b.1 | $CH_2CH_3$ |
| C-303 | T-47 | D2b.1 | $CH_2CH_3$ |
| C-304 | T-48 | D2b.1 | $CH_2CH_3$ |
| C-305 | T-49 | D2b.1 | $CH_2CH_3$ |
| C-306 | T-50 | D2b.1 | $CH_2CH_3$ |
| C-307 | T-51 | D2b.1 | $CH_2CH_3$ |
| C-308 | T-52 | D2b.1 | $CH_2CH_3$ |
| C-309 | T-53 | D2b.1 | $CH_2CH_3$ |
| C-310 | T-54 | D2b.1 | $CH_2CH_3$ |
| C-311 | T-55 | D2b.1 | $CH_2CH_3$ |
| C-312 | T-56 | D2b.1 | $CH_2CH_3$ |
| C-313 | T-57 | D2b.1 | $CH_2CH_3$ |
| C-314 | T-58 | D2b.1 | $CH_2CH_3$ |
| C-315 | T-59 | D2b.1 | $CH_2CH_3$ |
| C-316 | T-60 | D2b.1 | $CH_2CH_3$ |
| C-317 | T-61 | D2b.1 | $CH_2CH_3$ |
| C-318 | T-62 | D2b.1 | $CH_2CH_3$ |
| C-319 | T-63 | D2b.1 | $CH_2CH_3$ |
| C-320 | T-64 | D2b.1 | $CH_2CH_3$ |
| C-321 | T-1 | D25a.1 | $CH_2CH_3$ |
| C-322 | T-2 | D25a.1 | $CH_2CH_3$ |
| C-323 | T-3 | D25a.1 | $CH_2CH_3$ |
| C-324 | T-4 | D25a.1 | $CH_2CH_3$ |
| C-325 | T-5 | D25a.1 | $CH_2CH_3$ |

TABLE A-continued

| No. | T | $R^4$ | $R^1$ |
|---|---|---|---|
| C-326 | T-6 | D25a.1 | $CH_2CH_3$ |
| C-327 | T-7 | D25a.1 | $CH_2CH_3$ |
| C-328 | T-8 | D25a.1 | $CH_2CH_3$ |
| C-329 | T-9 | D25a.1 | $CH_2CH_3$ |
| C-330 | T-10 | D25a.1 | $CH_2CH_3$ |
| C-331 | T-11 | D25a.1 | $CH_2CH_3$ |
| C-332 | T-12 | D25a.1 | $CH_2CH_3$ |
| C-333 | T-13 | D25a.1 | $CH_2CH_3$ |
| C-334 | T-14 | D25a.1 | $CH_2CH_3$ |
| C-335 | T-15 | D25a.1 | $CH_2CH_3$ |
| C-336 | T-16 | D25a.1 | $CH_2CH_3$ |
| C-337 | T-17 | D25a.1 | $CH_2CH_3$ |
| C-338 | T-18 | D25a.1 | $CH_2CH_3$ |
| C-339 | T-19 | D25a.1 | $CH_2CH_3$ |
| C-340 | T-20 | D25a.1 | $CH_2CH_3$ |
| C-341 | T-21 | D25a.1 | $CH_2CH_3$ |
| C-342 | T-22 | D25a.1 | $CH_2CH_3$ |
| C-343 | T-23 | D25a.1 | $CH_2CH_3$ |
| C-344 | T-24 | D25a.1 | $CH_2CH_3$ |
| C-345 | T-25 | D25a.1 | $CH_2CH_3$ |
| C-346 | T-26 | D25a.1 | $CH_2CH_3$ |
| C-347 | T-27 | D25a.1 | $CH_2CH_3$ |
| C-348 | T-28 | D25a.1 | $CH_2CH_3$ |
| C-349 | T-29 | D25a.1 | $CH_2CH_3$ |
| C-350 | T-30 | D25a.1 | $CH_2CH_3$ |
| C-351 | T-31 | D25a.1 | $CH_2CH_3$ |
| C-352 | T-32 | D25a.1 | $CH_2CH_3$ |
| C-353 | T-33 | D25a.1 | $CH_2CH_3$ |
| C-354 | T-34 | D25a.1 | $CH_2CH_3$ |
| C-355 | T-35 | D25a.1 | $CH_2CH_3$ |
| C-356 | T-36 | D25a.1 | $CH_2CH_3$ |
| C-357 | T-37 | D25a.1 | $CH_2CH_3$ |
| C-358 | T-38 | D25a.1 | $CH_2CH_3$ |
| C-359 | T-39 | D25a.1 | $CH_2CH_3$ |
| C-360 | T-40 | D25a.1 | $CH_2CH_3$ |
| C-361 | T-41 | D25a.1 | $CH_2CH_3$ |
| C-362 | T-42 | D25a.1 | $CH_2CH_3$ |
| C-363 | T-43 | D25a.1 | $CH_2CH_3$ |
| C-364 | T-44 | D25a.1 | $CH_2CH_3$ |
| C-365 | T-45 | D25a.1 | $CH_2CH_3$ |
| C-366 | T-46 | D25a.1 | $CH_2CH_3$ |
| C-367 | T-47 | D25a.1 | $CH_2CH_3$ |
| C-368 | T-48 | D25a.1 | $CH_2CH_3$ |
| C-369 | T-49 | D25a.1 | $CH_2CH_3$ |
| C-370 | T-50 | D25a.1 | $CH_2CH_3$ |
| C-371 | T-51 | D25a.1 | $CH_2CH_3$ |
| C-372 | T-52 | D25a.1 | $CH_2CH_3$ |
| C-373 | T-53 | D25a.1 | $CH_2CH_3$ |
| C-374 | T-54 | D25a.1 | $CH_2CH_3$ |
| C-375 | T-55 | D25a.1 | $CH_2CH_3$ |
| C-376 | T-56 | D25a.1 | $CH_2CH_3$ |
| C-377 | T-57 | D25a.1 | $CH_2CH_3$ |
| C-378 | T-58 | D25a.1 | $CH_2CH_3$ |
| C-379 | T-59 | D25a.1 | $CH_2CH_3$ |
| C-380 | T-60 | D25a.1 | $CH_2CH_3$ |
| C-381 | T-61 | D25a.1 | $CH_2CH_3$ |
| C-382 | T-62 | D25a.1 | $CH_2CH_3$ |
| C-383 | T-63 | D25a.1 | $CH_2CH_3$ |
| C-384 | T-64 | D25a.1 | $CH_2CH_3$ |
| C-385 | T-1 | D9b | $CH_2CH_3$ |
| C-386 | T-2 | D9b | $CH_2CH_3$ |
| C-387 | T-3 | D9b | $CH_2CH_3$ |
| C-388 | T-4 | D9b | $CH_2CH_3$ |
| C-389 | T-5 | D9b | $CH_2CH_3$ |
| C-390 | T-6 | D9b | $CH_2CH_3$ |
| C-391 | T-7 | D9b | $CH_2CH_3$ |
| C-392 | T-8 | D9b | $CH_2CH_3$ |
| C-393 | T-9 | D9b | $CH_2CH_3$ |
| C-394 | T-10 | D9b | $CH_2CH_3$ |
| C-395 | T-11 | D9b | $CH_2CH_3$ |
| C-396 | T-12 | D9b | $CH_2CH_3$ |
| C-397 | T-13 | D9b | $CH_2CH_3$ |
| C-398 | T-14 | D9b | $CH_2CH_3$ |
| C-399 | T-15 | D9b | $CH_2CH_3$ |
| C-400 | T-16 | D9b | $CH_2CH_3$ |
| C-401 | T-17 | D9b | $CH_2CH_3$ |
| C-402 | T-18 | D9b | $CH_2CH_3$ |
| C-403 | T-19 | D9b | $CH_2CH_3$ |

TABLE A-continued

| No. | T | $R^4$ | $R^1$ |
|---|---|---|---|
| C-404 | T-20 | D9b | $CH_2CH_3$ |
| C-405 | T-21 | D9b | $CH_2CH_3$ |
| C-406 | T-22 | D9b | $CH_2CH_3$ |
| C-407 | T-23 | D9b | $CH_2CH_3$ |
| C-408 | T-24 | D9b | $CH_2CH_3$ |
| C-409 | T-25 | D9b | $CH_2CH_3$ |
| C-410 | T-26 | D9b | $CH_2CH_3$ |
| C-411 | T-27 | D9b | $CH_2CH_3$ |
| C-412 | T-28 | D9b | $CH_2CH_3$ |
| C-413 | T-29 | D9b | $CH_2CH_3$ |
| C-414 | T-30 | D9b | $CH_2CH_3$ |
| C-415 | T-31 | D9b | $CH_2CH_3$ |
| C-416 | T-32 | D9b | $CH_2CH_3$ |
| C-417 | T-33 | D9b | $CH_2CH_3$ |
| C-418 | T-34 | D9b | $CH_2CH_3$ |
| C-419 | T-35 | D9b | $CH_2CH_3$ |
| C-420 | T-36 | D9b | $CH_2CH_3$ |
| C-421 | T-37 | D9b | $CH_2CH_3$ |
| C-422 | T-38 | D9b | $CH_2CH_3$ |
| C-423 | T-39 | D9b | $CH_2CH_3$ |
| C-424 | T-40 | D9b | $CH_2CH_3$ |
| C-425 | T-41 | D9b | $CH_2CH_3$ |
| C-426 | T-42 | D9b | $CH_2CH_3$ |
| C-427 | T-43 | D9b | $CH_2CH_3$ |
| C-428 | T-44 | D9b | $CH_2CH_3$ |
| C-429 | T-45 | D9b | $CH_2CH_3$ |
| C-430 | T-46 | D9b | $CH_2CH_3$ |
| C-431 | T-47 | D9b | $CH_2CH_3$ |
| C-432 | T-48 | D9b | $CH_2CH_3$ |
| C-433 | T-49 | D9b | $CH_2CH_3$ |
| C-434 | T-50 | D9b | $CH_2CH_3$ |
| C-435 | T-51 | D9b | $CH_2CH_3$ |
| C-436 | T-52 | D9b | $CH_2CH_3$ |
| C-437 | T-53 | D9b | $CH_2CH_3$ |
| C-438 | T-54 | D9b | $CH_2CH_3$ |
| C-439 | T-55 | D9b | $CH_2CH_3$ |
| C-440 | T-56 | D9b | $CH_2CH_3$ |
| C-441 | T-57 | D9b | $CH_2CH_3$ |
| C-442 | T-58 | D9b | $CH_2CH_3$ |
| C-443 | T-59 | D9b | $CH_2CH_3$ |
| C-444 | T-60 | D9b | $CH_2CH_3$ |
| C-445 | T-61 | D9b | $CH_2CH_3$ |
| C-446 | T-62 | D9b | $CH_2CH_3$ |
| C-447 | T-63 | D9b | $CH_2CH_3$ |
| C-448 | T-64 | D9b | $CH_2CH_3$ |
| C-449 | T-1 | $CH_2$—CN | $CH_2CH_3$ |
| C-450 | T-2 | $CH_2$—CN | $CH_2CH_3$ |
| C-451 | T-3 | $CH_2$—CN | $CH_2CH_3$ |
| C-452 | T-4 | $CH_2$—CN | $CH_2CH_3$ |
| C-453 | T-5 | $CH_2$—CN | $CH_2CH_3$ |
| C-454 | T-6 | $CH_2$—CN | $CH_2CH_3$ |
| C-455 | T-7 | $CH_2$—CN | $CH_2CH_3$ |
| C-456 | T-8 | $CH_2$—CN | $CH_2CH_3$ |
| C-457 | T-9 | $CH_2$—CN | $CH_2CH_3$ |
| C-458 | T-10 | $CH_2$—CN | $CH_2CH_3$ |
| C-459 | T-11 | $CH_2$—CN | $CH_2CH_3$ |
| C-460 | T-12 | $CH_2$—CN | $CH_2CH_3$ |
| C-461 | T-13 | $CH_2$—CN | $CH_2CH_3$ |
| C-462 | T-14 | $CH_2$—CN | $CH_2CH_3$ |
| C-463 | T-15 | $CH_2$—CN | $CH_2CH_3$ |
| C-464 | T-16 | $CH_2$—CN | $CH_2CH_3$ |
| C-465 | T-17 | $CH_2$—CN | $CH_2CH_3$ |
| C-466 | T-18 | $CH_2$—CN | $CH_2CH_3$ |
| C-467 | T-19 | $CH_2$—CN | $CH_2CH_3$ |
| C-468 | T-20 | $CH_2$—CN | $CH_2CH_3$ |
| C-469 | T-21 | $CH_2$—CN | $CH_2CH_3$ |
| C-470 | T-22 | $CH_2$—CN | $CH_2CH_3$ |
| C-471 | T-23 | $CH_2$—CN | $CH_2CH_3$ |
| C-472 | T-24 | $CH_2$—CN | $CH_2CH_3$ |
| C-473 | T-25 | $CH_2$—CN | $CH_2CH_3$ |
| C-474 | T-26 | $CH_2$—CN | $CH_2CH_3$ |
| C-475 | T-27 | $CH_2$—CN | $CH_2CH_3$ |
| C-476 | T-28 | $CH_2$—CN | $CH_2CH_3$ |
| C-477 | T-29 | $CH_2$—CN | $CH_2CH_3$ |
| C-478 | T-30 | $CH_2$—CN | $CH_2CH_3$ |
| C-479 | T-31 | $CH_2$—CN | $CH_2CH_3$ |
| C-480 | T-32 | $CH_2$—CN | $CH_2CH_3$ |
| C-481 | T-33 | $CH_2$—CN | $CH_2CH_3$ |

TABLE A-continued

| No. | T | $R^4$ | $R^1$ |
|---|---|---|---|
| C-482 | T-34 | $CH_2$—CN | $CH_2CH_3$ |
| C-483 | T-35 | $CH_2$—CN | $CH_2CH_3$ |
| C-484 | T-36 | $CH_2$—CN | $CH_2CH_3$ |
| C-485 | T-37 | $CH_2$—CN | $CH_2CH_3$ |
| C-486 | T-38 | $CH_2$—CN | $CH_2CH_3$ |
| C-487 | T-39 | $CH_2$—CN | $CH_2CH_3$ |
| C-488 | T-40 | $CH_2$—CN | $CH_2CH_3$ |
| C-489 | T-41 | $CH_2$—CN | $CH_2CH_3$ |
| C-490 | T-42 | $CH_2$—CN | $CH_2CH_3$ |
| C-491 | T-43 | $CH_2$—CN | $CH_2CH_3$ |
| C-492 | T-44 | $CH_2$—CN | $CH_2CH_3$ |
| C-493 | T-45 | $CH_2$—CN | $CH_2CH_3$ |
| C-494 | T-46 | $CH_2$—CN | $CH_2CH_3$ |
| C-495 | T-47 | $CH_2$—CN | $CH_2CH_3$ |
| C-496 | T-48 | $CH_2$—CN | $CH_2CH_3$ |
| C-497 | T-49 | $CH_2$—CN | $CH_2CH_3$ |
| C-498 | T-50 | $CH_2$—CN | $CH_2CH_3$ |
| C-499 | T-51 | $CH_2$—CN | $CH_2CH_3$ |
| C-500 | T-52 | $CH_2$—CN | $CH_2CH_3$ |
| C-501 | T-53 | $CH_2$—CN | $CH_2CH_3$ |
| C-502 | T-54 | $CH_2$—CN | $CH_2CH_3$ |
| C-503 | T-55 | $CH_2$—CN | $CH_2CH_3$ |
| C-504 | T-56 | $CH_2$—CN | $CH_2CH_3$ |
| C-505 | T-57 | $CH_2$—CN | $CH_2CH_3$ |
| C-506 | T-58 | $CH_2$—CN | $CH_2CH_3$ |
| C-507 | T-59 | $CH_2$—CN | $CH_2CH_3$ |
| C-508 | T-60 | $CH_2$—CN | $CH_2CH_3$ |
| C-509 | T-61 | $CH_2$—CN | $CH_2CH_3$ |
| C-510 | T-62 | $CH_2$—CN | $CH_2CH_3$ |
| C-511 | T-63 | $CH_2$—CN | $CH_2CH_3$ |
| C-512 | T-64 | $CH_2$—CN | $CH_2CH_3$ |
| C-513 | T-1 | D2b.1 | $CH(CH_3)_2$ |
| C-514 | T-2 | D2b.1 | $CH(CH_3)_2$ |
| C-515 | T-3 | D2b.1 | $CH(CH_3)_2$ |
| C-516 | T-4 | D2b.1 | $CH(CH_3)_2$ |
| C-517 | T-5 | D2b.1 | $CH(CH_3)_2$ |
| C-518 | T-6 | D2b.1 | $CH(CH_3)_2$ |
| C-519 | T-7 | D2b.1 | $CH(CH_3)_2$ |
| C-520 | T-8 | D2b.1 | $CH(CH_3)_2$ |
| C-521 | T-9 | D2b.1 | $CH(CH_3)_2$ |
| C-522 | T-10 | D2b.1 | $CH(CH_3)_2$ |
| C-523 | T-11 | D2b.1 | $CH(CH_3)_2$ |
| C-524 | T-12 | D2b.1 | $CH(CH_3)_2$ |
| C-525 | T-13 | D2b.1 | $CH(CH_3)_2$ |
| C-526 | T-14 | D2b.1 | $CH(CH_3)_2$ |
| C-527 | T-15 | D2b.1 | $CH(CH_3)_2$ |
| C-528 | T-16 | D2b.1 | $CH(CH_3)_2$ |
| C-529 | T-17 | D2b.1 | $CH(CH_3)_2$ |
| C-530 | T-18 | D2b.1 | $CH(CH_3)_2$ |
| C-531 | T-19 | D2b.1 | $CH(CH_3)_2$ |
| C-532 | T-20 | D2b.1 | $CH(CH_3)_2$ |
| C-533 | T-21 | D2b.1 | $CH(CH_3)_2$ |
| C-534 | T-22 | D2b.1 | $CH(CH_3)_2$ |
| C-535 | T-23 | D2b.1 | $CH(CH_3)_2$ |
| C-536 | T-24 | D2b.1 | $CH(CH_3)_2$ |
| C-537 | T-25 | D2b.1 | $CH(CH_3)_2$ |
| C-538 | T-26 | D2b.1 | $CH(CH_3)_2$ |
| C-539 | T-27 | D2b.1 | $CH(CH_3)_2$ |
| C-540 | T-28 | D2b.1 | $CH(CH_3)_2$ |
| C-541 | T-29 | D2b.1 | $CH(CH_3)_2$ |
| C-542 | T-30 | D2b.1 | $CH(CH_3)_2$ |
| C-543 | T-31 | D2b.1 | $CH(CH_3)_2$ |
| C-544 | T-32 | D2b.1 | $CH(CH_3)_2$ |
| C-545 | T-33 | D2b.1 | $CH(CH_3)_2$ |
| C-546 | T-34 | D2b.1 | $CH(CH_3)_2$ |
| C-547 | T-35 | D2b.1 | $CH(CH_3)_2$ |
| C-548 | T-36 | D2b.1 | $CH(CH_3)_2$ |
| C-549 | T-37 | D2b.1 | $CH(CH_3)_2$ |
| C-550 | T-38 | D2b.1 | $CH(CH_3)_2$ |
| C-551 | T-39 | D2b.1 | $CH(CH_3)_2$ |
| C-552 | T-40 | D2b.1 | $CH(CH_3)_2$ |
| C-553 | T-41 | D2b.1 | $CH(CH_3)_2$ |
| C-554 | T-42 | D2b.1 | $CH(CH_3)_2$ |
| C-555 | T-43 | D2b.1 | $CH(CH_3)_2$ |
| C-556 | T-44 | D2b.1 | $CH(CH_3)_2$ |
| C-557 | T-45 | D2b.1 | $CH(CH_3)_2$ |
| C-558 | T-46 | D2b.1 | $CH(CH_3)_2$ |
| C-559 | T-47 | D2b.1 | $CH(CH_3)_2$ |

TABLE A-continued

| No. | T | $R^4$ | $R^1$ |
|---|---|---|---|
| C-560 | T-48 | D2b.1 | $CH(CH_3)_2$ |
| C-561 | T-49 | D2b.1 | $CH(CH_3)_2$ |
| C-562 | T-50 | D2b.1 | $CH(CH_3)_2$ |
| C-563 | T-51 | D2b.1 | $CH(CH_3)_2$ |
| C-564 | T-52 | D2b.1 | $CH(CH_3)_2$ |
| C-565 | T-53 | D2b.1 | $CH(CH_3)_2$ |
| C-566 | T-54 | D2b.1 | $CH(CH_3)_2$ |
| C-567 | T-55 | D2b.1 | $CH(CH_3)_2$ |
| C-568 | T-56 | D2b.1 | $CH(CH_3)_2$ |
| C-569 | T-57 | D2b.1 | $CH(CH_3)_2$ |
| C-570 | T-58 | D2b.1 | $CH(CH_3)_2$ |
| C-571 | T-59 | D2b.1 | $CH(CH_3)_2$ |
| C-572 | T-60 | D2b.1 | $CH(CH_3)_2$ |
| C-573 | T-61 | D2b.1 | $CH(CH_3)_2$ |
| C-574 | T-62 | D2b.1 | $CH(CH_3)_2$ |
| C-575 | T-63 | D2b.1 | $CH(CH_3)_2$ |
| C-576 | T-64 | D2b.1 | $CH(CH_3)_2$ |
| C-577 | T-1 | D25a.1 | $CH(CH_3)_2$ |
| C-578 | T-2 | D25a.1 | $CH(CH_3)_2$ |
| C-579 | T-3 | D25a.1 | $CH(CH_3)_2$ |
| C-580 | T-4 | D25a.1 | $CH(CH_3)_2$ |
| C-581 | T-5 | D25a.1 | $CH(CH_3)_2$ |
| C-582 | T-6 | D25a.1 | $CH(CH_3)_2$ |
| C-583 | T-7 | D25a.1 | $CH(CH_3)_2$ |
| C-584 | T-8 | D25a.1 | $CH(CH_3)_2$ |
| C-585 | T-9 | D25a.1 | $CH(CH_3)_2$ |
| C-586 | T-10 | D25a.1 | $CH(CH_3)_2$ |
| C-587 | T-11 | D25a.1 | $CH(CH_3)_2$ |
| C-588 | T-12 | D25a.1 | $CH(CH_3)_2$ |
| C-589 | T-13 | D25a.1 | $CH(CH_3)_2$ |
| C-590 | T-14 | D25a.1 | $CH(CH_3)_2$ |
| C-591 | T-15 | D25a.1 | $CH(CH_3)_2$ |
| C-592 | T-16 | D25a.1 | $CH(CH_3)_2$ |
| C-593 | T-17 | D25a.1 | $CH(CH_3)_2$ |
| C-594 | T-18 | D25a.1 | $CH(CH_3)_2$ |
| C-595 | T-19 | D25a.1 | $CH(CH_3)_2$ |
| C-596 | T-20 | D25a.1 | $CH(CH_3)_2$ |
| C-597 | T-21 | D25a.1 | $CH(CH_3)_2$ |
| C-598 | T-22 | D25a.1 | $CH(CH_3)_2$ |
| C-599 | T-23 | D25a.1 | $CH(CH_3)_2$ |
| C-600 | T-24 | D25a.1 | $CH(CH_3)_2$ |
| C-601 | T-25 | D25a.1 | $CH(CH_3)_2$ |
| C-602 | T-26 | D25a.1 | $CH(CH_3)_2$ |
| C-603 | T-27 | D25a.1 | $CH(CH_3)_2$ |
| C-604 | T-28 | D25a.1 | $CH(CH_3)_2$ |
| C-605 | T-29 | D25a.1 | $CH(CH_3)_2$ |
| C-606 | T-30 | D25a.1 | $CH(CH_3)_2$ |
| C-607 | T-31 | D25a.1 | $CH(CH_3)_2$ |
| C-608 | T-32 | D25a.1 | $CH(CH_3)_2$ |
| C-609 | T-33 | D25a.1 | $CH(CH_3)_2$ |
| C-610 | T-34 | D25a.1 | $CH(CH_3)_2$ |
| C-611 | T-35 | D25a.1 | $CH(CH_3)_2$ |
| C-612 | T-36 | D25a.1 | $CH(CH_3)_2$ |
| C-613 | T-37 | D25a.1 | $CH(CH_3)_2$ |
| C-614 | T-38 | D25a.1 | $CH(CH_3)_2$ |
| C-615 | T-39 | D25a.1 | $CH(CH_3)_2$ |
| C-616 | T-40 | D25a.1 | $CH(CH_3)_2$ |
| C-617 | T-41 | D25a.1 | $CH(CH_3)_2$ |
| C-618 | T-42 | D25a.1 | $CH(CH_3)_2$ |
| C-619 | T-43 | D25a.1 | $CH(CH_3)_2$ |
| C-620 | T-44 | D25a.1 | $CH(CH_3)_2$ |
| C-621 | T-45 | D25a.1 | $CH(CH_3)_2$ |
| C-622 | T-46 | D25a.1 | $CH(CH_3)_2$ |
| C-623 | T-47 | D25a.1 | $CH(CH_3)_2$ |
| C-624 | T-48 | D25a.1 | $CH(CH_3)_2$ |
| C-625 | T-49 | D25a.1 | $CH(CH_3)_2$ |
| C-626 | T-50 | D25a.1 | $CH(CH_3)_2$ |
| C-627 | T-51 | D25a.1 | $CH(CH_3)_2$ |
| C-628 | T-52 | D25a.1 | $CH(CH_3)_2$ |
| C-629 | T-53 | D25a.1 | $CH(CH_3)_2$ |
| C-630 | T-54 | D25a.1 | $CH(CH_3)_2$ |
| C-631 | T-55 | D25a.1 | $CH(CH_3)_2$ |
| C-632 | T-56 | D25a.1 | $CH(CH_3)_2$ |
| C-633 | T-57 | D25a.1 | $CH(CH_3)_2$ |
| C-634 | T-58 | D25a.1 | $CH(CH_3)_2$ |
| C-635 | T-59 | D25a.1 | $CH(CH_3)_2$ |
| C-636 | T-60 | D25a.1 | $CH(CH_3)_2$ |
| C-637 | T-61 | D25a.1 | $CH(CH_3)_2$ |

TABLE A-continued

| No. | T | $R^4$ | $R^1$ |
|---|---|---|---|
| C-638 | T-62 | D25a.1 | $CH(CH_3)_2$ |
| C-639 | T-63 | D25a.1 | $CH(CH_3)_2$ |
| C-640 | T-64 | D25a.1 | $CH(CH_3)_2$ |
| C-641 | T-1 | D9b | $CH(CH_3)_2$ |
| C-642 | T-2 | D9b | $CH(CH_3)_2$ |
| C-643 | T-3 | D9b | $CH(CH_3)_2$ |
| C-644 | T-4 | D9b | $CH(CH_3)_2$ |
| C-645 | T-5 | D9b | $CH(CH_3)_2$ |
| C-646 | T-6 | D9b | $CH(CH_3)_2$ |
| C-647 | T-7 | D9b | $CH(CH_3)_2$ |
| C-648 | T-8 | D9b | $CH(CH_3)_2$ |
| C-649 | T-9 | D9b | $CH(CH_3)_2$ |
| C-650 | T-10 | D9b | $CH(CH_3)_2$ |
| C-651 | T-11 | D9b | $CH(CH_3)_2$ |
| C-652 | T-12 | D9b | $CH(CH_3)_2$ |
| C-653 | T-13 | D9b | $CH(CH_3)_2$ |
| C-654 | T-14 | D9b | $CH(CH_3)_2$ |
| C-655 | T-15 | D9b | $CH(CH_3)_2$ |
| C-656 | T-16 | D9b | $CH(CH_3)_2$ |
| C-657 | T-17 | D9b | $CH(CH_3)_2$ |
| C-658 | T-18 | D9b | $CH(CH_3)_2$ |
| C-659 | T-19 | D9b | $CH(CH_3)_2$ |
| C-660 | T-20 | D9b | $CH(CH_3)_2$ |
| C-661 | T-21 | D9b | $CH(CH_3)_2$ |
| C-662 | T-22 | D9b | $CH(CH_3)_2$ |
| C-663 | T-23 | D9b | $CH(CH_3)_2$ |
| C-664 | T-24 | D9b | $CH(CH_3)_2$ |
| C-665 | T-25 | D9b | $CH(CH_3)_2$ |
| C-666 | T-26 | D9b | $CH(CH_3)_2$ |
| C-667 | T-27 | D9b | $CH(CH_3)_2$ |
| C-668 | T-28 | D9b | $CH(CH_3)_2$ |
| C-669 | T-29 | D9b | $CH(CH_3)_2$ |
| C-670 | T-30 | D9b | $CH(CH_3)_2$ |
| C-671 | T-31 | D9b | $CH(CH_3)_2$ |
| C-672 | T-32 | D9b | $CH(CH_3)_2$ |
| C-673 | T-33 | D9b | $CH(CH_3)_2$ |
| C-674 | T-34 | D9b | $CH(CH_3)_2$ |
| C-675 | T-35 | D9b | $CH(CH_3)_2$ |
| C-676 | T-36 | D9b | $CH(CH_3)_2$ |
| C-677 | T-37 | D9b | $CH(CH_3)_2$ |
| C-678 | T-38 | D9b | $CH(CH_3)_2$ |
| C-679 | T-39 | D9b | $CH(CH_3)_2$ |
| C-680 | T-40 | D9b | $CH(CH_3)_2$ |
| C-681 | T-41 | D9b | $CH(CH_3)_2$ |
| C-682 | T-42 | D9b | $CH(CH_3)_2$ |
| C-683 | T-43 | D9b | $CH(CH_3)_2$ |
| C-684 | T-44 | D9b | $CH(CH_3)_2$ |
| C-685 | T-45 | D9b | $CH(CH_3)_2$ |
| C-686 | T-46 | D9b | $CH(CH_3)_2$ |
| C-687 | T-47 | D9b | $CH(CH_3)_2$ |
| C-688 | T-48 | D9b | $CH(CH_3)_2$ |
| C-689 | T-49 | D9b | $CH(CH_3)_2$ |
| C-690 | T-50 | D9b | $CH(CH_3)_2$ |
| C-691 | T-51 | D9b | $CH(CH_3)_2$ |
| C-692 | T-52 | D9b | $CH(CH_3)_2$ |
| C-693 | T-53 | D9b | $CH(CH_3)_2$ |
| C-694 | T-54 | D9b | $CH(CH_3)_2$ |
| C-695 | T-55 | D9b | $CH(CH_3)_2$ |
| C-696 | T-56 | D9b | $CH(CH_3)_2$ |
| C-697 | T-57 | D9b | $CH(CH_3)_2$ |
| C-698 | T-58 | D9b | $CH(CH_3)_2$ |
| C-699 | T-59 | D9b | $CH(CH_3)_2$ |
| C-700 | T-60 | D9b | $CH(CH_3)_2$ |
| C-701 | T-61 | D9b | $CH(CH_3)_2$ |
| C-702 | T-62 | D9b | $CH(CH_3)_2$ |
| C-703 | T-63 | D9b | $CH(CH_3)_2$ |
| C-704 | T-64 | D9b | $CH(CH_3)_2$ |
| C-705 | T-1 | $CH_2$—CN | $CH(CH_3)_2$ |
| C-706 | T-2 | $CH_2$—CN | $CH(CH_3)_2$ |
| C-707 | T-3 | $CH_2$—CN | $CH(CH_3)_2$ |
| C-708 | T-4 | $CH_2$—CN | $CH(CH_3)_2$ |
| C-709 | T-5 | $CH_2$—CN | $CH(CH_3)_2$ |
| C-710 | T-6 | $CH_2$—CN | $CH(CH_3)_2$ |
| C-711 | T-7 | $CH_2$—CN | $CH(CH_3)_2$ |
| C-712 | T-8 | $CH_2$—CN | $CH(CH_3)_2$ |
| C-713 | T-9 | $CH_2$—CN | $CH(CH_3)_2$ |
| C-714 | T-10 | $CH_2$—CN | $CH(CH_3)_2$ |
| C-715 | T-11 | $CH_2$—CN | $CH(CH_3)_2$ |

TABLE A-continued

| No. | T | $R^4$ | $R^1$ |
|---|---|---|---|
| C-716 | T-12 | $CH_2$—CN | $CH(CH_3)_2$ |
| C-717 | T-13 | $CH_2$—CN | $CH(CH_3)_2$ |
| C-718 | T-14 | $CH_2$—CN | $CH(CH_3)_2$ |
| C-719 | T-15 | $CH_2$—CN | $CH(CH_3)_2$ |
| C-720 | T-16 | $CH_2$—CN | $CH(CH_3)_2$ |
| C-721 | T-17 | $CH_2$—CN | $CH(CH_3)_2$ |
| C-722 | T-18 | $CH_2$—CN | $CH(CH_3)_2$ |
| C-723 | T-19 | $CH_2$—CN | $CH(CH_3)_2$ |
| C-724 | T-20 | $CH_2$—CN | $CH(CH_3)_2$ |
| C-725 | T-21 | $CH_2$—CN | $CH(CH_3)_2$ |
| C-726 | T-22 | $CH_2$—CN | $CH(CH_3)_2$ |
| C-727 | T-23 | $CH_2$—CN | $CH(CH_3)_2$ |
| C-728 | T-24 | $CH_2$—CN | $CH(CH_3)_2$ |
| C-729 | T-25 | $CH_2$—CN | $CH(CH_3)_2$ |
| C-730 | T-26 | $CH_2$—CN | $CH(CH_3)_2$ |
| C-731 | T-27 | $CH_2$—CN | $CH(CH_3)_2$ |
| C-732 | T-28 | $CH_2$—CN | $CH(CH_3)_2$ |
| C-733 | T-29 | $CH_2$—CN | $CH(CH_3)_2$ |
| C-734 | T-30 | $CH_2$—CN | $CH(CH_3)_2$ |
| C-735 | T-31 | $CH_2$—CN | $CH(CH_3)_2$ |
| C-736 | T-32 | $CH_2$—CN | $CH(CH_3)_2$ |
| C-737 | T-33 | $CH_2$—CN | $CH(CH_3)_2$ |
| C-738 | T-34 | $CH_2$—CN | $CH(CH_3)_2$ |
| C-739 | T-35 | $CH_2$—CN | $CH(CH_3)_2$ |
| C-740 | T-36 | $CH_2$—CN | $CH(CH_3)_2$ |
| C-741 | T-37 | $CH_2$—CN | $CH(CH_3)_2$ |
| C-742 | T-38 | $CH_2$—CN | $CH(CH_3)_2$ |
| C-743 | T-39 | $CH_2$—CN | $CH(CH_3)_2$ |
| C-744 | T-40 | $CH_2$—CN | $CH(CH_3)_2$ |
| C-745 | T-41 | $CH_2$—CN | $CH(CH_3)_2$ |
| C-746 | T-42 | $CH_2$—CN | $CH(CH_3)_2$ |
| C-747 | T-43 | $CH_2$—CN | $CH(CH_3)_2$ |
| C-748 | T-44 | $CH_2$—CN | $CH(CH_3)_2$ |
| C-749 | T-45 | $CH_2$—CN | $CH(CH_3)_2$ |
| C-750 | T-46 | $CH_2$—CN | $CH(CH_3)_2$ |
| C-751 | T-47 | $CH_2$—CN | $CH(CH_3)_2$ |
| C-752 | T-48 | $CH_2$—CN | $CH(CH_3)_2$ |
| C-753 | T-49 | $CH_2$—CN | $CH(CH_3)_2$ |
| C-754 | T-50 | $CH_2$—CN | $CH(CH_3)_2$ |
| C-755 | T-51 | $CH_2$—CN | $CH(CH_3)_2$ |
| C-756 | T-52 | $CH_2$—CN | $CH(CH_3)_2$ |
| C-757 | T-53 | $CH_2$—CN | $CH(CH_3)_2$ |
| C-758 | T-54 | $CH_2$—CN | $CH(CH_3)_2$ |
| C-759 | T-55 | $CH_2$—CN | $CH(CH_3)_2$ |
| C-760 | T-56 | $CH_2$—CN | $CH(CH_3)_2$ |
| C-761 | T-57 | $CH_2$—CN | $CH(CH_3)_2$ |
| C-762 | T-58 | $CH_2$—CN | $CH(CH_3)_2$ |
| C-763 | T-59 | $CH_2$—CN | $CH(CH_3)_2$ |
| C-764 | T-60 | $CH_2$—CN | $CH(CH_3)_2$ |
| C-765 | T-61 | $CH_2$—CN | $CH(CH_3)_2$ |
| C-766 | T-62 | $CH_2$—CN | $CH(CH_3)_2$ |
| C-767 | T-63 | $CH_2$—CN | $CH(CH_3)_2$ |
| C-768 | T-64 | $CH_2$—CN | $CH(CH_3)_2$ |
| C-769 | T-1 | D2b.1 | $CH_2$—$C_6H_5$ |
| C-770 | T-2 | D2b.1 | $CH_2$—$C_6H_5$ |
| C-771 | T-3 | D2b.1 | $CH_2$—$C_6H_5$ |
| C-772 | T-4 | D2b.1 | $CH_2$—$C_6H_5$ |
| C-773 | T-5 | D2b.1 | $CH_2$—$C_6H_5$ |
| C-774 | T-6 | D2b.1 | $CH_2$—$C_6H_5$ |
| C-775 | T-7 | D2b.1 | $CH_2$—$C_6H_5$ |
| C-776 | T-8 | D2b.1 | $CH_2$—$C_6H_5$ |
| C-777 | T-9 | D2b.1 | $CH_2$—$C_6H_5$ |
| C-778 | T-10 | D2b.1 | $CH_2$—$C_6H_5$ |
| C-779 | T-11 | D2b.1 | $CH_2$—$C_6H_5$ |
| C-780 | T-12 | D2b.1 | $CH_2$—$C_6H_5$ |
| C-781 | T-13 | D2b.1 | $CH_2$—$C_6H_5$ |
| C-782 | T-14 | D2b.1 | $CH_2$—$C_6H_5$ |
| C-783 | T-15 | D2b.1 | $CH_2$—$C_6H_5$ |
| C-784 | T-16 | D2b.1 | $CH_2$—$C_6H_5$ |
| C-785 | T-17 | D2b.1 | $CH_2$—$C_6H_5$ |
| C-786 | T-18 | D2b.1 | $CH_2$—$C_6H_5$ |
| C-787 | T-19 | D2b.1 | $CH_2$—$C_6H_5$ |
| C-788 | T-20 | D2b.1 | $CH_2$—$C_6H_5$ |
| C-789 | T-21 | D2b.1 | $CH_2$—$C_6H_5$ |
| C-790 | T-22 | D2b.1 | $CH_2$—$C_6H_5$ |
| C-791 | T-23 | D2b.1 | $CH_2$—$C_6H_5$ |
| C-792 | T-24 | D2b.1 | $CH_2$—$C_6H_5$ |
| C-793 | T-25 | D2b.1 | $CH_2$—$C_6H_5$ |

TABLE A-continued

| No. | T | $R^4$ | $R^1$ |
|---|---|---|---|
| C-794 | T-26 | D2b.1 | $CH_2$—$C_6H_5$ |
| C-795 | T-27 | D2b.1 | $CH_2$—$C_6H_5$ |
| C-796 | T-28 | D2b.1 | $CH_2$—$C_6H_5$ |
| C-797 | T-29 | D2b.1 | $CH_2$—$C_6H_5$ |
| C-798 | T-30 | D2b.1 | $CH_2$—$C_6H_5$ |
| C-799 | T-31 | D2b.1 | $CH_2$—$C_6H_5$ |
| C-800 | T-32 | D2b.1 | $CH_2$—$C_6H_5$ |
| C-801 | T-33 | D2b.1 | $CH_2$—$C_6H_5$ |
| C-802 | T-34 | D2b.1 | $CH_2$—$C_6H_5$ |
| C-803 | T-35 | D2b.1 | $CH_2$—$C_6H_5$ |
| C-804 | T-36 | D2b.1 | $CH_2$—$C_6H_5$ |
| C-805 | T-37 | D2b.1 | $CH_2$—$C_6H_5$ |
| C-806 | T-38 | D2b.1 | $CH_2$—$C_6H_5$ |
| C-807 | T-39 | D2b.1 | $CH_2$—$C_6H_5$ |
| C-808 | T-40 | D2b.1 | $CH_2$—$C_6H_5$ |
| C-809 | T-41 | D2b.1 | $CH_2$—$C_6H_5$ |
| C-810 | T-42 | D2b.1 | $CH_2$—$C_6H_5$ |
| C-811 | T-43 | D2b.1 | $CH_2$—$C_6H_5$ |
| C-812 | T-44 | D2b.1 | $CH_2$—$C_6H_5$ |
| C-813 | T-45 | D2b.1 | $CH_2$—$C_6H_5$ |
| C-814 | T-46 | D2b.1 | $CH_2$—$C_6H_5$ |
| C-815 | T-47 | D2b.1 | $CH_2$—$C_6H_5$ |
| C-816 | T-48 | D2b.1 | $CH_2$—$C_6H_5$ |
| C-817 | T-49 | D2b.1 | $CH_2$—$C_6H_5$ |
| C-818 | T-50 | D2b.1 | $CH_2$—$C_6H_5$ |
| C-819 | T-51 | D2b.1 | $CH_2$—$C_6H_5$ |
| C-820 | T-52 | D2b.1 | $CH_2$—$C_6H_5$ |
| C-821 | T-53 | D2b.1 | $CH_2$—$C_6H_5$ |
| C-822 | T-54 | D2b.1 | $CH_2$—$C_6H_5$ |
| C-823 | T-55 | D2b.1 | $CH_2$—$C_6H_5$ |
| C-824 | T-56 | D2b.1 | $CH_2$—$C_6H_5$ |
| C-825 | T-57 | D2b.1 | $CH_2$—$C_6H_5$ |
| C-826 | T-58 | D2b.1 | $CH_2$—$C_6H_5$ |
| C-827 | T-59 | D2b.1 | $CH_2$—$C_6H_5$ |
| C-828 | T-60 | D2b.1 | $CH_2$—$C_6H_5$ |
| C-829 | T-61 | D2b.1 | $CH_2$—$C_6H_5$ |
| C-830 | T-62 | D2b.1 | $CH_2$—$C_6H_5$ |
| C-831 | T-63 | D2b.1 | $CH_2$—$C_6H_5$ |
| C-832 | T-64 | D2b.1 | $CH_2$—$C_6H_5$ |
| C-833 | T-1 | D25a.1 | $CH_2$—$C_6H_5$ |
| C-834 | T-2 | D25a.1 | $CH_2$—$C_6H_5$ |
| C-835 | T-3 | D25a.1 | $CH_2$—$C_6H_5$ |
| C-836 | T-4 | D25a.1 | $CH_2$—$C_6H_5$ |
| C-837 | T-5 | D25a.1 | $CH_2$—$C_6H_5$ |
| C-838 | T-6 | D25a.1 | $CH_2$—$C_6H_5$ |
| C-839 | T-7 | D25a.1 | $CH_2$—$C_6H_5$ |
| C-840 | T-8 | D25a.1 | $CH_2$—$C_6H_5$ |
| C-841 | T-9 | D25a.1 | $CH_2$—$C_6H_5$ |
| C-842 | T-10 | D25a.1 | $CH_2$—$C_6H_5$ |
| C-843 | T-11 | D25a.1 | $CH_2$—$C_6H_5$ |
| C-844 | T-12 | D25a.1 | $CH_2$—$C_6H_5$ |
| C-845 | T-13 | D25a.1 | $CH_2$—$C_6H_5$ |
| C-846 | T-14 | D25a.1 | $CH_2$—$C_6H_5$ |
| C-847 | T-15 | D25a.1 | $CH_2$—$C_6H_5$ |
| C-848 | T-16 | D25a.1 | $CH_2$—$C_6H_5$ |
| C-849 | T-17 | D25a.1 | $CH_2$—$C_6H_5$ |
| C-850 | T-18 | D25a.1 | $CH_2$—$C_6H_5$ |
| C-851 | T-19 | D25a.1 | $CH_2$—$C_6H_5$ |
| C-852 | T-20 | D25a.1 | $CH_2$—$C_6H_5$ |
| C-853 | T-21 | D25a.1 | $CH_2$—$C_6H_5$ |
| C-854 | T-22 | D25a.1 | $CH_2$—$C_6H_5$ |
| C-855 | T-23 | D25a.1 | $CH_2$—$C_6H_5$ |
| C-856 | T-24 | D25a.1 | $CH_2$—$C_6H_5$ |
| C-857 | T-25 | D25a.1 | $CH_2$—$C_6H_5$ |
| C-858 | T-26 | D25a.1 | $CH_2$—$C_6H_5$ |
| C-859 | T-27 | D25a.1 | $CH_2$—$C_6H_5$ |
| C-860 | T-28 | D25a.1 | $CH_2$—$C_6H_5$ |
| C-861 | T-29 | D25a.1 | $CH_2$—$C_6H_5$ |
| C-862 | T-30 | D25a.1 | $CH_2$—$C_6H_5$ |
| C-863 | T-31 | D25a.1 | $CH_2$—$C_6H_5$ |
| C-864 | T-32 | D25a.1 | $CH_2$—$C_6H_5$ |
| C-865 | T-33 | D25a.1 | $CH_2$—$C_6H_5$ |
| C-866 | T-34 | D25a.1 | $CH_2$—$C_6H_5$ |
| C-867 | T-35 | D25a.1 | $CH_2$—$C_6H_5$ |
| C-868 | T-36 | D25a.1 | $CH_2$—$C_6H_5$ |
| C-869 | T-37 | D25a.1 | $CH_2$—$C_6H_5$ |
| C-870 | T-38 | D25a.1 | $CH_2$—$C_6H_5$ |
| C-871 | T-39 | D25a.1 | $CH_2$—$C_6H_5$ |

TABLE A-continued

| No. | T | $R^4$ | $R^1$ |
|---|---|---|---|
| C-872 | T-40 | D25a.1 | $CH_2—C_6H_5$ |
| C-873 | T-41 | D25a.1 | $CH_2—C_6H_5$ |
| C-874 | T-42 | D25a.1 | $CH_2—C_6H_5$ |
| C-875 | T-43 | D25a.1 | $CH_2—C_6H_5$ |
| C-876 | T-44 | D25a.1 | $CH_2—C_6H_5$ |
| C-877 | T-45 | D25a.1 | $CH_2—C_6H_5$ |
| C-878 | T-46 | D25a.1 | $CH_2—C_6H_5$ |
| C-879 | T-47 | D25a.1 | $CH_2—C_6H_5$ |
| C-880 | T-48 | D25a.1 | $CH_2—C_6H_5$ |
| C-881 | T-49 | D25a.1 | $CH_2—C_6H_5$ |
| C-882 | T-50 | D25a.1 | $CH_2—C_6H_5$ |
| C-883 | T-51 | D25a.1 | $CH_2—C_6H_5$ |
| C-884 | T-52 | D25a.1 | $CH_2—C_6H_5$ |
| C-885 | T-53 | D25a.1 | $CH_2—C_6H_5$ |
| C-886 | T-54 | D25a.1 | $CH_2—C_6H_5$ |
| C-887 | T-55 | D25a.1 | $CH_2—C_6H_5$ |
| C-888 | T-56 | D25a.1 | $CH_2—C_6H_5$ |
| C-889 | T-57 | D25a.1 | $CH_2—C_6H_5$ |
| C-890 | T-58 | D25a.1 | $CH_2—C_6H_5$ |
| C-891 | T-59 | D25a.1 | $CH_2—C_6H_5$ |
| C-892 | T-60 | D25a.1 | $CH_2—C_6H_5$ |
| C-893 | T-61 | D25a.1 | $CH_2—C_6H_5$ |
| C-894 | T-62 | D25a.1 | $CH_2—C_6H_5$ |
| C-895 | T-63 | D25a.1 | $CH_2—C_6H_5$ |
| C-896 | T-64 | D25a.1 | $CH_2—C_6H_5$ |
| C-897 | T-1 | D9b | $CH_2—C_6H_5$ |
| C-898 | T-2 | D9b | $CH_2—C_6H_5$ |
| C-899 | T-3 | D9b | $CH_2—C_6H_5$ |
| C-900 | T-4 | D9b | $CH_2—C_6H_5$ |
| C-901 | T-5 | D9b | $CH_2—C_6H_5$ |
| C-902 | T-6 | D9b | $CH_2—C_6H_5$ |
| C-903 | T-7 | D9b | $CH_2—C_6H_5$ |
| C-904 | T-8 | D9b | $CH_2—C_6H_5$ |
| C-905 | T-9 | D9b | $CH_2—C_6H_5$ |
| C-906 | T-10 | D9b | $CH_2—C_6H_5$ |
| C-907 | T-11 | D9b | $CH_2—C_6H_5$ |
| C-908 | T-12 | D9b | $CH_2—C_6H_5$ |
| C-909 | T-13 | D9b | $CH_2—C_6H_5$ |
| C-910 | T-14 | D9b | $CH_2—C_6H_5$ |
| C-911 | T-15 | D9b | $CH_2—C_6H_5$ |
| C-912 | T-16 | D9b | $CH_2—C_6H_5$ |
| C-913 | T-17 | D9b | $CH_2—C_6H_5$ |
| C-914 | T-18 | D9b | $CH_2—C_6H_5$ |
| C-915 | T-19 | D9b | $CH_2—C_6H_5$ |
| C-916 | T-20 | D9b | $CH_2—C_6H_5$ |
| C-917 | T-21 | D9b | $CH_2—C_6H_5$ |
| C-918 | T-22 | D9b | $CH_2—C_6H_5$ |
| C-919 | T-23 | D9b | $CH_2—C_6H_5$ |
| C-920 | T-24 | D9b | $CH_2—C_6H_5$ |
| C-921 | T-25 | D9b | $CH_2—C_6H_5$ |
| C-922 | T-26 | D9b | $CH_2—C_6H_5$ |
| C-923 | T-27 | D9b | $CH_2—C_6H_5$ |
| C-924 | T-28 | D9b | $CH_2—C_6H_5$ |
| C-925 | T-29 | D9b | $CH_2—C_6H_5$ |
| C-926 | T-30 | D9b | $CH_2—C_6H_5$ |
| C-927 | T-31 | D9b | $CH_2—C_6H_5$ |
| C-928 | T-32 | D9b | $CH_2—C_6H_5$ |
| C-929 | T-33 | D9b | $CH_2—C_6H_5$ |
| C-930 | T-34 | D9b | $CH_2—C_6H_5$ |
| C-931 | T-35 | D9b | $CH_2—C_6H_5$ |
| C-932 | T-36 | D9b | $CH_2—C_6H_5$ |
| C-933 | T-37 | D9b | $CH_2—C_6H_5$ |
| C-934 | T-38 | D9b | $CH_2—C_6H_5$ |
| C-935 | T-39 | D9b | $CH_2—C_6H_5$ |
| C-936 | T-40 | D9b | $CH_2—C_6H_5$ |
| C-937 | T-41 | D9b | $CH_2—C_6H_5$ |
| C-938 | T-42 | D9b | $CH_2—C_6H_5$ |
| C-939 | T-43 | D9b | $CH_2—C_6H_5$ |
| C-940 | T-44 | D9b | $CH_2—C_6H_5$ |
| C-941 | T-45 | D9b | $CH_2—C_6H_5$ |
| C-942 | T-46 | D9b | $CH_2—C_6H_5$ |
| C-943 | T-47 | D9b | $CH_2—C_6H_5$ |
| C-944 | T-48 | D9b | $CH_2—C_6H_5$ |
| C-945 | T-49 | D9b | $CH_2—C_6H_5$ |
| C-946 | T-50 | D9b | $CH_2—C_6H_5$ |
| C-947 | T-51 | D9b | $CH_2—C_6H_5$ |
| C-948 | T-52 | D9b | $CH_2—C_6H_5$ |
| C-949 | T-53 | D9b | $CH_2—C_6H_5$ |

TABLE A-continued

| No. | T | $R^4$ | $R^1$ |
|---|---|---|---|
| C-950 | T-54 | D9b | $CH_2—C_6H_5$ |
| C-951 | T-55 | D9b | $CH_2—C_6H_5$ |
| C-952 | T-56 | D9b | $CH_2—C_6H_5$ |
| C-953 | T-57 | D9b | $CH_2—C_6H_5$ |
| C-954 | T-58 | D9b | $CH_2—C_6H_5$ |
| C-955 | T-59 | D9b | $CH_2—C_6H_5$ |
| C-956 | T-60 | D9b | $CH_2—C_6H_5$ |
| C-957 | T-61 | D9b | $CH_2—C_6H_5$ |
| C-958 | T-62 | D9b | $CH_2—C_6H_5$ |
| C-959 | T-63 | D9b | $CH_2—C_6H_5$ |
| C-960 | T-64 | D9b | $CH_2—C_6H_5$ |
| C-961 | T-1 | $CH_2—CN$ | $CH_2—C_6H_5$ |
| C-962 | T-2 | $CH_2—CN$ | $CH_2—C_6H_5$ |
| C-963 | T-3 | $CH_2—CN$ | $CH_2—C_6H_5$ |
| C-964 | T-4 | $CH_2—CN$ | $CH_2—C_6H_5$ |
| C-965 | T-5 | $CH_2—CN$ | $CH_2—C_6H_5$ |
| C-966 | T-6 | $CH_2—CN$ | $CH_2—C_6H_5$ |
| C-967 | T-7 | $CH_2—CN$ | $CH_2—C_6H_5$ |
| C-968 | T-8 | $CH_2—CN$ | $CH_2—C_6H_5$ |
| C-969 | T-9 | $CH_2—CN$ | $CH_2—C_6H_5$ |
| C-970 | T-10 | $CH_2—CN$ | $CH_2—C_6H_5$ |
| C-971 | T-11 | $CH_2—CN$ | $CH_2—C_6H_5$ |
| C-972 | T-12 | $CH_2—CN$ | $CH_2—C_6H_5$ |
| C-973 | T-13 | $CH_2—CN$ | $CH_2—C_6H_5$ |
| C-974 | T-14 | $CH_2—CN$ | $CH_2—C_6H_5$ |
| C-975 | T-15 | $CH_2—CN$ | $CH_2—C_6H_5$ |
| C-976 | T-16 | $CH_2—CN$ | $CH_2—C_6H_5$ |
| C-977 | T-17 | $CH_2—CN$ | $CH_2—C_6H_5$ |
| C-978 | T-18 | $CH_2—CN$ | $CH_2—C_6H_5$ |
| C-979 | T-19 | $CH_2—CN$ | $CH_2—C_6H_5$ |
| C-980 | T-20 | $CH_2—CN$ | $CH_2—C_6H_5$ |
| C-981 | T-21 | $CH_2—CN$ | $CH_2—C_6H_5$ |
| C-982 | T-22 | $CH_2—CN$ | $CH_2—C_6H_5$ |
| C-983 | T-23 | $CH_2—CN$ | $CH_2—C_6H_5$ |
| C-984 | T-24 | $CH_2—CN$ | $CH_2—C_6H_5$ |
| C-985 | T-25 | $CH_2—CN$ | $CH_2—C_6H_5$ |
| C-986 | T-26 | $CH_2—CN$ | $CH_2—C_6H_5$ |
| C-987 | T-27 | $CH_2—CN$ | $CH_2—C_6H_5$ |
| C-988 | T-28 | $CH_2—CN$ | $CH_2—C_6H_5$ |
| C-989 | T-29 | $CH_2—CN$ | $CH_2—C_6H_5$ |
| C-990 | T-30 | $CH_2—CN$ | $CH_2—C_6H_5$ |
| C-991 | T-31 | $CH_2—CN$ | $CH_2—C_6H_5$ |
| C-992 | T-32 | $CH_2—CN$ | $CH_2—C_6H_5$ |
| C-993 | T-33 | $CH_2—CN$ | $CH_2—C_6H_5$ |
| C-994 | T-34 | $CH_2—CN$ | $CH_2—C_6H_5$ |
| C-995 | T-35 | $CH_2—CN$ | $CH_2—C_6H_5$ |
| C-996 | T-36 | $CH_2—CN$ | $CH_2—C_6H_5$ |
| C-997 | T-37 | $CH_2—CN$ | $CH_2—C_6H_5$ |
| C-998 | T-38 | $CH_2—CN$ | $CH_2—C_6H_5$ |
| C-999 | T-39 | $CH_2—CN$ | $CH_2—C_6H_5$ |
| C-1000 | T-40 | $CH_2—CN$ | $CH_2—C_6H_5$ |
| C-1001 | T-41 | $CH_2—CN$ | $CH_2—C_6H_5$ |
| C-1002 | T-42 | $CH_2—CN$ | $CH_2—C_6H_5$ |
| C-1003 | T-43 | $CH_2—CN$ | $CH_2—C_6H_5$ |
| C-1004 | T-44 | $CH_2—CN$ | $CH_2—C_6H_5$ |
| C-1005 | T-45 | $CH_2—CN$ | $CH_2—C_6H_5$ |
| C-1006 | T-46 | $CH_2—CN$ | $CH_2—C_6H_5$ |
| C-1007 | T-47 | $CH_2—CN$ | $CH_2—C_6H_5$ |
| C-1008 | T-48 | $CH_2—CN$ | $CH_2—C_6H_5$ |
| C-1009 | T-49 | $CH_2—CN$ | $CH_2—C_6H_5$ |
| C-1010 | T-50 | $CH_2—CN$ | $CH_2—C_6H_5$ |
| C-1011 | T-51 | $CH_2—CN$ | $CH_2—C_6H_5$ |
| C-1012 | T-52 | $CH_2—CN$ | $CH_2—C_6H_5$ |
| C-1013 | T-53 | $CH_2—CN$ | $CH_2—C_6H_5$ |
| C-1014 | T-54 | $CH_2—CN$ | $CH_2—C_6H_5$ |
| C-1015 | T-55 | $CH_2—CN$ | $CH_2—C_6H_5$ |
| C-1016 | T-56 | $CH_2—CN$ | $CH_2—C_6H_5$ |
| C-1017 | T-57 | $CH_2—CN$ | $CH_2—C_6H_5$ |
| C-1018 | T-58 | $CH_2—CN$ | $CH_2—C_6H_5$ |
| C-1019 | T-59 | $CH_2—CN$ | $CH_2—C_6H_5$ |
| C-1020 | T-60 | $CH_2—CN$ | $CH_2—C_6H_5$ |
| C-1021 | T-61 | $CH_2—CN$ | $CH_2—C_6H_5$ |
| C-1022 | T-62 | $CH_2—CN$ | $CH_2—C_6H_5$ |
| C-1023 | T-63 | $CH_2—CN$ | $CH_2—C_6H_5$ |
| C-1024 | T-64 | $CH_2—CN$ | $CH_2—C_6H_5$ |
| C-1025 | T-1 | D2b.1 | $CH_2CH{=}CH_2$ |
| C-1026 | T-2 | D2b.1 | $CH_2CH{=}CH_2$ |
| C-1027 | T-3 | D2b.1 | $CH_2CH{=}CH_2$ |

TABLE A-continued

| No. | T | $R^4$ | $R^1$ |
|---|---|---|---|
| C-1028 | T-4 | D2b.1 | $CH_2CH{=}CH_2$ |
| C-1029 | T-5 | D2b.1 | $CH_2CH{=}CH_2$ |
| C-1030 | T-6 | D2b.1 | $CH_2CH{=}CH_2$ |
| C-1031 | T-7 | D2b.1 | $CH_2CH{=}CH_2$ |
| C-1032 | T-8 | D2b.1 | $CH_2CH{=}CH_2$ |
| C-1033 | T-9 | D2b.1 | $CH_2CH{=}CH_2$ |
| C-1034 | T-10 | D2b.1 | $CH_2CH{=}CH_2$ |
| C-1035 | T-11 | D2b.1 | $CH_2CH{=}CH_2$ |
| C-1036 | T-12 | D2b.1 | $CH_2CH{=}CH_2$ |
| C-1037 | T-13 | D2b.1 | $CH_2CH{=}CH_2$ |
| C-1038 | T-14 | D2b.1 | $CH_2CH{=}CH_2$ |
| C-1039 | T-15 | D2b.1 | $CH_2CH{=}CH_2$ |
| C-1040 | T-16 | D2b.1 | $CH_2CH{=}CH_2$ |
| C-1041 | T-17 | D2b.1 | $CH_2CH{=}CH_2$ |
| C-1042 | T-18 | D2b.1 | $CH_2CH{=}CH_2$ |
| C-1043 | T-19 | D2b.1 | $CH_2CH{=}CH_2$ |
| C-1044 | T-20 | D2b.1 | $CH_2CH{=}CH_2$ |
| C-1045 | T-21 | D2b.1 | $CH_2CH{=}CH_2$ |
| C-1046 | T-22 | D2b.1 | $CH_2CH{=}CH_2$ |
| C-1047 | T-23 | D2b.1 | $CH_2CH{=}CH_2$ |
| C-1048 | T-24 | D2b.1 | $CH_2CH{=}CH_2$ |
| C-1049 | T-25 | D2b.1 | $CH_2CH{=}CH_2$ |
| C-1050 | T-26 | D2b.1 | $CH_2CH{=}CH_2$ |
| C-1051 | T-27 | D2b.1 | $CH_2CH{=}CH_2$ |
| C-1052 | T-28 | D2b.1 | $CH_2CH{=}CH_2$ |
| C-1053 | T-29 | D2b.1 | $CH_2CH{=}CH_2$ |
| C-1054 | T-30 | D2b.1 | $CH_2CH{=}CH_2$ |
| C-1055 | T-31 | D2b.1 | $CH_2CH{=}CH_2$ |
| C-1056 | T-32 | D2b.1 | $CH_2CH{=}CH_2$ |
| C-1057 | T-33 | D2b.1 | $CH_2CH{=}CH_2$ |
| C-1058 | T-34 | D2b.1 | $CH_2CH{=}CH_2$ |
| C-1059 | T-35 | D2b.1 | $CH_2CH{=}CH_2$ |
| C-1060 | T-36 | D2b.1 | $CH_2CH{=}CH_2$ |
| C-1061 | T-37 | D2b.1 | $CH_2CH{=}CH_2$ |
| C-1062 | T-38 | D2b.1 | $CH_2CH{=}CH_2$ |
| C-1063 | T-39 | D2b.1 | $CH_2CH{=}CH_2$ |
| C-1064 | T-40 | D2b.1 | $CH_2CH{=}CH_2$ |
| C-1065 | T-41 | D2b.1 | $CH_2CH{=}CH_2$ |
| C-1066 | T-42 | D2b.1 | $CH_2CH{=}CH_2$ |
| C-1067 | T-43 | D2b.1 | $CH_2CH{=}CH_2$ |
| C-1068 | T-44 | D2b.1 | $CH_2CH{=}CH_2$ |
| C-1069 | T-45 | D2b.1 | $CH_2CH{=}CH_2$ |
| C-1070 | T-46 | D2b.1 | $CH_2CH{=}CH_2$ |
| C-1071 | T-47 | D2b.1 | $CH_2CH{=}CH_2$ |
| C-1072 | T-48 | D2b.1 | $CH_2CH{=}CH_2$ |
| C-1073 | T-49 | D2b.1 | $CH_2CH{=}CH_2$ |
| C-1074 | T-50 | D2b.1 | $CH_2CH{=}CH_2$ |
| C-1075 | T-51 | D2b.1 | $CH_2CH{=}CH_2$ |
| C-1076 | T-52 | D2b.1 | $CH_2CH{=}CH_2$ |
| C-1077 | T-53 | D2b.1 | $CH_2CH{=}CH_2$ |
| C-1078 | T-54 | D2b.1 | $CH_2CH{=}CH_2$ |
| C-1079 | T-55 | D2b.1 | $CH_2CH{=}CH_2$ |
| C-1080 | T-56 | D2b.1 | $CH_2CH{=}CH_2$ |
| C-1081 | T-57 | D2b.1 | $CH_2CH{=}CH_2$ |
| C-1082 | T-58 | D2b.1 | $CH_2CH{=}CH_2$ |
| C-1083 | T-59 | D2b.1 | $CH_2CH{=}CH_2$ |
| C-1084 | T-60 | D2b.1 | $CH_2CH{=}CH_2$ |
| C-1085 | T-61 | D2b.1 | $CH_2CH{=}CH_2$ |
| C-1086 | T-62 | D2b.1 | $CH_2CH{=}CH_2$ |
| C-1087 | T-63 | D2b.1 | $CH_2CH{=}CH_2$ |
| C-1088 | T-64 | D2b.1 | $CH_2CH{=}CH_2$ |
| C-1089 | T-1 | D25a.1 | $CH_2CH{=}CH_2$ |
| C-1090 | T-2 | D25a.1 | $CH_2CH{=}CH_2$ |
| C-1091 | T-3 | D25a.1 | $CH_2CH{=}CH_2$ |
| C-1092 | T-4 | D25a.1 | $CH_2CH{=}CH_2$ |
| C-1093 | T-5 | D25a.1 | $CH_2CH{=}CH_2$ |
| C-1094 | T-6 | D25a.1 | $CH_2CH{=}CH_2$ |
| C-1095 | T-7 | D25a.1 | $CH_2CH{=}CH_2$ |
| C-1096 | T-8 | D25a.1 | $CH_2CH{=}CH_2$ |
| C-1097 | T-9 | D25a.1 | $CH_2CH{=}CH_2$ |
| C-1098 | T-10 | D25a.1 | $CH_2CH{=}CH_2$ |
| C-1099 | T-11 | D25a.1 | $CH_2CH{=}CH_2$ |
| C-1100 | T-12 | D25a.1 | $CH_2CH{=}CH_2$ |
| C-1101 | T-13 | D25a.1 | $CH_2CH{=}CH_2$ |
| C-1102 | T-14 | D25a.1 | $CH_2CH{=}CH_2$ |
| C-1103 | T-15 | D25a.1 | $CH_2CH{=}CH_2$ |
| C-1104 | T-16 | D25a.1 | $CH_2CH{=}CH_2$ |
| C-1105 | T-17 | D25a.1 | $CH_2CH{=}CH_2$ |

TABLE A-continued

| No. | T | $R^4$ | $R^1$ |
|---|---|---|---|
| C-1106 | T-18 | D25a.1 | $CH_2CH{=}CH_2$ |
| C-1107 | T-19 | D25a.1 | $CH_2CH{=}CH_2$ |
| C-1108 | T-20 | D25a.1 | $CH_2CH{=}CH_2$ |
| C-1109 | T-21 | D25a.1 | $CH_2CH{=}CH_2$ |
| C-1110 | T-22 | D25a.1 | $CH_2CH{=}CH_2$ |
| C-1111 | T-23 | D25a.1 | $CH_2CH{=}CH_2$ |
| C-1112 | T-24 | D25a.1 | $CH_2CH{=}CH_2$ |
| C-1113 | T-25 | D25a.1 | $CH_2CH{=}CH_2$ |
| C-1114 | T-26 | D25a.1 | $CH_2CH{=}CH_2$ |
| C-1115 | T-27 | D25a.1 | $CH_2CH{=}CH_2$ |
| C-1116 | T-28 | D25a.1 | $CH_2CH{=}CH_2$ |
| C-1117 | T-29 | D25a.1 | $CH_2CH{=}CH_2$ |
| C-1118 | T-30 | D25a.1 | $CH_2CH{=}CH_2$ |
| C-1119 | T-31 | D25a.1 | $CH_2CH{=}CH_2$ |
| C-1120 | T-32 | D25a.1 | $CH_2CH{=}CH_2$ |
| C-1121 | T-33 | D25a.1 | $CH_2CH{=}CH_2$ |
| C-1122 | T-34 | D25a.1 | $CH_2CH{=}CH_2$ |
| C-1123 | T-35 | D25a.1 | $CH_2CH{=}CH_2$ |
| C-1124 | T-36 | D25a.1 | $CH_2CH{=}CH_2$ |
| C-1125 | T-37 | D25a.1 | $CH_2CH{=}CH_2$ |
| C-1126 | T-38 | D25a.1 | $CH_2CH{=}CH_2$ |
| C-1127 | T-39 | D25a.1 | $CH_2CH{=}CH_2$ |
| C-1128 | T-40 | D25a.1 | $CH_2CH{=}CH_2$ |
| C-1129 | T-41 | D25a.1 | $CH_2CH{=}CH_2$ |
| C-1130 | T-42 | D25a.1 | $CH_2CH{=}CH_2$ |
| C-1131 | T-43 | D25a.1 | $CH_2CH{=}CH_2$ |
| C-1132 | T-44 | D25a.1 | $CH_2CH{=}CH_2$ |
| C-1133 | T-45 | D25a.1 | $CH_2CH{=}CH_2$ |
| C-1134 | T-46 | D25a.1 | $CH_2CH{=}CH_2$ |
| C-1135 | T-47 | D25a.1 | $CH_2CH{=}CH_2$ |
| C-1136 | T-48 | D25a.1 | $CH_2CH{=}CH_2$ |
| C-1137 | T-49 | D25a.1 | $CH_2CH{=}CH_2$ |
| C-1138 | T-50 | D25a.1 | $CH_2CH{=}CH_2$ |
| C-1139 | T-51 | D25a.1 | $CH_2CH{=}CH_2$ |
| C-1140 | T-52 | D25a.1 | $CH_2CH{=}CH_2$ |
| C-1141 | T-53 | D25a.1 | $CH_2CH{=}CH_2$ |
| C-1142 | T-54 | D25a.1 | $CH_2CH{=}CH_2$ |
| C-1143 | T-55 | D25a.1 | $CH_2CH{=}CH_2$ |
| C-1144 | T-56 | D25a.1 | $CH_2CH{=}CH_2$ |
| C-1145 | T-57 | D25a.1 | $CH_2CH{=}CH_2$ |
| C-1146 | T-58 | D25a.1 | $CH_2CH{=}CH_2$ |
| C-1147 | T-59 | D25a.1 | $CH_2CH{=}CH_2$ |
| C-1148 | T-60 | D25a.1 | $CH_2CH{=}CH_2$ |
| C-1149 | T-61 | D25a.1 | $CH_2CH{=}CH_2$ |
| C-1150 | T-62 | D25a.1 | $CH_2CH{=}CH_2$ |
| C-1151 | T-63 | D25a.1 | $CH_2CH{=}CH_2$ |
| C-1152 | T-64 | D25a.1 | $CH_2CH{=}CH_2$ |
| C-1153 | T-1 | D9b | $CH_2CH{=}CH_2$ |
| C-1154 | T-2 | D9b | $CH_2CH{=}CH_2$ |
| C-1155 | T-3 | D9b | $CH_2CH{=}CH_2$ |
| C-1156 | T-4 | D9b | $CH_2CH{=}CH_2$ |
| C-1157 | T-5 | D9b | $CH_2CH{=}CH_2$ |
| C-1158 | T-6 | D9b | $CH_2CH{=}CH_2$ |
| C-1159 | T-7 | D9b | $CH_2CH{=}CH_2$ |
| C-1160 | T-8 | D9b | $CH_2CH{=}CH_2$ |
| C-1161 | T-9 | D9b | $CH_2CH{=}CH_2$ |
| C-1162 | T-10 | D9b | $CH_2CH{=}CH_2$ |
| C-1163 | T-11 | D9b | $CH_2CH{=}CH_2$ |
| C-1164 | T-12 | D9b | $CH_2CH{=}CH_2$ |
| C-1165 | T-13 | D9b | $CH_2CH{=}CH_2$ |
| C-1166 | T-14 | D9b | $CH_2CH{=}CH_2$ |
| C-1167 | T-15 | D9b | $CH_2CH{=}CH_2$ |
| C-1168 | T-16 | D9b | $CH_2CH{=}CH_2$ |
| C-1169 | T-17 | D9b | $CH_2CH{=}CH_2$ |
| C-1170 | T-18 | D9b | $CH_2CH{=}CH_2$ |
| C-1171 | T-19 | D9b | $CH_2CH{=}CH_2$ |
| C-1172 | T-20 | D9b | $CH_2CH{=}CH_2$ |
| C-1173 | T-21 | D9b | $CH_2CH{=}CH_2$ |
| C-1174 | T-22 | D9b | $CH_2CH{=}CH_2$ |
| C-1175 | T-23 | D9b | $CH_2CH{=}CH_2$ |
| C-1176 | T-24 | D9b | $CH_2CH{=}CH_2$ |
| C-1177 | T-25 | D9b | $CH_2CH{=}CH_2$ |
| C-1178 | T-26 | D9b | $CH_2CH{=}CH_2$ |
| C-1179 | T-27 | D9b | $CH_2CH{=}CH_2$ |
| C-1180 | T-28 | D9b | $CH_2CH{=}CH_2$ |
| C-1181 | T-29 | D9b | $CH_2CH{=}CH_2$ |
| C-1182 | T-30 | D9b | $CH_2CH{=}CH_2$ |
| C-1183 | T-31 | D9b | $CH_2CH{=}CH_2$ |

TABLE A-continued

| No. | T | $R^4$ | $R^1$ |
|---|---|---|---|
| C-1184 | T-32 | D9b | $CH_2CH{=}CH_2$ |
| C-1185 | T-33 | D9b | $CH_2CH{=}CH_2$ |
| C-1186 | T-34 | D9b | $CH_2CH{=}CH_2$ |
| C-1187 | T-35 | D9b | $CH_2CH{=}CH_2$ |
| C-1188 | T-36 | D9b | $CH_2CH{=}CH_2$ |
| C-1189 | T-37 | D9b | $CH_2CH{=}CH_2$ |
| C-1190 | T-38 | D9b | $CH_2CH{=}CH_2$ |
| C-1191 | T-39 | D9b | $CH_2CH{=}CH_2$ |
| C-1192 | T-40 | D9b | $CH_2CH{=}CH_2$ |
| C-1193 | T-41 | D9b | $CH_2CH{=}CH_2$ |
| C-1194 | T-42 | D9b | $CH_2CH{=}CH_2$ |
| C-1195 | T-43 | D9b | $CH_2CH{=}CH_2$ |
| C-1196 | T-44 | D9b | $CH_2CH{=}CH_2$ |
| C-1197 | T-45 | D9b | $CH_2CH{=}CH_2$ |
| C-1198 | T-46 | D9b | $CH_2CH{=}CH_2$ |
| C-1199 | T-47 | D9b | $CH_2CH{=}CH_2$ |
| C-1200 | T-48 | D9b | $CH_2CH{=}CH_2$ |
| C-1201 | T-49 | D9b | $CH_2CH{=}CH_2$ |
| C-1202 | T-50 | D9b | $CH_2CH{=}CH_2$ |
| C-1203 | T-51 | D9b | $CH_2CH{=}CH_2$ |
| C-1204 | T-52 | D9b | $CH_2CH{=}CH_2$ |
| C-1205 | T-53 | D9b | $CH_2CH{=}CH_2$ |
| C-1206 | T-54 | D9b | $CH_2CH{=}CH_2$ |
| C-1207 | T-55 | D9b | $CH_2CH{=}CH_2$ |
| C-1208 | T-56 | D9b | $CH_2CH{=}CH_2$ |
| C-1209 | T-57 | D9b | $CH_2CH{=}CH_2$ |
| C-1210 | T-58 | D9b | $CH_2CH{=}CH_2$ |
| C-1211 | T-59 | D9b | $CH_2CH{=}CH_2$ |
| C-1212 | T-60 | D9b | $CH_2CH{=}CH_2$ |
| C-1213 | T-61 | D9b | $CH_2CH{=}CH_2$ |
| C-1214 | T-62 | D9b | $CH_2CH{=}CH_2$ |
| C-1215 | T-63 | D9b | $CH_2CH{=}CH_2$ |
| C-1216 | T-64 | D9b | $CH_2CH{=}CH_2$ |
| C-1217 | T-1 | $CH_2$—CN | $CH_2CH{=}CH_2$ |
| C-1218 | T-2 | $CH_2$—CN | $CH_2CH{=}CH_2$ |
| C-1219 | T-3 | $CH_2$—CN | $CH_2CH{=}CH_2$ |
| C-1220 | T-4 | $CH_2$—CN | $CH_2CH{=}CH_2$ |
| C-1221 | T-5 | $CH_2$—CN | $CH_2CH{=}CH_2$ |
| C-1222 | T-6 | $CH_2$—CN | $CH_2CH{=}CH_2$ |
| C-1223 | T-7 | $CH_2$—CN | $CH_2CH{=}CH_2$ |
| C-1224 | T-8 | $CH_2$—CN | $CH_2CH{=}CH_2$ |
| C-1225 | T-9 | $CH_2$—CN | $CH_2CH{=}CH_2$ |
| C-1226 | T-10 | $CH_2$—CN | $CH_2CH{=}CH_2$ |
| C-1227 | T-11 | $CH_2$—CN | $CH_2CH{=}CH_2$ |
| C-1228 | T-12 | $CH_2$—CN | $CH_2CH{=}CH_2$ |
| C-1229 | T-13 | $CH_2$—CN | $CH_2CH{=}CH_2$ |
| C-1230 | T-14 | $CH_2$—CN | $CH_2CH{=}CH_2$ |
| C-1231 | T-15 | $CH_2$—CN | $CH_2CH{=}CH_2$ |
| C-1232 | T-16 | $CH_2$—CN | $CH_2CH{=}CH_2$ |
| C-1233 | T-17 | $CH_2$—CN | $CH_2CH{=}CH_2$ |
| C-1234 | T-18 | $CH_2$—CN | $CH_2CH{=}CH_2$ |
| C-1235 | T-19 | $CH_2$—CN | $CH_2CH{=}CH_2$ |
| C-1236 | T-20 | $CH_2$—CN | $CH_2CH{=}CH_2$ |
| C-1237 | T-21 | $CH_2$—CN | $CH_2CH{=}CH_2$ |
| C-1238 | T-22 | $CH_2$—CN | $CH_2CH{=}CH_2$ |
| C-1239 | T-23 | $CH_2$—CN | $CH_2CH{=}CH_2$ |
| C-1240 | T-24 | $CH_2$—CN | $CH_2CH{=}CH_2$ |
| C-1241 | T-25 | $CH_2$—CN | $CH_2CH{=}CH_2$ |
| C-1242 | T-26 | $CH_2$—CN | $CH_2CH{=}CH_2$ |
| C-1243 | T-27 | $CH_2$—CN | $CH_2CH{=}CH_2$ |
| C-1244 | T-28 | $CH_2$—CN | $CH_2CH{=}CH_2$ |
| C-1245 | T-29 | $CH_2$—CN | $CH_2CH{=}CH_2$ |
| C-1246 | T-30 | $CH_2$—CN | $CH_2CH{=}CH_2$ |
| C-1247 | T-31 | $CH_2$—CN | $CH_2CH{=}CH_2$ |
| C-1248 | T-32 | $CH_2$—CN | $CH_2CH{=}CH_2$ |
| C-1249 | T-33 | $CH_2$—CN | $CH_2CH{=}CH_2$ |
| C-1250 | T-34 | $CH_2$—CN | $CH_2CH{=}CH_2$ |
| C-1251 | T-35 | $CH_2$—CN | $CH_2CH{=}CH_2$ |
| C-1252 | T-36 | $CH_2$—CN | $CH_2CH{=}CH_2$ |
| C-1253 | T-37 | $CH_2$—CN | $CH_2CH{=}CH_2$ |
| C-1254 | T-38 | $CH_2$—CN | $CH_2CH{=}CH_2$ |
| C-1255 | T-39 | $CH_2$—CN | $CH_2CH{=}CH_2$ |
| C-1256 | T-40 | $CH_2$—CN | $CH_2CH{=}CH_2$ |
| C-1257 | T-41 | $CH_2$—CN | $CH_2CH{=}CH_2$ |
| C-1258 | T-42 | $CH_2$—CN | $CH_2CH{=}CH_2$ |
| C-1259 | T-43 | $CH_2$—CN | $CH_2CH{=}CH_2$ |
| C-1260 | T-44 | $CH_2$—CN | $CH_2CH{=}CH_2$ |
| C-1261 | T-45 | $CH_2$—CN | $CH_2CH{=}CH_2$ |
| C-1262 | T-46 | $CH_2$—CN | $CH_2CH{=}CH_2$ |
| C-1263 | T-47 | $CH_2$—CN | $CH_2CH{=}CH_2$ |
| C-1264 | T-48 | $CH_2$—CN | $CH_2CH{=}CH_2$ |
| C-1265 | T-49 | $CH_2$—CN | $CH_2CH{=}CH_2$ |
| C-1266 | T-50 | $CH_2$—CN | $CH_2CH{=}CH_2$ |
| C-1267 | T-51 | $CH_2$—CN | $CH_2CH{=}CH_2$ |
| C-1268 | T-52 | $CH_2$—CN | $CH_2CH{=}CH_2$ |
| C-1269 | T-53 | $CH_2$—CN | $CH_2CH{=}CH_2$ |
| C-1270 | T-54 | $CH_2$—CN | $CH_2CH{=}CH_2$ |
| C-1271 | T-55 | $CH_2$—CN | $CH_2CH{=}CH_2$ |
| C-1272 | T-56 | $CH_2$—CN | $CH_2CH{=}CH_2$ |
| C-1273 | T-57 | $CH_2$—CN | $CH_2CH{=}CH_2$ |
| C-1274 | T-58 | $CH_2$—CN | $CH_2CH{=}CH_2$ |
| C-1275 | T-59 | $CH_2$—CN | $CH_2CH{=}CH_2$ |
| C-1276 | T-60 | $CH_2$—CN | $CH_2CH{=}CH_2$ |
| C-1277 | T-61 | $CH_2$—CN | $CH_2CH{=}CH_2$ |
| C-1278 | T-62 | $CH_2$—CN | $CH_2CH{=}CH_2$ |
| C-1279 | T-63 | $CH_2$—CN | $CH_2CH{=}CH_2$ |
| C-1280 | T-64 | $CH_2$—CN | $CH_2CH{=}CH_2$ |
| C-1281 | T-1 | D2b.1 | $CH_2CF_3$ |
| C-1282 | T-2 | D2b.1 | $CH_2CF_3$ |
| C-1283 | T-3 | D2b.1 | $CH_2CF_3$ |
| C-1284 | T-4 | D2b.1 | $CH_2CF_3$ |
| C-1285 | T-5 | D2b.1 | $CH_2CF_3$ |
| C-1286 | T-6 | D2b.1 | $CH_2CF_3$ |
| C-1287 | T-7 | D2b.1 | $CH_2CF_3$ |
| C-1288 | T-8 | D2b.1 | $CH_2CF_3$ |
| C-1289 | T-9 | D2b.1 | $CH_2CF_3$ |
| C-1290 | T-10 | D2b.1 | $CH_2CF_3$ |
| C-1291 | T-11 | D2b.1 | $CH_2CF_3$ |
| C-1292 | T-12 | D2b.1 | $CH_2CF_3$ |
| C-1293 | T-13 | D2b.1 | $CH_2CF_3$ |
| C-1294 | T-14 | D2b.1 | $CH_2CF_3$ |
| C-1295 | T-15 | D2b.1 | $CH_2CF_3$ |
| C-1296 | T-16 | D2b.1 | $CH_2CF_3$ |
| C-1297 | T-17 | D2b.1 | $CH_2CF_3$ |
| C-1298 | T-18 | D2b.1 | $CH_2CF_3$ |
| C-1299 | T-19 | D2b.1 | $CH_2CF_3$ |
| C-1300 | T-20 | D2b.1 | $CH_2CF_3$ |
| C-1301 | T-21 | D2b.1 | $CH_2CF_3$ |
| C-1302 | T-22 | D2b.1 | $CH_2CF_3$ |
| C-1303 | T-23 | D2b.1 | $CH_2CF_3$ |
| C-1304 | T-24 | D2b.1 | $CH_2CF_3$ |
| C-1305 | T-25 | D2b.1 | $CH_2CF_3$ |
| C-1306 | T-26 | D2b.1 | $CH_2CF_3$ |
| C-1307 | T-27 | D2b.1 | $CH_2CF_3$ |
| C-1308 | T-28 | D2b.1 | $CH_2CF_3$ |
| C-1309 | T-29 | D2b.1 | $CH_2CF_3$ |
| C-1310 | T-30 | D2b.1 | $CH_2CF_3$ |
| C-1311 | T-31 | D2b.1 | $CH_2CF_3$ |
| C-1312 | T-32 | D2b.1 | $CH_2CF_3$ |
| C-1313 | T-33 | D2b.1 | $CH_2CF_3$ |
| C-1314 | T-34 | D2b.1 | $CH_2CF_3$ |
| C-1315 | T-35 | D2b.1 | $CH_2CF_3$ |
| C-1316 | T-36 | D2b.1 | $CH_2CF_3$ |
| C-1317 | T-37 | D2b.1 | $CH_2CF_3$ |
| C-1318 | T-38 | D2b.1 | $CH_2CF_3$ |
| C-1319 | T-39 | D2b.1 | $CH_2CF_3$ |
| C-1320 | T-40 | D2b.1 | $CH_2CF_3$ |
| C-1321 | T-41 | D2b.1 | $CH_2CF_3$ |
| C-1322 | T-42 | D2b.1 | $CH_2CF_3$ |
| C-1323 | T-43 | D2b.1 | $CH_2CF_3$ |
| C-1324 | T-44 | D2b.1 | $CH_2CF_3$ |
| C-1325 | T-45 | D2b.1 | $CH_2CF_3$ |
| C-1326 | T-46 | D2b.1 | $CH_2CF_3$ |
| C-1327 | T-47 | D2b.1 | $CH_2CF_3$ |
| C-1328 | T-48 | D2b.1 | $CH_2CF_3$ |
| C-1329 | T-49 | D2b.1 | $CH_2CF_3$ |
| C-1330 | T-50 | D2b.1 | $CH_2CF_3$ |
| C-1331 | T-51 | D2b.1 | $CH_2CF_3$ |
| C-1332 | T-52 | D2b.1 | $CH_2CF_3$ |
| C-1333 | T-53 | D2b.1 | $CH_2CF_3$ |
| C-1334 | T-54 | D2b.1 | $CH_2CF_3$ |
| C-1335 | T-55 | D2b.1 | $CH_2CF_3$ |
| C-1336 | T-56 | D2b.1 | $CH_2CF_3$ |
| C-1337 | T-57 | D2b.1 | $CH_2CF_3$ |
| C-1338 | T-58 | D2b.1 | $CH_2CF_3$ |
| C-1339 | T-59 | D2b.1 | $CH_2CF_3$ |

TABLE A-continued

| No. | T | $R^4$ | $R^1$ |
|---|---|---|---|
| C-1340 | T-60 | D2b.1 | $CH_2CF_3$ |
| C-1341 | T-61 | D2b.1 | $CH_2CF_3$ |
| C-1342 | T-62 | D2b.1 | $CH_2CF_3$ |
| C-1343 | T-63 | D2b.1 | $CH_2CF_3$ |
| C-1344 | T-64 | D2b.1 | $CH_2CF_3$ |
| C-1345 | T-1 | D25a.1 | $CH_2CF_3$ |
| C-1346 | T-2 | D25a.1 | $CH_2CF_3$ |
| C-1347 | T-3 | D25a.1 | $CH_2CF_3$ |
| C-1348 | T-4 | D25a.1 | $CH_2CF_3$ |
| C-1349 | T-5 | D25a.1 | $CH_2CF_3$ |
| C-1350 | T-6 | D25a.1 | $CH_2CF_3$ |
| C-1351 | T-7 | D25a.1 | $CH_2CF_3$ |
| C-1352 | T-8 | D25a.1 | $CH_2CF_3$ |
| C-1353 | T-9 | D25a.1 | $CH_2CF_3$ |
| C-1354 | T-10 | D25a.1 | $CH_2CF_3$ |
| C-1355 | T-11 | D25a.1 | $CH_2CF_3$ |
| C-1356 | T-12 | D25a.1 | $CH_2CF_3$ |
| C-1357 | T-13 | D25a.1 | $CH_2CF_3$ |
| C-1358 | T-14 | D25a.1 | $CH_2CF_3$ |
| C-1359 | T-15 | D25a.1 | $CH_2CF_3$ |
| C-1360 | T-16 | D25a.1 | $CH_2CF_3$ |
| C-1361 | T-17 | D25a.1 | $CH_2CF_3$ |
| C-1362 | T-18 | D25a.1 | $CH_2CF_3$ |
| C-1363 | T-19 | D25a.1 | $CH_2CF_3$ |
| C-1364 | T-20 | D25a.1 | $CH_2CF_3$ |
| C-1365 | T-21 | D25a.1 | $CH_2CF_3$ |
| C-1366 | T-22 | D25a.1 | $CH_2CF_3$ |
| C-1367 | T-23 | D25a.1 | $CH_2CF_3$ |
| C-1368 | T-24 | D25a.1 | $CH_2CF_3$ |
| C-1369 | T-25 | D25a.1 | $CH_2CF_3$ |
| C-1370 | T-26 | D25a.1 | $CH_2CF_3$ |
| C-1371 | T-27 | D25a.1 | $CH_2CF_3$ |
| C-1372 | T-28 | D25a.1 | $CH_2CF_3$ |
| C-1373 | T-29 | D25a.1 | $CH_2CF_3$ |
| C-1374 | T-30 | D25a.1 | $CH_2CF_3$ |
| C-1375 | T-31 | D25a.1 | $CH_2CF_3$ |
| C-1376 | T-32 | D25a.1 | $CH_2CF_3$ |
| C-1377 | T-33 | D25a.1 | $CH_2CF_3$ |
| C-1378 | T-34 | D25a.1 | $CH_2CF_3$ |
| C-1379 | T-35 | D25a.1 | $CH_2CF_3$ |
| C-1380 | T-36 | D25a.1 | $CH_2CF_3$ |
| C-1381 | T-37 | D25a.1 | $CH_2CF_3$ |
| C-1382 | T-38 | D25a.1 | $CH_2CF_3$ |
| C-1383 | T-39 | D25a.1 | $CH_2CF_3$ |
| C-1384 | T-40 | D25a.1 | $CH_2CF_3$ |
| C-1385 | T-41 | D25a.1 | $CH_2CF_3$ |
| C-1386 | T-42 | D25a.1 | $CH_2CF_3$ |
| C-1387 | T-43 | D25a.1 | $CH_2CF_3$ |
| C-1388 | T-44 | D25a.1 | $CH_2CF_3$ |
| C-1389 | T-45 | D25a.1 | $CH_2CF_3$ |
| C-1390 | T-46 | D25a.1 | $CH_2CF_3$ |
| C-1391 | T-47 | D25a.1 | $CH_2CF_3$ |
| C-1392 | T-48 | D25a.1 | $CH_2CF_3$ |
| C-1393 | T-49 | D25a.1 | $CH_2CF_3$ |
| C-1394 | T-50 | D25a.1 | $CH_2CF_3$ |
| C-1395 | T-51 | D25a.1 | $CH_2CF_3$ |
| C-1396 | T-52 | D25a.1 | $CH_2CF_3$ |
| C-1397 | T-53 | D25a.1 | $CH_2CF_3$ |
| C-1398 | T-54 | D25a.1 | $CH_2CF_3$ |
| C-1399 | T-55 | D25a.1 | $CH_2CF_3$ |
| C-1400 | T-56 | D25a.1 | $CH_2CF_3$ |
| C-1401 | T-57 | D25a.1 | $CH_2CF_3$ |
| C-1402 | T-58 | D25a.1 | $CH_2CF_3$ |
| C-1403 | T-59 | D25a.1 | $CH_2CF_3$ |
| C-1404 | T-60 | D25a.1 | $CH_2CF_3$ |
| C-1405 | T-61 | D25a.1 | $CH_2CF_3$ |
| C-1406 | T-62 | D25a.1 | $CH_2CF_3$ |
| C-1407 | T-63 | D25a.1 | $CH_2CF_3$ |
| C-1408 | T-64 | D25a.1 | $CH_2CF_3$ |
| C-1409 | T-1 | D9b | $CH_2CF_3$ |
| C-1410 | T-2 | D9b | $CH_2CF_3$ |
| C-1411 | T-3 | D9b | $CH_2CF_3$ |
| C-1412 | T-4 | D9b | $CH_2CF_3$ |
| C-1413 | T-5 | D9b | $CH_2CF_3$ |
| C-1414 | T-6 | D9b | $CH_2CF_3$ |
| C-1415 | T-7 | D9b | $CH_2CF_3$ |
| C-1416 | T-8 | D9b | $CH_2CF_3$ |
| C-1417 | T-9 | D9b | $CH_2CF_3$ |

TABLE A-continued

| No. | T | $R^4$ | $R^1$ |
|---|---|---|---|
| C-1418 | T-10 | D9b | $CH_2CF_3$ |
| C-1419 | T-11 | D9b | $CH_2CF_3$ |
| C-1420 | T-12 | D9b | $CH_2CF_3$ |
| C-1421 | T-13 | D9b | $CH_2CF_3$ |
| C-1422 | T-14 | D9b | $CH_2CF_3$ |
| C-1423 | T-15 | D9b | $CH_2CF_3$ |
| C-1424 | T-16 | D9b | $CH_2CF_3$ |
| C-1425 | T-17 | D9b | $CH_2CF_3$ |
| C-1426 | T-18 | D9b | $CH_2CF_3$ |
| C-1427 | T-19 | D9b | $CH_2CF_3$ |
| C-1428 | T-20 | D9b | $CH_2CF_3$ |
| C-1429 | T-21 | D9b | $CH_2CF_3$ |
| C-1430 | T-22 | D9b | $CH_2CF_3$ |
| C-1431 | T-23 | D9b | $CH_2CF_3$ |
| C-1432 | T-24 | D9b | $CH_2CF_3$ |
| C-1433 | T-25 | D9b | $CH_2CF_3$ |
| C-1434 | T-26 | D9b | $CH_2CF_3$ |
| C-1435 | T-27 | D9b | $CH_2CF_3$ |
| C-1436 | T-28 | D9b | $CH_2CF_3$ |
| C-1437 | T-29 | D9b | $CH_2CF_3$ |
| C-1438 | T-30 | D9b | $CH_2CF_3$ |
| C-1439 | T-31 | D9b | $CH_2CF_3$ |
| C-1440 | T-32 | D9b | $CH_2CF_3$ |
| C-1441 | T-33 | D9b | $CH_2CF_3$ |
| C-1442 | T-34 | D9b | $CH_2CF_3$ |
| C-1443 | T-35 | D9b | $CH_2CF_3$ |
| C-1444 | T-36 | D9b | $CH_2CF_3$ |
| C-1445 | T-37 | D9b | $CH_2CF_3$ |
| C-1446 | T-38 | D9b | $CH_2CF_3$ |
| C-1447 | T-39 | D9b | $CH_2CF_3$ |
| C-1448 | T-40 | D9b | $CH_2CF_3$ |
| C-1449 | T-41 | D9b | $CH_2CF_3$ |
| C-1450 | T-42 | D9b | $CH_2CF_3$ |
| C-1451 | T-43 | D9b | $CH_2CF_3$ |
| C-1452 | T-44 | D9b | $CH_2CF_3$ |
| C-1453 | T-45 | D9b | $CH_2CF_3$ |
| C-1454 | T-46 | D9b | $CH_2CF_3$ |
| C-1455 | T-47 | D9b | $CH_2CF_3$ |
| C-1456 | T-48 | D9b | $CH_2CF_3$ |
| C-1457 | T-49 | D9b | $CH_2CF_3$ |
| C-1458 | T-50 | D9b | $CH_2CF_3$ |
| C-1459 | T-51 | D9b | $CH_2CF_3$ |
| C-1460 | T-52 | D9b | $CH_2CF_3$ |
| C-1461 | T-53 | D9b | $CH_2CF_3$ |
| C-1462 | T-54 | D9b | $CH_2CF_3$ |
| C-1463 | T-55 | D9b | $CH_2CF_3$ |
| C-1464 | T-56 | D9b | $CH_2CF_3$ |
| C-1465 | T-57 | D9b | $CH_2CF_3$ |
| C-1466 | T-58 | D9b | $CH_2CF_3$ |
| C-1467 | T-59 | D9b | $CH_2CF_3$ |
| C-1468 | T-60 | D9b | $CH_2CF_3$ |
| C-1469 | T-61 | D9b | $CH_2CF_3$ |
| C-1470 | T-62 | D9b | $CH_2CF_3$ |
| C-1471 | T-63 | D9b | $CH_2CF_3$ |
| C-1472 | T-64 | D9b | $CH_2CF_3$ |
| C-1473 | T-1 | $CH_2$—CN | $CH_2CF_3$ |
| C-1474 | T-2 | $CH_2$—CN | $CH_2CF_3$ |
| C-1475 | T-3 | $CH_2$—CN | $CH_2CF_3$ |
| C-1476 | T-4 | $CH_2$—CN | $CH_2CF_3$ |
| C-1477 | T-5 | $CH_2$—CN | $CH_2CF_3$ |
| C-1478 | T-6 | $CH_2$—CN | $CH_2CF_3$ |
| C-1479 | T-7 | $CH_2$—CN | $CH_2CF_3$ |
| C-1480 | T-8 | $CH_2$—CN | $CH_2CF_3$ |
| C-1481 | T-9 | $CH_2$—CN | $CH_2CF_3$ |
| C-1482 | T-10 | $CH_2$—CN | $CH_2CF_3$ |
| C-1483 | T-11 | $CH_2$—CN | $CH_2CF_3$ |
| C-1484 | T-12 | $CH_2$—CN | $CH_2CF_3$ |
| C-1485 | T-13 | $CH_2$—CN | $CH_2CF_3$ |
| C-1486 | T-14 | $CH_2$—CN | $CH_2CF_3$ |
| C-1487 | T-15 | $CH_2$—CN | $CH_2CF_3$ |
| C-1488 | T-16 | $CH_2$—CN | $CH_2CF_3$ |
| C-1489 | T-17 | $CH_2$—CN | $CH_2CF_3$ |
| C-1490 | T-18 | $CH_2$—CN | $CH_2CF_3$ |
| C-1491 | T-19 | $CH_2$—CN | $CH_2CF_3$ |
| C-1492 | T-20 | $CH_2$—CN | $CH_2CF_3$ |
| C-1493 | T-21 | $CH_2$—CN | $CH_2CF_3$ |
| C-1494 | T-22 | $CH_2$—CN | $CH_2CF_3$ |
| C-1495 | T-23 | $CH_2$—CN | $CH_2CF_3$ |

TABLE A-continued

| No. | T | $R^4$ | $R^1$ |
|---|---|---|---|
| C-1496 | T-24 | $CH_2$—CN | $CH_2CF_3$ |
| C-1497 | T-25 | $CH_2$—CN | $CH_2CF_3$ |
| C-1498 | T-26 | $CH_2$—CN | $CH_2CF_3$ |
| C-1499 | T-27 | $CH_2$—CN | $CH_2CF_3$ |
| C-1500 | T-28 | $CH_2$—CN | $CH_2CF_3$ |
| C-1501 | T-29 | $CH_2$—CN | $CH_2CF_3$ |
| C-1502 | T-30 | $CH_2$—CN | $CH_2CF_3$ |
| C-1503 | T-31 | $CH_2$—CN | $CH_2CF_3$ |
| C-1504 | T-32 | $CH_2$—CN | $CH_2CF_3$ |
| C-1505 | T-33 | $CH_2$—CN | $CH_2CF_3$ |
| C-1506 | T-34 | $CH_2$—CN | $CH_2CF_3$ |
| C-1507 | T-35 | $CH_2$—CN | $CH_2CF_3$ |
| C-1508 | T-36 | $CH_2$—CN | $CH_2CF_3$ |
| C-1509 | T-37 | $CH_2$—CN | $CH_2CF_3$ |
| C-1510 | T-38 | $CH_2$—CN | $CH_2CF_3$ |
| C-1511 | T-39 | $CH_2$—CN | $CH_2CF_3$ |
| C-1512 | T-40 | $CH_2$—CN | $CH_2CF_3$ |
| C-1513 | T-41 | $CH_2$—CN | $CH_2CF_3$ |
| C-1514 | T-42 | $CH_2$—CN | $CH_2CF_3$ |
| C-1515 | T-43 | $CH_2$—CN | $CH_2CF_3$ |
| C-1516 | T-44 | $CH_2$—CN | $CH_2CF_3$ |
| C-1517 | T-45 | $CH_2$—CN | $CH_2CF_3$ |
| C-1518 | T-46 | $CH_2$—CN | $CH_2CF_3$ |
| C-1519 | T-47 | $CH_2$—CN | $CH_2CF_3$ |
| C-1520 | T-48 | $CH_2$—CN | $CH_2CF_3$ |
| C-1521 | T-49 | $CH_2$—CN | $CH_2CF_3$ |
| C-1522 | T-50 | $CH_2$—CN | $CH_2CF_3$ |
| C-1523 | T-51 | $CH_2$—CN | $CH_2CF_3$ |
| C-1524 | T-52 | $CH_2$—CN | $CH_2CF_3$ |
| C-1525 | T-53 | $CH_2$—CN | $CH_2CF_3$ |
| C-1526 | T-54 | $CH_2$—CN | $CH_2CF_3$ |
| C-1527 | T-55 | $CH_2$—CN | $CH_2CF_3$ |
| C-1528 | T-56 | $CH_2$—CN | $CH_2CF_3$ |
| C-1529 | T-57 | $CH_2$—CN | $CH_2CF_3$ |
| C-1530 | T-58 | $CH_2$—CN | $CH_2CF_3$ |
| C-1531 | T-59 | $CH_2$—CN | $CH_2CF_3$ |
| C-1532 | T-60 | $CH_2$—CN | $CH_2CF_3$ |
| C-1533 | T-61 | $CH_2$—CN | $CH_2CF_3$ |
| C-1534 | T-62 | $CH_2$—CN | $CH_2CF_3$ |
| C-1535 | T-63 | $CH_2$—CN | $CH_2CF_3$ |
| C-1536 | T-64 | $CH_2$—CN | $CH_2CF_3$ |

The compound of formula (I) according to the present invention can be prepared according to the following syntheses routes, e.g. according to the preparation methods and preparation schemes as described below.

The compounds of formula (I) according to the present invention can be prepared analogously to the methods described in WO2014/167084 and WO2017/093214, in particular according to the preparation methods and preparation schemes as described e.g. below.

The compounds used as starting materials for the syntheses of the compounds according to the present invention can generally be prepared by standard methods of organic chemistry. If not otherwise specified, the definitions of the variables such as $R^1$, and A of the structures given in the schemes have the same meaning as defined above.

The compound of formula (Ia) according to the present invention can be prepared according to the following syntheses routes, e.g. according to the preparation methods and preparation schemes as described below.

Scheme 1

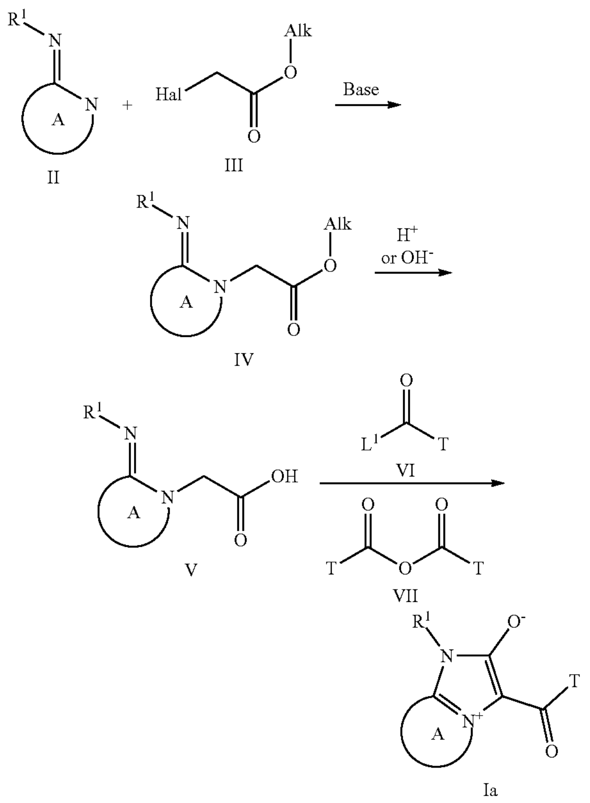

The compound of formula (Ia) according to the present invention can be prepared according to the following syntheses routes, e.g. according to the preparation methods and preparation schemes as described below.

The compounds of formula (Ia) according to the present invention can be prepared analogously to the methods described in WO2018/189077, WO2018/208595 and WO2019/086474, in particular according to the preparation methods and preparation schemes as described e.g. below.

The compounds used as starting materials for the syntheses of the compounds according to the present invention can generally be prepared by standard methods of organic chemistry. If not otherwise specified, the definitions of the variables such as R1, R2 and R3 of the structures given in the schemes have the same meaning as defined above.

Compounds of type II are known in the literature (see, for example, W02009099929, W02012092115, WO2011057022, WO2011017342) or can be prepared in analogy to literature known procedures. Compounds like III are commercially available. Compound of type IV can be prepared from compound II and compound III in the presence of base, like for example sodium hydride, using organic solvents like dimethylformamide. Compound V could be achieved by treating compound IV with, for example, trifluoracetic acid in organic solvents like dichloromethane or lithium hydroxide in tetrahydrofuran.

Compound Ia could be synthesized from compound V and compound VI or VII in the presence of base, like for example triethylamine, cesium carbonate, potassium carbonate, DBU. And using organic solvents like dichloromethane, tetrahydrofuran, DMF, acetonitrile, dichloromethane, ethyl acetate or toluene. Reaction temperature typically varies from 25° C. to 100° C. (Scheme 1).

In general, compounds of formula I could be synthesized according to the scheme described above. In case when the some of the compounds are not directly accessible using the described scheme, they can be synthesized through the derivatization of other compounds of formula I, for example using the chemical transformations like hydrolysis, aminolysis, substitution, esterification, amide formation, reduction, etherification, oxidation, olefination, halogenation, acylation, alkylation and other transformations.

Compounds of Formula I wherein Y is S can be prepared from compounds of formula Ia by treatment with a thionating reagent such as $P_4S_{10}$ or Lawessen's Reagent (2,4-bis (4-methoxy-phenyl)-'1,3-dithia-2,4-diphosphetane 2,4-disulfide). This type of reactions described in the literature, for example Tetrafedron, 63(48), 11862-11877, 2007 or Advanced Organic Chemistry: Reactions, Mechanisms and Structure, Fourth Edition by Jerry March, 1992 (Wiley New York, N.Y.) 1184-1185.

Structures of formula Ib and Ic could be prepared from compound V and compounds VIII and IX respectively, in the presence of a base, for example triethylamine. Compounds VIII and IX, where X is a halogen, are commercially available or known from the literature (Scheme 2).

Scheme 2

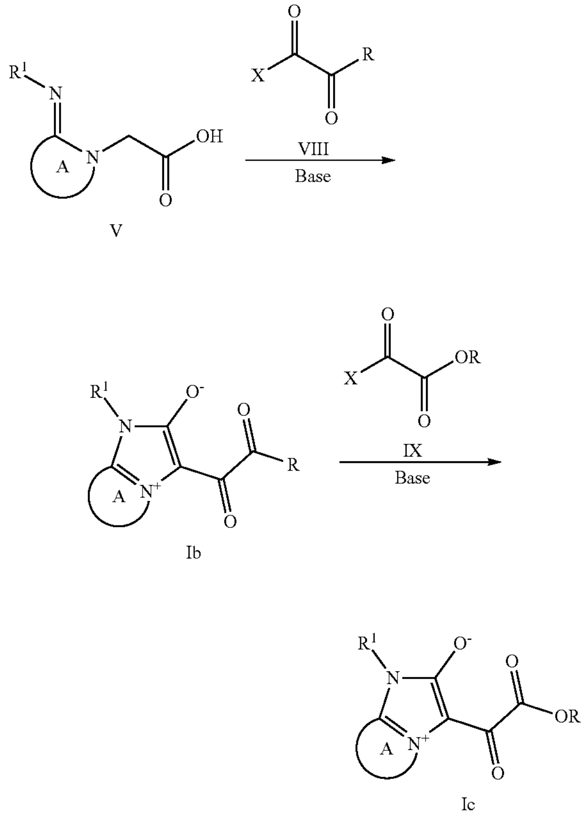

Additionally, compound of formula Ic and Id could be achieved in two steps from compound V, by reacting compound V with oxalyl chloride in the presence of a base, for example triethylamine. Followed by reaction of the intermediate X with alcohols of formula XI or amines of formula XII in the presence of a base, for example triethylamine. Alcohols X and amines XI are commercially available or known from the literature (Scheme 3).

Scheme 3

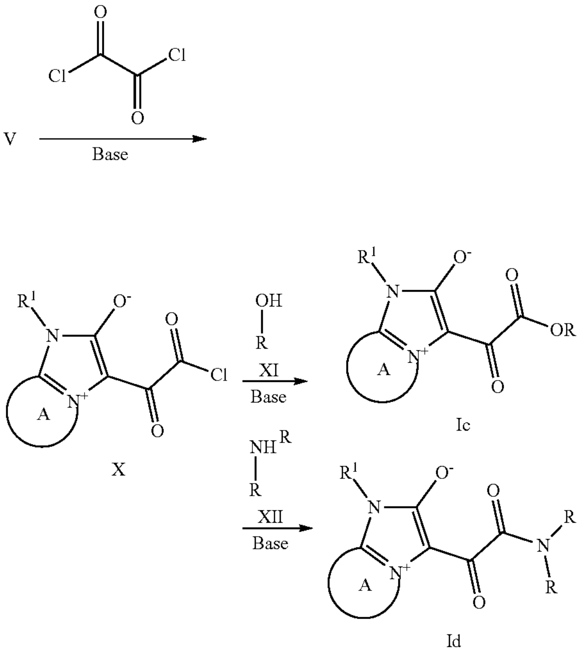

Compounds of formula Ie could be synthesized from compounds of formula V and compound of formula XIII, in the presence of a base, for example triethylamine. Compounds of formula XIII, where X is a halogen, are commercially available or known in the literature.

Scheme 4

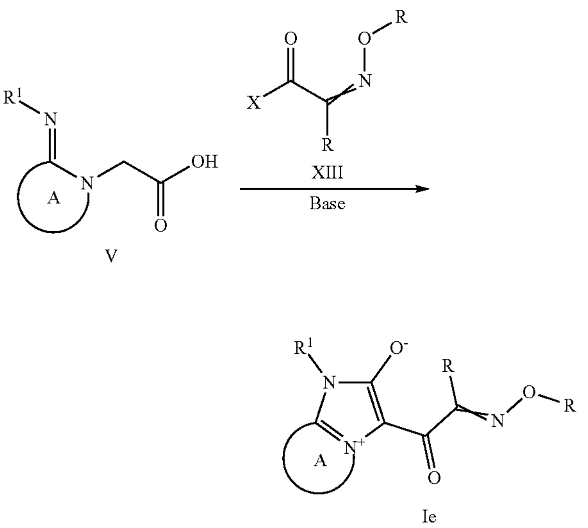

Compounds of formula Ig and Ih could be prepared from the compound of formula If, using amine XIV and hydrazine XV respectively, in the presence of base such as, for example, triethylamine (Scheme 5). Compounds XIV and XV are commercially available or known in the literature.

Scheme 5

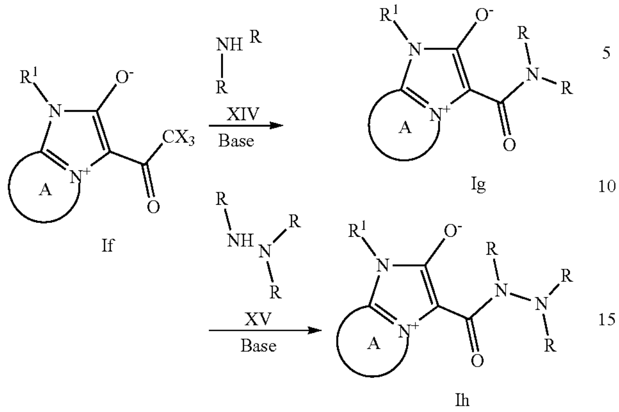

If individual compounds cannot be prepared via the above described routes, they can be prepared by derivatization of other compounds of formula (I) or by customary modifications of the synthesis routes described.

For example, in individual cases, certain compounds of formula (I) can advantageously be prepared from other compounds of formula (I) by derivatization, e.g. by ester hydrolysis, amidation, esterification, ether cleavage, olefination, reduction, oxidation and the like, or by customary modifications of the synthesis routes described.

The reaction mixtures are worked up in the customary manner, for example by mixing with water, separating the phases, and, if appropriate, purifying the crude products by chromatography, for example on alumina or silica gel.

As used herein, the term "compound(s) of the present invention" or "compound(s) according to the invention" refers to the compound(s) of formula (I) as defined above, which are also referred to as "compound(s) of formula I" or "compound(s) I" or "formula I compound(s)", and includes their salts, tautomers, stereoisomers, and N-oxides.

As used herein, the term "compound(s) of the present invention" or "compound(s) according to the invention" refers to the compound(s) of formula (I) as defined above, which are also referred to as "compound(s) of formula I" or "compound(s) I" or "formula I compound(s)", and includes their salts, tautomers, stereoisomers, and N-oxides.

Mixtures

The present invention also relates to a mixture of at least one compound of the invention with at least one mixing partner as defined herein. Preferred are binary mixtures of one compound of the invention as component I with one mixing partner as defined herein as component II. Preferred weight ratios for such binary mixtures are from 5000:1 to 1:5000, preferably from 1000:1 to 1:1000, more preferably from 100:1 to 1:100, particularly from 10:1 to 1:10. In such binary mixtures, components I and II may be used in equal amounts, or an excess of component I, or an excess of component II may be used.

Mixing partners can be selected from pesticides, in particular insecticides, nematicides, and acaricides, fungicides, herbicides, plant growth regulators, fertilizers. Preferred mixing partners are insecticides, nematicides and fungicides.

The following list M of pesticides, grouped and numbered according the Mode of Action Classification of the Insecticide Resistance Action Committee (IRAC), together with which the compounds of the invention can be used and with which potential synergistic effects might be produced, is intended to illustrate the possible combinations, but not to impose any limitation:

M.1 Acetylcholine esterase (AChE) inhibitors: M.1A carbamates, e.g. aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or M.1B organophosphates, e.g. acephate, azamethiphos, azinphos-ethyl, azinphosmethyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxy-aminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, and vamidothion;

M.2. GABA-gated chloride channel antagonists: M.2A cyclodiene organochlorine compounds, e.g. endosulfan or chlordane; or M.2B fiproles (phenylpyrazoles), e.g. ethiprole, fipronil, flufiprole, pyrafluprole, and pyriprole;

M.3 Sodium channel modulators from the class of M.3A pyrethroids, e.g. acrinathrin, allethrin, d-cis-trans allethrin, d-trans allethrin, bifenthrin, kappa-bifenthrin, bioallethrin, bioallethrin S-cyclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin, metofluthrin, momfluorothrin, epsilon-momfluorothrin, permethrin, phenothrin, prallethrin, profluthrin, pyrethrin (pyrethrum), resmethrin, silafluofen, tefluthrin, kappa-tefluthrin, tetramethylfluthrin, tetramethrin, tralomethrin, and transfluthrin; or M.3B sodium channel modulators such as DDT or methoxychlor;

M.4 Nicotinic acetylcholine receptor agonists (nAChR): M.4A neonicotinoids, e.g. acetamiprid, clothianidin, cycloxaprid, dinotefuran, imidacloprid, nitenpyram, thiacloprid and thiamethoxam; or the compounds M.4A.1 4,5-Dihydro-N-nitro-1-(2-oxiranylmethyl)-1H-imidazol-2-amine, M.4A.2: (2E−)-1-[(6-Chloropyridin-3-yl)methyl]-N'-nitro-2-pentylidenehydrazinecarboximidamide; or M4.A.3: 1-[(6-Chloropyridin-3-yl)methyl]-7-methyl-8-nitro-5-propoxy-1,2,3,5,6,7-hexahydroimidazo[1,2-a]pyridine; or M.4B nicotine; M.4C sulfoxaflor; M.4D flupyradifurone; M.4E triflumezopyrim, M.4E.1a) (3R)-3-(2-chlorothiazol-5-yl)-8-methyl-5-oxo-6-phenyl-2,3-dihydrothiazolo[3,2-a]pyrimidin-8-ium-7-olate, M.4E.1b) (3S)-3-(6-chloro-3-pyridyl)-8-methyl-5-oxo-6-phenyl-2,3-dihydrothiazolo[3,2-a]pyrimidin-8-ium-7-olate, M.4E.1c) (3S)-8-methyl-5-oxo-6-phenyl-3-pyrimidin-5-yl-2,3-dihydrothiazolo[3,2-a]pyrimidin-8-ium-7-olate, M.4E.1d) (3R)-3-(2-chlorothiazol-5-yl)-8-methyl-5-oxo-6-[3-(trifluoromethyl)phenyl]-2,3-dihydrothiazolo[3,2-a]pyrimidin-8-ium-7-olate; M.4E.1e) (3R)-3-(2-chlorothiazol-5-yl)-6-(3,5-dichlorophenyl)-8-methyl-5-oxo-2,3-dihydrothiazolo[3,2-a]pyrimidin-8-ium-7-olate, M.4E.1f) (3R)-3-(2-chlorothiazol-5-yl)-8-ethyl-5-oxo-6-phenyl-2,3-dihydrothiazolo[3,2-a]pyrimidin-8-ium-7-olate;

M.5 Nicotinic acetylcholine receptor allosteric activators: spinosyns, e.g. spinosad or spinetoram;

M.6 Chloride channel activators from the class of avermectins and milbemycins, e.g. abamectin, emamectin benzoate, ivermectin, lepimectin, or milbemectin;

M.7 Juvenile hormone mimics, such as M.7A juvenile hormone analogues hydroprene, kinoprene, and methoprene; or M.7B fenoxycarb, or M.7C pyriproxyfen;

M.8 miscellaneous non-specific (multi-site) inhibitors, e.g. M.8A alkyl halides as methyl bromide and other alkyl halides, M.8B chloropicrin, M.8C sulfuryl fluoride, M.8D borax, or M.8E tartar emetic;

M.9 Chordotonal organ TRPV channel modulators, e.g. M.9B pymetrozine; pyrifluquinazon;

M.10 Mite growth inhibitors, e.g. M.10A clofentezine, hexythiazox, and diflovidazin, or M.10B etoxazole;

M.11 Microbial disruptors of insect midgut membranes, e.g. *Bacillus thuringiensis* or *Bacillus sphaericus* and the insecticidal proteins they produce such as *Bacillus thuringiensis* subsp. *israelensis, Bacillus sphaericus, Bacillus thuringiensis* subsp. *aizawai, Bacillus thuringiensis* subsp. *kurstaki* and *Bacillus thuringiensis* subsp. *tenebrionis*, or the Bt crop proteins: Cry1Ab, Cry1Ac, Cry1Fa, Cry2Ab, mCry3A, Cry3Ab, Cry3Bb, and Cry34/35Ab1;

M.12 Inhibitors of mitochondrial ATP synthase, e.g. M.12A diafenthiuron, or M.12B organotin miticides such as azocyclotin, cyhexatin, or fenbutatin oxide, M.12C propargite, or M.12D tetradifon;

M.13 Uncouplers of oxidative phosphorylation via disruption of the proton gradient, e.g. chlorfenapyr, DNOC, or sulfluramid;

M.14 Nicotinic acetylcholine receptor (nAChR) channel blockers, e.g. nereistoxin analogues bensultap, cartap hydrochloride, thiocyclam, or thiosultap sodium;

M.15 Inhibitors of the chitin biosynthesis type 0, such as benzoylureas e.g. bistrifluron, chlorfluazuron, diflubenzuron, flucycloxuron, flufenoxuron, hexaflumuron, lufenuron, novaluron, noviflumuron, teflubenzuron, or triflumuron;

M.16 Inhibitors of the chitin biosynthesis type 1, e.g. buprofezin;

M.17 Moulting disruptors, Dipteran, e.g. cyromazine;

M.18 Ecdyson receptor agonists such as diacylhydrazines, e.g. methoxyfenozide, tebufenozide, halofenozide, fufenozide, or chromafenozide;

M.19 Octopamin receptor agonists, e.g. amitraz;

M.20 Mitochondrial complex III electron transport inhibitors, e.g. M.20A hydramethylnon, M.20B acequinocyl, M.20C fluacrypyrim; or M.20D bifenazate;

M.21 Mitochondrial complex I electron transport inhibitors, e.g. M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, e.g. M.22A indoxacarb, M.22B metaflumizone, or M.22B.1: 2-[2-(4-Cyanophenyl)-1-[3-(trifluoromethyl)phenyl]ethylidene]-N-[4-(difluoro-methoxy)phenyl]-hydrazinecarboxamide or M.22B.2: N-(3-Chloro-2-methylphenyl)-2-[(4-chlorophenyl)[4-[methyl(methylsulfonyl)amino]phenyl]methylene]-hydrazinecarboxamide;

M.23 Inhibitors of the of acetyl CoA carboxylase, such as Tetronic and Tetramic acid derivatives, e.g. spirodiclofen, spiromesifen, or spirotetramat; M.23.1 spiropidion;

M.24 Mitochondrial complex IV electron transport inhibitors, e.g. M.24A phosphine such as aluminium phosphide, calcium phosphide, phosphine or zinc phosphide, or M.24B cyanide;

M.25 Mitochondrial complex II electron transport inhibitors, such as beta-ketonitrile derivatives, e.g. cyenopyrafen or cyflumetofen;

M.28 Ryanodine receptor-modulators from the class of diamides, e.g. flubendiamide, chlorantraniliprole, cyantraniliprole, tetraniliprole, M.28.1: (R)-3-Chlor-N1-{2-methyl-4-[1,2,2,2-tetrafluoro-1-(trifluoromethyl)ethyl]phenyl}-N2-(1-methyl-2-methylsulfonylethyl)phthalamid, M.28.2: (S)-3-Chloro-N1-{2-methyl-4-[1,2,2,2-tetrafluoro-1-(trifluoromethyl)ethyl]phenyl}-N2-(1-methyl-2-methylsulfonylethyl)phthalamid, M.28.3: cyclaniliprole, or M.28.4: methyl-2-[3,5-dibromo-2-({[3-bromo-1-(3-chloropyridin-2-yl)-1H-pyrazol-5-yl]carbonyl}amino)benzoyl]-1,2-dimethylhydrazine-carboxylate; M.28.5i) N-[2-(5-Amino-1,3,4-thiadiazol-2-yl)-4-chloro-6-methylphenyl]-3-bromo-1-(3-chloro-2-pyridinyl)-1H-pyrazole-5-carboxamide; M.28.5j) 3-Chloro-1-(3-chloro-2-pyridinyl)-N-[2,4-dichloro-6-[[(1-cyano-1-methylethyl)amino]carbonyl]phenyl]-1H-pyrazole-5-carboxamide; M.28.5k) tetrachlorantraniliprole; M.28.5l) N-[4-Chloro-2-[[(1,1-dimethylethyl)amino]carbonyl]-6-methylphenyl]-1-(3-chloro-2-pyridinyl)-3-(fluoromethoxy)-1H-pyrazole-5-carboxamide; or M.28.6: cyhalodiamide; or M.29: Chordotonal organ Modulators—undefined target site, e.g. flonicamid;

M.UN. insecticidal active compounds of unknown or uncertain mode of action, e.g. afidopyropen, afoxolaner, azadirachtin, amidoflumet, benzoximate, broflanilide, bromopropylate, chinomethionat, cryolite, dicloromezotiaz, dicofol, flufenerim, flometoquin, fluensulfone, fluhexafon, fluopyram, fluralaner, metaldehyde, metoxadiazone, piperonyl butoxide, pyflubumide, pyridalyl, tioxazafen, M.UN.3: 11-(4-chloro-2,6-dimethylphenyl)-12-hydroxy-1,4-dioxa-9-azadispiro[4.2.4.2]-tetradec-11-en-10-one, M.UN.4: 3-(4'-fluoro-2,4-dimethylbiphenyl-3-yl)-4-hydroxy-8-oxa-1-azaspiro[4.5]dec-3-en-2-one, M.UN.5: 1-[2-fluoro-4-methyl-5-[(2,2,2-trifluoroethyl)sulfinyl]phenyl]-3-(trifluoromethyl)-1H-1,2,4-triazole-5-amine, or actives on basis of *Bacillus firmus* (Votivo, I-1582);

M.UN.6: flupyrimin;

M.UN.8: fluazaindolizine; M.UN.9.a): 4-[5-(3,5-dichlorophenyl)-5-(trifluoromethyl)-4H-isoxazol-3-yl]-2-methyl-N-(1-oxothietan-3-yl)benzamide; M.UN.9.b): fluxametamide; M.UN.10: 5-[3-[2,6-dichloro-4-(3,3-dichloroallyloxy)phenoxy]propoxy]-1H-pyrazole;

M.UN.11.i) 4-cyano-N-[2-cyano-5-[[2,6-dibromo-4-[1,2,2,3,3,3-hexafluoro-1-(trifluoromethyl)-propyl]phenyl]carbamoyl]phenyl]-2-methyl-benzamide; M.UN.11.j) 4-cyano-3-[(4-cyano-2-methyl-benzoyl)amino]-N-[2, 6-dichloro-4-[1,2,2,3,3,3-hexafluoro-1-(trifluoromethyl)propyl]phenyl]-2-fluoro-benzamide; M.UN.11.k) N-[5-[[2-chloro-6-cyano-4-[1,2,2,3,3,3-hexafluoro-1-(trifluoromethyl)propyl]phenyl]carbamoyl]-2-cyano-phenyl]-4-cyano-2-methyl-benzamide; M.UN.11.l) N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide; M.UN.11.m) N-[5-[[2-bromo-6-chloro-4-[1,2,2,3,3,3-hexafluoro-1-(trifluoromethyl)propyl]phenyl]carbamoyl]-2-cyano-phenyl]-4-cyano-2-methyl-benzamide; M.UN.11.n) 4-cyano-N-[2-cyano-5-[[2,6-dichloro-4-[1,2,2,3,3,3-hexafluoro-1-(trifluoromethyl)propyl]phenyl]carbamoyl]phenyl]-2-methyl-benzamide; M.UN.11.o) 4-cyano-N-[2-cyano-5-[[2,6-dichloro-4-[1,2,2,2-tetrafluoro-1-(trifluoromethyl)ethyl]phenyl]carbamoyl]phenyl]-2-methyl-benzamide; M.UN.11.p) N-[5-[[2-bromo-6-chloro-4-[1,2,2,2-tetrafluoro-1-(trifluoromethyl)ethyl]phenyl]carbamoyl]-2-cyano-phenyl]-4-cyano-2-methyl-benzamide; or M.UN.12.a) 2-(1,3-Dioxan-2-yl)-6-[2-(3-pyridinyl)-5-thiazolyl]-pyridine; M.UN.12.b) 2-[6-[2-(5-Fluoro-3-pyridinyl)-5-thiazolyl]-2-pyridinyl]-pyrimidine; M.UN.12.c) 2-[6-[2-(3-Pyridinyl)-5-thiazolyl]-2-pyridinyl]-pyrimidine; M.UN.12.d) N-Methylsulfonyl-6-[2-(3-pyridyl)thiazol-5-yl]pyridine-2-carboxamide; M.UN.12.e) N-Methylsulfonyl-6-[2-(3-pyridyl)thiazol-5-yl]pyridine-2-carboxamide;

M.UN.14a) 1-[(6-Chloro-3-pyridinyl)methyl]-1,2,3,5,6,7-hexahydro-5-methoxy-7-methyl-8-nitro-imidazo[1,2-a]pyridine; or M.UN.14b) 1-[(6-Chloropyridin-3-yl)methyl]-7-methyl-8-nitro-1,2,3,5,6,7-hexahydroimidazo[1,2-a]pyridin-5-ol;

M.UN.16a) 1-isopropyl-N,5-dimethyl-N-pyridazin-4-yl-pyrazole-4-carboxamide; or M.UN.16b) 1-(1,2-dimethylpropyl)-N-ethyl-5-methyl-N-pyridazin-4-yl-pyrazole-4-carboxamide; M.UN.16c) N,5-dimethyl-N-pyridazin-4-yl-1-(2,2,2-trifluoro-1-methyl-ethyl)pyrazole-4-carboxamide; M.UN.16d) 1-[1-(1-cyanocyclopropyl)ethyl]-N-ethyl-5-methyl-N-pyridazin-4-yl-pyrazole-4-carboxamide; M.UN.16e) N-ethyl-1-(2-fluoro-1-methyl-propyl)-5-methyl-N-pyridazin-4-yl-pyrazole-4-carboxamide; M.UN.16f) 1-(1,2-dimethylpropyl)-N,5-dimethyl-N-pyridazin-4-yl-pyrazole-4-carboxamide; M.UN.16g) 1-[1-(1-cyanocyclopropyl)ethyl]-N,5-dimethyl-N-pyridazin-4-yl-pyrazole-4-carboxamide; M.UN.16h) N-methyl-1-(2-fluoro-1-methyl-propyl]-5-methyl-N-pyridazin-4-yl-pyrazole-4-carboxamide; M.UN.16i) 1-(4,4-difluorocyclohexyl)-N-ethyl-5-methyl-N-pyridazin-4-yl-pyrazole-4-carboxamide; or M.UN.16j) 1-(4,4-difluorocyclohexyl)-N,5-dimethyl-N-pyridazin-4-yl-pyrazole-4-carboxamide, M.UN.17a) N-(1-methylethyl)-2-(3-pyridinyl)-2H-indazole-4-carboxamide; M.UN.17b) N-cyclopropyl-2-(3-pyridinyl)-2H-indazole-4-carboxamide; M.UN.17c) N-cyclohexyl-2-(3-pyridinyl)-2H-indazole-4-carboxamide; M.UN.17d) 2-(3-pyridinyl)-N-(2,2,2-trifluoroethyl)-2H-indazole-4-carboxamide; M.UN.17e) 2-(3-pyridinyl)-N-[(tetrahydro-2-furanyl)methyl]-2H-indazole-5-carboxamide; M.UN.17f) methyl 2-[[2-(3-pyridinyl)-2H-indazol-5-yl]carbonyl]hydrazinecarboxylate; M.UN.17g) N-[(2,2-difluorocyclopropyl)methyl]-2-(3-pyridinyl)-2H-indazole-5-carboxamide; M.UN.17h) N-(2,2-difluoropropyl)-2-(3-pyridinyl)-2H-indazole-5-carboxamide; M.UN.17i) 2-(3-pyridinyl)-N-(2-pyrimidinylmethyl)-2H-indazole-5-carboxamide; M.UN.17j) N-[(5-methyl-2-pyrazinyl)methyl]-2-(3-pyridinyl)-2H-indazole-5-carboxamide, M.UN.18. tyclopyrazoflor;

M.UN.19 sarolaner, M.UN.20 lotilaner;

M.UN.21 N-[4-Chloro-3-[[(phenylmethyl)amino]carbonyl]phenyl]-1-methyl-3-(1,1,2,2,2-pentafluoroethyl)-4-(trifluoromethyl)-1H-pyrazole-5-carboxamide; M.UN.22a 2-(3-ethylsulfonyl-2-pyridyl)-3-methyl-6-(trifluoromethyl)imidazo[4,5-b]pyridine, or M.UN.22b 2-[3-ethylsulfonyl-5-(trifluoromethyl)-2-pyridyl]-3-methyl-6-(trifluoromethyl)imidazo[4,5-b]pyridine;

M.UN.23 Isocycloseram;

M.UN.24a) N-[4-chloro-3-(cyclopropylcarbamoyl)phenyl]-2-methyl-5-(1,1,2,2,2-pentafluoroethyl)-4-(trifluoromethyl)pyrazole-3-carboxamide or M.UN.24b) N-[4-chloro-3-[(1-cyanocyclopropyl)carbamoyl]phenyl]-2-methyl-5-(1,1,2,2,2-pentafluoroethyl)-4-(trifluoromethyl)pyrazole-3-carboxamide; M.UN.25 acynonapyr; M.UN.26 benzpyrimoxan; M.UN.27 tigolaner; M.UN.28 Oxazosulfyl;

M.UN.29a) [(2S,3R,4R,5S,6S)-3,5-dimethoxy-6-methyl-4-propoxy-tetrahydropyran-2-yl] N-[4-[1-[4-(trifluoromethoxy)phenyl]-1,2,4-triazol-3-yl]phenyl]carbamate; M.UN.29b) [(2S,3R,4R,5S,6S)-3,4,5-trimethoxy-6-methyl-tetrahydropyran-2-yl] N-[4-[1-[4-(trifluoromethoxy)phenyl]-1,2,4-triazol-3-yl]phenyl]carbamate; M.UN.29c) [(2S,3R,4R,5S,6S)-3,5-dimethoxy-6-methyl-4-propoxy-tetrahydropyran-2-yl] N-[4-[1-[4-(1,1,2,2,2-pentafluoroethoxy)phenyl]-1,2,4-triazol-3-yl]phenyl]carbamate; M.UN.29d) [(2S,3R,4R,5S,6S)-3,4,5-trimethoxy-6-methyl-tetrahydropyran-2-yl] N-[4-[1-[4-(1,1,2,2,2-pentafluoroethoxy)phenyl]-1,2,4-triazol-3-yl]phenyl]carbamate; M.UN.29.e) (2Z)-3-(2-isopropylphenyl)-2-[(E)-[4-[1-[4-(trifluoromethoxy)phenyl]-1,2,4-triazol-3-yl]phenyl]methylenehydrazono]thiazolidin-4-one or M.UN.29f) (2Z)-3-(2-isopropylphenyl)-2-[(E)-[4-[1-[4-(1,1,2,2,2-pentafluoroethoxy)phenyl]-1,2,4-triazol-3-yl]phenyl]methylenehydrazono]thiazolidin-4-one;

M.UN.30a) 2-(6-chloro-3-ethylsulfonyl-imidazo[1,2-a]pyridin-2-yl)-3-methyl-6-(trifluoromethyl)imidazo[4,5-b]pyridine, M.UN.30b) 2-(6-bromo-3-ethylsulfonyl-imidazo[1,2-a]pyridin-2-yl)-3-methyl-6-(trifluoromethyl)imidazo[4,5-b]pyridine, M.UN.30c) 2-(3-ethylsulfonyl-6-iodo-imidazo[1,2-a]pyridin-2-yl)-3-methyl-6-(trifluoromethyl)imidazo[4,5-b]pyridine, M.UN.30d) 2-[3-ethylsulfonyl-6-(trifluoromethyl)imidazo[1,2-a]pyridin-2-yl]-3-methyl-6-(trifluoromethyl)imidazo[4,5-b]pyridine, M.UN.30e) 2-(7-chloro-3-ethylsulfonyl-imidazo[1,2-a]pyridin-2-yl)-3-methyl-6-(trifluoromethyl)imidazo[4,5-b]pyridine, M.UN.30f) 2-(3-ethylsulfonyl-7-iodo-imidazo[1,2-a]pyridin-2-yl)-3-methyl-6-(trifluoromethyl)imidazo[4,5-b]pyridine, M.UN.30g) 3-ethylsulfonyl-6-iodo-2-[3-methyl-6-(trifluoromethyl)imidazo[4,5-b]pyridin-2-yl]imidazo[1,2-a]pyridine-8-carbonitrile, M.UN.30h) 2-[3-ethylsulfonyl-8-fluoro-6-(trifluoromethyl)imidazo[1,2-a]pyridin-2-yl]-3-methyl-6-(trifluoromethyl)imidazo[4,5-b]pyridine, M.UN.30i) 2-[3-ethylsulfonyl-7-(trifluoromethyl)imidazo[1,2-a]pyridin-2-yl]-3-methyl-6-(trifluoromethylsulfinyl)imidazo[4,5-b]pyridine, M.UN.30j) 2-[3-ethylsulfonyl-7-(trifluoromethyl)imidazo[1,2-a]pyridin-2-yl]-3-methyl-6-(trifluoromethyl)imidazo[4,5-c]pyridine, M.UN.30k) 2-(6-bromo-3-ethylsulfonyl-imidazo[1,2-a]pyridin-2-yl)-6-(trifluoromethyl)pyrazolo[4,3-c] pyridine.

The commercially available compounds of the group M listed above may be found in The Pesticide Manual, 17th Edition, C. MacBean, British Crop Protection Council (2015) among other publications. The online Pesticide Manual is updated regularly.

The M.4 cycloxaprid is known from WO2010/069266 and WO2011/069456. M.4A.1 is known from CN 103814937; CN105367557, CN 105481839. M.4A.2, guadipyr, is known from WO 2013/003977, and M.4A.3 (approved as paichongding in China) is known from WO 2007/101369. M.4E.1a) to M.4E.1f) are known from WO2018177970. M.22B.1 is described in CN10171577 and M.22B.2 in CN102126994. Spiropidion M.23.1 is known from WO 2014/191271. M.28.1 and M.28.2 are known from WO2007/101540. M.28.3 is described in WO2005/077934. M.28.4 is described in WO2007/043677. M.28.5a) to M.28.5d) and M.28.5h) are described in WO 2007/006670, WO2013/024009 and WO 2013/024010, M.28.5i) is described in WO2011/085575, M.28.5j) in WO2008/134969, M.28.5k) in US2011/046186 and M.28.5l) in WO2012/034403. M.28.6 can be found in WO2012/034472. M.UN.3 is known from WO2006/089633 and M.UN.4 from WO2008/067911. M.UN.5 is described in WO2006/043635, and biological control agents on the basis of *Bacillus firmus* are described in WO2009/124707. Flupyrimin is described in WO2012/029672. M.UN.8 is known from WO2013/055584. M.UN.9.a) is described in WO2013/050317. M.UN.9.b) is described in WO2014/126208. M.UN.10 is known from WO2010/060379. Broflanilide and M.UN.11.b) to M.UN.11.h) are described in WO2010/018714, and M.UN.11i) to M.UN.11.p) in WO 2010/127926. M.UN.12.a) to M.UN.12.c) are known from WO2010/006713, M.UN.12.d) and M.UN.12.e) are known from WO2012/000896. M.UN.14a) and M.UN.14b) are known from WO2007/101369. M.UN.16.a) to M.UN.16h) are described in WO2010/034737, WO2012/084670, and WO2012/143317, resp., and M.UN.16i) and M.UN.16j) are described in WO2015/055497. M.UN.17a) to M.UN.17.j) are described in WO2015/038503. M.UN.18 Tycloprazoflor is described in US2014/0213448. M.UN.19 is described in WO2014/036056. M.UN.20 is known from WO2014/090918. M.UN.21 is known from EP2910126. M.UN.22a and M.UN.22b are known from WO2015/059039 and WO2015/190316. M.UN.23a and M.UN.23b are known from WO2013/050302. M.UN.24a) and M.UN.24b) are known from WO2012/126766. Acynonapyr M.UN.25 is known from WO 2011/105506. Benzpyrimoxan M.UN.26 is known from WO2016/104516. M.UN.27 is known from WO2016/174049. M.UN.28 Oxazosulfyl is known from WO2017/104592. M.UN.29a) to M.UN.29f) are known from WO2009/102736 or WO2013116053. M.UN.30 is known from WO2013/050302. M.UN.30a) to M.UN.30k) are known from WO2018/052136.

The following list of fungicides, in conjunction with which the compounds of the present invention can be used, is intended to illustrate the possible combinations but does not limit them:

A) Respiration Inhibitors

Inhibitors of complex III at $Q_o$ site: azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxystrobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneaminooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxylmethyl]phenyl]-N-methoxy-carbamate (A.1.22), metyltetrapole (A.1.25), (Z,2E)-5-[1-(2,4-dichlorophenyl)pyrazol-3-yl]-oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), pyriminostrobin (A.1.36), bifujunzhi (A.1.37), 2-(ortho-((2,5-dimethylphenyl-oxymethylen)phenyl)-3-methoxy-acrylic acid methylester (A.1.38);

inhibitors of complex III at $Q_i$ site: cyazofamid (A.2.1), amisulbrom (A.2.2), [(6S,7R,8R)-8-benzyl-3-[(3-hydroxy-4-methoxy-pyridine-2-carbonyl)amino]-6-methyl-4,9-dioxo-1,5-dioxonan-7-yl] 2-methylpropanoate (A.2.3), fenpicoxamid (A.2.4), florylpicoxamid (A.2.5);

inhibitors of complex II: benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.15), penthiopyrad (A.3.16), pydiflumetofen (A.3.17), pyraziflumid (A.3.18), sedaxane (A.3.19), tecloftalam (A.3.20), thifluzamide (A.3.21), inpyrfluxam (A.3.22), pyrapropoyne (A.3.23), fluindapyr (A.3.28), N-[2-[2-chloro-4-(trifluoromethyl)phenoxy]phenyl]-3-(difluoromethyl)-5-fluoro-1-methyl-pyrazole-4-carboxamide (A.3.29), methyl (E)-2-[2-[(5-cyano-2-methyl-phenoxy)methyl]phenyl]-3-methoxy-prop-2-enoate (A.3.30), isoflucypram (A.3.31), 2-(difluoromethyl)-N-(1,1,3-trimethyl-indan-4-yl)pyridine-3-carboxamide (A.3.32), 2-(difluoromethyl)-N-[(3R)-1,1,3-trimethylindan-4-yl]pyridine-3-carboxamide (A.3.33), 2-(difluoromethyl)-N-(3-ethyl-1,1-dimethyl-indan-4-yl)pyridine-3-carboxamide (A.3.34), 2-(difluoromethyl)-N-[(3R)-3-ethyl-1,1-dimethyl-indan-4-yl]pyridine-3-carboxamide (A.3.35), 2-(difluoromethyl)-N-(1,1-dimethyl-3-propyl-indan-4-yl)pyridine-3-carboxamide (A.3.36), 2-(difluoromethyl)-N-[(3R)-1,1-dimethyl-3-propyl-indan-4-yl]pyridine-3-carboxamide (A.3.37), 2-(difluoromethyl)-N-(3-isobutyl-1,1-dimethyl-indan-4-yl)pyridine-3-carboxamide (A.3.38), 2-(difluoromethyl)-N-[(3R)-3-isobutyl-1,1-dimethyl-indan-4-yl]pyridine-3-carboxamide (A.3.39);

other respiration inhibitors: diflumetorim (A.4.1); nitrophenyl derivates: binapacryl (A.4.2), dinobuton (A.4.3), dinocap (A.4.4), fluazinam (A.4.5), meptyldinocap (A.4.6), ferimzone (A.4.7); organometal compounds: fentin salts, e. g. fentin-acetate (A.4.8), fentin chloride (A.4.9) or fentin hydroxide (A.4.10); ametoctradin (A.4.11); silthiofam (A.4.12);

B) Sterol Biosynthesis Inhibitors (SBI Fungicides)

C14 demethylase inhibitors: triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 2-(2,4-difluorophenyl)-1,1-difluoro-3-(tetrazol-1-yl)-1-[5-[4-(2,2,2-trifluoroethoxy)phenyl]-2-pyridyl]propan-2-ol (B.1.31), 2-(2,4-difluorophenyl)-1,1-difluoro-3-(tetrazol-1-yl)-1-[5-[4-(trifluoromethoxy)phenyl]-2-pyridyl]propan-2-ol (B.1.32), ipfentrifluconazole (B.1.37), mefentrifluconazole (B.1.38), 2-(chloromethyl)-2-methyl-5-(p-tolylmethyl)-1-(1,2,4-triazol-1-ylmethyl)cyclopentanol (B.1.43); imidazoles: imazalil (B.1.44), pefurazoate (B.1.45), prochloraz (B.1.46), triflumizol (B.1.47); pyrimidines, pyridines, piperazines: fenarimol (B.1.49), pyrifenox (B.1.50), triforine (B.1.51), [3-(4-chloro-2-fluoro-phenyl)-5-(2,4-difluorophenyl)isoxazol-4-yl]-(3-pyridyl)methanol (B.1.52);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

Other Sterol biosynthesis inhibitors: chlorphenomizole (B.4.1);

C) Nucleic Acid Synthesis Inhibitors phenylamides or acyl amino acid fungicides: benalaxyl (C.1.1), benalaxyl-M (C.1.2), kiralaxyl (C.1.3), metalaxyl (C.1.4), metalaxyl-M (C.1.5), ofurace (C.1.6), oxadixyl (C.1.7);

other nucleic acid synthesis inhibitors: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7), 5-fluoro-2-(4-chlorophenylmethoxy)pyrimidin-4 amine (C.2.8);

D) Inhibitors of Cell Division and Cytoskeleton tubulin inhibitors: benomyl (D.1.1), carbendazim (D.1.2), fuberidazole (D1.3), thiabendazole (D.1.4), thiophanate-methyl (D.1.5), pyridachlometyl (D.1.6), N-ethyl-2-[(3-ethynyl-8-methyl-6-quinolyl)oxy]butanamide (D.1.8), N-ethyl-2-[(3-ethynyl-8-methyl-6-quinolyl)oxy]-2-methylsulfanyl-acetamide (D.1.9), 2-[(3-ethynyl-8-methyl-6-quinolyl)oxy]-N-(2-fluoroethyl)butanamide (D.1.10), 2-[(3-ethynyl-8-methyl-6-quinolyl)oxy]-N-(2-fluoroethyl)-2-methoxy-acetamide (D.1.11), 2-[(3-ethynyl-8-methyl-6-quinolyl)oxy]-N-propyl-butanamide (D.1.12), 2-[(3-ethynyl-8-methyl-6-quinolyl)oxy]-2-methoxy-N-propyl-acetamide (D.1.13), 2-[(3-ethynyl-8-methyl-6-quinolyl)oxy]-2-methylsulfanyl-N-propyl-acetamide (D.1.14), 2-[(3-ethynyl-8-methyl-6-quinolyl)oxy]-N-(2-fluoroethyl)-2-methylsulfanyl-acetamide (D.1.15), 4-(2-bromo-4-fluoro-phenyl)-N-(2-chloro-6-fluoro-phenyl)-2,5-dimethyl-pyrazol-3-amine (D.1.16);

other cell division inhibitors: diethofencarb (D.2.1), ethaboxam (D.2.2), pencycuron (D.2.3), fluopicolide (D.2.4), zoxamide (D.2.5), metrafenone (D.2.6), pyriofenone (D.2.7);

E) Inhibitors of Amino Acid and Protein Synthesis methionine synthesis inhibitors: cyprodinil (E.1.1), mepanipyrim (E.1.2), pyrimethanil (E.1.3);

protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6);

F) Signal Transduction Inhibitors

MAP/histidine kinase inhibitors: fluoroimid (F.1.1), iprodione (F.1.2), procymidone (F.1.3), vinclozolin (F.1.4), fludioxonil (F.1.5);

G protein inhibitors: quinoxyfen (F.2.1);

G) Lipid and Membrane Synthesis Inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7);

compounds affecting cell membrane permeability and fatty acids: propamocarb (G.4.1);

inhibitors of oxysterol binding protein: oxathiapiprolin (G.5.1), fluoxapiprolin (G.5.3), 4-[1-[2-[3-(difluoromethyl)-5-methyl-pyrazol-1-yl]acetyl]-4-piperidyl]-N-tetralin-1-yl-pyridine-2-carboxamide (G.5.4), 4-[1-[2-[3,5-bis(difluoromethyl)pyrazol-1-yl]acetyl]-4-piperidyl]-N-tetralin-1-yl-pyridine-2-carboxamide (G.5.5), 4-[1-[2-[3-(difluoromethyl)-5-(trifluoromethyl)pyrazol-1-yl]acetyl]-4-piperidyl]-N-tetralin-1-yl-pyridine-2-carboxamide (G.5.6), 4-[1-[2-[5-cyclopropyl-3-(difluoromethyl)pyrazol-1-yl]acetyl]-4-piperidyl]-N-tetralin-1-yl-pyridine-2-carboxamide (G.5.7), 4-[1-[2-[5-methyl-3-(trifluoromethyl)pyrazol-1-yl]acetyl]-4-piperidyl]-N-tetralin-1-yl-pyridine-2-carboxamide (G.5.8), 4-[1-[2-[5-(difluoromethyl)-3-(trifluoromethyl)pyrazol-1-yl]acetyl]-4-piperidyl]-N-tetralin-1-yl-pyridine-2-carboxamide (G.5.9), 4-[1-[2-[3,5-bis(trifluoromethyl)pyrazol-1-yl]acetyl]-4-piperidyl]-N-tetralin-1-yl-pyridine-2-carboxamide (G.5.10), (4-[1-[2-[5-cyclopropyl-3-(trifluoromethyl)pyrazol-1-yl]acetyl]-4-piperidyl]-N-tetralin-1-yl-pyridine-2-carboxamide (G.5.11);

H) Inhibitors with Multi Site Action inorganic active substances: Bordeaux mixture (H.1.1), copper (H.1.2), copper acetate (H.1.3), copper hydroxide (H.1.4), copper oxychloride (H.1.5), basic copper sulfate (H.1.6), sulfur (H.1.7);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds: anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H-[1,4]dithiino[2,3-c:5,6-c']dipyrrole-1,3,5,7(2H,6H)-tetraone (H.4.10);

I) Cell Wall Synthesis Inhibitors inhibitors of glucan synthesis: validamycin (I.1.1), polyoxin B (I.1.2);

melanin synthesis inhibitors: pyroquilon (I.2.1), tricyclazole (I.2.2), carpropamid (I.2.3), dicyclomet (I.2.4), fenoxanil (I.2.5);

J) Plant Defence Inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), calcium phosphonate (J.1.11), potassium phosphonate (J.1.12), potassium or sodium bicarbonate (J.1.9), 4-cyclopropyl-N-(2,4-dimethoxyphenyl)thiadiazole-5-carboxamide (J.1.10);

K) Unknown Mode of Action bronopol (K.1.1), chinomethionat (K.1.2), cyflufenamid (K.1.3), cymoxanil (K.1.4), dazomet (K.1.5), debacarb (K.1.6), diclocymet (K.1.7), diclomezine (K.1.8), difenzoquat (K.1.9), difenzoquat-methylsulfate (K.1.10), diphenylamin (K.1.11), fenitropan (K.1.12), fenpyrazamine (K.1.13), flumetover (K.1.14), flusulfamide (K.1.15), flutianil (K.1.16), harpin (K.1.17), methasulfocarb (K.1.18), nitrapyrin (K.1.19), nitrothal-isopropyl (K.1.20), tolprocarb (K.1.21), oxin-copper (K.1.22), proquinazid (K.1.23), tebufloquin (K.1.24), tecloftalam (K.1.25), triazoxide (K.1.26), N'-(4-(4-chloro-3-trifluoromethyl-phenoxy)-2,5-dimethyl-phenyl)-N-ethyl-N-methyl formamidine (K.1.27), N'-(4-(4-fluoro-3-trifluoromethyl-phenoxy)-2,5-dimethyl-phenyl)-N-ethyl-N-methyl formamidine (K.1.28), N'-[4-[[3-[(4-chlorophenyl)methyl]-1,2,4-thiadiazol-5-yl]oxy]-2,5-dimethyl-phenyl]-N-ethyl-N-methyl-formamidine (K.1.29), N'-(5-bromo-6-indan-2-yloxy-2-methyl-3-pyridyl)-N-ethyl-N-methyl-formamidine (K.1.30), N'-[5-bromo-6-[1-(3,5-difluorophenyl)ethoxy]-2-methyl-3-pyridyl]-N-ethyl-N-methyl-formamidine (K.1.31), N'-[5-bromo-6-(4-isopropylcyclohexoxy)-2-methyl-3-pyridyl]-N-ethyl-N-methyl-formamidine (K.1.32), N'-[5-bromo-2-methyl-6-(1-phenylethoxy)-3-pyridyl]-N-ethyl-N-methyl-formamidine (K.1.33), N'-(2-methyl-5-trifluoromethyl-4-(3-trimethylsilanyl-propoxy)-phenyl)-N-ethyl-N-methyl formamidine (K.1.34), N'-(5-difluoromethyl-2-methyl-4-(3-trimethylsilanyl-propoxy)-phenyl)-N-ethyl-N-methyl formamidine (K.1.35), 2-(4-chloro-phenyl)-N-[4-(3,4-dimethoxy-phenyl)-isoxazol-5-yl]-2-prop-2-ynyloxy-acetamide (K.1.36), 3-[5-(4-chloro-phenyl)-2,3-dimethyl-isoxazolidin-3-yl]-pyridine (pyrisoxazole) (K.1.37), 3-[5-(4-methylphenyl)-2,3-dimethyl-isoxazolidin-3 yl]-pyridine (K.1.38), 5-chloro-1-(4,6-dimethoxy-pyrimidin-2-yl)-2-methyl-1H-benzoimidazole (K.1.39), ethyl (Z)-3-amino-2-cyano-3-phenyl-prop-2-enoate (K.1.40), picarbutrazox (K.1.41), pentyl N-[6-[[(Z)-[(1-methyltetrazol-5-yl)-phenyl-methylene]amino]oxymethyl]-2-pyridyl]carbamate (K.1.42), but-3-ynyl N-[6-[[(Z)-[(1-methyltetrazol-5-yl)-phenyl-methylene]amino]oxymethyl]-2-pyridyl]carbamate (K.1.43), ipflufenoquin (K.1.44), quinofumelin (K.1.47), 2-(6-benzyl-2-pyridyl)quinazoline (K.1.50), 2-[6-(3-fluoro-4-methoxy-phenyl)-5-methyl-2-pyridyl]quinazoline (K.1.51), dichlobentiazox (K.1.52), N'-(2,5-dimethyl-4-phenoxy-phenyl)-N-ethyl-N-methyl-formamidine (K.1.53), pyrifenamine (K.1.54).

The fungicides described by common names, their preparation and their activity e.g. against harmful fungi is known; these substances are commercially available.

The active substances referred to as component 2, their preparation and their activity e. g. against harmful fungi is known; these substances are commercially available. The compounds described by IUPAC nomenclature, their preparation and their pesticidal activity are also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 10/139271, WO 11/028657, WO 12/168188, WO 07/006670, WO 11/77514; WO 13/047749, WO 10/069882, WO 13/047441, WO 03/16303, WO 09/90181, WO 13/007767, WO 13/010862, WO 13/127704, WO 13/024009, WO 13/24010, WO 13/047441, WO 13/162072, WO 13/092224, WO 11/135833, CN 1907024, CN 1456054, CN 103387541, CN 1309897, WO 12/84812, CN 1907024, WO 09094442, WO 14/60177, WO 13/116251, WO 08/013622, WO 15/65922, WO 94/01546, EP 2865265, WO 07/129454, WO 12/165511, WO 11/081174, WO 13/47441). Some compounds are identified by their CAS Registry Number which is separated by hyphens into three parts, the first consisting from two up to seven digits, the second consisting of two digits, and the third consisting of a single digit.

Biopesticides

Suitable mixing partners for the compounds of the present invention also include biopesticides.

Biopesticides have been defined as a form of pesticides based on micro-organisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/). Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classified as microbial pesticides, even though they are multicellular.

(2) Biochemical pesticides are naturally occurring substances or structurally-similar and functionally identical to a naturally-occurring substance and extracts from biological sources that control pests or provide other crop protection uses as defined below, but have non-toxic mode of actions (such as growth or developmental regulation, attractants, repellents or defence activators (e.g. induced resistance) and are relatively non-toxic to mammals.

Biopesticides for use against crop diseases have already established themselves on a variety of crops. For example, biopesticides already play an important role in controlling downy mildew diseases. Their benefits include: a 0-Day Pre-Harvest Interval, the ability to use under moderate to severe disease pressure, and the ability to use in mixture or in a rotational program with other registered pesticides.

A major growth area for biopesticides is in the area of seed treatments and soil amendments. Biopesticidal seed treatments are e.g. used to control soil borne fungal pathogens that cause seed rots, damping-off, root rot and seedling blights. They can also be used to control internal seed borne fungal pathogens as well as fungal pathogens that are on the surface of the seed. Many biopesticidal products also show capacities to stimulate plant host defenses and other physiological processes that can make treated crops more resistant to a variety of biotic and abiotic stresses or can regulate plant growth. Many biopesticidal products also show capacities to stimulate plant health, plant growth and/or yield enhancing activity.

The following list of biopesticides, in conjunction with which the compounds of the present invention can be used, is intended to illustrate the possible combinations but does not limit them:

L) Biopesticides

L1) Microbial pesticides with fungicidal, bactericidal, viricidal and/or plant defense activator activity: *Ampelomyces quisqualis, Aspergillus flavus, Aureobasidium pullulans, Bacillus altitudinis, B. amyloliquefaciens, B. amyloliquefaciens* ssp. *plantarum* (also referred to as *B. velezensis*), *B. megaterium, B. mojavensis, B. mycoides, B. pumilus, B. simplex, B. solisalsi, B. subtilis, B. subtilis* var. *amyloliquefaciens, B. velezensis, Candida oleophila, C. saitoana, Clavibacter michiganensis* (bacteriophages), *Coniothyrium minitans, Cryphonectria parasitica, Cryptococcus albidus, Dilophosphora alopecuri, Fusarium oxysporum, Clonostachys rosea f. catenulate* (also named *Gliocladium catenulatum*), *Gliocladium roseum, Lysobacter antibioticus, L. enzymogenes, Metschnikowia fructicola, Microdochium dimerum, Microsphaeropsis ochracea, Muscodor albus, Paenibacillus alvei, Paenibacillus epiphyticus, P. polymyxa, Pantoea vagans, Penicillium bilaiae, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseoviridis, S. lydicus, S. violaceusniger, Talaromyces flavus, Trichoderma asperelloides, T. asperellum, T. atroviride, T. fertile, T. gamsii, T. harmatum, T. harzianum, T. polysporum, T. stromaticum, T. virens, T. viride, Typhula phacorrhiza, Ulocladium oudemansii, Verticillium dahlia*, zucchini yellow mosaic virus (avirulent strain);

L2) Biochemical pesticides with fungicidal, bactericidal, viricidal and/or plant defense activator activity: harpin protein, *Reynoutria sachalinensis* extract;

L3) Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai, B. t.* ssp. *israelensis, B. t.* ssp. *galleriae, B. t.* ssp. *kurstaki, B. t.* ssp. *tenebrionis, Beauveria bassiana, B. brongniartii, Burkholderia* spp., *Chromobacterium subtsugae, Cydia pomonella* granulovirus (CpGV), *Cryptophlebia leucotreta* granulovirus (CrleGV), *Flavobacterium* spp., *Helicoverpa armigera* nucleopolyhedrovirus (HearNPV), *Helicoverpa zea* nucleopolyhedrovirus (HzNPV), *Helicoverpa zea* single capsid nucleopolyhedrovirus (HzSNPV), *Heterorhabditis bacteriophora, Isaria fumosorosea, Lecanicillium longisporum, L. muscarium, Metarhizium anisopliae, M. anisopliae* var. *anisopliae, M. anisopliae* var. *acridum, Nomuraea rileyi, Paecilomyces fumosoroseus, P. lilacinus, Paenibacillus popilliae, Pasteuria* spp., *P. nishizawae, P. penetrans, P. ramosa, P. thornea, P. usgae, Pseudomonas fluorescens, Spodoptera littoralis* nucleopolyhedrovirus (SpliNPV), *Steinernema carpocapsae, S. feltiae, S. kraussei, Streptomyces galbus, S. microflavus;*

L4) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, (R)-1-octen-3-ol, pentatermanone, (E,Z,Z)-3,8,11-tetradecatrienyl acetate, (Z,E)-9,12-tetradecadien-1-yl acetate, (Z)-7-tetradecen-2-one, (Z)-9-tetradecen-1-yl acetate, (Z)-11-tetradecenal, (Z)-11-tetradecen-1-ol, extract of *Chenopodium ambrosiodes*, Neem oil, Quillay extract;

L5) Microbial pesticides with plant stress reducing, plant growth regulator, plant growth promoting and/or yield enhancing activity: *Azospirillum amazonense, A. brasilense, A. lipoferum, A. irakense, A. halopraeferens, Bradyrhizobium* spp., *B. elkanii, B. japonicum, B. liaoningense, B. lupini, Delftia acidovorans, Glomus intraradices, Mesorhizobium* spp., *Rhizobium leguminosarum* bv. *phaseoli, R. l.* bv. *trifolii, R. l.* bv. *viciae, R. tropici, Sinorhizobium meliloti.*

The biopesticides from group L1) and/or L2) may also have insecticidal, acaricidal, molluscidal, pheromone, nematicidal, plant stress reducing, plant growth regulator, plant growth promoting and/or yield enhancing activity. The biopesticides from group L3) and/or L4) may also have fungicidal, bactericidal, viricidal, plant defense activator, plant stress reducing, plant growth regulator, plant growth promoting and/or yield enhancing activity. The biopesticides from group L5) may also have fungicidal, bactericidal, viricidal, plant defense activator, insecticidal, acaricidal, molluscidal, pheromone and/or nematicidal activity.

Many of these biopesticides have been deposited under deposition numbers mentioned herein (the prefices such as ATCC or DSM refer to the acronym of the respective culture collection, are referred to in litera-ture, registered and/or are commercially available: mixtures of *Aureobasidium pullulans* DSM 14940 and DSM 14941 isolated in 1989 in Konstanz, Germany (e. g. blastospores in BlossomProtect® from bio-ferm GmbH, Austria), *Azospirillum brasilense* Sp245 originally isolated in wheat region of South Brazil (Passo Fundo) at least prior to 1980 (BR 11005; e. g. GELFIX® Gramíneas from BASF Agricultural Specialties Ltd., Brazil), *A. brasilense* strains Ab-V5 and Ab-V6 (e. g. in AzoMax from Novozymes BioAg Produtos papra Agricultura Ltda., Quattro Barras, Brazil or Simbiose-Maíz® from Simbiose-Agro, Brazil; Plant Soil 331, 413-425, 2010), *Bacillus amyloliquefaciens* strain AP-188 (NRRL B-50615 and B-50331; U.S. Pat. No. 8,445,255); *B. amyloliquefaciens* ssp. *plantarum* strains formerly also sometimes referred to as *B. subtilis*, recently together with *B. methylotrophicus*, and *B. velezensis* classified as *B. velezensis* (Int. J. Syst. Evol. Microbiol. 66, 1212-1217, 2016): *B. a.* ssp. *plantarum* or *B. velezensis* D747 isolated from air in Kikugawa-shi, Japan (US 20130236522 A1; FERM BP-8234; e. g. Double Nickel™ 55 WDG from Certis LLC, USA), *B. a.* ssp. *plantarum* or *B. velezensis* FZB24 isolated from soil in Brandenburg, Germany (also called SB3615; DSM 96-2; J. Plant Dis. Prot. 105, 181-197, 1998; e. g. Taegro® from Novozyme Biologicals, Inc., USA), *B. a.* ssp. *plantarum* or *B. velezensis* FZB42 isolated from soil in Brandenburg, Germany (DSM 23117; J. Plant Dis. Prot. 105, 181-197, 1998; e. g. RhizoVital® 42 from AbiTEP GmbH, Germany), *B. a.* ssp. *plantarum* or *B. velezensis* MBI600 isolated from faba bean in Sutton Bonington, Nottinghamshire, U.K. at least before 1988 (also called 1430; NRRL B-50595; US 2012/0149571 A1; e. g. Integral® from BASF Corp., USA), *B. a.* ssp. *plantarum* or *B. velezensis* QST-713 isolated from peach orchard in 1995 in California, U.S.A. (NRRL B-21661; e. g. Serenade® MAX from Bayer Crop Science LP, USA), *B. a.* ssp. *plantarum* or *B. velezensis* TJ1000 isolated in 1992 in South Dakota, U.S.A. (also called 1BE; ATCC BAA-390; CA 2471555 A1; e. g. QuickRoots™ from TJ Technologies, Watertown, SD, USA); *B. firmus* CNCM I-1582, a variant of parental strain EIP-N1 (CNCM I-1556) isolated from soil of central plain area of Israel (WO 2009/126473, U.S. Pat. No. 6,406,690; e. g. Votivo® from Bayer CropScience LP, USA), *B. pumilus* GHA 180 isolated from apple tree rhizosphere in Mexico (IDAC 260707-01; e. g. PRO-MIX® BX from Premier Horticulture, Quebec, Canada), *B. pumilus* INR-7 otherwise referred to as BU-F22 and BU-F33 isolated at least before 1993 from cucumber infested by *Erwinia tracheiphila* (NRRL B-50185, NRRL B-50153; U.S. Pat. No. 8,445,255), *B. pumilus* KFP9F isolated from the rhizosphere of grasses in South Africa at least before 2008 (NRRL B-50754; WO 2014/029697; e. g. BAC-UP or FUSION-P from BASF Agricultural Specialities (Pty) Ltd., South Africa), *B. pumilus* QST 2808 was isolated from soil collected in Pohnpei, Federated States of Micronesia, in 1998 (NRRL B-30087; e. g. Sonata® or Ballad® Plus from Bayer Crop Science LP, USA), *B. simplex* ABU 288 (NRRL B-50304; U.S. Pat. No. 8,445,255), *B. subtilis* FB17 also called UD 1022 or UD10-22 isolated from red beet roots in North America (ATCC PTA-11857; System. Appl. Microbiol. 27, 372-379, 2004; US 2010/0260735; WO 2011/109395); *B. thuringiensis* ssp. *aizawai* ABTS-1857 isolated from soil taken from a lawn in Ephraim, Wisconsin, U.S.A., in 1987 (also called ABG-6346; ATCC SD-1372; e. g. XenTari® from BioFa AG, Münsingen, Germany), *B. t.* ssp. *kurstaki* ABTS-351 identical to HD-1 isolated in 1967 from diseased Pink Bollworm black larvae in Brownsville, Texas, U.S.A. (ATCC SD-1275; e. g. Dipel® DF from Valent BioSciences, IL, USA), *B. t.* ssp. *kurstaki* SB4 isolated from *E. saccharina* larval cadavers (NRRL B-50753; e. g. Beta Pro® from BASF Agricultural Specialities (Pty) Ltd., South Africa), *B. t.* ssp. *tenebrionis* NB-176-1, a mutant of strain NB-125, a wild type strain isolated in 1982 from a dead pupa of the beetle *Tenebrio molitor* (DSM 5480; EP 585 215 B1; e. g. Novodor® from Valent BioSciences, Switzerland), *Beauveria bassiana* GHA (ATCC 74250; e. g. BotaniGard® 22WGP from Laverlam Int. Corp., USA), *B. bassiana* JW-1 (ATCC 74040; e. g. Naturalis® from CBC (Europe) S.r.l., Italy), *B. bassiana* PPRI 5339 isolated from the larva of the tortoise beetle *Conchyloctenia punctata* (NRRL 50757; e. g. BroadBand® from BASF Agricultural Specialities (Pty) Ltd., South Africa), *Bradyrhizobium elkanii* strains SEMIA 5019 (also called 29W) isolated in Rio de Janeiro, Brazil and SEMIA 587 isolated in 1967 in the State of Rio Grande do Sul, from an area previously inoculated with a North American isolate, and used in commercial inoculants since 1968 (Appl. Environ. Microbiol. 73(8), 2635, 2007; e. g. GELFIX 5 from BASF Agricultural Specialties Ltd., Brazil), *B. japonicum* 532c isolated from Wisconsin field in U.S.A. (Nitragin 61A152; Can. J. Plant. Sci. 70, 661-666, 1990; e. g. in Rhizoflo®, Histick®, Hicoat® Super from BASF Agricultural Specialties Ltd., Canada), *B. japonicum* E-109 variant of strain USDA 138 (INTA E109, SEMIA 5085; Eur. J. Soil Biol. 45, 28-35, 2009; Biol. Fertil. Soils 47, 81-89, 2011); *B. japonicum* strains deposited at SEMIA known from Appl. Environ. Microbiol. 73(8), 2635, 2007: SEMIA 5079 isolated from soil in Cerrados region, Brazil by Embrapa-Cerrados used in commercial inoculants since 1992 (CPAC 15; e. g. GELFIX 5 or ADHERE 60 from BASF Agricultural Specialties Ltd., Brazil), *B. japonicum* SEMIA 5080 obtained under lab conditions by Embrapa-Cerrados in Brazil and used in commercial inoculants since 1992, being a natural variant of SEMIA 586 (CB1809) originally isolated in U.S.A. (CPAC 7; e. g. GELFIX 5 or ADHERE 60 from BASF Agricultural Specialties Ltd., Brazil); *Burkholderia* sp. A396 isolated from soil in Nikko, Japan, in 2008 (NRRL B-50319; WO 2013/032693; Marrone Bio Innovations, Inc., USA), *Coniothyrium minitans* CON/M/91-08 isolated from oilseed rape (WO 1996/021358; DSM 9660; e. g. Contans® WG, Intercept® WG from Bayer CropScience AG, Germany), harpin (alpha-beta) protein (Science 257, 85-88, 1992; e. g. Messenger™ or HARP-N-Tek from Plant Health Care plc, U.K.), *Helicoverpa armigera* nucleopolyhedrovirus (HearNPV) (J. Invertebrate Pathol. 107, 112-126, 2011; e. g. Helicovex® from Adermatt Biocontrol, Switzerland; Diplomata® from Koppert, Brazil; Vivus® Max from AgBiTech Pty Ltd., Queensland, Australia), *Helicoverpa zea* single capsid nucleopolyhedrovirus (HzSNPV) (e. g. Gemstar® from Certis LLC, USA), *Helicoverpa zea* nucleopolyhedrovirus ABA-NPV-U (e. g. Heligen® from AgBiTech Pty Ltd., Queensland, Australia), *Heterorhabditis bacteriophora* (e. g. Nemasys® G from BASF Agricultural Specialities Limited, UK), *Isaria fumosorosea* Apopka-97 isolated from mealy bug on gynura in Apopka, Florida, U.S.A. (ATCC 20874; Biocontrol Science Technol. 22(7), 747-761, 2012; e. g. PFR-97™ or PreFeRal® from Certis LLC, USA), *Metarhizium anisopliae* var. *anisopliae* F52 also called 275 or V275 isolated from codling moth in Austria (DSM 3884, ATCC 90448; e. g. Met52® Novozymes Biologicals BioAg Group, Canada), *Metschnikowia fructicola* 277 isolated from grapes in the central part of Israel (U.S. Pat. No. 6,994,849; NRRL Y-30752; e. g. formerly Shemer® from Agrogreen, Israel), *Paecilomyces ilacinus* 251 isolated from infected nematode eggs in the Philippines (AGAL 89/030550; WO1991/02051; Crop Protection 27, 352-361, 2008; e. g. BioAct® from Bayer CropScience AG, Germany and MeloCon® from Certis, USA), *Paenibacillus alvei* NAS6G6 isolated from the rhizosphere of grasses in South Africa at least before 2008 (WO 2014/029697; NRRL B-50755; e.g. BAC-UP from BASF Agricultural Specialities (Pty) Ltd., South Africa), *Paenibacillus* strains isolated from soil samples from a variety of European locations including Germany: *P. epiphyticus* Lu17015 (WO 2016/020371; DSM 26971), *P. polymyxa* ssp. *plantarum* Lu16774 (WO 2016/020371; DSM 26969), *P. p.* ssp. *plantarum* strain Lu17007 (WO 2016/020371; DSM 26970); *Pasteuria nishizawae* Pn1 isolated from a soybean field in the mid-2000s in Illinois, U.S.A. (ATCC SD-5833; Federal Register 76(22), 5808, Feb. 2, 2011; e.g. Clariva™ PN from Syngenta Crop Protection, LLC, USA), *Penicillium bilaiae* (also called *P. bilaii*) strains ATCC 18309 (=ATCC 74319), ATCC 20851 and/or ATCC 22348 (=ATCC 74318) originally isolated from soil in Alberta, Canada (Fertilizer Res. 39, 97-103, 1994; Can. J. Plant Sci. 78(1), 91-102, 1998; U.S. Pat. No. 5,026,417, WO 1995/017806; e. g. Jump Start®, Provide® from Novozymes Biologicals BioAg Group, Canada), *Reynoutria sachalinensis* extract (EP 0307510 B1; e. g. Regalia® SC from Marrone BioInnovations, Davis, CA, USA or Milsana® from BioFa AG, Germany), *Steinernema carpocapsae* (e. g. Millenium® from BASF Agricultural Specialities Limited, UK), *S. feltiae* (e. g. Nemashield® from BioWorks, Inc., USA; Nemasys® from BASF Agricultural Specialities Limited, UK), *Streptomyces microflavus* NRRL B-50550 (WO 2014/124369; Bayer CropScience, Germany), *Trichoderma asperelloides* JM41R isolated in South Africa (NRRL 50759; also referred to as *T. fertile*; e. g. Trichoplus® from BASF Agricultural Specialities (Pty) Ltd., South Africa), *T. harzianum* T-22 also called KRL-AG2 (ATCC 20847; BioControl 57, 687-696, 2012; e. g. Plantshield® from BioWorks Inc., USA or SabrEx™ from Advanced Biological Marketing Inc., Van Wert, OH, USA).

According to the invention, the solid material (dry matter) of the biopesticides (with the exception of oils such as Neem oil) are considered as active components (e.g. to be obtained after drying or evaporation of the extraction or suspension medium in case of liquid formulations of the microbial pesticides).

In accordance with the present invention, the weight ratios and percentages used herein for a biological extract such as Quillay extract are based on the total weight of the dry content (solid material) of the respective extract(s).

The total weight ratios of compositions comprising at least one microbial pesticide in the form of viable microbial cells including dormant forms, can be determined using the amount of CFU of the respective microorganism to calculate the total weight of the respective active component with the following equation that $1\times10^{10}$ CFU equals one gram of total weight of the respective active component. Colony forming unit is measure of viable microbial cells, in particular fungal and bacterial cells. In addition, here "CFU" may also be understood as the number of (juvenile) individual nematodes in case of (entomopathogenic) nematode biopesticides, such as *Steinernema feltiae.*

When mixtures comprising microbial pesticides are employed in crop protection, the application rates preferably range from about $1\times10^{6}$ to $5\times10^{15}$ (or more) CFU/ha, preferably from about $1\times10^{8}$ to about $1\times10^{13}$ CFU/ha, and even more preferably from about $1\times10^{9}$ to about $1\times10^{12}$ CFU/ha. In the case of (entomopathogenic) nematodes as microbial pesticides (e. g. *Steinernema feltiae*), the application rates preferably range inform about $1\times10^{5}$ to $1\times10^{12}$ (or more), more preferably from $1\times10^{8}$ to $1\times10^{11}$, even more preferably from $5\times10^{8}$ to $1\times10^{10}$ individuals (e. g. in the form of eggs, juvenile or any other live stages, preferably in an infective juvenile stage) per ha.

When mixtures comprising microbial pesticides are employed in seed treatment, the application rates with respect to plant propagation material preferably range from about $1\times10^{6}$ to $1\times10^{12}$ (or more) CFU/seed. Preferably, the concentration is about $1\times10^{6}$ to about $1\times10^{9}$ CFU/seed. In the case of the microbial pesticides II, the application rates with respect to plant propagation material also preferably range from about $1\times10^{7}$ to $1\times10^{14}$ (or more) CFU per 100 kg of seed, preferably from $1\times10^{9}$ to about $1\times10^{12}$ CFU per 100 kg of seed.

Formulations

The invention also relates to agrochemical compositions comprising an auxiliary and at least one compound of the present invention or a mixture thereof.

An agrochemical composition comprises a pesticidally effective amount of a compound of the present invention or a mixture thereof. The term "pesticidally effective amount" is defined below.

The compounds of the present invention or the mixtures thereof can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl-sulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinylalcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compounds of the present invention on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:

i) Water-Soluble Concentrates (SL, LS)

10-60 wt % of a compound I according to the invention and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible Concentrates (DC)

5-25 wt % of a compound I according to the invention and 1-10 wt % dispersant (e. g. polyvinylpyrrolidone) are dissolved in up to 100 wt % organic solvent (e.g. cyclohexanone). Dilution with water gives a dispersion.

iii) Emulsifiable Concentrates (EC)

15-70 wt % of a compound I according to the invention and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)

5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)

In an agitated ball mill, 20-60 wt % of a compound I according to the invention are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a compound I according to the invention are ground finely with addition of up to 100 wt % dispersants and wetting agents (e.g. sodium lignosulfonate and alcohol ethoxylate) and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.

ix) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable microemulsion.

x) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of a polyurea microcapsule. The monomers amount to 1-10 wt %. The wt % relate to the total CS composition.

xi) Dustable Powders (DP, DS)

1-10 wt % of a compound I according to the invention are ground finely and mixed intimately with up to 100 wt % solid carrier, e.g. finely divided kaolin.

xii) Granules (GR, FG)

0.5-30 wt % of a compound I according to the invention is ground finely and associated with up to 100 wt % solid carrier (e.g. silicate). Granulation is achieved by extrusion, spray-drying or the fluidized bed.

xiii) Ultra-Low Volume Liquids (UL)

1-50 wt % of a compound I according to the invention are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e. g. components comprising compounds of the present invention and/or mixing partners as defined above, may be mixed by the user in a spray tank and further auxiliaries and additives may be added, if appropriate.

In a further embodiment, either individual components of the composition according to the invention or partially premixed components, e. g. components comprising compounds of the present invention and/or mixing partners as defined above, can be applied jointly (e.g. after tank mix) or consecutively.

Application Methods

The compounds of the present invention are suitable for use in protecting crops, plants, plant propagation materials, such as seeds, or soil or water, in which the plants are growing, from attack or infestation by animal pests. Therefore, the present invention also relates to a plant protection method, which comprises contacting crops, plants, plant propagation materials, such as seeds, or soil or water, in which the plants are growing, to be protected from attack or infestation by animal pests, with a pesticidally effective amount of a compound of the present invention.

The compounds of the present invention are also suitable for use in combating or controlling animal pests. Therefore, the present invention also relates to a method of combating or controlling animal pests, which comprises contacting the animal pests, their habitat, breeding ground, or food supply, or the crops, plants, plant propagation materials, such as seeds, or soil, or the area, material or environment in which the animal pests are growing or may grow, with a pesticidally effective amount of a compound of the present invention.

The compounds of the present invention are effective through both contact and ingestion. Furthermore, the compounds of the present invention can be applied to any and all developmental stages, such as egg, larva, pupa, and adult.

The compounds of the present invention can be applied as such or in form of compositions comprising them as defined above. Furthermore, the compounds of the present invention can be applied together with a mixing partner as defined above or in form of compositions comprising said mixtures as defined above. The components of said mixture can be applied simultaneously, jointly or separately, or in succession, that is immediately one after another and thereby creating the mixture "in situ" on the desired location, e.g. the plant, the sequence, in the case of separate application, generally not having any effect on the result of the control measures.

The application can be carried out both before and after the infestation of the crops, plants, plant propagation materials, such as seeds, soil, or the area, material or environment by the pests.

Suitable application methods include inter alia soil treatment, seed treatment, in furrow application, and foliar application. Soil treatment methods include drenching the soil, drip irrigation (drip application onto the soil), dipping roots, tubers or bulbs, or soil injection. Seed treatment techniques include seed dressing, seed coating, seed dusting, seed soaking, and seed pelleting. In furrow applications typically include the steps of making a furrow in cultivated land, seeding the furrow with seeds, applying the pesticidally active compound to the furrow, and closing the furrow. Foliar application refers to the application of the pesticidally active compound to plant foliage, e.g. through spray equipment. For foliar applications, it can be advantageous to modify the behavior of the pests by use of pheromones in combination with the compounds of the present invention. Suitable pheromones for specific crops and pests are known to a skilled person and publicly available from databases of pheromones and semiochemicals, such as http://www.pherobase.com.

As used herein, the term "contacting" includes both direct contact (applying the compounds/compositions directly on the animal pest or plant—typically to the foliage, stem or roots of the plant) and indirect contact (applying the compounds/compositions to the locus, i.e. habitat, breeding ground, plant, seed, soil, area, material or environment in which a pest is growing or may grow, of the animal pest or plant).

The term "animal pest" includes arthropods, gastropods, and nematodes. Preferred animal pests according to the invention are arthropods, preferably insects and arachnids, in particular insects. Insects, which are of particular relevance for crops, are typically referred to as crop insect pests.

The term "crop" refers to both, growing and harvested crops.

The term "plant" includes cereals, e.g. durum and other wheat, rye, barley, triticale, oats, rice, or maize (fodder maize and sugar maize/sweet and field corn); beet, e.g. sugar beet or fodder beet; fruits, such as pomes, stone fruits or soft fruits, e.g. apples, pears, plums, peaches, nectarines, almonds, cherries, papayas, strawberries, raspberries, blackberries or gooseberries; leguminous plants, such as beans, lentils, peas, alfalfa or soybeans; oil plants, such as rapeseed (oilseed rape), turnip rape, mustard, olives, sunflowers, coconut, cocoa beans, castor oil plants, oil palms, ground nuts or soybeans; cucurbits, such as squashes, pumpkins, cucumber or melons; fiber plants, such as cotton, flax, hemp or jute; citrus fruit, such as oranges, lemons, grapefruits or mandarins; vegetables, such as eggplant, spinach, lettuce (e.g. iceberg lettuce), chicory, cabbage, asparagus, cabbages, carrots, onions, garlic, leeks, tomatoes, potatoes, cucurbits or sweet peppers; lauraceous plants, such as avocados, cinnamon or camphor; energy and raw material plants, such as corn, soybean, rapeseed, sugar cane or oil palm; tobacco; nuts, e.g. walnuts; pistachios; coffee; tea; bananas; vines (table grapes and grape juice grape vines); hop; sweet leaf (also called Stevia); natural rubber plants or ornamental and forestry plants, such as flowers (e.g. carnation, petunias, geranium/pelargoniums, pansies and impatiens), shrubs, broad-leaved trees (e.g. poplar) or evergreens, e.g. conifers; eucalyptus; turf; lawn; grass such as grass for animal feed or ornamental uses. Preferred plants include potatoes sugar beets, tobacco, wheat, rye, barley, oats, rice, corn, cotton, soybeans, rapeseed, legumes, sunflowers, coffee or sugar cane; fruits; vines; ornamentals; or vegetables, such as cucumbers, tomatoes, beans or squashes.

The term "cultivated plants" is to be understood as including plants which have been modified by mutagenesis or genetic engineering in order to provide a new trait to a plant or to modify an already present trait.

Mutagenesis includes techniques of random mutagenesis using X-rays or mutagenic chemicals, but also techniques of targeted mutagenesis, in order to create mutations at a specific locus of a plant genome. Targeted mutagenesis techniques frequently use oligonucleotides or proteins like CRISPR/Cas, zinc-finger nucleases, TALENs or meganucleases to achieve the targeting effect.

Genetic engineering usually uses recombinant DNA techniques to create modifications in a plant genome which under natural circumstances cannot readily be obtained by cross breeding, mutagenesis or natural recombination. Typically, one or more genes are integrated into the genome of a plant in order to add a trait or improve a trait. These integrated genes are also referred to as transgenes in the art, while plant comprising such transgenes are referred to as transgenic plants. The process of plant transformation usually produces several transformation events, which differ in the genomic locus in which a transgene has been integrated. Plants comprising a specific transgene on a specific genomic locus are usually described as comprising a specific "event", which is referred to by a specific event name. Traits which have been introduced in plants or have been modified include in particular herbicide tolerance, insect resistance, increased yield and tolerance to abiotic conditions, like drought.

Herbicide tolerance has been created by using mutagenesis as well as using genetic engineering. Plants which have been rendered tolerant to acetolactate synthase (ALS) inhibitor herbicides by conventional methods of mutagenesis and breeding comprise plant varieties commercially available under the name Clearfield®. However, most of the herbicide tolerance traits have been created via the use of transgenes.

Herbicide tolerance has been created to glyphosate, glufosinate, 2,4-D, dicamba, oxynil herbicides, like bromoxynil and ioxynil, sulfonylurea herbicides, ALS inhibitor herbicides and 4-hydroxyphenylpyruvate dioxygenase (HPPD) inhibitors, like isoxaflutole and mesotrione.

Transgenes which have been used to provide herbicide tolerance traits comprise: for tolerance to glyphosate: cp4 epsps, epsps grg23ace5, mepsps, 2mepsps, gat4601, gat4621 and goxv247, for tolerance to glufosinate: pat and bar, for tolerance to 2,4-D: aad-1 and aad-12, for tolerance to dicamba: dmo, for tolerance to oxynil herbicides: bxn, for tolerance to sulfonylurea herbicides: zm-hra, csr1-2, gm-hra, S4-HrA, for tolerance to ALS inhibitor herbicides: csr1-2, for tolerance to HPPD inhibitor herbicides: hppdPF, W336 and avhppd-03.

Transgenic corn events comprising herbicide tolerance genes are for example, but not excluding others, DAS40278, MON801, MON802, MON809, MON810, MON832, MON87411, MON87419, MON87427, MON88017, MON89034, NK603, GA21, MZHG0JG, HCEM485, VCO-Ø1981-5, 676, 678, 680, 33121, 4114, 59122, 98140, Bt10, Bt176, CBH-351, DBT418, DLL25, MS3, MS6, MZIR098, T25, TC1507 and TC6275.

Transgenic soybean events comprising herbicide tolerance genes are for example, but not excluding others, GTS 40-3-2, MON87705, MON87708, MON87712, MON87769, MON89788, A2704-12, A2704-21, A5547-127, A5547-35, DP356043, DAS44406-6, DAS68416-4, DAS-81419-2, GU262, SYHTØH2, W62, W98, FG72 and CV127.

Transgenic cotton events comprising herbicide tolerance genes are for example, but not excluding others, 19-51a, 31707, 42317, 81910, 281-24-236, 3006-210-23, BXN10211, BXN10215, BXN10222, BXN10224, MON1445, MON1698, MON88701, MON88913, GHB119, GHB614, LLCotton25, T303-3 and T304-40.

Transgenic canola events comprising herbicide tolerance genes are for example, but not excluding others, MON88302, HCR-1, HCN10, HCN28, HCN92, MS1, MS8, PHY14, PHY23, PHY35, PHY36, RF1, RF2 and RF3.

Insect resistance has mainly been created by transferring bacterial genes for insecticidal proteins to plants. Transgenes which have most frequently been used are toxin genes of *Bacillus* spec. and synthetic variants thereof, like cry1A, cry1Ab, cry1Ab-Ac, cry1Ac, cry1A.105, cry1F, cry1Fa2, cry2Ab2, cry2Ae, mcry3A, ecry3.1Ab, cry3Bb1, cry34Ab1, cry35Ab1, cry9C, vip3A(a), vip3Aa20. However, also genes of plant origin have been transferred to other plants. In particular genes coding for protease inhibitors, like CpTI and pinII. A further approach uses transgenes in order to produce double stranded RNA in plants to target and down-regulate insect genes. An example for such a transgene is dvsnf7.

Transgenic corn events comprising genes for insecticidal proteins or double stranded RNA are for example, but not excluding others, Bt10, Bt11, Bt176, MON801, MON802, MON809, MON810, MON863, MON87411, MON88017, MON89034, 33121, 4114, 5307, 59122, TC1507, TC6275, CBH-351, MIR162, DBT418 and MZIR098.

Transgenic soybean events comprising genes for insecticidal proteins are for example, but not excluding others, MON87701, MON87751 and DAS-81419.

Transgenic cotton events comprising genes for insecticidal proteins are for example, but not excluding others, SGK321, MON531, MON757, MON1076, MON15985, 31707, 31803, 31807, 31808, 42317, BNLA-601, Event1, COT67B, COT102, T303-3, T304-40, GFM Cry1A, GK12, MLS 9124, 281-24-236, 3006-210-23, GHB119 and SGK321.

Increased yield has been created by increasing ear biomass using the transgene athb17, being present in corn event MON87403, or by enhancing photosynthesis using the transgene bbx32, being present in the soybean event MON87712.

Cultivated plants comprising a modified oil content have been created by using the transgenes: gm-fad2-1, Pj.D6D, Nc.Fad3, fad2-1A and fatb1-A. Soybean events comprising at least one of these genes are: 260-05, MON87705 and MON87769.

Tolerance to abiotic conditions, in particular to tolerance to drought, has been created by using the transgene cspB, comprised by the corn event MON87460 and by using the transgene Hahb-4, comprised by soybean event IND-ØØ41Ø-5.

Traits are frequently combined by combining genes in a transformation event or by combining different events during the breeding process. Preferred combination of traits are herbicide tolerance to different groups of herbicides, insect tolerance to different kind of insects, in particular tolerance to lepidopteran and coleopteran insects, herbicide tolerance with one or several types of insect resistance, herbicide tolerance with increased yield as well as a combination of herbicide tolerance and tolerance to abiotic conditions.

Plants comprising singular or stacked traits as well as the genes and events providing these traits are well known in the art. For example, detailed information as to the mutagenized or integrated genes and the respective events are available from websites of the organizations "International Service for the Acquisition of Agri-biotech Applications (ISAAA)" and the "Center for Environmental Risk Assessment (CERA)", Further information on specific events and methods to detect them can be found for canola events MS1, MS8, RF3, GT73, MON88302, KK179 in WO01/031042, WO01/041558, WO01/041558, WO02/036831, WO11/153186, WO13/003558, for cotton events MON1445, MON15985, MON531(MON15985), LLCotton25, MON88913, COT102, 281-24-236, 3006-210-23, COT67B, GHB614, T304-40, GHB119, MON88701, 81910 in WO02/034946, WO02/100163, WO02/100163, WO03/013224, WO04/072235, WO04/039986, WO05/103266, WO05/103266, WO06/128573, WO07/017186, WO08/122406, WO08/151780, WO12/134808, WO13/112527, for corn events GA21, MON810, DLL25, TC1507, MON863, MIR604, LY038, MON88017, 3272, 59122, NK603, MIR162, MON89034, 98140, 32138, MON87460, 5307, 4114, MON87427, DAS40278, MON87411, 33121, MON87403, MON87419 in WO98/044140, U.S. Ser. No. 02/102,582, U.S. Ser. No. 03/126,634, WO04/099447, WO04/011601, WO05/103301, WO05/061720, WO05/059103, WO06/098952, WO06/039376, US2007/292854, WO07/142840, WO07/140256, WO08/112019, WO09/103049, WO09/111263, WO10/077816, WO11/084621, WO11/062904, WO11/022469, WO13/169923, WO14/116854, WO15/053998, WO15/142571, for potato events E12, F10, J3, J55, V11, X17, Y9 in WO14/178910, WO14/178913, WO14/178941, WO14/179276, WO16/183445, WO17/062831, WO17/062825, for rice events LLRICE06, LLRICE601, LLRICE62 in WO00/026345, WO00/026356, WO00/026345 for soybean events H7-1, MON89788, A2704-12, A5547-127, DP305423, DP356043, MON87701, MON87769, CV127, MON87705, DAS68416-4, MON87708, MON87712, SYHT0H2, DAS81419, DAS81419xDAS44406-6, MON87751 in WO04/074492, WO06/130436, WO06/108674, WO06/108675, WO08/054747, WO08/002872, WO09/064652, WO09/102873, WO10/080829, WO10/037016, WO11/066384, WO11/034704, WO12/051199, WO12/082548, WO13/016527, WO13/016516, WO14/201235.

The use of compositions according to the invention on cultivated plants may result in effects which are specific to a cultivated plant comprising a certain gene or event. These effects might involve changes in growth behavior or changed resistance to biotic or abiotic stress factors. Such effects may in particular comprise enhanced yield, enhanced resistance or tolerance to insects, nematodes, fungal, bacterial, mycoplasma, viral or viroid pathogens as well as early vigour, early or delayed ripening, cold or heat tolerance as well as changed amino acid or fatty acid spectrum or content.

It has surprisingly been found that the pesticidal activity of the compounds of the present invention may be enhanced by the insecticidal trait of a modified plant. Furthermore, it has been found that the compounds of the present invention are suitable for preventing insects to become resistant to the insecticidal trait or for combating pests, which already have become resistant to the insecticidal trait of a modified plant. Moreover, the compounds of the present invention are suitable for combating pests, against which the insecticidal trait is not effective, so that a complementary insecticidal activity can advantageously be used.

The term "plant propagation material" refers to all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "seed" embraces seeds and plant propagules of all kinds including but not limited to true seeds, seed pieces, suckers, corms, bulbs, fruit, tubers, grains, cuttings, cut shoots and the like, and means in a preferred embodiment true seeds.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment, in furrow application or of application to the pests dwelling place or nest, the quantity of active ingredient ranges from 0.0001 to 500 g per 100 $m^2$, preferably from 0.001 to 20 g per 100 $m^2$.

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare, more desirably from 10 g to 50 g per hectare, e.g., 10 to 20 g per hectare, 20 to 30 g per hectare, 30 to 40 g per hectare, or 40 to 50 g per hectare.

The compounds of the invention are particularly suitable for use in the treatment of seeds in order to protect the seeds from insect pests, in particular from soil-living insect pests, and the resulting seedling's roots and shoots against soil pests and foliar insects. The invention therefore also relates to a method for the protection of seeds from insects, in particular from soil insects, and of the seedling's roots and shoots from insects, in particular from soil and foliar insects, said method comprising treating the seeds before sowing and/or after pregermination with a compound of the invention. The protection of the seedling's roots and shoots is preferred. More preferred is the protection of seedling's shoots from piercing and sucking insects, chewing insects and nematodes.

The term "seed treatment" comprises all suitable seed treatment techniques known in the art, such as seed dressing, seed coating, seed dusting, seed soaking, seed pelleting, and in-furrow application methods. Preferably, the seed treatment application of the active compound is carried out by spraying or by dusting the seeds before sowing of the plants and before emergence of the plants.

The invention also comprises seeds coated with or containing the active compound. The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is for example seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, Brassica species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment of seeds from plants, which have been modified by mutagenesis or genetic engineering, and which e.g. tolerate the action of herbicides or fungicides or insecticides. Such modified plants have been described in detail above.

Conventional seed treatment formulations include for example flowable concentrates FS, solutions LS, suspoemulsions (SE), powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter. Preferably, the formulations are applied such that germination is not included.

The active substance concentrations in ready-to-use formulations, which may be obtained after two-to-tenfold dilution, are preferably from 0.01 to 60% by weight, more preferably from 0.1 to 40% by weight.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of the compounds of the invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

In the treatment of seed, the application rates of the compounds of the invention are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed, e.g. from 1 g to 100 g or from 5 g to 100 g per 100 kg of seed.

The invention therefore also relates to seed comprising a compound of the invention, or an agriculturally useful salt thereof, as defined herein. The amount of the compound of the invention or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

The compounds of the invention may also be used for improving the health of a plant. Therefore, the invention also relates to a method for improving plant health by treating a plant, plant propagation material and/or the locus where the plant is growing or is to grow with an effective and non-phytotoxic amount of a compound of the invention.

As used herein "an effective and non-phytotoxic amount" means that the compound is used in a quantity which allows to obtain the desired effect but which does not give rise to any phytotoxic symptom on the treated plant or on the plant grown from the treated propagule or treated soil.

The terms "plant" and "plant propagation material" are defined above.

"Plant health" is defined as a condition of the plant and/or its products which is determined by several aspects alone or in combination with each other such as yield (for example increased biomass and/or increased content of valuable ingredients), quality (for example improved content or composition of certain ingredients or shelf life), plant vigour (for example improved plant growth and/or greener leaves ("greening effect"), tolerance to abiotic (for example drought) and/or biotic stress (for example disease) and production efficiency (for example, harvesting efficiency, processability).

The above identified indicators for the health condition of a plant may be interdependent and may result from each other. Each indicator is defined in the art and can be determined by methods known to a skilled person.

The compounds of the invention are also suitable for use against non-crop insect pests. For use against said non-crop pests, compounds of the invention can be used as bait composition, gel, general insect spray, aerosol, as ultra-low volume application and bed net (impregnated or surface applied). Furthermore, drenching and rodding methods can be used.

As used herein, the term "non-crop insect pest" refers to pests, which are particularly relevant for non-crop targets, such as ants, termites, wasps, flies, ticks, mosquitoes, bed bugs, crickets, or cockroaches.

The bait can be a liquid, a solid or a semisolid preparation (e.g. a gel). The bait employed in the composition is a product, which is sufficiently attractive to incite insects such as ants, termites, wasps, flies, mosquitoes, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature (e.g. http://www.pherobase.com), and are known to those skilled in the art.

For use in bait compositions, the typical content of active ingredient is from 0.001 weight % to 15 weight %, desirably from 0.001 weight % to 5% weight % of active compound.

Formulations of the compounds of the invention as aerosols (e.g in spray cans), oil sprays or pump sprays are highly suitable for professional or non-professional users for controlling pests such as flies, fleas, ticks, bed bugs, mosquitoes or cockroaches. Aerosol recipes are preferably composed of the active compound, solvents, furthermore auxiliaries such as emulsifiers, perfume oils, if appropriate stabilizers, and, if required, propellants.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder.

The compounds of the invention and its compositions can be used for protecting wooden materials such as trees, board fences, sleepers, frames, artistic artifacts, etc. and buildings, but also construction materials, furniture, leathers, fibers, vinyl articles, electric wires and cables etc. from ants, termites and/or wood or textile destroying beetles, and for controlling ants and termites from doing harm to crops or human beings (e.g. when the pests invade into houses and public facilities or nest in yards, orchards or parks).

Customary application rates in the protection of materials are, for example, from 0.001 g to 2000 g or from 0.01 g to 1000 g of active compound per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

Pests

The compounds of the invention are especially suitable for efficiently combating animal pests such as arthropods, gastropods and nematodes including but not limited to:

insects from the order of Lepidoptera, for example *Achroia grisella, Acleris* spp. such as *A. fimbriana, A. gloverana, A. variana; Acrolepiopsis assectella, Acronicta major, Adoxophyes* spp. such as *A. cyrtosema, A. orana; Aedia leucomelas, Agrotis* spp. such as *A. exclamationis, A. fucosa, A. ipsilon, A. orthogoma, A. segetum, A. subterranea; Alabama argillacea, Aleurodicus dispersus, Alsophila pometaria, Ampelophaga rubiginosa, Amyelois transitella, Anacampsis sarcitella, Anagasta kuehniella, Anarsia lineatella, Anisota senatoria, Antheraea pernyi, Anticarsia* (=*Thermesia*) spp. such as *A. gemmatalis; Apamea* spp., *Aproaerema modicella, Archips* spp. such as *A. argyrospila, A. fuscocupreanus, A. rosana, A. xyloseanus; Argyresthia conjugella, Argyroploce* spp., *Argyrotaenia* spp. such as *A. velutinana; Athetis mindara, Austroasca viridigrisea, Autographa gamma, Autographa nigrisigna, Barathra brassicae, Bedellia* spp., *Bonagota salubricola, Borbo cinnara, Bucculatrix thurberiella, Bupalus piniarius, Busseola* spp., *Cacoecia* spp. such as *C. murinana, C. podana; Cactoblastis cactorum, Cadra cautella, Calingo braziliensis, Caloptilis theivora, Capua reticulana, Carposina* spp. such as *C. niponensis, C. sasakii; Cephus* spp., *Chaetocnema aridula, Cheimatobia brumata, Chilo* spp. such as *C. indicus, C. suppressalis, C. partellus; Choreutis pariana, Choristoneura* spp. such as *C. conflictana, C. fumiferana, C. longicellana, C. murinana, C. occidentalis, C. rosaceana; Chrysodeixis* (=*Pseudoplusia*) spp. such as *C. eriosoma, C. includens; Cirphis unipuncta, Clysia ambiguella, Cnaphalocerus* spp., *Cnaphalocrocis medinalis, Cnephasia* spp., *Cochylis hospes, Coleophora* spp., *Colias eurytheme, Conopomorpha* spp., *Conotrachelus* spp., *Copitarsia* spp., *Corcyra cephalonica, Crambus caliginosellus, Crambus teterrellus, Crocidosema* (=*Epinotia*) *aporema, Cydalima* (=*Diaphania*) *perspectalis, Cydia* (=*Carpocapsa*) spp. such as *C. pomonella, C. latiferreana; Dalaca noctuides, Datana integerrima, Dasychira pinicola, Dendrolimus* spp. such as *D. pini, D. spectabilis, D. sibiricus; Desmia funeralis, Diaphania* spp. such as *D. nitidalis, D. hyalinata; Diatraea grandiosella, Diatraea saccharalis, Diphthera festiva, Earias* spp. such as *E. insulana, E. vittella; Ecdytolopha aurantianu, Egira* (=*Xylomyges*) *curialis, Elasmopalpus lignosellus, Eldana*

*saccharina, Endopiza viteana, Ennomos subsignaria, Eoreuma loftini, Ephestia* spp. such as *E. cautella, E. elutella, E. kuehniella; Epinotia aporema, Epiphyas postvittana, Erannis tiliaria, Erionota thrax, Etiella* spp., *Eulia* spp., *Eupoecilia ambiguella, Euproctis chrysorrhoea, Euxoa* spp., *Evetria bouliana, Faronta albilinea, Feltia* spp. such as *F. subterranean; Galleria mellonella, Gracillaria* spp., *Grapholita* spp. such as *G. funebrana, G. molesta, G. inopinata; Halysidota* spp., *Harrisina americana, Hedylepta* spp., *Helicoverpa* spp. such as *H. armigera* (=*Heliothis armigera*), *H. zea* (=*Heliothis zea*); *Heliothis* spp. such as *H. assulta, H. subflexa, H. virescens; Hellula* spp. such as *H. undalis, H. rogatalis; Helocoverpa gelotopoeon, Hemileuca oliviae, Herpetogramma licarsisalis, Hibernia defoliaria, Hofmannophila pseudospretella, Homoeosoma electellum, Homona magnanima, Hypena scabra, Hyphantria cunea, Hyponomeuta padella, Hyponomeuta malinellus, Kakivoria flavofasciata, Keiferia lycopersicella, Lambdina fiscellaria fiscellaria, Lambdina fiscellaria lugubrosa, Lamprosema indicata, Laspeyresia molesta, Leguminivora glycinivorella, Lerodea eufala, Leucinodes orbonalis, Leucoma salicis, Leucoptera* spp. such as *L. coffeella, L. scitella; Leuminivora lycinivorella, Lithocolletis blancardella, Lithophane antennata, Llattia octo* (=*Amyna axis*), *Lobesia botrana, Lophocampa* spp., *Loxagrotis albicosta, Loxostege* spp. such as *L. sticticalis, L. cereralis; Lymantria* spp. such as *L. dispar, L. monacha; Lyonetia clerkella, Lyonetia prunifoliella, Malacosoma* spp. such as *M. americanum, M. californicum, M. constrictum, M. neustria; Mamestra* spp. such as *M. brassicae, M. configurata; Mamstra brassicae, Manduca* spp. such as *M. quinquemaculata, M. sexta; Marasmia* spp, *Marmara* spp., *Maruca testulalis, Megalopyge lanata, Melanchra picta, Melanitis leda, Mocis* spp. such as *M. lapites, M. repanda; Mocis latipes, Monochroa fragariae, Mythimna separata, Nemapogon cloacella, Neoleucinodes elegantalis, Nepytia* spp., *Nymphula* spp., *Oiketicus* spp., *Omiodes indicata, Omphisa anastomosalis, Operophtera brumata, Orgyia pseudotsugata, Oria* spp., *Orthaga thyrisalis, Ostrinia* spp. such as *O. nubilalis; Oulema oryzae, Paleacrita vernata, Panolis flammea, Parnara* spp., *Papaipema nebris, Papilio cresphontes, Paramyelois transitella, Paranthrene regalis, Paysandisia archon, Pectinophora* spp. such as *P. gossypiella; Peridroma saucia, Perileucoptera* spp., such as *P. coffeella; Phalera bucephala, Phryganidia californica, Phthorimaea* spp. such as *P. operculella; Phyllocnistis citrella, Phyllonorycter* spp. such as *P. blancardella, P. crataegella, P. issikii, P. ringoniella; Pieris* spp. such as *P. brassicae, P. rapae, P. napi; Pilocrocis tripunctata, Plathypena scabra, Platynota* spp. such as *P. flavedana, P. idaeusalis, P. stultana; Platyptilia carduidactyla, Plebejus argus, Plodia interpunctella, Plusia* spp, *Plutella maculipennis, Plutella xylostella, Pontia protodica, Prays* spp., *Prodenia* spp., *Proxenus lepigone, Pseudaletia* spp. such as *P. sequax, P. unipuncta; Pyrausta nubilalis, Rachiplusia nu, Richia albicosta, Rhizobius ventralis, Rhyacionia frustrana, Sabulodes aegrotata, Schizura concinna, Schoenobius* spp., *Schreckensteinia festaliella, Scirpophaga* spp. such as *S. incertulas, S. innotata; Scotia segetum, Sesamia* spp. such as *S. inferens, Seudyra subflava, Sitotroga cerealella, Sparganothis pilleriana, Spilonota lechriaspis, S. ocellana, Spodoptera* (=*Lamphygma*) spp. such as *S. cosmoides, S. eridania, S. exigua, S. frugiperda, S. latisfascia, S. littoralis, S. litura, S. omithogalli; Stigmella* spp., *Stomopteryx subsecivella, Strymon bazochii, Sylepta derogata, Synanthedon* spp. such as *S. exitiosa, Tecia solanivora, Telehin licus, Thaumatopoea pityocampa, Thaumatotibia* (=*Cryptophlebia*) *leucotreta, Thaumetopoea pityocampa, Thecla* spp., *Theresimima ampelophaga, Thyrinteina* spp, *Tildenia inconspicuella, Tinea* spp. such as *T. cloacella, T. pellionella; Tineola bisselliella, Tortrix* spp. such as *T. viridana; Trichophaga tapetzella, Trichoplusia* spp. such as *T. ni; Tuta* (=*Scrobipalpula*) *absoluta, Udea* spp. such as *U. rubigalis, U. rubigalis; Virachola* spp., *Yponomeuta padella*, and *Zeiraphera canadensis;* insects from the order of Coleoptera, for example *Acalymma vittatum, Acanthoscehdes obtectus, Adoretus* spp., *Agelastica alni, Agrilus* spp. such as *A. anxius, A. planipennis, A. sinuatus; Agriotes* spp. such as *A. fuscicollis, A. lineatus, A. obscurus; Alphitobius diaperinus, Amphimallus solstitialis, Anisandrus dispar, Anisoplia austriaca, Anobium punctatum, Anomala corpulenta, Anomala rufocuprea, Anoplophora* spp. such as *A. glabripennis; Anthonomus* spp. such as *A. eugenii, A. grandis, A. pomorum; Anthrenus* spp., *Aphthona euphoridae, Apion* spp., *Apogonia* spp., *Athous haemorrhoidalis, Atomaria* spp. such as *A. linearis; Attagenus* spp., *Aulacophora femoralis, Blastophagus piniperda, Blitophaga undata, Bruchidius obtectus, Bruchus* spp. such as *B. lentis, B. pisorum, B. rufimanus; Byctiscus betulae, Callidiellum rufipenne, Callopistria floridensis, Callosobruchus chinensis, Cameraria ohridella, Cassida nebulosa, Cerotoma trifurcata, Cetonia aurata, Ceuthorhynchus* spp. such as *C. assimilis, C. napi; Chaetocnema tibialis, Cleonus mendicus, Conoderus* spp. such as *C. vespertinus; Conotrachelus nenuphar, Cosmopolites* spp., *Costelytra zealandica, Crioceris asparagi, Cryptolestes ferrugineus, Cryptorhynchus lapathi, Ctenicera* spp. such as *C. destructor; Curculio* spp., *Cylindrocopturus* spp., *Cyclocephala* spp., *Dactylispa balyi, Dectes texanus, Dermestes* spp., *Diabrotica* spp. such as *D. undecimpunctata, D. speciosa, D. longicornis, D. semipunctata, D. virgifera; Diaprepes abbreviates, Dichocrocis* spp., *Dicladispa armigera, Diloboderus abderus, Diocalandra frumenti* (*Diocalandra stigmaticollis*), *Enaphalodes rufulus, Epilachna* spp. such as *E. varivestis, E. vigintioctomaculata; Epitrix* spp. such as *E. hirtipennis, E. similaris; Eutheola humilis, Eutinobothrus brasiliensis, Faustinus cubae, Gibbium psylloides, Gnathocerus cornutus, Hellula undalis, Heteronychus arator, Hylamorpha elegans, Hylobius abietis, Hylotrupes bajulus, Hypera* spp. such as *H. brunneipennis, H. postica; Hypomeces squamosus, Hypothenemus* spp., *Ips typographus, Lachnosterna consanguinea, Lasioderma serricorne, Latheticus oryzae, Lathridius* spp., *Lema* spp. such as *L. bilineata, L. melanopus; Leptinotarsa* spp. such as *L. decemlineata; Leptispa pygmaea, Limonius californicus, Lissorhoptrus oryzophilus, Lixus* spp., *Luperodes* spp., *Lyctus* spp. such as *L. bruneus; Liogenys fuscus, Macrodactylus* spp. such as *M. subspinosus; Maladera matrida, Megaplatypus mutates, Megascelis* spp., *Melanotus communis, Meligethes* spp. such as *M. aeneus; Melolontha* spp. such as *M. hippocastani, M. melolontha; Metamasius hemipterus, Microtheca* spp., *Migdolus* spp. such as *M. fryanus, Monochamus* spp. such as *M. alternatus; Naupactus xanthographus, Niptus*

*hololeucus, Oberia brevis, Oemona hirta, Oryctes rhinoceros, Oryzaephilus surinamensis, Oryzaphagus oryzae, Otiorrhynchus sulcatus, Otiorrhynchus ovatus, Otiorrhynchus sulcatus, Oulema melanopus, Oulema oryzae, Oxycetonia jucunda, Phaedon* spp. such as *P. brassicae, P. cochleariae; Phoracantha recurva, Phyllobius pyri, Phyllopertha horticola, Phyllophaga* spp. such as *P. helleri; Phyllotreta* spp. such as *P. chrysocephala, P. nemorum, P. striolata, P. vittula; Phyllopertha horticola, Popillia japonica, Premnotrypes* spp., *Psacothea hilaris, Psylliodes chrysocephala, Prostephanus truncates, Psylliodes* spp., *Ptinus* spp., *Pulga saltona, Rhizopertha dominica, Rhynchophorus* spp. such as *R. billineatus, R. ferrugineus, R. palmarum, R. phoenicis, R. vulneratus; Saperda candida, Scolytus schevyrewi, Scyphophorus acupunctatus, Sitona lineatus, Sitophilus* spp. such as *S. granaria, S. oryzae, S. zeamais; Sphenophorus* spp. such as *S. levis; Stegobium paniceum, Sternechus* spp. such as *S. subsignatus; Strophomorphus ctenotus, Symphyletes* spp., *Tanymecus* spp., *Tenebrio molitor, Tenebrioides mauretanicus, Tribolium* spp. such as *T. castaneum; Trogoderma* spp., *Tychius* spp., *Xylotrechus* spp. such as *X. pyrrhoderus*; and, *Zabrus* spp. such as *Z. tenebrioides;* insects from the order of Diptera e.g. *Aedes* spp. such as *A. aegypti, A. albopictus, A. vexans; Anastrepha ludens, Anopheles* spp. such as *A. albimanus, A. crucians, A. freeborni, A. gambiae, A. leucosphyrus, A. maculipennis, A. minimus, A. quadrimaculatus, A. sinensis; Bactrocera invadens, Bibio hortulanus, Calliphora erythrocephala, Calliphora vicina, Ceratitis capitata, Chrysomyia* spp. such as *C. bezziana, C. hominivorax, C. macellaria; Chrysops atlanticus, Chrysops discalis, Chrysops silacea, Cochliomyia* spp. such as *C. hominivorax; Contarinia* spp. such as *C. sorghicola; Cordylobia anthropophaga, Culex* spp. such as *C. nigripalpus, C. pipiens, C. quinquefasciatus, C. tarsalis, C. tritaeniorhynchus; Culicoides furens, Culiseta inornata, Culiseta melanura, Cuterebra* spp., *Dacus cucurbitae, Dacus oleae, Dasineura brassicae, Dasineura oxycoccana, Delia* spp. such as *D. antique, D. coarctata, D. platura, D. radicum; Dermatobia hominis, Drosophila* spp. such as *D. suzukii, Fannia* spp. such as *F. canicularis; Gastraphilus* spp. such as *G. intestinalis; Geomyza tipunctata, Glossina* spp. such as *G. fuscipes, G. morsitans, G. palpalis, G. tachinoides; Haematobia irritans, Haplodiplosis equestris, Hippelates* spp., *Hylemyia* spp. such as *H. platura; Hypoderma* spp. such as *H. lineata; Hyppobosca* spp., *Hydrellia philippina, Leptoconops torrens, Liriomyza* spp. such as *L. sativae, L. trifolii; Lucilia* spp. such as *L. caprina, L. cuprina, L. sericata; Lycoria pectoralis, Mansonia titillanus, Mayetiola* spp. such as *M. destructor; Musca* spp. such as *M. autumnalis, M. domestica; Muscina stabulans, Oestrus* spp. such as *O. ovis; Opomyza forum, Oscinella* spp. such as *O. frit; Orseolia oryzae, Pegomya hysocyami, Phlebotomus argentipes, Phorbia* spp. such as *P. antiqua, P. brassicae, P. coarctata; Phytomyza gymnostoma, Prosimulium mixtum, Psila rosae, Psorophora columbiae, Psorophora discolor, Rhagoletis* spp. such as *R. cerasi, R. cingulate, R. indifferens, R. mendax, R. pomonella; Rivellia quadrifasciata, Sarcophaga* spp. such as *S. haemorrhoidalis; Simulium vittatum, Sitodiplosis mosellana, Stomoxys* spp. such as *S. calcitrans; Tabanus* spp. such as *T. atratus, T. bovinus, T. lineola, T. similis; Tannia* spp., *Thecodiplosis japonensis, Tipula oleracea, Tipula paludosa*, and *Wohlfahrtia* spp;

insects from the order of Thysanoptera for example, *Baliothrips biformis, Dichromothrips corbetti, Dichromothrips* ssp., *Echinothrips americanus, Enneothrips flavens, Frankliniella* spp. such as *F. fusca, F. occidentalis, F. tritici; Heliothrips* spp., *Hercinothrips femoralis, Kakothrips* spp., *Microcephalothrips abdominalis, Neohydatothrips samayunkur, Pezothrips kellyanus, Rhipiphorothrips cruentatus, Scirtothrips* spp. such as *S. citri, S. dorsalis, S. perseae; Stenchaetothrips* spp, *Taeniothrips cardamoni, Taeniothrips inconsequens, Thrips* spp. such as *T. imagines, T. hawaiiensis, T. oryzae, T. palmi, T. parvispinus, T. tabaci;* insects from the order of Hemiptera for example, *Acizzia jamatonica, Acrosternum* spp. such as *A. hilare; Acyrthosipon* spp. such as *A. onobrychis, A. pisum; Adelges laricis, Adelges tsugae, Adelphocoris* spp., such as *A. rapidus, A. superbus; Aeneolamia* spp., *Agonoscena* spp., *Aulacorthum solani, Aleurocanthus woglumi, Aleurodes* spp., *Aleurodicus disperses, Aleurolobus barodensis, Aleurothrixus* spp., *Amrasca* spp., *Anasa tristis, Antestiopsis* spp., *Anuraphis cardui, Aonidiella* spp., *Aphanostigma piri, Aphidula nasturtii, Aphis* spp. such as *A. craccivora, A. fabae, A. forbesi, A. gossypii, A. grossulariae, A. maidiradicis, A. pomi, A. sambuci, A. schneideri, A. spiraecola; Arboridia apicalis, Arilus critatus, Aspidiella* spp., *Aspidiotus* spp., *Atanus* spp., *Aulacaspis yasumatsui, Aulacorthum solani, Bactericera cockerelli* (*Paratrioza cockerelli*), *Bemisia* spp. such as *B. argentifolii, B. tabaci* (*Aleurodes tabaci*); *Blissus* spp. such as *B. leucopterus; Brachycaudus* spp. such as *B. cardui, B. helichrysi, B. persicae, B. prunicola; Brachycolus* spp., *Brachycorynella asparagi, Brevicoryne brassicae, Cacopsylla* spp. such as *C. fulguralis, C. pyricola* (*Psylla piri*); *Calligypona marginata, Calocoris* spp., *Campylomma livida, Capitophorus horni, Carneocephala fulgida, Cavelerius* spp., *Ceraplastes* spp., *Ceratovacuna lanigera, Ceroplastes ceriferus, Cerosipha gossypii, Chaetosiphon fragaefolii, Chionaspis tegalensis, Chlorita onukii, Chromaphis juglandicola, Chrysomphalus ficus, Cicadulina mbila, Cimex* spp. such as *C. hemipterus, C. lectularius; Coccomytilus halli, Coccus* spp. such as *C. hesperidum, C. pseudomagnoliarum; Corythucha arcuata, Creontiades dilutus, Cryptomyzus ribis, Chrysomphalus aonidum, Cryptomyzus ribis, Ctenarytaina spatulata, Cyrtopeltis notatus, Dalbulus* spp., *Dasynus piperis, Dialeurodes* spp. such as *D. citrifolii; Dalbulus maidis, Diaphorina* spp. such as *D. citri; Diaspis* spp. such as *D. bromeliae; Dichelops furcatus, Diconocoris hewetti, Doralis* spp., *Dreyfusia nordmannianae, Dreyfusia piceae, Drosicha* spp., *Dysaphis* spp. such as *D. plantaginea, D. pyri, D. radicola; Dysaulacorthum pseudosolani, Dysdercus* spp. such as *D. cingulatus, D. intermedius; Dysmicoccus* spp., *Edessa* spp., *Geocoris* spp., *Empoasca* spp. such as *E. fabae, E. solana; Epidiaspis leperii, Eriosoma* spp. such as *E. lanigerum, E. pyricola; Erythroneura* spp., *Eurygaster* spp. such as *E. integriceps; Euscelis bilobatus, Euschistus* spp. such as *E. heros, E. impictiventris, E. servus; Fiorinia theae, Geococcus coffeae, Glycaspis brimblecombei, Halyomorpha* spp. such as *H. halys; Heliopeltis* spp., *Homalodisca vitripennis* (=*H. coagulata*), *Horcias nobilellus, Hyalopterus pruni, Hyperomyzus lactucae, Icerya* spp. such as *I. purchase; Idiocerus* spp., *Idioscopus* spp., *Laodel-*

*phax striatellus, Lecanium* spp., *Lecanoideus floccissimus, Lepidosaphes* spp. such as *L. ulmi; Leptocorisa* spp., *Leptoglossus phyllopus, Lipaphis erysimi, Lygus* spp. such as *L. hesperus, L. lineolaris, L. pratensis; Maconellicoccus hirsutus, Marchalina hellenica, Macropes excavatus, Macrosiphum* spp. such as *M. rosae, M. avenae, M. euphorbiae; Macrosteles quadrilineatus, Mahanarva fimbriolata, Megacopta cribraria, Megoura viciae, Melanaphis pyrarius, Melanaphis sacchari, Melanocallis* (=*Tinocallis*) *caryaefoliae, Metcafiella* spp., *Metopolophium dirhodum, Monellia costalis, Monelliopsis pecanis, Myzocallis coryli, Murgantia* spp., *Myzus* spp. such as *M. ascalonicus, M. cerasi, M. nicotianae, M. persicae, M. varians; Nasonovia ribis-nigri, Neotoxoptera formosana, Neomegalotomus* spp, *Nephotettix* spp. such as *N. malayanus, N. nigropictus, N. parvus, N. virescens; Nezara* spp. such as *N. viridula; Nilaparvata lugens, Nysius huttoni, Oebalus* spp. such as *O. pugnax; Oncometopia* spp., *Orthezia praelonga, Oxycaraenus hyalinipennis, Parabemisia myricae, Parlatoria* spp., *Parthenolecanium* spp. such as *P. corn, P. persicae; Pemphigus* spp. such as *P. bursarius, P. populivenae; Peregrinus maidis, Perkinsiella saccharicida, Phenacoccus* spp. such as *P. aceris, P. gossypii; Phloeomyzus passerinii, Phorodon humuli, Phylloxera* spp. such as *P. devastatrix, Piesma quadrata, Piezodorus* spp. such as *P. guildinii; Pinnaspis aspidistrae, Planococcus* spp. such as *P. citri, P. ficus; Prosapia bicincta, Protopulvinaria pyriformis, Psallus seriatus, Pseudacysta persea, Pseudaulacaspis pentagona, Pseudococcus* spp. such as *P. comstocki; Psylla* spp. such as *P. mali; Pteromalus* spp., *Pulvinaria amygdali, Pyrilla* spp., *Quadraspidiotus* spp., such as *Q. perniciosus; Quesada gigas, Rastrococcus* spp., *Reduvius senilis, Rhizoecus americanus, Rhodnius* spp., *Rhopalomyzus ascalonicus, Rhopalosiphum* spp. such as *R. pseudobrassicas, R. insertum, R. maidis, R. padi; Sagatodes* spp., *Sahlbergella singularis, Saissetia* spp., *Sappaphis mala, Sappaphis mali, Scaptocoris* spp., *Scaphoides titanus, Schizaphis graminum, Schizoneura lanuginosa, Scotinophora* spp., *Selenaspidus articulatus, Sitobion avenae, Sogata* spp., *Sogatella furcifera, Solubea insularis, Spissistilus festinus* (=*Stictocephala festina*), *Stephanitis nashi, Stephanitis pyrioides, Stephanitis takeyai, Tenalaphara malayensis, Tetraleurodes perseae, Therioaphis maculate, Thyanta* spp. such as *T. accerra, T. perditor; Tibraca* spp., *Tomaspis* spp., *Toxoptera* spp. such as *T. aurantii; Trialeurodes* spp. such as *T. abutilonea, T. ricin, T. vaporariorum; Triatoma* spp., *Trioza* spp., *Typhlocyba* spp., *Unaspis* spp. such as *U. citri, U. yanonensis*; and *Viteus vitifolii,*

Insects from the order Hymenoptera for example *Acanthomyops interjectus, Athalia rosae, Atta* spp. such as *A. capiguara, A. cephalotes, A. cephalotes, A. laevigata, A. robusta, A. sexdens, A. texana, Bombus* spp., *Brachymyrmex* spp., *Camponotus* spp. such as *C. floridanus, C. pennsylvanicus, C. modoc; Cardiocondyla nuda, Chalibion* sp, *Crematogaster* spp., *Dasymutilla occidentalis, Diprion* spp., *Dolichovespula maculata, Dorymyrmex* spp., *Dryocosmus kuriphilus, Formica* spp., *Hoplocampa* spp. such as *H. minuta, H. testudinea; Iridomyrmex humilis, Lasius* spp. such as *L. niger, Linepithema humile, Liometopum* spp., *Leptocybe invasa, Monomorium* spp. such as *M. pharaonis, Monomorium, Nylandria fulva, Pachycondyla chinensis, Paratrechina longicornis, Paravespula* spp., such as *P. germanica, P. pennsylvanica, P. vulgaris; Pheidole* spp. such as *P. megacephala; Pogonomyrmex* spp. such as *P. barbatus, P. californicus, Polistes rubiginosa, Prenolepis impairs, Pseudomyrmex gracilis, Schelipron* spp., *Sirex cyaneus, Solenopsis* spp. such as *S. geminata, S.invicta, S. molesta, S. richteri, S. xyloni, Sphecius speciosus, Sphex* spp., *Tapinoma* spp. such as *T. melanocephalum, T. sessile; Tetramorium* spp. such as *T. caespitum, T. bicarinatum, Vespa* spp. such as *V. crabro; Vespula* spp. such as *V. squamosal; Wasmannia auropunctata, Xylocopa* sp;

Insects from the order Orthoptera for example *Acheta domesticus, Calliptamus italicus, Chortoicetes terminifera, Ceuthophilus* spp., *Diastrammena asynamora, Dociostaurus maroccanus, Gryllotalpa* spp. such as *G. africana, G. gryllotalpa; Gryllus* spp., *Hieroglyphus daganensis, Kraussaria angulifera, Locusta* spp. such as *L. migratoria, L. pardalina; Melanoplus* spp. such as *M. bivittatus, M. femurrubrum, M. mexicanus, M. sanguinipes, M. spretus; Nomadacris septemfasciata, Oedaleus senegalensis, Scapteriscus* spp., *Schistocerca* spp. such as *S. americana, S. gregaria, Stemopelmatus* spp., *Tachycines asynamorus*, and *Zonozerus variegatus;*

Pests from the Class Arachnida for example Acari, e.g. of the families Argasidae, Ixodidae and Sarcoptidae, such as *Amblyomma* spp. (e.g. *A. americanum, A. variegatum, A. maculatum*), *Argas* spp. such as *A. persicu*), *Boophilus* spp. such as *B. annulatus, B. decoloratus, B. microplus, Dermacentor* spp. such as *D. silvarum, D. andersoni, D. variabilis, Hyalomma* spp. such as *H. truncatum, Ixodes* spp. such as *I. ricinus, I. rubicundus, I. scapularis, I. holocyclus, I. pacificus, Rhipicephalus sanguineus, Ornithodorus* spp. such as *O. moubata, O. hermsi, O. turicata, Ornithonyssus bacoti, Otobius megnini, Dermanyssus gallinae, Psoroptes* spp. such as *P. ovis, Rhipicephalus* spp. such as *R. sanguineus, R. appendiculatus, Rhipicephalus evertsi, Rhizoglyphus* spp., *Sarcoptes* spp. such as *S. scabiei*; and Family Eriophyidae including *Aceria* spp. such as *A. sheldoni, A. anthocoptes, Acallitus* spp., *Aculops* spp. such as *A. lycopersici, A. pelekassi; Aculus* spp. such as *A. schlechtendali; Colomerus vitis, Epitrimerus pyri, Phyllocoptruta oleivora; Eriophytes ribis* and *Eriophyes* spp. such as *Eriophyes sheldoni*; Family Tarsonemidae including *Hemitarsonemus* spp., *Phytonemus pallidus* and *Polyphagotarsonemus latus, Stenotarsonemus* spp. *Steneotarsonemus spinki*; Family Tenuipalpidae including *Brevipalpus* spp. such as *B. phoenicis*; Family Tetranychidae including *Eotetranychus* spp., *Eutetranychus* spp., *Oligonychus* spp., *Petrobia latens, Tetranychus* spp. such as *T. cinnabarinus, T. evansi, T. kanzawai, T, pacificus, T. phaseulus, T. telarius* and *T. urticae; Bryobia praetiosa; Panonychus* spp. such as *P. ulmi, P. citri; Metatetranychus* spp. and *Oligonychus* spp. such as *O. pratensis, O. perseae, Vasates lycopersici; Raoiella indica*, Family Carpoglyphidae including *Carpoglyphus* spp.; *Penthaleidae* spp. such as *Halotydeus destructor*, Family Demodicidae with species such as *Demodex* spp.; Family Trombicidea including *Trombicula* spp.; Family Macronyssidae including *Ornothonyssus* spp.; Family Pyemotidae including *Pyemotes tritici; Tyrophagus putrescentiae*; Family Acaridae including *Acarus siro*; Family Araneida including *Latrodectus mactans, Tegenaria agrestis, Chiracanthium* sp, *Lycosa* sp *Achaearanea tepidariorum* and *Loxosceles reclusa;*

Pests from the Phylum Nematoda, for example, plant parasitic nematodes such as root-knot nematodes, *Meloidogyne* spp. such as *M. hapla, M. incognita, M. javanica*; cyst-forming nematodes, *Globodera* spp. such as *G. rostochiensis; Heterodera* spp. such as *H. avenae, H. glycines, H. schachtii, H. trifolii*; Seed gall nematodes, *Anguina* spp.; Stem and foliar nematodes, *Aphelenchoides* spp. such as *A. besseyi*; Sting nematodes, *Belonolaimus* spp. such as *B. longicaudatus*; Pine nematodes, *Bursaphelenchus* spp. such as *B. lignicolus, B. xylophilus*; Ring nematodes, *Criconema* spp., *Criconemella* spp. such as *C. xenoplax* and *C. ornata*; and, *Criconemoides* spp. such as *Criconemoides informis; Mesocriconema* spp.; Stem and bulb nematodes, *Ditylenchus* spp. such as *D. destructor, D. dipsaci*; Awl nematodes, *Dolichodorus* spp.; Spiral nematodes, *Heliocotylenchus multicinctus*; Sheath and sheathoid nematodes, *Hemicycliophora* spp. and *Hemicriconemoides* spp.; *Hirshmanniella* spp.; Lance nematodes, *Hoploaimus* spp.; False rootknot nematodes, *Nacobbus* spp.; Needle nematodes, *Longidorus* spp. such as *L. elongatus*; Lesion nematodes, *Pratylenchus* spp. such as *P. brachyurus, P. neglectus, P. penetrans, P. curvitatus, P. goodeyi*; Burrowing nematodes, *Radopholus* spp. such as *R. similis; Rhadopholus* spp.; *Rhodopholus* spp.; Reniform nematodes, *Rotylenchus* spp. such as *R. robustus, R. reniformis; Scutellonema* spp.; Stubby-root nematode, *Trichodorus* spp. such as *T. obtusus, T. primitivus; Paratrichodorus* spp. such as *P. minor*; Stunt nematodes, *Tylenchorhynchus* spp. such as *T. claytoni, T. dubius*; Citrus nematodes, *Tylenchulus* spp. such as *T. semipenetrans*; Dagger nematodes, *Xiphinema* spp.; and other plant parasitic nematode species;

Insects from the order Blattodea for example *Macrotermes* spp. such as *M. natalensis; Cornitermes cumulans, Procornitermes* spp., *Globitermes sulfureus, Neocapritermes* spp. such as *N. opacus, N. parvus; Odontotermes* spp., *Nasutitermes* spp. such as *N. corniger, Coptotermes* spp. such as *C. formosanus, C. gestroi, C. acinaciformis; Reticulitermes* spp. such as *R. hesperus, R. tibialis, R. speratus, R. flavipes, R. grassei, R. lucifugus, R. virginicus; Heterotermes* spp. such as *H. aureus, H. longiceps, H. tenuis; Cryptotermes* spp. such as *C. brevis, C. cavifrons; Incisitermes* spp. such as *I. minor, I. snyderi; Marginitermes hubbardi, Kalotermes flavicollis, Neotermes* spp. such as *N. castaneus, Zootermopsis* spp. such as *Z. angusticollis, Z. nevadensis, Mastotermes* spp. such as *M. darwiniensis; Blatta* spp. such as *B. orientalis, B. lateralis; Blattella* spp. such as *B. asahinae, B. germanica; Rhyparobia maderae, Panchlora nivea, Periplaneta* spp. such as *P. americana, P. australasiae, P. brunnea, P. fuliginosa, P. japonica; Supella longipalpa, Parcoblatta pennsylvanica, Eurycotis floridana, Pycnoscelus surinamensis,*

Insects from the order Siphonoptera for example *Cediopsylla simples, Ceratophyllus* spp., *Ctenocephalides* spp. such as *C. felis, C. canis, Xenopsylla cheopis, Pulex irritans, Trichodectes canis, Tunga penetrans*, and *Nosopsyllus fasciatus,*

Insects from the order Thysanura for example *Lepisma saccharina, Ctenolepisma urbana*, and *Thermobia domestica,*

Pests from the class Chilopoda for example *Geophilus* spp., *Scutigera* spp. such as *Scutigera coleoptrata;*

Pests from the class Diplopoda for example *Blaniulus guttulatus, Julus* spp., *Narceus* spp., Pests from the class Symphyla for example *Scutigerella immaculata,*

Insects from the order Dermaptera, for example *Forficula auricularia,*

Insects from the order Collembola, for example *Onychiurus* spp., such as *Onychiurus armatus,*

Pests from the order Isopoda for example, *Armadillidium vulgare, Oniscus asellus, Porcellio scaber,*

Insects from the order Phthiraptera, for example *Damalinia* spp., *Pediculus* spp. such as *Pediculus humanus capitis, Pediculus humanus corporis, Pediculus humanus humanus; Pthirus pubis, Haematopinus* spp. such as *Haematopinus eurysternus, Haematopinus suis; Linognathus* spp. such as *Linognathus vituli; Bovicola bovis, Menopon gallinae, Menacanthus stramineus* and *Solenopotes capillatus, Trichodectes* spp., Examples of further pest species which may be controlled by compounds of formula (I) include: from the Phylum Mollusca, class Bivalvia, for example, *Dreissena* spp.; class Gastropoda, for example, *Arion* spp., *Biomphalaria* spp., *Bulinus* spp., *Deroceras* spp., *Galba* spp., *Lymnaea* spp., *Oncomelania* spp., *Pomacea canaliclata, Succinea* spp.; from the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp., *Dictyocaulus filaria, Diphyllobothrium latum, Dracunculus medinensis, Echinococcus granulosus, Echinococcus multilocularis, Enterobius vermicularis, Faciola* spp., *Haemonchus* spp. such as *Haemonchus contortus; Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercora lis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

Animal Health

The compounds of the invention are suitable for use in treating or protecting animals against infestation or infection by parasites. Therefore, the invention also relates to the use of a compound of the invention for the manufacture of a medicament for the treatment or protection of animals against infestation or infection by parasites. Furthermore, the invention relates to a method of treating or protecting animals against infestation and infection by parasites, which comprises orally, topically or parenterally administering or applying to the animals a parasiticidally effective amount of a compound of the invention.

The present invention also relates to the non-therapeutic use of compounds of the invention for treating or protecting animals against infestation and infection by parasites. Moreover, the invention relates to a non-therapeutic method of treating or protecting animals against infestation and infection by parasites, which comprises applying to a locus a parasiticidally effective amount of a compound of the invention.

The compounds of the invention are further suitable for use in combating or controlling parasites in and on animals. Furthermore, the invention relates to a method of combating or controlling parasites in and on animals, which comprises contacting the parasites with a parasitically effective amount of a compound of the invention.

The invention also relates to the non-therapeutic use of compounds of the invention for controlling or combating parasites. Moreover, the invention relates to a non-therapeutic method of combating or controlling parasites, which comprises applying to a locus a parasiticidally effective amount of a compound of the invention.

The compounds of the invention can be effective through both contact (via soil, glass, wall, bed net, carpet, blankets or animal parts) and ingestion (e.g. baits). Furthermore, the compounds of the invention can be applied to any and all developmental stages.

The compounds of the invention can be applied as such or in form of compositions comprising the compounds of the invention.

The compounds of the invention can also be applied together with a mixing partner, which acts against pathogenic parasites, e.g. with synthetic coccidiosis compounds, polyetherantibiotics such as Amprolium, Robenidin, Toltrazuril, Monensin, Salinomycin, Maduramicin, Lasalocid, Narasin or Semduramicin, or with other mixing partners as defined above, or in form of compositions comprising said mixtures.

The compounds of the invention and compositions comprising them can be applied orally, parenterally or topically, e.g. dermally. The compounds of the invention can be systemically or non-systemically effective.

The application can be carried out prophylactically, therapeutically or non-therapeutically. Furthermore, the application can be carried out preventively to places at which occurrence of the parasites is expected.

As used herein, the term "contacting" includes both direct contact (applying the compounds/compositions directly on the parasite, including the application directly on the animal or excluding the application directly on the animal, e.g. at it's locus for the latter) and indirect contact (applying the compounds/compositions to the locus of the parasite). The contact of the parasite through application to its locus is an example of a non-therapeutic use of the compounds of the invention.

The term "locus" means the habitat, food supply, breeding ground, area, material or environment in which a parasite is growing or may grow outside of the animal.

As used herein, the term "parasites" includes endo- and ectoparasites. In some embodiments of the invention, endoparasites can be preferred. In other embodiments, ectoparasites can be preferred. Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the invention are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans*, and *Nosopsyllus fasciatus*; cockroaches (Blattaria—Blattodea), e.g. *Blattella germanica, Blattella asahinae, Periplaneta americana, Periplaneta japonica, Periplaneta brunnea, Periplaneta fuliginosa, Periplaneta australasiae*, and *Blatta orientalis*; flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola*, and *Tabanus similis*; lice (Phthiraptera), e.g. *Pediculus humanus capitis, Pediculus humanus humanus, Pthirus pubis, Haematopinus eurysternus, Haematopinus suis, Linognathus vituli, Bovicola bovis, Menopon gallinae, Menacanthus stramineus* and *Solenopotes capillatus*; ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Amblyomma maculatum, Ornithodorus hermsi, Ornithodorus turicata* and parasitic mites (Mesostigmata), e.g. *Ornithonyssus bacoti* and *Dermanyssus gallinae*; Actinedida (Prostigmata) und Acaridida (Astigmata), e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp; Bugs (Heteropterida): *Cimex lectularius, Cimex hemipterus, Reduvius senilis, Triatoma* spp., *Rhodnius* ssp., *Panstrongylus* ssp., and *Arilus critatus*; Anoplurida, e.g. *Haematopinus* spp., *Linognathus* spp., *Pediculus* spp., *Phtirus* spp., and *Solenopotes* spp.; Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp.; Roundworms Nematoda: Wipeworms and Trichinosis (Trichosyringida), e.g. Trichinellidae (*Trichinella* spp.), (Trichuridae) *Trichuris* spp., *Capillaria* spp.; Rhabditida, e.g. *Rhabditis* spp., *Strongyloides* spp., *Helicephalobus* spp.; Strongylida, e.g. *Strongylus* spp., *Ancylostoma* spp., *Necator americanus, Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp., *Aleurostrongylus abstrusus*, and *Dioctophyma renale*; Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi*; Camallanida, e.g. *Dracunculus medinensis* (guinea worm); Spirurida, e.g. *Thelazia* spp., *Wuchereria* spp., *Brugia* spp., *Onchocerca* spp., *Dirofilari* spp.a, *Dipetalonema* spp., *Setaria* spp., *Elaeophora* spp., *Spirocerca lupi*, and *Habronema* spp.; Thorny headed worms (Acanthocephala), e.g. *Acanthocephalus* spp., *Macracanthorhynchus hirudinaceus* and *Oncicola* spp.; Planarians (Plathelminthes): Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp.; Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

As used herein, the term "animal" includes warm-blooded animals (including humans) and fish. Preferred are mammals, such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels. Particularly preferred are domestic animals, such as dogs or cats.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Generally, it is favorable to apply the compounds of the invention in total amounts of 0.5 mg/kg to 100 mg/kg per day, preferably 1 mg/kg to 50 mg/kg per day.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:

Solutions such as oral solutions, concentrates for oral administration after dilution, solutions for use on the skin or in body cavities, pouring-on formulations, gels;

Emulsions and suspensions for oral or dermal administration; semi-solid preparations;

Formulations in which the active compound is processed in an ointment base or in an oil-in-water or water-in-oil emulsion base;

Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further auxiliaries such as acids, bases, buffer salts, preservatives, and solubilizers. Suitable auxiliaries for injection solutions are known in the art. The solutions are filtered and filled sterile.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on. Solutions for use on the skin are prepared according to the state of the art and according to what is described above for injection solutions, sterile procedures not being necessary.

Gels are applied to or spread on the skin or introduced into body cavities. Gels are prepared by treating solutions which have been prepared as described in the case of the injection solutions with sufficient thickener that a clear material having an ointment-like consistency results. Suitable thickeners are known in the art.

Pour-on formulations are poured or sprayed onto limited areas of the skin, the active compound penetrating the skin and acting systemically. Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added. Suitable such auxiliaries are known in the art.

Emulsions can be administered orally, dermally or as injections. Emulsions are either of the water-in-oil type or of the oil-in-water type. They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances. Suitable hydrophobic phases (oils), suitable hydrophilic phases, suitable emulsifiers, and suitable further auxiliaries for emulsions are known in the art.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers. Suitable suspending agents, and suitable other auxiliaries for suspensions including wetting agents are known in the art.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form. Suitable auxiliaries for this purpose are known in the art.

The compositions which can be used in the invention can comprise generally from about 0.001 to 95% of the compound of the invention.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

Topical application may be conducted with compound-containing shaped articles such as collars, medallions, ear tags, bands for fixing at body parts, and adhesive strips and foils.

Generally it is favorable to apply solid formulations which release compounds of the invention in total amounts of 10 mg/kg to 300 mg/kg, preferably 20 mg/kg to 200 mg/kg, most preferably 25 mg/kg to 160 mg/kg body weight of the treated animal in the course of three weeks.

EXAMPLES

With appropriate modification of the starting materials, the procedures as described in the preparation examples below were used to obtain further compounds of formula I. The compounds obtained in this manner are listed in the table X that follows, together with physical data. The following examples illustrate the invention.

A. Preparation of Compounds

Materials: Unless otherwise noted, reagents and solvents were purchased at highest commercial quality and used without further purification. Dry tetrahydrofuran (THF), ethylacetate (EtOAc), dimethylsulfoxide (DMSO), acetone, ethanol (EtOH), benzene, dimethylformamide, (DMF), diisopropylethylamine (DIPEA), hexafluorophosphate azabenzotriazole tetramethyl uronium (HATU), pyridine, and CH2Cl2 were purchased from commercial providers.

All reactions were monitored by thin-layer chromatography (TLC) using Merck silica gel 60 $F_2$54 pre-coated plates (0.25 mm). Flash chromatography was carried out with Kanto Chemical silica gel (Kanto Chemical, silica gel 60N, spherical neutral, 0.040-0.050 mm, Cat.-No. 37563-84). $^1$H NMR spectra were recorded on JEOL JNM-ECA-500 (500 MHz). Chemical shifts are expressed in ppm downfield from the internal solvent peaks for acetone-$d_6$ ($^1$H; δ=2.05 ppm) and $CD_3OD$ ($^1$H; δ=3.30 ppm), and J values are given in Hertz. The following abbreviations were used to explain the multiplicities: s=singlet, d=doublet, t=triplet, q=quartet, dd=double doublet, dt=double triplet, m=multiplet, br=broad. High-resolution mass spectra were measured on a JEOL JMS-T100LP.

Characterization: The compounds were characterized by coupled High Performance Liquid Chromatography with mass spectrometry (H PLC/MS). Method A: UHPLC-MS on Shimadzu Nexera UHPLC & Shimadzu LCMS 20-20 ESI. Analytical UHPLC column: Phenomenex Kinetex 1.7 μm XB-C18 100A; 50×2.1 mm; mobile phase: A: water+0.1% TFA; B: acetonitrile; gradient: 5-100% B in 1.50 minutes; 100% B 0.20 min; flow: 0.8-1.0 mL/min in 1.50 minutes at 60° C. MS-method: ESI positive; mass range (m/z) 100-700.

Synthesis Example A

Example 1: (C-1)

5-benzoyl-3-(6-chloro-3-pyridyl)-7-ethyl-2,3-dihydroimidazo[2,1-b]thiazol-4-ium-6-olate

Step 1: 4-(6-chloro-3-pyridyl)-N-ethyl-thiazolidin-2-imine 10 g of [2-chloro-1-(6-chloro-3-pyridyl)ethyl]ammonium chloride was dissolved in 250 ml ethanol at RT. 9.8 g ethyl isothiocyanate and 11.2 g triethyl amine was added and the resulting mixture was stirred for 2 days at RT. 110 ml of 1M aq. NaOH was added and the reaction mixture was heated to reflux for three hours. The solvent was removed, and the residue was triturated with acetone. The solid residue was removed by filtration and the organic phase was concentrated and purified by column chromatography. This yielded 4.62 g of the desired product.

Step 2: 2-[(2Z)-4-(6-chloro-3-pyridyl)-2-ethylimino-thiazolidin-3-yl]acetic acid Under an Argon atmosphere, 214 mg sodium hydride (60%) was dispersed in 4 ml DMF at 0° C. 500 mg 4-(6-chloro-3-pyridyl)-N-ethyl-thiazolidin-2-imine was dissolved in 4 ml DMF and added dropwise. The mixture was stirred at 0° C. for 1.5 hours. followed by 834 mg of t-butyl bromo acetate was added and the resulting mixture was stirred at RT overnight. The reaction was quenched with saturated ammonium chloride solution an extracted with ethyl acetate. The organic phases were dried over sodium sulfate and the solvent was removed. 280 mg of the resulting ester was dissolved in 3 ml methylene chloride at 0° C. and 2.2 ml trifluoro acetic acid was added dropwise and stirred over night at RT. Removal of the solvents yielded 380 mg of desired product. This was used in the next step without further purification.

Step 3: 5-benzoyl-3-(6-chloro-3-pyridyl)-7-ethyl-2,3-dihydroimidazo[2,1-b]thiazol-4-ium-6-olate 200 mg 2-[(2Z)-4-(6-chloro-3-pyridyl)-2-ethylimino-thiazolidin-3-yl]acetic acid from the previous step was dissolved in dichloromethane at RT. 188 mg of benzoyl chloride and 270 mg of triethylamine was added and the resulting mixture was stirred at RT overnight. The solvents were evaporated, and the resulting residue was purified by column chromatography. Yield: 54 mg of the desired compound.

Example 2: (C-12)

5-benzoyl-3-(6-chloro-3-pyridyl)-7-ethyl-2,3-dihydroimidazo[2,1-b]thiazol-4-ium-6-olate

Step 1: 4-(2-chlorothiazol-5-yl)-N,1-dimethyl-imidazolidin-2-imine 4.5 g of [1-(2-chlorothiazol-5-yl)-2-(methylamino)ethyl] ammonium chloride was dissolved in 100 ml toluene at RT.

3.3 g methyl isothiocyanate and 11.2 g was added and the resulting mixture was heated to reflux for four hours. The solvent was removed, and the organic phase was concentrated and purified by column chromatography. This yielded 1.25 g of the desired product.

Step 2 2-[[4-(2-chlorothiazol-5-yl)-1-methyl-4,5-dihydroimidazol-2-yl]-methyl amino]acetic acid Under an Argon atmosphere, 183 mg sodium hydride (60%) was dispersed in 3 ml DMF at 0° C. 700 mg 4-(2-chlorothiazol-5-yl)-N,1-dimethyl-imidazolidin-2-imine was dissolved in 4 ml DMF and added dropwise followed by 888 mg of t-butyl bromo acetate in 3 ml DMF and the resulting mixture was stirred at RT for four hours. The reaction was quenched with saturated ammonium chloride solution an extracted with methylene chloride. The organic phases were dried over sodium sulfate and the solvent was removed. 1.1 g of the resulting product was purified with reverse phase column chromatography to yield 300 mg of the desired ester. This product was dissolved in 3 ml methylene chloride at 0° C. and 2.2 ml trifluoro acetic acid were added dropwise and stirred overnight at RT. Removal of the solvents yielded 167 mg of desired product. This was used in the next step without further purification.

Step 3: 5-benzoyl-3-(6-chloro-3-pyridyl)-7-ethyl-2,3-dihydroimidazo[2,1-b]thiazol-4-ium-6-olate To a stirred solution of 400 mg 2-[[4-(2-chlorothiazol-5-yl)-1-methyl-4,5-dihydroimidazol-2-yl]-methyl amino]acetic acid in acetonitrile was added 1 g triethylamine and 677 mg benzoic anhydride at RT. The reaction mixture was heated at 85° C. for overnight. The reaction mixture was concentrated under reduced pressure to afford a brown color semisolid. The crude material was triturated with 10% MTBE in heptane and decanted twice. The organic solution was dried over sodium sulphate and concentrated under reduced pressure to get crude material which was purified by column chromatography. This yielded 100 mg of the desired material.

With appropriate modification of the starting materials or intermediates thereof, the procedures as described in the preparation examples above were used to obtain further compounds of formula I. The compounds obtained in this manner are listed in the below table, together with physical data.

| Compound number | LS code | Structure | HPLC/MS | Rt min |
|---|---|---|---|---|
| C-1. | 6137279 | 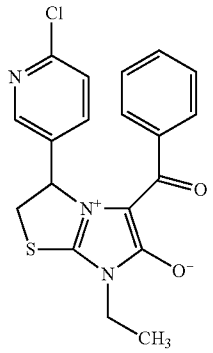 [SMILES: CCn1c([O-])c(C(=O)c2ccccc2)[n+]2c1SCC2c1ccc(Cl)nc1] | 385.8 | 0.889 |
| C-2. | 6118084 | 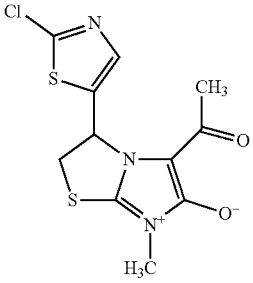 [SMILES: CC(=O)c1c([O-])[n+](C)c2n1C(c1cnc(Cl)s1)CS2] | 315.7 | 0.688 |
| C-3. | 6126293 | 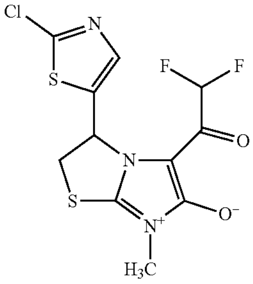 [SMILES: C[n+]1c([O-])c(C(=O)C(F)F)n2c1SCC2c1cnc(Cl)s1] | 351.9 | 0.804 |

-continued
| Compound number | LS code | Structure | HPLC/MS | Rt min |
|---|---|---|---|---|
| C-4. | 6126326 | 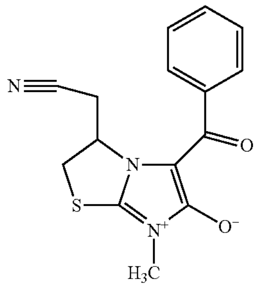 [SMILES: C[n+]1c([O-])c(C(=O)c2ccccc2)n2c1SCC2CC#N] | 300 | 1.195 |
| C-5. | 6126330 | 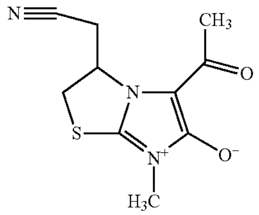 | 238 | 0.917 |
| C-6. | 6127658 | 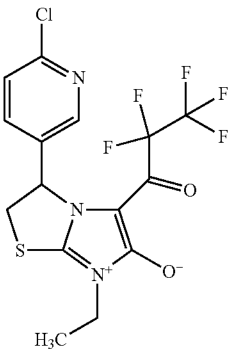 [SMILES: CC[n+]1c([O-])c(C(=O)C(F)(F)C(F)(F)F)n2c1SCC2c1ccc(Cl)nc1] | 427.9 | 1.005 |
| C-7. | 6128278 | 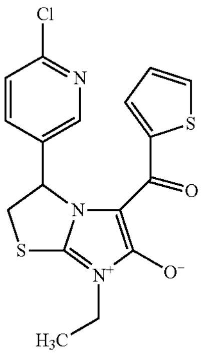 [SMILES: CC[n+]1c([O-])c(C(=O)c2cccs2)n2c1SCC2c1ccc(Cl)nc1] | 391.9 | 0.933 |
| C-8. | 6129145 | 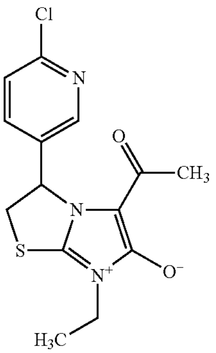 [SMILES: CC[n+]1c([O-])c(C(C)=O)n2c1SCC2c1ccc(Cl)nc1] | 323.8 | 0.742 |

-continued
| Compound number | LS code | Structure | HPLC/MS | Rt min |
|---|---|---|---|---|
| C-9. | 6129596 | 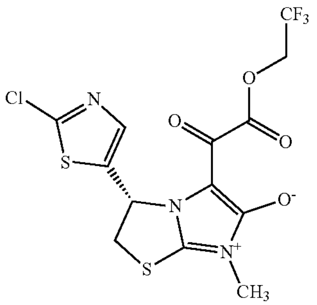 [SMILES: C[n+]1c([O-])c(C(=O)C(=O)OCC(F)(F)F)n2c1SC[C@@H]2c1cnc(Cl)s1] | 427.8 | 0.906 |
| C-10. | 6129597 | 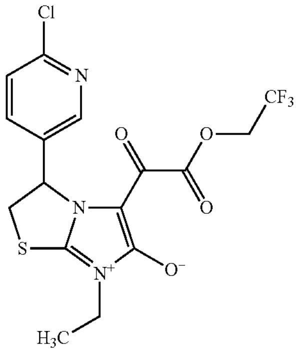 [SMILES: CC[n+]1c([O-])c(C(=O)C(=O)OCC(F)(F)F)n2c1SCC2c1ccc(Cl)nc1] | 435.8 | 0.947 |
| C-11. | 6137394 | 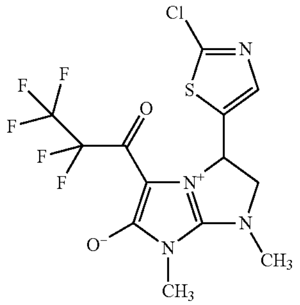 [SMILES: CN1CC(c2cnc(Cl)s2)[n+]2c(C(=O)C(F)(F)C(F)(F)F)c([O-])n(C)c21] | 417 | 1.57 |
| C-12. | 6137395 | 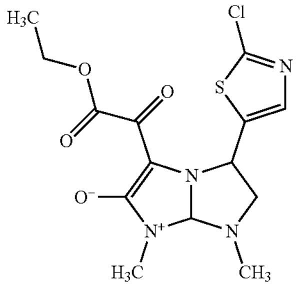 [SMILES: CCOC(=O)C(=O)C1=C([O-])[NH+](C)C2N(C)CC(c3cnc(Cl)s3)N12] | 375 | 1.38 |
| C-13. | 6129141 | 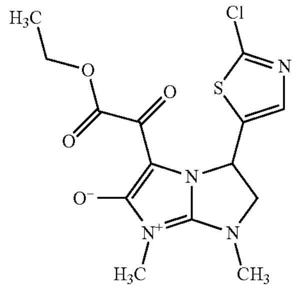 [SMILES: CCOC(=O)C(=O)c1c([O-])[n+](C)c2n1C(c1cnc(Cl)s1)CN2C] | 370.8 | 0.923 |

-continued

| Compound number | LS code | Structure | HPLC/MS | Rt min |
|---|---|---|---|---|
| C-14. | 6129411 | 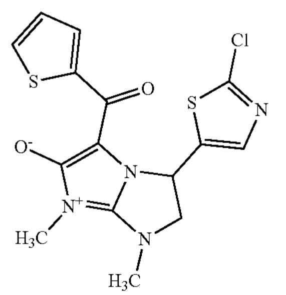 [SMILES: CN1CC(c2cnc(Cl)s2)n2c(C(=O)c3cccs3)c([O-])[n+](C)c21] | 380.9 | 0.838 |

B. Biological Examples

The activity of the compounds of formula (I) of the present invention could be demonstrated and evaluated in biological tests described in the following. If not otherwise specified, the test solutions are prepared as follows: The active compound is dissolved at the desired concentration in a mixture of 1:1 (vol:vol) distilled water:acteone. The test solution is prepared at the day of use. Test solutions are prepared in general at concentrations of 2500 ppm, 1000 ppm, 500 ppm, 300 ppm, 100 ppm and 30 ppm (wt/vol).

Boll Weevil (*Anthonomus grandis*)

For evaluating control of boll weevil (*Anthonomus grandis*) the test unit consisted of 96-well-microtiter plates containing an insect diet and 5-10 *A. grandis* eggs. The compounds were formulated using a solution containing 75% v/v water and 25% v/v DMSO. Different concentrations of formulated compounds were sprayed onto the insect diet at 5 µl, using a custom built micro atomizer, at two replications. After application, microtiter plates were incubated at about 25±1° C. and about 75±5% relative humidity for 5 days. Egg and larval mortality was then visually assessed. In this test, compounds C-6, C-7, C-8 and C-12 at 2500 ppm showed over 75% mortality in comparison with untreated controls.

Tobacco Budworm (*Heliothis virescens*)

For evaluating control of tobacco budworm (*Heliothis virescens*) the test unit consisted of 96-well-microtiter plates containing an insect diet and 15-25 *H. virescens* eggs. The compounds were formulated using a solution containing 75% v/v water and 25% v/v DMSO. Different concentrations of formulated compounds were sprayed onto the insect diet at 10 µl, using a custom built micro atomizer, at two replications. After application, microtiter plates were incubated at about 28±1° C. and about 80±5% relative humidity for 5 days. Egg and larval mortality was then visually assessed. In this test, compounds C-3, C-6 and C-12 at 2500 ppm showed over 75% mortality in comparison with untreated controls.

Vetch Aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications. After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed. In this test, compounds C-1, C-2, C-3, C-4, C-6, C-7, C-8, C-9 and C-10 at 2500 ppm showed over 75% mortality in comparison with untreated controls.

Green Peach Aphid (*Myzus persicae*)

For evaluating control of green peach aphid (*Myzus persicae*) through systemic means the test unit consisted of 96-well-microtiter plates containing liquid artificial diet under an artificial membrane. The compounds were formulated using a solution containing 75% v/v water and 25% v/v DMSO. Different concentrations of formulated compounds were pipetted into the aphid diet, using a custom built pipetter, at two replications. After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed. In this test, compounds C-1, C-2, C-3, C-4, C-6, C-7, C-8, C-9, C-10 and C-12 at 2500 ppm showed over 75% mortality in comparison with untreated controls.

We claim:

1. A compound of formula I,

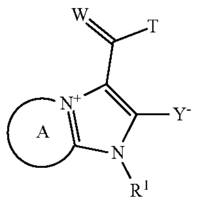

I

Y is O or S;

W is O, S, or $NOR^{15}$;

T is $R^5$, $OR^6$, $-N(R^7)(R^8)$, $-N(R^{7a})-N(R^7)(R^8)$, $C(=Z)R^{12}$, $C(=Z)OR^{13}$, or $C(=O)NR^{14a}R^{14b}$;

Z is O, S, or $N-OR^{15}$;

$R^1$ is $NO_2$ or CN, or $R^1$ is $C_1$-$C_6$-alkyl, $C_2$-$C_8$-alkenyl, $C_2$-$C_8$-alkynyl, $C_3$-$C_{10}$-cycloalkyl, $C_4$-$C_{10}$-cycloalkenyl, $C_5$-$C_{14}$-cycloalkylcycloalkyl, or a three- to eleven-membered saturated, or partially unsaturated or aromatic carbo- or heterocyclic ring or ring system, which may contain 1 to 4 heteroatoms selected from $N(R^c)_p$, O, and S, wherein S may be oxidized, and wherein the aforementioned groups and the carbo- or heterocyclic rings system may be unsubstituted, partially or fully substituted with $R^a$;

or $R^1$ is $C(=O)R^b$, $C(=O)OR^e$, $NR^bR^c$, $C(=O)NR^bR^c$, $C(=S)NR^bR^c$, $SO_2NR^bR^c$, $OC(=O)R^c$, $OC(=O)OR^e$, $OC(=O)NR^bR^e$, $N(R^c)C=O)R^c$, $N(R^c)C(=O)OR^e$, $N(R^c)C(=O)NR^bR^c$, $NR^cSO_2R^b$, $NR^cSO_2NR^bR^c$, $Si(R^d)_3$, $C(=NR^c)R^c$, $C(=NOR^c)R^c$, $C(=NNR^bR^c)R^c$, $C(=NN(C(=O)R^b)R^c)R^c$, $C(=NN(C=O)OR^c)(R^c)_2$, $S(=O)_o$ $(=NR^b)_qR^c$, or $N=CR^bR^c$;

A is a five-membered saturated or partially unsaturated ring, taken together with the carbon and nitrogen of the imidazole ring in formula (I), wherein each remaining ring member is selected from carbon atoms and up to 3 heteroatoms independently selected from up to 2 O, up to 2 S, and up to 3 N, wherein up to 2 carbon atom ring members are independently selected from C(=O) and C(=S), and the sulfur atom ring members are independently selected from $S(=O)_m$, wherein each ring member may be substituted with $R^a$ and/or $R^c$;

wherein the ring A is substituted with one $R^4$;

$R^4$ is Het or $R^{4a}$;

Het is selected from the group consisting of D-1, D-2, D-3, D-25, D-26, and D-27

D-1

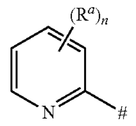

D-2

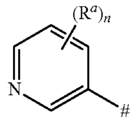

D-3

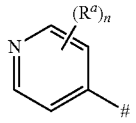

D-25

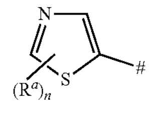

D-26

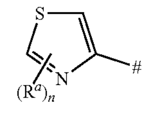

D-27

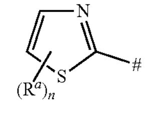

wherein n is 0 to 5;

o, q are each independently 0, 1, or 2, provided that the sum (o+q) is 0, 1, or 2 for each ring;

$R^{4a}$ is (a) CN or $R^{4a}$ is $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_7$-cycloalkyl, $C_3$-$C_7$-halocycloalkyl, $C_4$-$C_8$-alkylcycloalkyl, $C_4$-$C_8$-haloalkylcycloalkyl, $C_4$-$C_8$-cycloalkylalkyl, $C_4$-$C_8$-halocycloalkylalkyl, $C_1$-$C_6$-alkoxy, $C_1$-$C_6$-haloalkoxy, $C_2$-$C_6$-alkylcarbonyl, or $C_2$-$C_6$-haloalkylcarbonyl;

each optionally substituted with one or more substituents selected from the group consisting of CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=W)R^bR^c$, $OP(=W)(O_pR^c)R^b$, $OP(=W)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=W)NR^bR^c$, $NR^bNR^bSO_2NR^bR^c$, and $N=S(=O)_pR^cR^C$, or (b) phenyl optionally substituted with one or more substituents selected from the group consisting of halogen, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_1R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=W)R^bR^c$, $OP(=W)(O_pR^c)R^b$, $OP(=W)(OR^c)_2$, $N=CR^bR^c$, $NR^bN=CR^bR^c$, $NR^bNR^bR^c$, $NR^bC(=S)NR^bR^c$, $NR^bC(=NR^b)NR^bR^c$, $NR^bNR^bC(=W)NR^bR^c$, $NR^bNR^bSO_2NR^bR^c$, and $N=S(=O)_pR^cR^c$, or (c) phenyl optionally substituted with one or more substituents selected from the group consisting of $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl, $C_2$-$C_4$-haloalkynyl, $C_3$-$C_7$-cycloalkyl, $C_3$-$C_7$-halocycloalkyl, $C_4$-$C_8$-alkylcycloalkyl, $C_4$-$C_8$-haloalkylcycloalkyl, $C_4$-$C_8$-cycloalkylalkyl, $C_4$-$C_8$-halocycloalkylalkyl, $C_1$-$C_6$-alkoxy, $C_1$-$C_6$-haloalkoxy, $C_2$-$C_6$-alkylcarbonyl, and $C_2$-$C_6$-haloalkylcarbonyl, which groups may optionally be substituted with halogen, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $SF_5$, OCN, SCN, $Si(R^d)_3$, $C(=N(O)_pR^b)R^b$, $C(=NNR^bR^c)R^b$, $C(=NN(C(=O)O_pR^c)R^b)R^b$, $ON=CR^bR^c$, $ONR^bR^c$, $S(=O)_o(=NR^b)_qR^c$, $SO_2NR^b(=O)NR^bR^c$, $P(=W)R^bR^c$, $OP(=W)(O_pR^c)R^b$, $OP(=W)(OR^c)_2$, $N=CR^bR^c$, $NR^bN=CR^bR^c$, $NR^bNR^bR^c$, $NR^bC(=S)NR^bR^c$, $NR^bC(=NR^b)$ $NR^bR^c$, $NR^bNR^bC(=W)NR^bR^c$, $NR^bNR^bSO_2NR^bR^c$, or $N=S(=O)_pR^cR^c$;

$R^a$ is each independently halogen, $C_1$-$C_6$-alkyl, $C_1$-$C_6$-haloalkyl, $C_1$-$C_6$-alkoxy, $C_1$-$C_6$-haloalkoxy, $C_2$-$C_4$-alkenyl, $C_2$-$C_4$-alkynyl, $C_3$-$C_6$-cycloalkyl, CN, $OR^c$, $NR^bR^c$, $NO_2$, $C(=O)(O)_pR^c$, $OC(=O)(O)_pR^e$, $C(=O)NR^bR^c$, $OC(=O)NR^bR^e$, $NR^bC(=O)(O)_pR^e$, $NR^bC(=O)NR^bR^c$, $C(=S)NR^bR^c$, $S(O)_mR^b$, $SO_2NR^bR^c$, $OSO_2R^c$, $OSO_2NR^bR^c$, $NR^bSO_2R^c$, $NR^bSO_2NR^bR^c$, $N=S(=O)_pR^cR^c$, $S(=O)_p(=NR^b)_qR^c$, $SF_5$, OCN, SCN, $Si(R^d)_3$ or a three- to six-membered saturated, or partially unsaturated or aromatic carbo- or heterocyclic ring, which may contain 1 to 3 heteroatoms selected from N—$(R^c)_p$, O, and S which may be oxidized, and wherein the aforementioned groups and the carbo- or heterocyclic ring may be partially or fully substituted with $R^{aa}$, or two geminally bound groups $R^a$ together may form a group selected from =O, =S, =$CR^bR^c$, =$NR^c$, =$NOR^c$, and =$NNR^cR^c$;

$R^{aa}$ is each independently halogen, $C_1$-$C_6$-alkyl, $C_1$-$C_6$-haloalkyl, $C_1$-$C_6$-alkoxy or $C_1$-$C_6$-haloalkoxy;

$R^b$ is each independently hydrogen, $C_1$-$C_6$-alkyl, $C_1$-$C_6$-haloalkyl, $C_1$-$C_6$-alkoxy, $C_1$-$C_6$-haloalkoxy or a three- to six-membered saturated, or partially unsaturated or aromatic carbo- or heterocyclic ring, which may contain 1 to 3 heteroatoms selected from $N(R^c)_p$, O, and S, wherein S may be oxidized and which carbo- or heterocyclic ring may be partially or fully substituted with $R^{aa}$;

$R^c$ is each independently hydrogen, $C_1$-$C_4$-alkyl, $C_1$-$C_4$-haloalkyl, $C_1$-$C_4$-alkylcarbonyl, $C_1$-$C_6$ cycloalkyl, or a three- to six-membered saturated, partially unsaturated or aromatic carbo- or heterocyclic ring, which may contain 1 to 3 heteroatoms selected from $N(R^{aa})_p$, O, and S, wherein S may be oxidized and wherein the carbo- or heterocyclic ring may be partially or fully substituted with $R^{aa}$;

wherein two geminally bound groups $R^bR^b$, $R^cR^b$ or $R^cR^c$ together with the atom to which they are bound, may form a 3-, 4-, 5-, 6-, or 7-membered saturated, partially unsaturated or aromatic carbo- or heterocyclic ring, which may contain 1 to 2 heteroatoms or heteroatoms groups selected from N, O, S, NO, SO, and $SO_2$ and wherein the carbo- or heterocyclic ring may be partially or fully substituted with $R^a$;

$R^d$ is each independently hydrogen, or $R^d$ is each independently phenyl, $C_1$-$C_6$-alkyl, $C_2$-$C_6$-alkenyl, $C_2$-$C_6$-alkynyl, $C_3$-$C_8$-cycloalkyl, or $C_1$-$C_6$-alkoxyalkyl, wherein the above mentioned groups may be substituted with one or more halogen;

$R^e$ is each independently $C_1$-$C_4$-alkyl, $C_1$-$C_4$-haloalkyl, $C_1$-$C_4$-alkylcarbonyl, $C_1$-$C_6$ cycloalkyl, or a three- to six-membered saturated, partially unsaturated or aromatic carbo- or heterocyclic ring, which may contain 1 to 3 heteroatoms selected from $N(R^{aa})_p$, O, and S, wherein S may be oxidized and wherein the carbo- or heterocyclic ring may be partially or fully substituted with $R^{aa}$;

m is 0, 1, or 2;

p is 0 or 1;

$R^5$ is hydrogen, $C_1$-$C_8$-alkyl, $C_2$-$C_8$-alkenyl, $C_2$-$C_8$-alkynyl, wherein the three aforementioned groups may be independently from each other substituted with one to five substituents selected from halogen, $NO_2$, CN, OH, $C_1$-$C_6$-alkyl, $C_3$-$C_6$-cycloalkyl, $C_1$-$C_6$-alkoxy-$C_1$-$C_6$-alkyl, $C_1$-$C_6$-haloalkyl, $C_3$-$C_6$-halocycloalkyl, $C_3$-$C_6$-cycloalkyl-$C_1$-$C_6$-alkyl, $C_3$-$C_6$-halocycloalkyl-$C_1$-$C_6$-alkyl, cyano-$C_1$-$C_6$-alkyl, cyano-$C_1$-$C_6$-haloalkyl, O—$R^{51}$, —$S(O)_q$—$R^{52}$, —$N(R^{53})(R^{54})$, —C(=O)N$(R^{53})(R^{54})$, —O—C(=O)—$R^{55}$, —C(=O)—$OR^{55}$, —C(=O)—$R^{55}$, O—$SO_2$—$R^{56}$, aryl, hetaryl, heterocyclyl, and oxoheterocyclyl, wherein aryl, hetaryl, heterocyclyl, or oxoheterocyclyl may in turn be substituted with 1 to 3 substituents selected from halogen, $NO_2$, CN, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-$(C_1$-$C_6)$-alkylaminocarbonyl, $C_1$-$C_6$-alkylcarbonylamino, aryl, and hetaryl;

wherein aryl and hetaryl may be substituted with one or more, identical or different, halogen, CN, $NO_2$, hydroxy, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, or $C_1$-$C_6$-alkylthio;

or $R^5$ is $C_3$-$C_6$-cycloalkyl, $C_3$-$C_6$-heterocyclyl, $C_3$-$C_8$-oxo-heterocyclyl or $C_3$-$C_8$-dioxo-heterocyclyl, which groups may be independently from each other substituted with substituents selected from the group consisting of halogen, CN, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, $C_1$-$C_6$-alkylthio, $C_1$-$C_6$-alkylsulfinyl, $C_1$-$C_6$-alkylsulfonyl, aryl, hetaryl, aryl-$C_1$-$C_6$-alkyl, and hetaryl-$C_1$-$C_6$-alkyl, wherein aryl, hetaryl, aryl-$C_1$-$C_6$-alkyl and hetaryl-$C_1$-$C_6$-alkyl may be substituted with one to three halogen, CN, $NO_2$, $C_1$-$C_4$-alkyl, $C_1$-$C_4$-haloalkyl, $C_1$-$C_4$-alkoxy, and $C_1$-$C_4$-haloalkoxy;

or $R^5$ is aryl, $C_1$-$C_6$-alkylenedioxyaryl, or hetaryl, which groups may be independently from each other substituted with one to three substituents independently selected from the group consisting of halogen, $NO_2$, amino, CN, $SF_5$, SCN, OH, COOH, $CONH_2$, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_3$-$C_6$-cycloalkyl-$C_1$-$C_6$-alkyl, $C_3$-$C_6$-halocycloalkyl-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkoxy, cyano-$C_1$-$C_6$-alkyl, cyano-$C_1$-$C_6$-haloalkyl, $C_3$-$C_6$-cycloalkyl-$C_1$-$C_6$-alkyl, $C_2$-$C_6$-alkenyl, $C_2$-$C_6$-haloalkenyl, $C_2$-$C_6$-alkynyl, $C_2$-$C_6$-haloalkynyl, SH, $C_1$-$C_6$-alkylthio, $C_1$-$C_6$-alkylsulfonyl, $C_1$-$C_6$-alkylsulfinyl, $C_1$-$C_6$-haloalkylthio, $C_1$-$C_6$-haloalkylsulfonyl, $C_1$-$C_6$-haloalkylsulfinyl, $C_1$-$C_6$-alkylcarbonyl, $C_3$-$C_6$-cycloalkylcarbonyl, $C_3$-$C_6$-halocycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-haloalkoxycarbonyl, $C_1$-$C_6$-alkylamino, di-$(C_1$-$C_6)$-alkylamino, $C_3$-$C_6$-cycloalkylamino, di-$(C_3$-$C_6)$-cycloalkylamino, $C_1$-$C_6$-alkylcarbonylamino, $C_1$-$C_6$-haloalkylcarbonylamino, $C_3$-$C_6$-cycloalkylcarbonylamino, $C_3$-$C_6$-halocycloalkylcarbonylamino, $C_1$-$C_6$-alkylaminocarbonyl, $C_1$-$C_6$-haloalkylaminocarbonyl, $C_3$-$C_6$-cycloalkylaminocarbonyl, $C_3$-$C_6$-halocycloalkylaminocarbonyl, di-$(C_1$-$C_6)$-alkylaminocarbonyl, tri-$(C_1$-$C_6$-alkyl)-silyl, aryl, hetaryl, heterocyclyl, aryl-$C_1$-$C_6$-alkyl and hetaryl-$C_1$-$C_6$-alkyl, wherein aryl, hetaryl, aryl-$C_1$-$C_6$-alkyl and hetaryl-$C_1$-$C_6$-alkyl may each in turn optionally be substituted with 1 to 3 substituents selected independently of one another from halogen, CN, $NO_2$, $C_1$-$C_4$-alkyl, $C_1$-$C_4$-haloalkyl, $C_1$-$C_4$-alkoxy, and $C_1$-$C_4$-haloalkoxy;

q is 0, 1, or 2; q $R^{51}$ is hydrogen, or $R^{51}$ is $C_1$-$C_6$-alkyl, $C_2$-$C_6$-alkenyl, $C_2$-$C_6$-alkynyl, $C_3$-$C_6$-cycloalkyl or $C_3$-$C_6$-heterocyclyl, which groups may be independently from each other substituted with one to three halogen or one $NO_2$, CN, $C_3$-$C_6$-cycloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-alkylcarbonyl, $C_1$-$C_6$-alkoxyimino-$C_1$-$C_6$-alkyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, aryl, or hetaryl, wherein aryl and hetaryl may be substituted with one to three halogen, CN, $NO_2$, $C_1$-$C_4$-alkyl, $C_1$-$C_4$-haloalkyl, $C_1$-$C_4$-alkoxy, or $C_1$-$C_4$-haloalkoxy;

or $R^{51}$ is aryl or hetaryl, which groups may be independently from each other substituted with one to three halogen, $NO_2$, amino, CN, $SF_5$, SCN, $C_1$-$C_6$-alkylamino, di-($C_1$-$C_6$)-alkylamino, hydroxy, COOH, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_3$-$C_6$-halocycloalkyl-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, SH, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, or tri-($C_1$-$C_6$-alkyl)-silyl;

$R^{52}$ is $C_1$-$C_6$-alkyl, $C_2$-$C_6$-alkenyl, $C_2$-$C_6$-alkynyl, $C_3$-$C_6$-cycloalkyl or $C_3$-$C_6$-heterocyclyl, which groups may be independently from each other substituted with one to three halogen, $NO_2$, CN, $C_3$-$C_6$-cycloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-alkylcarbonyl, $C_1$-$C_6$-alkoxyimino-$C_1$-$C_6$-alkyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, aryl, or hetaryl, wherein aryl and hetaryl may be substituted with one to three halogen, CN, $NO_2$, $C_1$-$C_4$-alkyl, $C_1$-$C_4$-haloalkyl, $C_1$-$C_4$-alkoxy, or $C_1$-$C_4$-haloalkoxy;

or $R^{52}$ is aryl or hetaryl, which groups may be independently from each other substituted with one to three halogen, $NO_2$, amino, CN, $SF_5$, SCN, $C_1$-$C_6$-alkylamino, di-($C_1$-$C_6$)-alkylamino, hydroxy, COOH, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_3$-$C_6$-halocycloalkyl-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, or tri-($C_1$-$C_6$-alkyl)-silyl;

$R^{53}$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-alkoxy-$C_1$-$C_6$-alkyl, $C_1$-$C_6$-alkoxycarbonyl, $C_1$-$C_6$-alkylcarbonyl, aryl, hetaryl, arylcarbonyl or hetarylcarbonyl, wherein aryl and hetaryl may be substituted with one to three halogen, CN, $NO_2$, $C_1$-$C_4$-alkyl, $C_1$-$C_4$-haloalkyl, $C_1$-$C_4$-alkoxy, or $C_1$-$C_4$-haloalkoxy;

$R^{54}$ is hydrogen, or $R^{54}$ is $C_1$-$C_6$-alkyl, $C_2$-$C_6$-alkenyl, $C_2$-$C_6$-alkynyl, $C_3$-$C_6$-cycloalkyl or $C_3$-$C_6$-cycloalkyl-$C_1$-$C_6$-alkyl, which groups may be independently from each other substituted with one to five halogen or one CN, $NO_2$, hydroxy, $C_1$-$C_6$-alkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-alkoxycarbonyl, $C_1$-$C_6$-alkylcarbonyl, or tri-($C_1$-$C_6$-alkyl)-silyl;

or $R^{54}$ is aryl, hetaryl, aryl-$C_1$-$C_6$-alkyl, or hetaryl-$C_1$-$C_6$-alkyl, which groups may be independently from each other substituted with halogen, CN, $NO_2$, hydroxy, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl, or $C_2$-$C_6$-alkylcarbonyl, or $R^{53}$ and $R^{54}$ are connected through two to six carbon atoms and form a ring, which may comprise an additional atom selected from O, S, or N, and which may be substituted with one to four $C_1$-$C_2$-alkyl, halogen, CN, amino, or $C_1$-$C_2$-alkoxy;

$R^{55}$ is $C_1$-$C_6$-alkyl, $C_3$-$C_6$-cycloalkyl, $C_1$-$C_6$-haloalkyl, $C_3$-$C_6$-halocycloalkyl, $C_3$-$C_6$-cycloalkyl-$C_1$-$C_6$-alkyl, $C_3$-$C_6$-halocycloalkyl-$C_1$-$C_6$-alkyl, cyano-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, aryl, hetaryl, aryl-$C_1$-$C_6$-alkyl or hetaryl-$C_1$-$C_6$-alkyl, wherein aryl, hetaryl, aryl-$C_1$-$C_6$-alkyl, and hetaryl-$C_1$-$C_6$-alkyl, may be substituted with one or more, identical or different, halogen, CN, $NO_2$, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, or $C_1$-$C_6$-alkoxy-$C_1$-$C_6$-alkyl;

$R^{56}$ is $C_1$-$C_6$-alkyl, $C_3$-$C_6$-cycloalkyl, $C_3$-$C_6$-halocycloalkyl, $C_3$-$C_6$-cycloalkyl-$C_1$-$C_6$-alkyl, $C_3$-$C_6$-halocycloalkyl-$C_1$-$C_6$-alkyl, cyano-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, aryl, hetaryl or aryl-$C_1$-$C_6$-alkyl, wherein aryl, hetaryl, and aryl-$C_1$-$C_6$-alkyl may be substituted with one or more, identical or different, halogen, CN, $NO_2$, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, or $C_1$-$C_6$-alkoxy-$C_1$-$C_6$-alkyl;

$R^6$ is $C_1$-$C_6$-alkyl, $C_3$-$C_6$-cycloalkyl, $C_1$-$C_6$-haloalkyl, $C_3$-$C_6$-halocycloalkyl, $C_3$-$C_6$-cycloalkyl-$C_1$-$C_6$-alkyl, $C_3$-$C_6$-halocycloalkyl-$C_1$-$C_6$-alkyl, cyano-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, aryl, hetaryl, aryl-$C_1$-$C_6$-alkyl, or hetaryl-$C_1$-$C_6$-alkyl, wherein aryl, hetaryl, aryl-$C_1$-$C_6$-alkyl, and hetaryl-$C_1$-$C_6$-alkyl, may be substituted with one or more, identical or different, halogen, CN, $NO_2$, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, or $C_1$-$C_6$-alkoxy-$C_1$-$C_6$-alkyl;

$R^7$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkoxy-$C_1$-$C_6$-alkyl, $C_1$-$C_6$-alkoxycarbonyl, or $C_1$-$C_6$-alkylcarbonyl;

$R^{7a}$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy-$C_1$-$C_6$-alkyl, $C_1$-$C_6$-alkoxycarbonyl, or $C_1$-$C_6$-alkylcarbonyl;

$R^8$ is hydrogen, $C_1$-$C_6$-alkyl, $C_2$-$C_6$-alkenyl, $C_2$-$C_6$-alkynyl, which groups may be independently from each other substituted with one to five halogen or one CN, $NO_2$, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_1$-$C_4$-alkylsulfimino-$C_1$-$C_4$-alkyl, $C_1$-$C_4$-alkylsulfimino-$C_2$-$C_5$-alkylcarbonyl, $C_1$-$C_4$-alkylsulfoximino, $C_1$-$C_4$-alkylsulfoximino-$C_1$-$C_4$-alkyl, $C_1$-$C_4$-alkylsulfoximino-$C_2$-$C_5$-alkylcarbonyl, $C_1$-$C_6$-alkoxycarbonyl, $C_1$-$C_6$-alkylcarbonyl, or $C_3$-$C_6$-trialkylsilyl;

or $R^8$ is aryl-$C_1$-$C_6$-alkyl, hetaryl-$C_1$-$C_6$-alkyl, $C_3$-$C_{12}$-cycloalkyl, $C_3$-$C_{12}$-cycloalkyl-$C_1$-$C_6$-alkyl, or $C_4$-$C_{12}$-bicycloalkyl, which groups may be substituted with halogen, CN, $NO_2$, hydroxy, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl, or $C_2$-$C_6$-alkylcarbonyl, or $R^8$ is a five- to ten-membered aromatic or heteroaromatic ring which may be substituted with one or more identical or different substituents, a four- to six-membered partially saturated ring, a saturated heterocyclic ring, or a saturated or aromatic heterobicyclic ring which may comprise one to three heteroatoms from O, S, or N and which may be substituted with one or more substituents, wherein the substituents are independently from each other halogen, CN, $NO_2$, hydroxy, amino, $C_1$-$C_6$-alkyl, $C_2$-$C_6$-alkynyl, $C_1$-$C_6$-haloalkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl, or $C_2$-$C_6$-alkylcarbonyl, or $R^7$ and $R^8$ are connected through two to six carbon atoms and form a ring, which may comprise an additional atom selected from O, S, or N, and which may be substituted with one to four $C_1$-$C_2$-alkyl, halogen, CN, amino, or $C_1$-$C_2$-alkoxy;

$R^{12}$ is (a) H, $C_1$-$C_6$-alkyl, $C_2$-$C_6$-alkenyl, $C_2$-$C_6$-alkynyl, $C_3$-$C_6$-cycloalkyl, or $C_3$-$C_6$-heterocyclyl, wherein $C_1$-$C_6$-alkyl, $C_2$-$C_6$-alkenyl, $C_2$-$C_6$-alkynyl, $C_3$-$C_6$-cycloalkyl, and $C_3$-$C_6$-heterocyclyl groups may each optionally be substituted with 1 to 3 substituents independently selected from halogen, $NO_2$, CN, $C_3$-$C_6$-cycloalkyl, $C_1$-$C_6$-alkoxy, $C_1$-$C_6$-haloalkoxy, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, $C_1$-$C_6$-alkylthio, $C_1$-$C_6$-haloalkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, $C_1$-$C_6$-alkylcarbonylamino, aryl, hetaryl, $C_3$-$C_6$-heterocyclyl, or $C_3$-$C_6$-oxoheterocyclyl;

wherein aryl, hetaryl, $C_3$-$C_6$-heterocyclyl, and $C_3$-$C_6$-oxoheterocyclyl may be substituted with one or more, identical or different, halogen, CN, $NO_2$, hydroxy, $C_1$-$C_6$-alkyl, $C_3$-$C_6$-cycloalkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy, $C_1$-$C_6$-alkoxy-$C_1$-$C_6$-alkyl, $C_1$-$C_6$-haloalkoxy-$C_1$-$C_6$-alkyl, $C_3$-$C_6$-cycloalkyl-$C_1$-$C_6$-alkyl, cyano-$C_1$-$C_6$-alkyl, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylthio, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, $C_1$-$C_6$-alkylcarbonylamino, aryl, or hetaryl;

or (b) aryl or heteroaryl, which is optionally substituted with 1 to 3 substituents independently selected from the group consisting of halogen, $NO_2$, CN, amino, $SF_5$, SCN, $C_1$-$C_6$-alkylamino, di-($C_1$-$C_6$)-alkylamino, OH, COOH, $C_1$-$C_6$-alkyl, $C_3$-$C_6$-cycloalkyl, $C_1$-$C_6$-alkoxy, $C_1$-$C_6$-haloalkyl, $C_1$-$C_6$-haloalkoxy, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_3$-$C_6$-halocycloalkyl-$C_1$-$C_6$-alkyl, $C_1$-$C_6$-alkoxy-$C_1$-$C_6$-alkyloxy, $C_1$-$C_6$-haloalkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, and tri-($C_1$-$C_6$-alkyl) silyl;

$R^{13}$ is H, $C_1$-$C_6$-alkyl, $C_2$-$C_6$-alkenyl, $C_2$-$C_6$-alkynyl, $C_3$-$C_6$-cycloalkyl, $C_3$-$C_6$-heterocyclyl, aryl, heteroaryl, aryl-$C_1$-$C_6$-alkyl, heteroaryl-$C_1$-$C_6$-alkyl, $C_3$-$C_6$-oxo-heterocyclyl or $C_3$-$C_6$-dioxo-heterocyclyl, wherein each of the aforementioned eleven groups may optionally be substituted with 1 to 3 substituents independently selected from the group consisting of halogen, $NO_2$, CN, $C_3$-$C_6$-cycloalkyl, $C_1$-$C_6$-alkoxy, $C_1$-$C_6$-haloalkoxy, $C_1$-$C_6$-alkoxyamino-$C_1$-$C_6$-alkyl, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfinyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, aryl, and heteroaryl, wherein aryl, heteroaryl, may be substituted with one or more, identical or different, halogen, CN, $NO_2$, OH, $C_1$-$C_6$-alkyl, $C_1$-$C_6$-haloalkyl, $C_1$-$C_6$-alkoxy, or $C_1$-$C_6$-haloalkoxy;

$R^{14a}$ is hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkoxy-$C_1$-$C_6$-alkyl, $C_1$-$C_6$-alkoxycarbonyl, or $C_1$-$C_6$-alkylcarbonyl;

$R^{14b}$ is hydrogen, $C_1$-$C_6$-alkyl, $C_2$-$C_6$-alkenyl, $C_2$-$C_6$-alkynyl, $C(=O)N(R^7)(R^8)$, wherein $C_1$-$C_6$-alkyl, $C_2$-$C_6$-alkenyl, and $C_2$-$C_6$-alkynyl may be independently from each other substituted with one to five halogen or one CN, $NO_2$, hydroxy, $C_1$-$C_6$-alkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_1$-$C_4$-alkylsulfimino-$C_1$-$C_4$-alkyl, $C_1$-$C_4$-alkylsulfimino-$C_2$-$C_5$-alkylcarbonyl, $C_1$-$C_4$-alkylsulfoximino, $C_1$-$C_4$-alkylsulfoximino-$C_1$-$C_4$-alkyl, $C_1$-$C_4$-alkylsulfoximino-$C_2$-$C_5$-alkylcarbonyl, $C_1$-$C_6$-alkoxycarbonyl, $C_1$-$C_6$-alkylcarbonyl, or $C_3$-$C_6$-trialkylsilyl;

or $R^{14b}$ is aryl-$C_1$-$C_6$-alkyl, hetaryl-$C_1$-$C_6$-alkyl, $C_3$-$C_{12}$-cycloalkyl, $C_3$-$C_{12}$-cycloalkyl-$C_1$-$C_6$-alkyl or $C_4$-$C_{12}$-bicycloalkyl, which groups may be substituted with halogen, CN, $NO_2$, hydroxy, amino, $C_1$-$C_6$-alkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl, or $C_2$-$C_6$-alkylcarbonyl, or $R^{14b}$ is a five- to six-membered aromatic or heteroaromatic ring which may be substituted with one or more identical or different substituents, a four- to six-membered partially saturated ring, a saturated heterocyclic ring, or a saturated or aromatic heterobicyclic ring which may comprise one to three heteroatoms from O, S, or N and which may be substituted with one or more substituents, wherein the substituents are independently from each other halogen, CN, $NO_2$, hydroxy, amino, $C_1$-$C_6$-alkyl, $C_2$-$C_6$-alkynyl, $C_1$-$C_6$-haloalkyl, $C_3$-$C_6$-cycloalkyl, $C_3$-$C_6$-cycloalkylamino, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkylsulfimino, $C_2$-$C_6$-alkoxycarbonyl, or $C_2$-$C_6$-alkylcarbonyl, or $R^{14a}$ and $R^{14b}$ are connected through two to six carbon atoms and form a ring, which may comprise an additional atom selected from O, S, or N, and which may be substituted with one to four $C_1$-$C_2$-alkyl, halogen, CN, amino, or $C_1$-$C_2$-alkoxy;

$R^{15}$ is H or $C_1$-$C_6$-alkyl, wherein alkyl group is optionally substituted with one or more substituents independently selected from the group consisting of halogen, $NO_2$, CN, $C_3$-$C_6$-cycloalkyl, $C_1$-$C_6$-alkoxy, $C_1$-$C_6$-haloalkoxy, aryl, and heteroaryl, wherein aryl and heteroaryl may optionally be substituted with one or more, identical or different, halogen, CN, $NO_2$, OH, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylcarbonyl, $C_1$-$C_6$-haloalkylcarbonyl, $C_1$-$C_6$-alkoxycarbonyl, $C_1$-$C_6$-alkylsulfinyl, $C_1$-$C_6$-alkylsulfonyl, $C_1$-$C_6$-haloalkylsulfonyl, or $C_1$-$C_6$-alkylcarbonylamino;

or a stereoisomer, tautomer, salt, or N-oxide thereof.

2. The compound of formula (I) according to claim 1, wherein Y is O.

3. The compound of formula (I) or a stereoisomer, tautomer, salt, or N-oxide thereof according to claim 1, wherein the ring A is a five-membered saturated or partially saturated ring, taken together with the carbon and nitrogen of the imidazole ring in formula (I), wherein each remaining ring member is selected from carbon atoms and up to 3 heteroatoms independently selected from up to 2 O, up to 2 S, and up to 3 N, wherein up to 2 carbon atom ring members are independently selected from C(═O) and C(═S), and the sulfur atom ring members are independently selected from $S(═O)_m$, wherein each ring member may be substituted with $R^a$ and/or $R^c$; and wherein the ring is substituted with one $R^4$.

4. The compound of formula (I) according to claim 1, is selected from a group of compounds of formulae II-1 to II-8 and II-16.

(II-1)

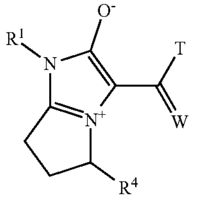

-continued (II-2)

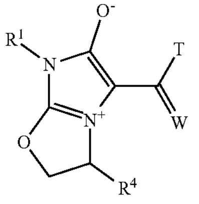

(II-3)

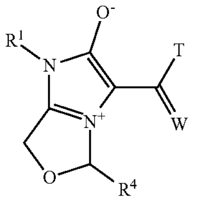

(II-4)

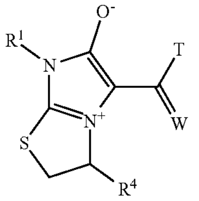

(II-5)

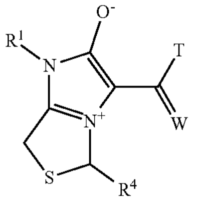

(II-6)

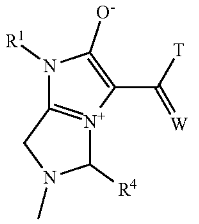

(II-7)

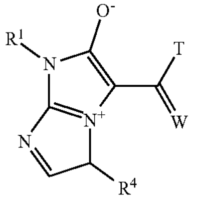

(II-8)

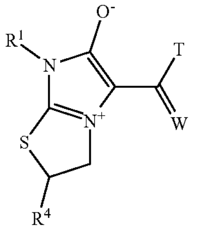

-continued (II-16)

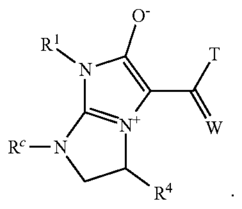

5. The compound of formula (I) according to claim 4, wherein the compound is of formula II-4 or II-16.

6. The compound of formula (I) according to claim 1, wherein W is O.

7. The compound of formula (I) or a stereoisomer, tautomer, salt, or N-oxide thereof according to claim 1, wherein T is $R^5$, $OR^6$, —$N(R^7)(R^8)$, —$N(R^{7a})$—$N(R^7)(R^8)$, C(═Z)$R^{12}$, or C(═Z)$OR^{13}$, wherein Z is O, S, or N—$OR^{15}$, $R^5$ is $C_1$-$C_8$-alkyl, which may be independently from each other substituted with one to five substituents selected from halogen, aryl, hetaryl, wherein aryl, hetaryl, may in turn be substituted with 1 to 3 halogen, or $R^5$ is aryl, or hetaryl, which groups may be independently from each other substituted with one to three substituents independently selected from the group consisting of halogen, CN, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, and $C_1$-$C_6$-alkylthio;

$R^7$ is hydrogen;

$R^{7a}$ is hydrogen;

$R^8$ is $C_1$-$C_6$-alkyl;

or $R^8$ is aryl-$C_1$-$C_6$-alkyl;

or $R^8$ is a five- to ten-membered aromatic ring which may be substituted with one or more halogen;

$R^{12}$ is $C_1$-$C_6$-alkyl, may each optionally be substituted with 1 to 3 substituents independently selected from halogen, and $C_1$-$C_6$-haloalkylthio;

$R^{13}$ is $C_1$-$C_6$-alkyl, may optionally be substituted with 1 to 3 halogens;

$R^{14a}$ is hydrogen;

$R^{14b}$ is C(═O)$N(R^7)(R^8)$;

$R^{15}$ is $C_1$-$C_6$-alkyl, optionally substituted with one or more halogen.

8. The compound of formula (I) according to claim 1, wherein $R^4$ is $CH_2CN$ or $CH_2CH_2CN$.

9. A composition comprising at least one compound of formula (I), as defined in claim 1, and at least one inert liquid and/or solid carrier.

10. A method for protecting crops, plants, plant propagation material and/or growing plants from attack or infestation by invertebrate pests comprising contacting or treating the crops, plants, plant propagation material and growing plants, or soil, material, surface, space, area or water in which the crops, plants, plant propagation material is stored or the plant is growing with a pesticidally effective amount of at least one compound of formula (I) or a stereoisomer, tautomer, salt, or N-oxide thereof as defined in claim 1.

11. A method for combating, controlling, preventing or protecting against infestation or infection by invertebrate pest, which method comprises contacting said pest or its food supply, habitat or breeding grounds with a pesticidally effective amount of at least one compound of formula I or a stereoisomer, tautomer, salt, or N-oxide thereof as defined in claim 1.

12. A non-therapeutic method for treating animals infested or infected by parasites or preventing animals of getting infected or infested by parasites or protecting animals against infestation or infection by parasites which comprises orally, topically or parenterally administering or applying to the animals a parasiticidally effective amount of a compound of formula I or a stereoisomer, tautomer, salt, or N-oxide thereof as defined in claim 1.

13. Seed comprising a compound of formula I as defined in claim 1 or a stereoisomer, tautomer, salt, or N-oxide thereof in an amount of from 0.1 g to 10 kg per 100 kg of seed.

14. The compound of claim 1 wherein the Het is selected from the group consisting of D-2a, D-2b, D-2c, and D-25a:

D-2a

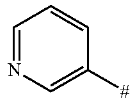

D-2b

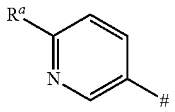

D-2c

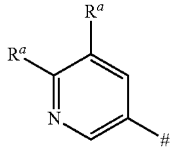

and

D-25a

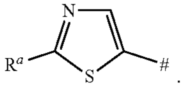

15. The compound of claim 14 wherein Het is D-25a substituted with Cl.

* * * * *